US011408007B2

(12) United States Patent
Isaacs et al.

(10) Patent No.: US 11,408,007 B2
(45) Date of Patent: Aug. 9, 2022

(54) COMPOSITIONS AND METHODS FOR BIOCONTAINMENT OF MICROORGANISMS

(71) Applicant: Yale University, New Haven, CT (US)

(72) Inventors: Farren J. Isaacs, Stamford, CT (US); Ryan Gallagher, New Haven, CT (US); Jaymin Patel, New Haven, CT (US); Alexis Rovner, Cambridge, MA (US)

(73) Assignee: YALE UNIVERSITY, New Haven, CT (US)

( * ) Notice: Subject to any disclaimer, the term of this patent is extended or adjusted under 35 U.S.C. 154(b) by 58 days.

(21) Appl. No.: 15/514,749

(22) PCT Filed: Sep. 28, 2015

(86) PCT No.: PCT/US2015/052613
§ 371 (c)(1),
(2) Date: Mar. 27, 2017

(87) PCT Pub. No.: WO2016/073079
PCT Pub. Date: May 12, 2016

(65) Prior Publication Data
US 2017/0240908 A1 Aug. 24, 2017

Related U.S. Application Data

(60) Provisional application No. 62/056,189, filed on Sep. 26, 2014.

(51) Int. Cl.
*C12N 15/70* (2006.01)
*C12N 15/79* (2006.01)
*C12N 15/74* (2006.01)
*C12N 1/36* (2006.01)
*C12P 1/00* (2006.01)
*C12N 15/10* (2006.01)
*C12N 1/20* (2006.01)
*C12P 21/02* (2006.01)
*C12P 1/04* (2006.01)
*C12R 1/19* (2006.01)

(52) U.S. Cl.
CPC .............. *C12N 15/70* (2013.01); *C12N 1/20* (2013.01); *C12N 1/205* (2021.05); *C12N 1/36* (2013.01); *C12N 15/102* (2013.01); *C12N 15/74* (2013.01); *C12N 15/79* (2013.01); *C12P 1/00* (2013.01); *C12P 1/04* (2013.01); *C12P 21/02* (2013.01); *C12R 2001/19* (2021.05)

(58) Field of Classification Search
None
See application file for complete search history.

(56) References Cited

U.S. PATENT DOCUMENTS

| | | |
|---|---|---|
| 4,495,280 A | 1/1985 | Bujard |
| 4,868,111 A | 9/1989 | Bujard |
| 5,362,646 A | 11/1994 | Bujard |
| 5,464,758 A | 11/1995 | Gossen |
| 5,589,362 A | 12/1996 | Bujard |
| 5,650,298 A | 7/1997 | Bujard |
| 5,654,168 A | 8/1997 | Bujard |
| 5,789,156 A | 8/1998 | Bujard |
| 5,814,618 A | 9/1998 | Bujard |
| 5,888,981 A | 3/1999 | Bujard |
| 5,922,927 A | 7/1999 | Bujard |
| 6,004,941 A | 12/1999 | Bujard |
| 6,087,166 A | 7/2000 | Baron |
| 6,136,954 A | 10/2000 | Bujard |
| 6,242,667 B1 | 6/2001 | Bujard |
| 6,252,136 B1 | 6/2001 | Bujard |
| 6,271,341 B1 | 8/2001 | Baron |
| 6,271,348 B1 | 8/2001 | Bujard |
| 6,783,756 B2 | 8/2004 | Bujard |
| 6,852,834 B2 | 2/2005 | Chilkoti |
| 8,153,432 B2 | 4/2012 | Church |
| 9,464,288 B2 | 10/2016 | Soll |
| 10,023,893 B2 | 7/2018 | Soll |
| 10,240,158 B2 | 3/2019 | Soll |
| 10,501,734 B2 | 12/2019 | Isaacs |
| 10,876,142 B2 | 12/2020 | Söll |
| 2003/0148422 A1 | 8/2003 | Doring |

(Continued)

FOREIGN PATENT DOCUMENTS

WO 1999058652 11/1999
WO 2002086075 10/2002

(Continued)

OTHER PUBLICATIONS

Precise manipulation of chromosomes in vivo enables genome-wide codon replacement, Science Jul. 15, 2011; 333(6040):348-353 (Year: 2011).*
Jaehwan Jeong (Genome-scale genetic engineering in *Escherichia coli* Biotechnology advances 31, 804-810, 2013 (Year: 2013).*
Lajoie et al (Genomically Recoded Organisms Expand Biological Functions Science vol. 342, pp. 357-360, Oct. 18, 2013). (Year: 2013).*
Genomically Recoded Organisms Expand Biological Functions Marc J. Lajoie, Science vol. 342 Oct. 18, 2013 (Year: 2013).*

(Continued)

*Primary Examiner* — Kagnew H Gebreyesus
(74) *Attorney, Agent, or Firm* — Pabst Patent Group LLP

(57) ABSTRACT

Methods and strategies for introducing genetic safeguards into microorganisms, genetically modified organisms (GMO) including the safeguards, and methods of use thereof are provided. The genetic safeguards generally impart a low escape frequency, are robust, and are modular. Safeguards with low escape frequency prevent the rise of mutants escaping defined media and limit growth in the wild. Robust safeguards retain wild-type levels of fitness while also maintaining containment in diverse growth conditions.

27 Claims, 24 Drawing Sheets

Specification includes a Sequence Listing.

(56) References Cited

U.S. PATENT DOCUMENTS

| | | | |
|---|---|---|---|
| 2014/0154744 | A1 | 6/2014 | Soll |
| 2017/0002347 | A1 | 1/2017 | Soll |
| 2017/0029858 | A1 | 2/2017 | Soll |
| 2017/0240908 | A1 | 8/2017 | Isaacs |
| 2018/0105854 | A1 | 4/2018 | Söll |
| 2020/0190500 | A1 | 6/2020 | Isaacs |
| 2020/0332336 | A1 | 10/2020 | Soll |

FOREIGN PATENT DOCUMENTS

| | | |
|---|---|---|
| WO | 2007005053 | 1/2007 |
| WO | 2008036392 | 5/2008 |
| WO | 2009048971 | 4/2009 |
| WO | 2009049223 | 4/2009 |
| WO | 2012087483 | 6/2012 |
| WO | 2013003597 | 1/2013 |
| WO | 2015048364 | 4/2015 |
| WO | 2015120287 | 8/2015 |

OTHER PUBLICATIONS

Altenhoefer, et al, "The probiotic *Escherichia coli* strain Nissle 1917 interferes with invasion of human intestinal epithelial cells by different enteroinvasive bacterial pathogens", FEMS Immunol. Med. Microbiol, 40:223-229 (2004).

Anderson, et al., "Environmentally controlled invasion of cancer cells by engineered bacteria," J. Mol. Biol., 355:619-27 (2006).

Baba, et al, "Construction of *Escherichia coli* K-12 in-frame, single-gene knockout mutants: the Keio collection", Mol. Syst. Biol, 2:2006-8 (2006).

Bain, et al, "Ribosome-mediated incorporation of a non-standard amino acid into a peptide through expansion of the genetic code" Nature, 356:537-9 (1992).

Bayer and Smolke, "Programmable ligand-controlled riboregulators of eukaryotic gene expression" Nat Biotechnol., 23(3):337-43 2005).

Berg, et al, "Summary statement of the Asilomar conference on recombinant DNA molecules", PNAS, 72:1981-4 (1975).

Betenbaugh, et al., "Effects of plasmid amplification and recombinant gene expression on the growth kinetics of recombinant *E. coli*", Biotechnol. Bioeng, 33:1425-36 (1989).

Brenner, et al, "Engineering microbial consortia: a new frontier in synthetic biology", Trends Biotechnol, 26:483-9 (2008).

Cai, et al., "Intrinsic biocontainment: Multiplex genome safeguards combine transcriptional and recombinational control of essential yeast genes", PNAS, 112(6):1803-8 (2015).

Callura, et al, "Tracking, tuning, and terminating microbial physiology using synthetic riboregulators", PNAS, 107:15898-903 (2010).

Calos and Miller, "The DNA sequence change resulting from the IQ1 mutation, which greatly increases promoter strength", Mol. Gen. Genet., 183:559-60 (1981).

Carr, et al, "Enhanced multiplex genome engineering through co-operative oligonucleotide co-selection", Nucleic Acids Res, 40:e132 (2012).

Cohen, et al, "Construction of biologically functional bacterial plasmids in vitro", PNAS., 70:3240-4 (1973).

Dang, et al., "Combination bacteriolytic therapy for the treatment of experimental tumors", PNAS, 98, 15155-15160 (2001).

Davis and Chin, "Designer proteins: applications of genetic code expansion in cell biology", Nat. Rev. Mol. Cell Biol., 13:168-82 (2012).

Devito, "Recombineering with tolC as a selectable/counter-selectable marker: remodeling the rRNA operons of *Escherichia coli*" Nucleic Acids Res., 36:e4 (2008).

Dumas, et al., "Designing logical codon reassignment—Expanding the chemistry in biology", Chem. Sci., 6:50-69 (2015).

Eggertsson, "Transfer ribonucleic acid-mediated suppression of termination codons in *Escherichia coli*", Microbiol. Rev, 52:354-74 (1988).

Ellis, et al, "High efficiency mutagenesis, repair, and engineering of chromosomal DNA using single-stranded oligonucleotides", PNAS., 98:6742-6 (2001).

Fan, et al, "Exploring the substrate range of wild-type aminoacyl-tRNA synthetases", ChemBioChem, 15:1805-9 (2014).

Farabaugh, et al, "Genetic studies of the lac repressor. VII. On the molecular nature of spontaneous hotspots in the lacI gene of *Escherichia coli*", J. Mol. Biol., 126:847-57 (1978).

Galan and Wolf-Waltz, et al, "Protein delivery into eukaryotic cells by type III secretion machines", Nature, 444:567-73 (2006).

Gallagher, et al,, "Multilayered genetic safeguards restricted growth of microorganisms to synthetic environments", poster SB60, presented at conference in London, England, Jul. 9-11, 2013.

Gallagher, et al, "Rapid editing and evolution of bacterial genomes using libraries of synthetic DNA", Nat. Protoc., 9:2301-16 (2014).

Gallagher, et al,, "Multilayered genetic safeguards limit growth of microorganisms to defined environments", Nucleic Acids Res., 43(3):1945-54 (2015).

Garmory, et al., "The use of live attenuated bacteria as a delivery system for heterologous antigens," J. Drug Target., 11:471-9 (2003).

GenBank accession CP006698, Synthetic *Escherichia coli* C321. deltaA, complete sequence, 4 pages, first appeared. Oct. 18, 2013, updated Jan. 21, 2015, accessed Aug. 25, 2017.

Gibson, et al, "Enzymatic assembly of DNA molecules up to several hundred kilobases", Nature Methods, 6:343-5 (2009).

Gregg, et al., "Rational optimization of tolC as a powerful dual selectable marker for genome engineering", Nucleic Acids Res., 42(7):4779-90 (2014).

Grillot-Courvalin, et al, "Functional gene transfer from intracellular bacteria to mammalian cells", Nat. Biotechnol, 16:862-6 (1998).

Hammerling, et al, "Bacteriophages use an expanded genetic code on evolutionary paths to higher fitness", Nature Chem. Biol, 10:178-80 (2014).

Hanahan, et al, "Hallmarks of cancer: the next generation", Cell, 144:646-74 (2011).

Holberger, et al, "Ribosomal protein S12 and aminoglycoside antibiotics modulate A-site mRNA cleavage and transfer-messenger RNA activity in *Escherichia coli*". J. Biol. Chem, 284:32188-200 (2009).

Isaacs, et al, Engineered riboregulators enable post-transcriptional control of gene expression, Nat. Biotechnol, 22:841-7 (2004).

Isaacs, et al, "Precise manipulation of chromosomes in vivo enables genome-wide codon replacement", Science, 333:348-53 (2011).

Jensen, et al, "Programmed cell death in bacteria: proteic plasmid stabilization systems", Mol. Microbiol., 17:205-210 (1995).

Jensen, et al., "A substrate-dependent biological containment system for Pseudomonas putida based on the *Escherichia coli* gef gene," Appl. Environ. Microbiol., 59, 3713-3717 (1993).

Kang, et al, "Immune responses dependent on antigen location in recombinant attenuated *Salmonella typhimurium* vaccines following oral immunization", Infect. Immun, 70:1739-49 (2003).

Kimman, et al., "Evidence-based biosafety: a review of the principles and effectiveness of microbiological containment measures", Clin. Microbiol., 21(3):403-25 (2008).

Knudsen, et. al, "Development of efficient suicide mechanisms for biological containment of bacteria", Appl. Environ. Microbiol, 57:85-92 (1991).

Knudson, et al, "Two genetic hits (more or less) to cancer", Nat. Rev. Cancer, 1:157-62 (2001).

Kong, et al, "Regulated programmed lysis of recombinant Salmonella in host tissues to release protective antigens and confer biological containment", PNAS, 105:9361-6 (2008).

Kotula, et al., "Programmable bacteria detect and record an environmental signal in the mammalian gut," PNAS, 111, 4838-43 (2014).

Kroll, et al., "Plasmid addiction systems: perspectives and aplications in biotechnology", Micro Biotech., 3(6):634-57 (2010).

Kumar, et al, "Predicting the effects of coding non-synonymous variants on protein function using the SIFT algorithm", Nature Protocols, 4:1073-81 (2009).

Lajoie, et al, "Genomically recoded organisms expand biological functions", Science, 342:357-360 (2013).

(56) References Cited

OTHER PUBLICATIONS

Lajoie, et al, "Probing the limits of genetic recoding in essential genes", Science, 342:361-363 (2013b).
Liu and Schultz, "Adding new chemistries to the genetic code", Annu. Rev. Biochem., 79:413-44 (2010).
Lutz and Bujard, "Independent and tight regulation of transcriptional units in *Escherichia coli* via the LacR/O, the TetR/O and AraC/I1-I2 regulatory elements.", Nucleic Acids Res, 25(6):1203-10 (1997).
Maisnier-Patin, et al, "Compensatory adaptation to the deleterious effect of antibiotic resistance in *Salmonella typhimurium*", Mol. Microbiol, 46:355-66 (2002).
Mandell, et al., "Biocontainment of genetically modified organisms by synthetic protein design", Nature, 518:(7537):55-60 (2015).
Marchler-Bauer, et al, "CDD: a Conserved Domain Database for protein classification", Nucleic Acids Res, 33:D192-6 (2005).
Moe-Behrens, et al., "Preparing synthetic biology for the world," Frontiers in Microbiology 4:5, doi:10.3389/fmicb. (2013).
Molin, et al, "Conditional Suicide System for Containment of Bacteria and Plasmids", Nat. Biotechnol, 5:1315-8 (1987).
Normanly, et al., "Construction of two *Escherichia coli* amber suppressor genes: tRNAPheCUA and tRNACysCUA", PNAS, 83:6548-52 (1986).
O'Donoghue, et al., "Upgrading protein synthesis for synthetic biology", Nature Chem. Biol, 9:594-8 (2013).
Otsuka, et al., "GenoBase: comprehensive resource database of *Escherichia coli* K-12.", Nucleic Acids Research, 43:database issue doi: 10.1093/nar/gku1164 (2015).
Paddon, et al., "High-level semi-synthetic production of the potent antimalarial artemisinin," Nature, 496:528-32 (2013).
Park, et al., "Expanding the genetic code of *Escherichia coli* with phosphoserine", Science, 333:1151-4 (2011).
Pieper and Reineke, "Engineering bacteria for bioremediation," Curr. Opin. Biotechnol., 11: 262-70 (2000).
Pinheiro, et al, "Synthetic genetic polymers capable of heredity and evolution", Science, 336:341-4 (2012).
Polisky, et al, "Specificity of substrate recognition by the EcoRI restriction endonuclease", PNAS, 72:3310-4 (1975).
Richmond, et al, "Genome-wide expression profiling in *Escherichia coli* K-12", Nucleic Acids Res, 27:3821-35 (1999).
Ritger, et al., "Fatal Laboratory-Acquired Infection with an Attenuated Yersinia Pestis Strain", CDC—Morbidity and Mortality Weekly Report, 60(07);201-205 ,Chicago, Il (2009).
Ronchel and Ramos, "Dual system to reinforce biological containment of recombinant bacteria designed for rhizoremediation," Appl Environ. Microbiol., 67, 2649-56 (2001).
Rovner, et al., "Recoded organisms engineered to depend on synthetic amino acids", Nature, 518(7537):89-93 (2015).
Schaaper, et al, "Spectra of spontaneous mutations in *Escherichia coli* strains defective in mismatch correction: the nature of in vivo DNA replication errors", PNAS, 84:6220-4 (1987).
Schmidt and de Lorenzo, "Synthetic constructs in/for the environment: managing the interplay between natural and engineered biology," FEBS Lett., 586, 2199-206 (2012).
Schultz, et al., "A genetically encoded infrared probe", J Am Chem Soc, 128:13984-5 (2006).
Seo, et al., "Transcription of an expanded genetic alphabet", J Am Chem Soc., 131(14):5046-7 (2009).
Sharan, et al, "Recombineering: a homologous recombination-based method of genetic engineering", Nature Protocols, 4:206-23 (2009).
Smith, et al., "Efficiency of the pTF-FC2 pas poison-antidote stability system in *Escherichia coli* is affected by the host strain, and antidote degradation requires the Ion protease", J Bacteriol., 180:5458-62 (1998).
Sørensen, et al., "Studying plasmid horizontal transfer in situ: a critical review", Nature Rev. Microbiol, 3:700-10 (2005).
Steidler, et al., "Biological containment of genetically modified Lactococcus lactis for intestinal delivery of human interleukin," Nat. Biotechnol., 21(7):785-9 (2003).

Steidler, et al., "Genetically engineered probiotics," Best Pract. Res. Clin. Gastroenterol., 17, 861-876 (2003b).
Szafranski, et al., "A new approach for containment of microorganisms: dual control of streptavidin expression by antisense RNA and the T7 transcription system", PNAS, 94:1059-63 (1997).
Torres, et al, "A dual lethal system to enhance containment of recombinant microorganisms", Microbiology, 149:3595-601 (2003).
Wang, et al., "Programming cells by multiplex genome engineering and accelerated evolution", Nature, 460:894-8 (2009).
Way, et al, "Integrating biological redesign: where synthetic biology came from and where it needs to go", Cell, 157:151-61 (2014).
Wilson, et al, "Restriction and modification systems", Annu. Rev. Genet, 25:585-627 (1991).
Wu, et al, "Isolation and characterization of a glucosamine-requiring mutant of *Escherichia coli* K-12 defective in glucosamine-6-phosphate synthetase", J. Bacteriol, 105:455-66 (1971).
Xiang, et al, "Short hairpin RNA-expressing bacteria elicit RNA interference in mammals", Nat. Biotechnol, 24:697-702 (2006).
Yamaguchi, et al., "Toxin-antitoxin systems in bacteria and archaea", Annu Rev Genet, 45:61☐79 (2011).
Young, et al, "An enhanced system for unnatural amino acid mutagenesis in *E. coli*", J. Mol. Biol, 395:361-74 (2010).
International Search Report for corresponding PCT Application PCT/US2015/052613 dated Jun. 1, 2016.
Johnson, et al., "RF1 Knockout Allows Ribosomal Incorporation of Unnatural Amino Acids at Multiple Sites", Nat. Chem. Biol., 7:779-786 (2011).
Lajoie, et al., "Supplemental Materials for Genomically recoded organisms expand biological functions", Science, Supplementary Materials, http://science.sciencemag.org/content/suppl/2013/10/16/342.6156.357.DC1, 78 pages, (2013).
Mukai, et al., "Codon reassignment in the *Escherichia coli* genetic code", Nucleic Acids Res., 38:8188-95 (2010).
Odonoghue, et al., "Near-cognate suppression of amber, opal and quaduplet codons competes with aminoacyl-tRNAPyl for genetic code expansion", FEBS Lett., 586(21):3931-3937 (2012).
Ohtake, et al., "Efficient Decoding of the UAG Triplet as a Full-Fledged Sense Codon Enhances the Growth of a prfA-Deficient Strain of *Escerichia coli*", Journal of Bacteriology, 194(10):2606-2613 (2012).
U.S. Appl. No. 17/107,555, filed Nov. 30, 2020, Isaacs.
Aerni, et al., "Revealing the amino acid composition of proteins within an expanded genetic code", Nucleic Acids Res., 43(2):e8 (2015).
Ambrogelly & Palioura, "Natural expansion of the genetic code" Nature Chemical Biology, 3:29-35 (2007).
Amiram, et al., "Evolution of translation machinery in recoded bacteria enables multi-site incorporation of nonstandard amino acids," Nature Biotechnology, 33:1272-1279 (2015).
Atkins and Baranov, "The distinction between recoding and codon reassignment", Genetics, 185:1535-6 (2010).
Best, et al., "Click Chemistry and Bioorthogonal Reactions: Unprecedented Selectivity in the Labeling of Biological Molecules" *Biochemistry*, 48(28):6571-6584 (2009).
Chin, "Expanding and reprogramming the genetic code of cells and animals", *Annu Rev Biochem*, 83:379-408 (2014).
Chin, et al., "Addition of p-azido-L-phenylalanine to the genetic code of *Escherichia coli*", *J Am Chem Soc*, 124:9026-7 (2002).
Furman, et al., "A genetically encoded aza-Michael acceptor for covalent cross-linking of protein-receptor complexes", *J Am Chem Soc*, 136:8411-7 (2014).
Gogarten & Townsend, "Horizontal gene transfer, genome innovation and evolution," *Nature Reviews Microbiology* 3:679-687 (2005).
Grosskopf & Soyer, "Synthetic microbial communities" *Current Opinion in Microbiology*, 18:72-77 (2014).
Heinemann, et al., "Enhanced phosphoserine insertion during *Escherichia coli* protein synthesis via partial UAG codon reassignment and release factor 1 deletion", *FEBS Lett*, 586:3716-22 (2012).
Ivanova, et al., "Stop codon reassignments in the wild." *Science*, 344:909-913 (2014).
Johnson, et al., "Residue-specific incorporation of non-canonical amino acids into proteins: recent developments and applications.", *Curr Opin Chem Biol*, 14:774-80 (2010).

(56) References Cited

OTHER PUBLICATIONS

Johnson, et al., "RF1 knockout allows ribosomal incorporation of unnatural amino acids at multiple sites", *Nat Chem Biol*, 7:779-86 (2011).
Johnson, et al., "RF1 knockout allows ribosomal incorporation of unnatural amino acids at multiple sites", *Nat Chem Biol*, 7:779-86 (2011) [Supplemental Material].
Kirshenbaum, et al., "Biosynthesis of proteins incorporating a versatile set of phenylalanine analogues", *Chembiochem*, 3:235-7 (2002).
*Knight, et al., "Rewiring the keyboard: evolvability of the genetic code." *Nature Reviews Genetics*, 2:49-58 (2001).
Kothakota, et al., "Biosynthesis of a Periodic Protein Containing 3-Thienylalanine: A Step Toward Genetically Engineered Conducting Polymers", *J Am Chem Soc*, 117:536-7 (1995).
Li, et al., "Biological applications of expanded genetic codes", *Chembiochem*, 15(16):2335-41 (2014).
Miyake-Stoner, et al., "Generating permissive site-specific unnatural aminoacyl-tRNA synthetases", *Biochemistry*, 49:1667-77 (2010).
Moe-Behrens, et al., "Preparing synthetic biology for the world," *Frontiers in Microbiology*, (2013);4:5, doi:10.3389/fmicb.2013.00005.
Nowatzki, et al., "Mechanically Tunable Thin Films of Photosensitive Artificial Proteins: Preparation and Characterization by Nanoindentation", *Macromolecules*, 41(5):1839-1845 (2008).
Wang, et al., "Addition of the keto functional group to the genetic code of *Escherichia coli*", PNAS, 100:56-61 (2003).
Wu, et al., "Multiple site-selective insertions of noncanonical amino acids into sequence-repetitive polypeptides", Chembiochem, 14:968-78 (2013).
Young, "An enhanced system for unnatural amino acid mutagenesis in *E. coli*." J. Mol. Biol, 395(2):361-74 (2010).
Young, et al., "An evolved aminoacyl-tRNA synthetase with atypical polysubstrate specificity", Biochemistry, 50:1894-900 (2011).
Pirman, "A flexible codon in genomically recoded *Escherichia coli* permits programmable protein phosphorylation," *Nature Communications*, 6:8130 (2015). DOI: https://doi.org/10.1038/ncomms9130, PMID: 26350500.
Schmidt and De Lorenzo, "Synthetic constructs in/for the environment: managing the interplay between natural and engineered biology," *FEBS Lett*, 586, 2199-2206 (2012).
Stokes, et al., "Enhancing the utility of unnatural amino acid synthetases by manipulating broad substrate specificit", *Mol Biosyst*, 5:1032-8 (2009).
Mukai, et al., "Reassignment of a rare sense codon to a noncanonical amino acid in *Escherichia coli*," *Nucleic Acids Res.*, 43:8111 (2015).

* cited by examiner

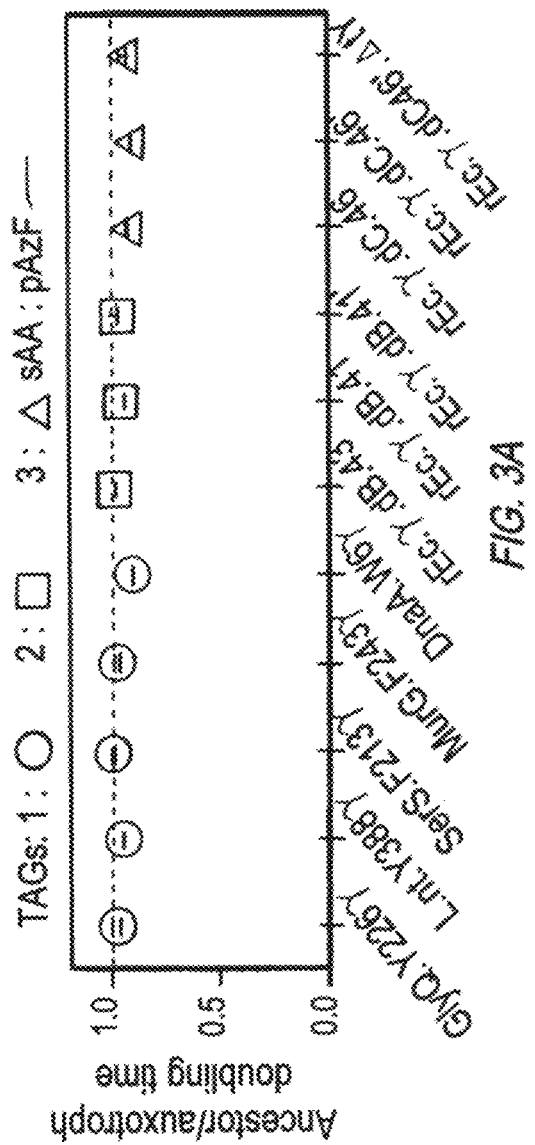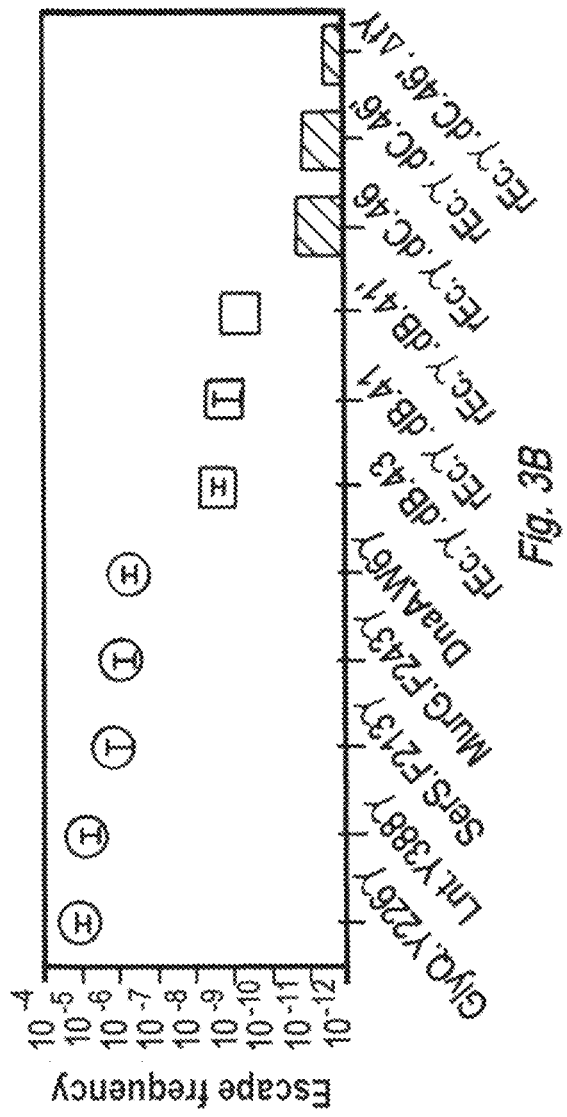
FIG. 3A
FIG. 3B

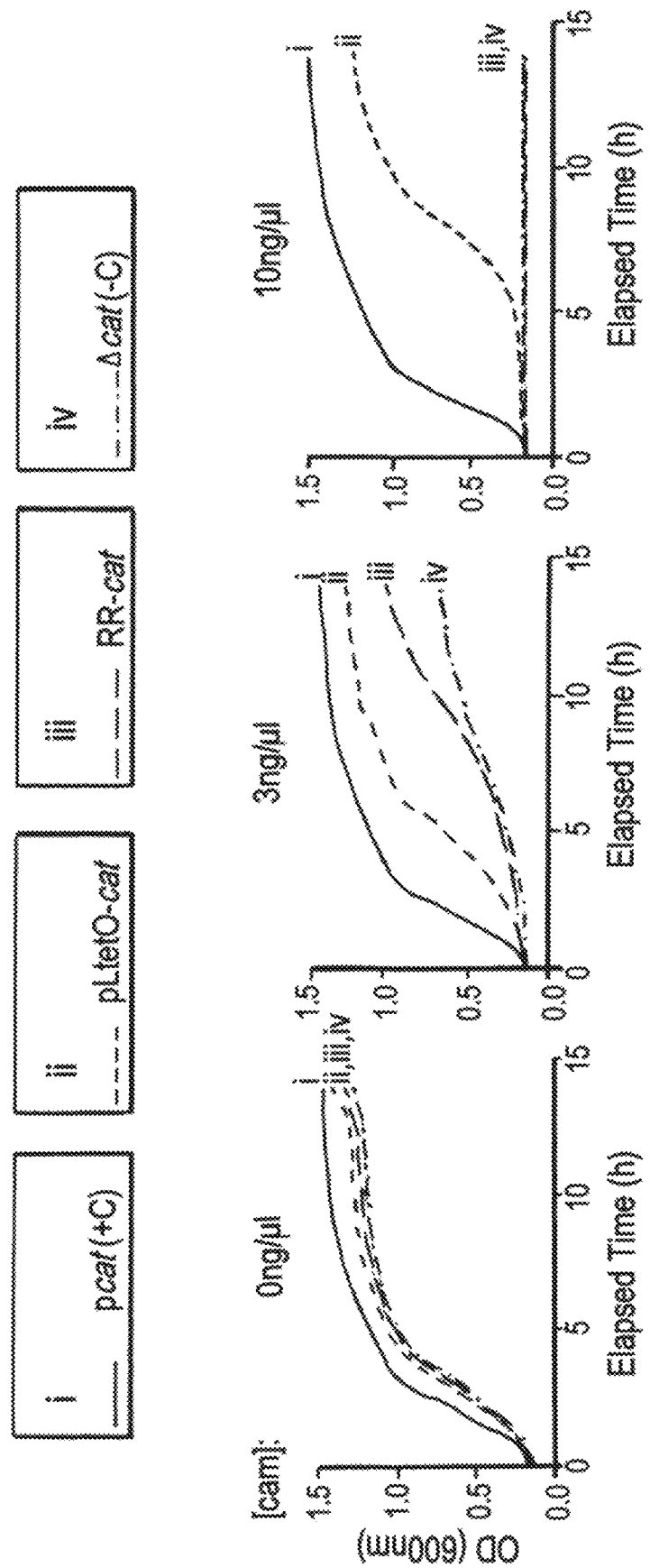

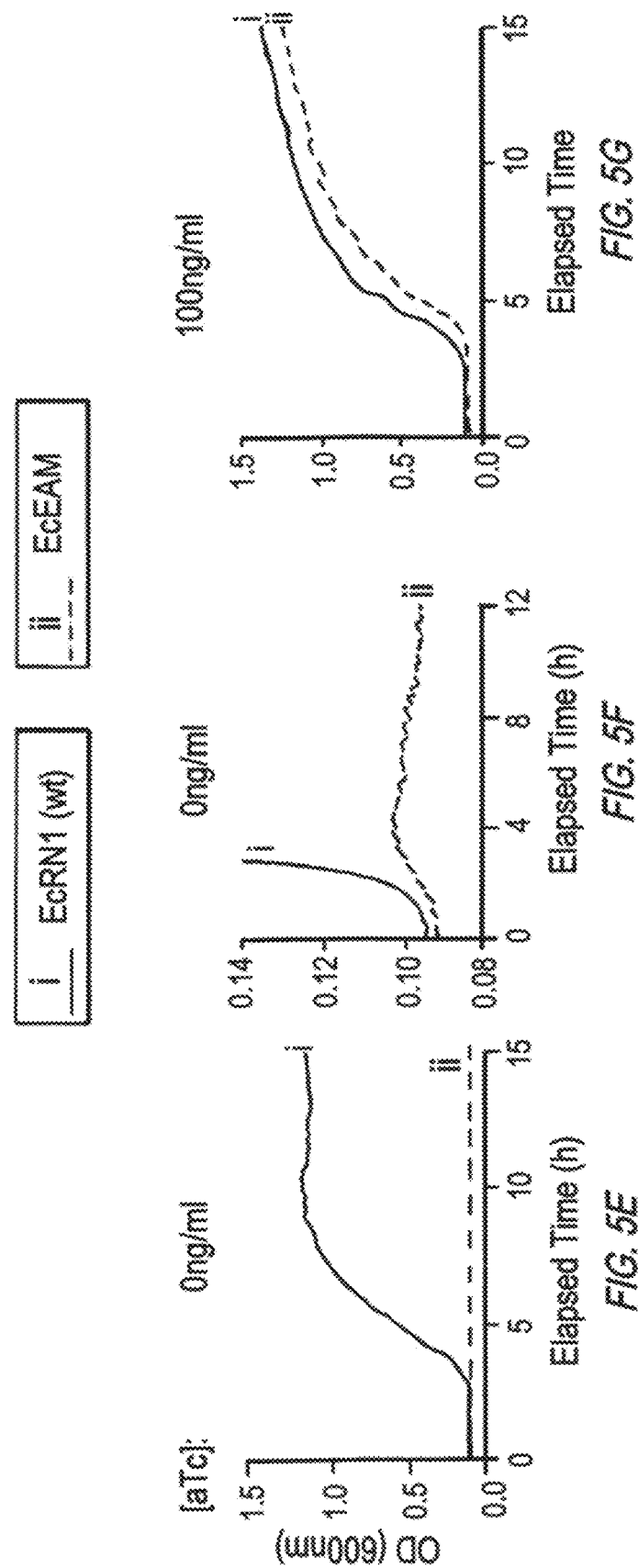

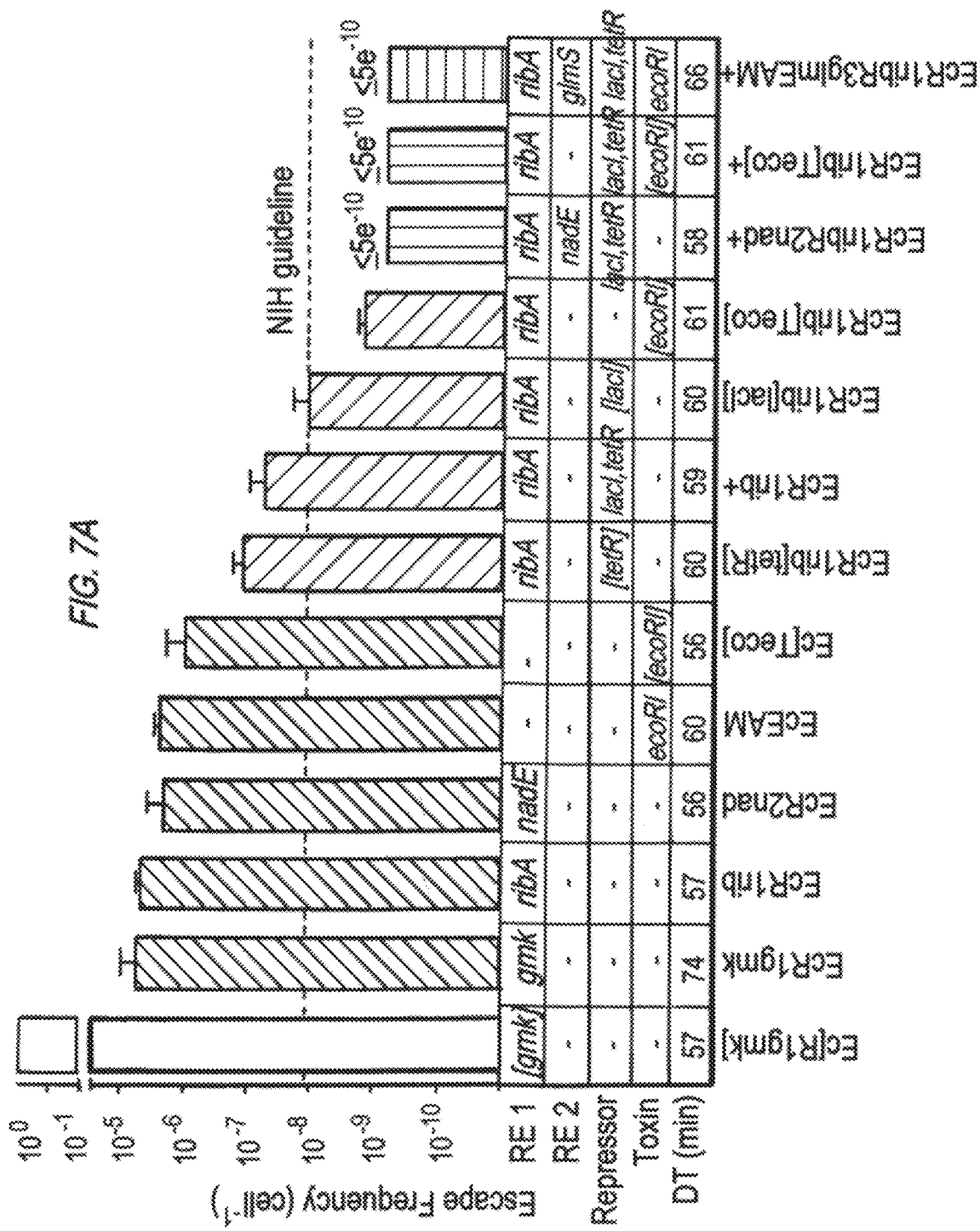

COMPOSITIONS AND METHODS FOR BIOCONTAINMENT OF MICROORGANISMS

CROSS-REFERENCE TO RELATED APPLICATIONS

This application is a 371 application of International Application No. PCT/US2015/052613, filed Sep. 28, 2015, which claims benefit of and priority to U.S. Provisional Application 62/056,189, entitled "Multilayered genetic safeguards for restricting growth of microorganisms to synthetic environments" filed Sep. 26, 2014, and where permissible are incorporated by reference in their entirety.

STATEMENT REGARDING FEDERALLY SPONSORED RESEARCH

This invention was made with government support under N66001-12-C-4020 awarded by the Defense Advanced Research Projects Agency. The government has certain rights in the invention.

REFERENCE TO SEQUENCE LISTING

The Sequence Listing submitted as a text file named "YU_6220_PCT_ST25.txt," created on Sep. 25, 2015, and having a size of 68,811 bytes is hereby incorporated by reference pursuant to 37 C.F.R. § 1.52(e)(5).

FIELD OF THE INVENTION

The field of the invention is generally related to compositions and methods for containment of microorganisms to defined synthetic environments.

BACKGROUND OF THE INVENTION

Since the advent of genetic engineering (Cohen, et al, *Proc. Natl. Acad. Sci. U.S.A.*, 70:3240-3244 (1973)), genetically modified organisms (GMOs) have enabled functional testing of mutations and production of valuable pharmaceutical or industrial compounds (Paddon, et al, *Nature*, 496: 528-532 (2013)). Advances in synthetic biology have led to GMOs with increasingly complex functions including production of fuels and medicines (Paddon, et al, *Nature*, 496:528-532 (2013)), and genetic circuits that can sense and respond to changing environments (Way, et al, *Cell*, 157: 151-161 (2014)). As sophisticated GMOs expand to applications in open systems such as environmental (Pieper, et al, *Curr. Opin. Biotechnol*, 11:262-270 (2000)) or clinical settings (Steidler, *Best Pract. Res. Clin. Gastroenterol*, 17:861-876 (2003)), there is a growing need for intrinsic biocontainment strategies—robust genetic safeguards that conditionally restrict the host cell's viability to defined environments (Schmidt, et al, *FEBS Lett*, 586:2199-2206 (2012)). Safety and security measures were first outlined in the 1975 Asilomar conference on recombinant DNA (Berg, et al, *Proc. Natl Acad. Sci. USA*, 72:1981-1984 (1975)). While guidelines for physical containment and safe use of organisms have been widely adopted, intrinsic biocontainment-biological barriers limiting the spread and survival of microorganisms in natural environments—remains a defining challenge.

Existing strategies for biocontainment are based on designs to control cell growth by engineered auxotrophy (Steidler, et al, *Nat. Biotechnol*, 21:785-789 (2003)), essential gene regulation (Kong, et al, *Proc. Natl. Acad. Sci. U.S.A.*, 105:9361-9366 (2008)) or toxin expression (Molin, et al, *Nat. Biotechnol*, 5:1315-1318 (1987); Szafranski, et al, *Proc. Natl. Acad. Sci. U.S.A.*, 94:1059-1063 (1997)). While the best-performing safeguards reach the $10^{-8}$ NIH standard (that is, one escape mutant per $10^8$ cells) (Health N.I.o. Office of Biotechnology Activities. Bethesda, Md.; 2013. Guidelines for Research Involving Recombinant DNA Molecules) for escape frequency of recombinant microorganisms (Ronchel, et al, *Appl. Environ. Microbiol*, 67:2649-2656 (2001); Jensen, et al, *Appl. Environ. Microbiol*, 59:3713-3717 (1993)), each approach carries risk. Auxotrophy can be complemented by metabolite cross-feeding (Ritger, et al., *Centers for Disease Control and Prevention—Morbidity and Mortality Weekly Report*, Vol. 63. Atlanta, Ga.; 2011. "Fatal Laboratory-Acquired Infection with an Attenuated *Yersinia* Pestis Strain"—Chicago, Ill., 2009) or by environmental availability of essential small molecules, yielding strains that grow in rich media and natural environments. Leaked expression of essential genes can permit viability (Kong, et al, *Proc. Natl. Acad. Sci. U.S.A.*, 105: 9361-9366 (2008)) and mutations lead to loss of toxins (Knudsenk, et. al, *Appl. Environ. Microbiol*, 57:85-92 (1991)). Attempts to implement redundant safeguards reduce the risk of escape, but at the price of decreased fitness (Moe-Behrens, et al, *Front. Microbiol*, 4:1-10 (2013); Torres, et al, *Microbiology*, 149:3595-3601 (2003), leading to a growth advantage for escaping mutants. In view of these drawbacks, there remains a need for improved biocontainment strategies. Specifically, there remains a need for an intrinsic biocontainment strategy able to restrict growth to environments containing synthetic small molecules could prevent a GMO's dissemination and enhance its safety.

It is an object of the invention to provide compositions and strategies that restrict growth of organisms to synthetic environments by engineering intrinsic biocontainment that solve the uncontrolled spread of genetically modified organisms.

It is another object of the invention to provide methods and strategies for introducing genetic safeguards into microorganisms.

It is a further object of the invention to provide genetically modified organisms (GMO) including genetic safeguards.

SUMMARY OF THE INVENTION

Methods and strategies for introducing genetic safeguards into microorganisms, genetically modified organisms (GMO) including the safeguards, and methods of use thereof are provided. The genetic safeguards generally impart a low or even undetectable escape frequency, are robust, and are modular. Safeguards with low escape frequency (e.g., less than $10^{-12}$) prevent the rise of mutants escaping defined media and limit growth in the wild. Robust safeguards retain wild-type levels of fitness while also maintaining containment in diverse growth conditions. This requirement demands that low escape frequency safeguards maintain their performance in rich or diverse environments, where provision of auxotrophic metabolites by other community members is possible. Modularity allows many different strategies to be combined in one strain enabling multilayered safeguards. Modularity also allows portability, such that the safeguards can be easily transferred to different organisms. To satisfy these three requirements, strategies are provided based on independently acting safeguards including natural and synthetic auxotrophy, engineered riboregulation, and engineered addiction that when introduced into microorganisms permit robust growth only in defined environments.

In some embodiments, the GMO is a genomically recoded organism (GRO) having a genome wherein at least one codon is reassigned creating an available sense codon for a recombinant tRNA which is present in at least one essential gene of interest. The recombinant tRNA can be charged by a paired recombinant aminoacyl-tRNA synthetase (aaRS) to permit site-specific incorporation of a synthetic amino acid (sAA) or non-standard amino acid (nsAA) into a nascent peptide chain during translation of the essential gene in the GRO. Typically, the GRO is derived from one in which all genomic iterations of a first stop codon sequence have been reassigned to a second stop codon sequence, the available sense codon consists of the sequence of the first stop codon (i.e., is reassigned sequence of the first stop codon), and the anticodon sequence for the recombinant tRNA recognizes the reassigned sense sequence. In particular embodiments the first stop codon sequence is TAG, and the second stop codon sequence is TAA. In such embodiments, the recombinant tRNA can include the anticodon for TAG. However, in some embodiments, a sense codon is reassigned, e.g., AGG or AGA to CGG, CGA, CGC, or CGG (arginine), e.g., as the principles can be extended to any set of synonymous or non-synonymous codons. The gene encoding release factor 1 (RF1) can be interrupted or deleted. In some embodiments, the reassigned sense codon is only present in the one or more essential genes of interest. By non-limiting example, the GRO can a variant of *E. coli* strain C321.ΔA (GenBank accession CP006698) wherein TAG is substituted for at least one codon in at least one essential gene of interest.

Any of the GRO can include a nucleic acid sequence encoding an expression control sequence operably linked a recombinant aaRS, a recombinant tRNA, or the combination thereof wherein the recombinant tRNA that can be charged by the aaRS to permit site-specific incorporation of a sAA or nsAA into a nascent peptide chain during translation of the essential gene in the GRO. It will be appreciated that the essential gene(s) can be recoded by mutating the gene directly at its endogenous site, or by deleting or otherwise interrupting the endogenous copies and expressing the reassigned copy extrachormasomally. Any of the heterologous nucleic acid sequences including the recoded essential gene (s), recombinant aaRA, recombinant tRNA, etc., can be expressed extrachromosomally by, for example, a vector. In the most preferred embodiments, one or more of the recoded essential gene(s), recombinant aaRA, recombinant tRNA are integrated into a chromosome of the GRO.

Exemplary aaRS include an amino acid sequence of any of SEQ ID NO:1-20, or a functional fragment thereof. An exemplary tRNA is encoded by the nucleic acid sequence of SEQ ID NO:21. Preferred synthetic or non-naturally occurring amino acids are pAcF, pIF, pAzF, and pCNF.

The GRO are typically viable when cultured under permissive conditions including the synthetic amino acid or non-standard amino acid. Such conditions result in translation of a full-length protein encoded by the essential gene. The protein includes one or more iterations of the non-standard or synthetic amino acid, but is nonetheless active and functional. Culturing of the GRO in non-permissive media that does not include the necessary synthetic amino acid or non-standard amino acid leads to truncation of the full-length protein encoded by the essential gene, and preferably results in reduced viability or non-viability of the GRO. In some embodiments, the escape frequency of the GRO in non-permissive media is $10^{-6}$ or lower, for example, between about $10^{-6}$ and about $10^{-12}$.

Additionally or alternatively the GMO can have (i) one or more essential genes whose expression is controlled by riboregulation; (ii) a polynucleotide including an inducible expression control sequence operably linked to a sequence encoding an agent toxic to the GMO; (iii) an engineered addiction system including (a) a polynucleotide including an expression control sequence operably linked to sequence encoding an agent toxic to the GMO, and (b) a polynucleotide including an inducible expression control sequence operably linked to a sequence encoding a rescue agent that neutralizes, inhibits, or otherwise reduces the toxicity of the toxic agent; and combinations thereof.

In some embodiments, the GMO is modified such that one or more essential genes are controlled by riboregulation. Typically, the one or more endogenous essential genes in the GMO is modified, interrupted, or deleted and compensated for by a cis-regulating fusion construct including an inducible expression control sequence operably linked to a sequence encoding a cis-repressive (crRNA) RNA operatively linked to a sequence encoding the open reading frame of the essential gene, wherein induction of the cis-regulating fusion construct causes transcription of a crRNA-essential gene mRNA fusion RNA, and wherein translation of the essential gene mRNA is repressed by a secondary structure Banned by the crRNA. In such embodiments, the GMO also typically also includes a trans-activating construct including an inducible expression control sequence operably linked to a sequence encoding a trans-activating RNA (taRNA) that can hybridize with the crRNA and relieve repression of translation.

Ribregulation can be established such that the product of the essential gene is translated only when the GMO is cultured under permissive conditions that include one or more supplemental agents that induce transcription of both the crRNA-essential gene mRNA fusion RNA and the taRNA. For example, in some embodiments, the expression control sequence of the cis-regulating fusion construct, the expression control sequence of the trans-activating construct, or both include a promoter that is directly induced by the presence of the supplemental agent. Exemplary promoters include pAra or pRha which are induced by arabinose or rhamnose, respectively. In some embodiments, the expression control sequence of the cis-regulating fusion construct, the expression control sequence of the trans-activating construct, or both includes a promoter that is repressed by a constitutively present repressor that prevents transcription of the crRNA-essential gene mRNA fusion RNA, and wherein promoter is indirectly induced in the presence of a supplemental agent that inhibits the repressor. Exemplary promoters include pLtetO, which is repressed by Tet Repressor Protein (TetR), and de-repressed (i.e., induced) by anhydrotetracycline (ATc), and pLlacO, which is repressed by lac Repressor (LacI) and de-repressed (i.e., induced) by isopropyl β-D-1-thiogalactopyranoside (IPTG).

The GMO can include one or more repressor constructs each including a constitutively active promoter operably linked to a nucleic acid sequence encoding the repressor. In some embodiments, the GMO includes at least two copies the nucleic acid sequence encoding the repressor. The promoter of the cis-regulating fusion construct and the trans-activating construct can be the same, but is preferably different. In some embodiments, the promoter of the cis-regulating fusion construct and the trans-activating construct are each independently selected from the group consisting of pLtetO, pLlacO, pAra, and pRha. Expression of two, three, four, five, or more essential genes can be controlled by riboregulation. The sequence of the cis-repressive RNA of each cis-regulating fusion construct can be the same or the cis-repressive RNA sequence for two or more fusion constructs can be different. Accordingly, the taRNA sequence, which is typically designed to complementary to the cis-repressive RNA sequence, can be the same or different for regulation of two or more different essential genes. In preferred embodiments, the one or more essential genes is selected from the group consisting of ribA, adk, pyrH, glmS, gmk, nadE, acpP, tmk, and lpxC.

The cis-regulating fusion construct, the trans-activating construct, or both can be extrachromosomal, for example, expressed from a vector. Preferably, the cis-regulating fusion construct, the trans-activating construct, or both are integrated into a chromosome of the GMO. The riborepressed GMO are typically viable when cultured under permissive conditions including the inducers needed to express the cis-regulating fusion construct and the trans-activating construct. Such conditions result in translation of a full-length protein encoded by the essential gene. Culturing of the GMO in non-permissive media that does not include the necessary inducers leads to non-transcription and non-translation the full-length protein encoded by the essential gene, and preferably results in reduced viability or non-viability of the GMO. In some embodiments, the escape frequency of the GMO in non-permissive media is $10^{-6}$ or lower, for example, between about $10^{-6}$ and about $10^{-12}$.

Some GMO include a polynucleotide including an inducible expression control sequence operably linked to a sequence encoding an agent toxic to the GMO. The expression control sequence can, for example, include an inducible promoter such as pAr or pRh, wherein growth permissive conditions do not include arabinose or rhamnose respectively. In some embodiments, the toxic agent is selected from the group consisting of EcoRI, ccdB, and pasB. In a particularly preferred embodiment, the toxic agent is EcoRI. The polynucleotide can be expressed extrachromosomally or integrated into the genome of the GRO.

The GMO with inducible toxicity are typically viable when cultured under permissive conditions that do not include the inducers needed to express the toxic agent. Such conditions prevent or otherwise fail to induce transcription and translation of the toxic agent. Culturing of the GMO in non-permissive media that includes the necessary inducer leads transcription and translation of the toxic agent, and preferably results in reduced viability or non-viability of the GMO. In some embodiments, the escape frequency of the GMO in non-permissive media is $10^{-6}$ or lower, for example, between about $10^{-6}$ and about $10^{-12}$.

Some GMO include an engineered addiction system. The engineered addiction system can include (a) a polynucleotide including an expression control sequence operably linked to sequence encoding an agent toxic to the GMO, and (b) a polynucleotide comprising an inducible expression control sequence operably linked to a sequence encoding a rescue agent that neutralizes, inhibits, or otherwise reduces the toxicity of the toxic agent. In some embodiments, the expression control sequence of (a) includes an inducible, or preferably constitutively active promoter. The toxic agent can be, for example, EcoRI, ccdB, and pasB. The expression control sequence of (b) can include a promoter that is repressed by a repressor that prevents transcription of the rescue agent, and wherein promoter is indirectly induced in the presence of a supplemental agent that inhibits the repressor. Exemplary rescue agent or antitoxin agents include EcoRI methylase, ccdA, and pasA. The promoter can be, for example, pLtetO, the repressor can be Tet Repressor Protein (TetR), and the supplemental agent can be anhydrotetracycline (ATc), or the promoter can be pLlacO, the repressor can be lac Repressor (LacI), and the supplemental agent can be isopropyl β-D-1-thiogalactopyranoside (IPTG). In some embodiments, the GMO includes one or more repressor constructs each including a constitutively active promoter operably linked to a nucleic acid sequence encoding the repressor. The GMO can include at least two copies the nucleic acid sequence encoding the repressor. Any of the constructs can be expressed extrachromasomally, for example by a vector, or integrated into the genome of the organism.

The GMO with an engineered addiction system are typically viable when cultured under permissive conditions including the inducer needed to de-repress or induce the rescue agent. Such conditions result in translation of a full-length protein encoded by the essential gene. Culturing of the GMO in non-permissive media that does not include the necessary inducers leads to non-transcription and non-translation the rescue agent encoded by the essential gene, leading to exposure of the organism to the toxic agent, and preferably results in reduced viability or non-viability of the GMO. In some embodiments, the escape frequency of the GMO in non-permissive media is $10^{-6}$ or lower, for example, between about $10^{-6}$ and about $10^{-12}$. In some embodiments the escape frequency is less than about $10^{-12}$.

Any of the GMO can be further modified, engineered, or tailored for a variety of applications. For example, the organisms can be modified to include a nucleic acid encoding an expression control sequence operably linked to a heterologous gene of interest. Preferred heterologous genes of interest include, but are not limited to, therapeutically or pharmaceutically active proteins; proteins that allows or improves the ability of the GRO to facilitate bioremediation; proteins that allow or improve the ability of the GRO to facilitate energy production; and proteins that allows or improves the ability of the GRO to facilitate agriculture. Methods of using such GRO generally include culturing them under permissive conditions until the task at hand is complete. Removal of or escape from permissive conditions to non-permissive conditions results in non-variability of the organism. Accordingly, the organisms can be said to be biocontained. The disclosed safeguards can be adapted to numerous organisms and culture systems; however, in the most preferred embodiments the organism is a bacterium such as *E. coli*.

BRIEF DESCRIPTION OF THE DRAWINGS

FIGS. 3A and 3B are plots showing the doubling time ratios for the non-contained ancestor to pAzF auxotroph with one or more TAGs at functional loci calculated from growth in 5 mM pAzF and 0.2% L-arabinose (3A) and the escape frequencies (3B). Bars represent escape frequencies below the detection limit; average escape frequencies are plotted.

FIG. 7A is a bar graphs showing escape frequencies (n=3, ±SD) on solid media for strains containing one, two, three, or four layers of genetic safeguards. NIH guidelines for work with engineered microorganisms advise a $10^{-8}$ escape frequency (Health N.I.o. Office of Biotechnology Activities. Bethesda, Md.; 2013. Guidelines for Research Involving Recombinant DNA Molecules) (dotted horizontal line). Strains are characterized by ribo-essential gene (RE 1 or 2), presence of supplemental repressors, presence of a toxin and doubling time (DT) in minutes. Plasmid-based ribo-essential gmk safeguard (gray) does not confer containment. Square brackets denote plasmid-based constructs. Limit of detection for solid media is ~$5 \times 10^{-10}$.

DETAILED DESCRIPTION OF THE INVENTION

I. Definitions

Figure 1A:
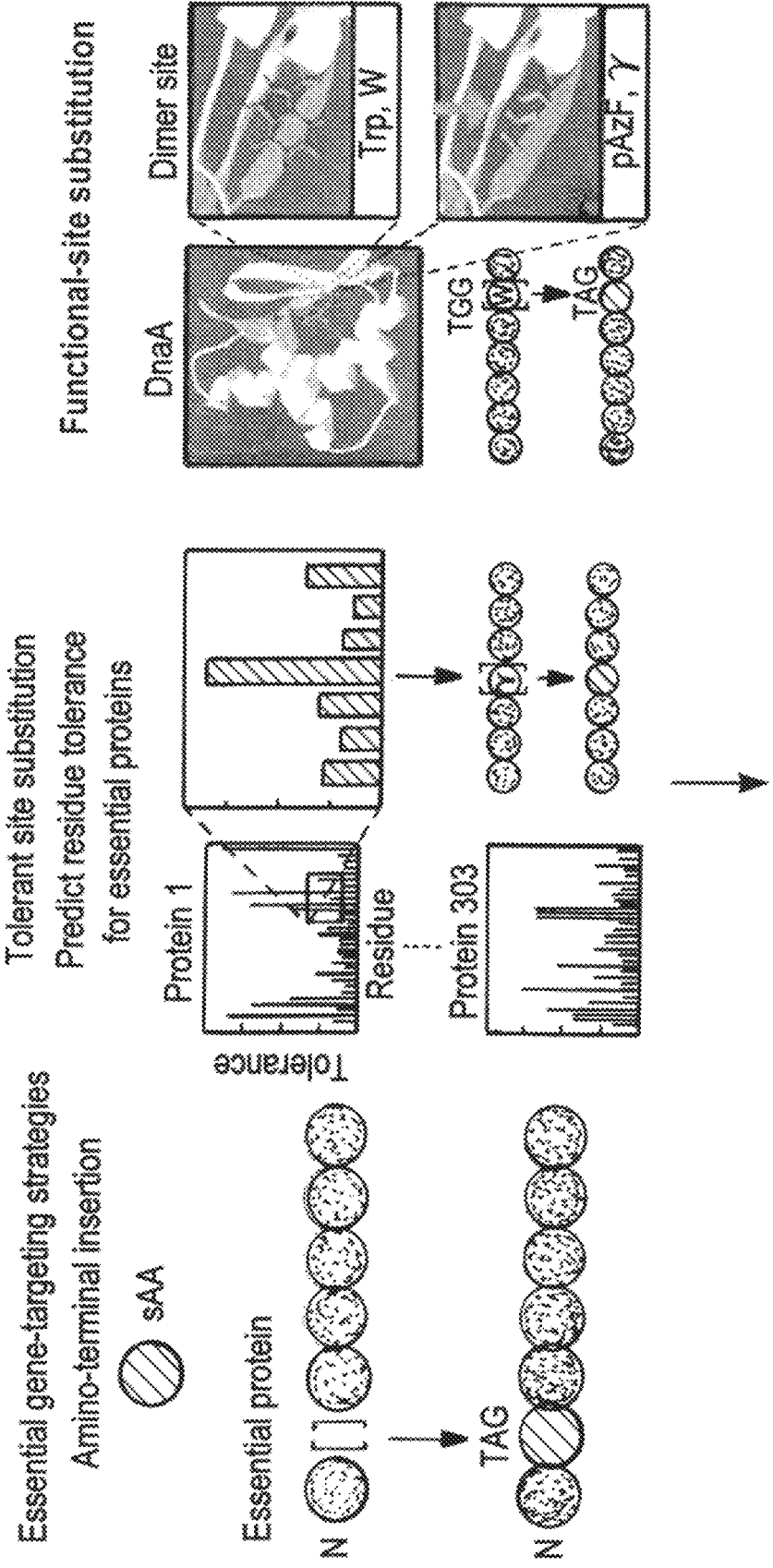
FIG. 1A is an illustration showing approaches used to identify suitable loci within essential proteins for sAA incorporation.

As used herein, the terms "transfer RNA" and "tRNA" refers to a set of genetically encoded RNAs that act during protein synthesis as adaptor molecules, matching individual amino acids to their corresponding codon on a messenger RNA (mRNA). In higher eukaryotes such as mammals, there is at least one tRNA for each of the 20 naturally occurring amino acids. In eukaryotes, including mammals, tRNAs are encoded by families of genes that are 73 to 150 base pairs long. tRNAs assume a secondary structure with four base paired stems known as the cloverleaf structure. The tRNA contains a stem and an anticodon. The anticodon is complementary to the codon specifying the tRNA's corresponding amino acid. The anticodon is in the loop that is opposite of the stem containing the terminal nucleotides. The 3' end of a tRNA is aminoacylated by a tRNA synthetase so that an amino acid is attached to the 3'end of the tRNA. This amino acid is delivered to a growing polypeptide chain as the anticodon sequence of the tRNA reads a codon triplet in an mRNA.

As used herein, the term "anticodon" refers to a unit made up of typically three nucleotides that correspond to the three bases of a codon on the mRNA. Each tRNA contains a specific anticodon triplet sequence that can base-pair to one or more codons for an amino acid or "stop codon." Known "stop codons" include, but are not limited to, the three codon bases, UAA known as ochre, UAG known as amber and UGA known as opal, which do not code for an amino acid but act as signals for the termination of protein synthesis. tRNAs do not decode stop codons naturally, but can and have been engineered to do so. Stop codons are usually recognized by enzymes (release factors) that cleave the polypeptide as opposed to encode an AA via a tRNA.

As used herein, the term "suppressor tRNA" refers to a tRNA that alters the reading of a messenger RNA (mRNA) in a given translation system. For example, a non-sense suppressor tRNA can read through a stop codon.

As used herein, the term "aminoacyl tRNA synthetase (AARS)" refers to an enzyme that catalyzes the esterification of a specific amino acid or its precursor to one of all its compatible cognate tRNAs to form an aminoacyl-tRNA. These charged aminoacyl tRNAs then participate in mRNA translation and protein synthesis. The AARS show high specificity for charging a specific tRNA with the appropriate amino acid. In general, there is at least one AARS for each of the twenty amino acids.

As used herein, the term "residue" as used herein refers to an amino acid that is incorporated into a protein. The amino acid may be a naturally occurring amino acid and, unless otherwise limited, may encompass known analogs of natural amino acids that can function in a similar manner as naturally occurring amino acids.

As used herein, the terms "polynucleotide" and "nucleic acid sequence" refers to a natural or synthetic molecule including two or more nucleotides linked by a phosphate group at the 3' position of one nucleotide to the 5' end of another nucleotide. The polynucleotide is not limited by length, and thus the polynucleotide can include deoxyribonucleic acid (DNA) or ribonucleic acid (RNA).

As used herein, the term "vector" refers to a polynucleotide capable of transporting into a cell another polynucleotide to which the vector sequence has been linked. The term "expression vector" includes any vector, (e.g., a plasmid, cosmid or phage chromosome) containing a gene construct in a form suitable for expression by a cell (e.g., linked to a transcriptional control element). "Plasmid" and "vector" are used interchangeably, as a plasmid is a commonly used form of vector.

As used herein, the term "operatively linked to" refers to the functional relationship of a nucleic acid with another nucleic acid sequence. Promoters, enhancers, transcriptional and translational stop sites, and other signal sequences are examples of nucleic acid sequences operatively linked to other sequences. For example, operative linkage of gene to a transcriptional control element refers to the physical and functional relationship between the gene and promoter such that the transcription of the gene is initiated from the promoter by an RNA polymerase that specifically recognizes, binds to and transcribes the DNA.

As used herein, the terms "transformation" and "transfection" refer to the introduction of a polynucleotide, e.g., an expression vector, into a recipient cell including introduction of a polynucleotide to the chromosomal DNA of the cell.

As used herein, the term "conservative variant" refers to a particular nucleic acid sequence that encodes identical or essentially identical amino acid sequences. Conservative substitution tables providing functionally similar amino acids are well known in the art. The following sets forth exemplary groups which contain natural amino acids that are "conservative substitutions" for one another. Conservative Substitution Groups 1 Alanine (A) Serine (S) Threonine (T); 2 Aspartic acid (D) Glutamic acid (E); 3 Asparagine (N) Glutamine (Q); 4 Arginine (R) Lysine (K); 5 Isoleucine (I) Leucine (L) Methionine (M) Valine (V); and 6 Phenylalanine (F) Tyrosine (Y) Tryptophan (W).

As used herein, the term "percent (%) sequence identity" or "homology" refers to the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

As used herein, the term "transgenic organism" refers to any organism, in which one or more of the cells of the organism contains heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. Suitable transgenic organisms include, but are not limited to, bacteria, cyanobacteria, fungi, plants and animals. The nucleic acids described herein can be introduced into the host by methods known in the art, for example infection, transfection, transformation or transconjugation.

As used herein, the term "eukaryote" or "eukaryotic" refers to organisms or cells or tissues derived from these organisms belonging to the phylogenetic domain Eukarya such as animals (e.g., mammals, insects, reptiles, and birds), ciliates, plants (e.g., monocots, dicots, and algae), fungi, yeasts, flagellates, microsporidia, and protists.

As used herein, the term "prokaryote" or "prokaryotic" refers to organisms including, but not limited to, organisms of the Eubacteria phylogenetic domain, such as *Escherichia coli, Thermus thermophilus*, and *Bacillus stearothermophilus*, or organisms of the Archaea phylogenetic domain such as, *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii*, and *Aeuropyrum pernix*.

As used herein, the term "construct" refers to a recombinant genetic molecule having one or more isolated polynucleotide sequences. Genetic constructs used for transgene expression in a host organism include in the 5'-3' direction, a promoter sequence; a sequence encoding a gene of interest; and a termination sequence. The construct may also include selectable marker gene(s) and other regulatory elements for expression.

As used herein, the term "gene" refers to a DNA sequence that encodes through its template or messenger RNA a sequence of amino acids characteristic of a specific peptide, polypeptide, or protein. The term "gene" also refers to a DNA sequence that encodes an RNA product, for example a functional RNA that does not encode a protein or polypeptide (e.g., miRNA, tRNA, etc.). The term gene as used herein with reference to genomic DNA includes intervening, non-coding regions as well as regulatory regions and can include 5' and 3'untranslated ends.

As used herein, the term "isolated" is meant to describe a compound of interest (e.g., nucleic acids) that is in an environment different from that in which the compound naturally occurs, e.g., separated from its natural milieu such as by concentrating a peptide to a concentration at which it is not found in nature. "Isolated" is meant to include compounds that are within samples that are substantially enriched for the compound of interest and/or in which the compound of interest is partially or substantially purified. Isolated nucleic acids are at least 60% free, preferably 75% free, and most preferably 90% free from other associated components.

As used herein, the term "purified" and like terms relate to the isolation of a molecule or compound in a form that is substantially free (at least 60% free, preferably 75% free, and most preferably 90% free) from other components normally associated with the molecule or compound in a native environment.

As used herein, the term "pharmaceutically acceptable carrier" encompasses any of the standard pharmaceutical carriers, such as a phosphate buffered saline solution, water and emulsions such as an oil/water or water/oil emulsion, and various types of wetting agents.

As used herein, the term "translation system" refers to the components necessary to incorporate an amino acid into a growing polypeptide chain (protein). Key components of a translation system generally include amino acids, ribosomes, tRNAs, AARRS, EF-Tu, and mRNA. The components described herein can be added to a translation system, in vivo or in vitro, to incorporate amino acids into a protein.

As used herein, the term "orthogonal translation system (OTS)" refers to at least an AARS and paired tRNA that are both heterologous to a host or translational system in which they can participate in translation of an mRNA including at least one codon that can hybridize to the anticodon of the tRNA.

As used herein, the terms "recoded organism" and "genomically recoded organism (GRO)" in the context of codons refer to an organism in which the genetic code of the organism has been altered such that a codon has been eliminated from the genetic code by reassignment to a synonymous or nonsynonymous codon.

As used herein, the term "polyspecific" refers to an AARS that can accept and incorporate two or more different non-standard amino acids.

As used herein, the terms "protein," "polypeptide," and "peptide" refers to a natural or synthetic molecule comprising two or more amino acids linked by the carboxyl group of one amino acid to the alpha amino group of another. The term polypeptide includes proteins and fragments thereof. The polypeptides can be "exogenous," meaning that they are "heterologous," i.e., foreign to the host cell being utilized, such as human polypeptide produced by a bacterial cell. Polypeptides are disclosed herein as amino acid residue sequences. Those sequences are written left to right in the direction from the amino to the carboxy terminus.

As used herein, "standard amino acid" and "canonical amino acid" refer to the twenty amino acids that are encoded directly by the codons of the universal genetic code denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, "non-standard amino acid (nsAA)" refers to any and all amino acids that are not a standard amino acid. nsAA can be created by enzymes through posttranslational modifications; or those that are not found in nature and are entirely synthetic (e.g., synthetic amino acids (sAA)). In both classes, the nsAAs can be made synthetically.

As used herein, "genetically modified organism (GMO)" refers to any organism whose genetic material has been modified (e.g., altered, supplemented, etc.) using genetic engineering techniques. The modification can be extrachromasomal (e.g., an episome, plasmid, etc.), by insertion or modification of the organism's genome, or a combination thereof.

As used herein, the term "vector" refers to a replicon, such as a plasmid, phage, or cosmid, into which another DNA segment may be inserted so as to bring about the replication of the inserted segment. The vectors can be expression vectors.

As used herein, the term "expression vector" refers to a vector that includes one or more expression control sequences.

As used herein, term "expression control sequence" refers to a DNA sequence that controls and regulates the transcription and/or translation of another DNA sequence. Control sequences that are suitable for prokaryotes, for example, include a promoter, optionally an operator sequence, a ribosome binding site, and the like. Eukaryotic cells are known to utilize promoters, polyadenylation signals, and enhancers.

As used herein, the term "promoter" refers to a regulatory nucleic acid sequence, typically located upstream (5') of a gene or protein coding sequence that, in conjunction with various elements, is responsible for regulating the expression of the gene or protein coding sequence. These include constitutive promoters, inducible promoters, tissue- and cell-specific promoters and developmentally-regulated promoters.

II. Strategies for Genetic Safeguards

Several genetic safeguards and methods of preparing genetically modified microorganisms including one or more safeguards are discussed in more detail below. It will be appreciated that genetic safeguards are modular in nature and can be used in any combination of two, three, four, five, six, or more to achieve user desired growth and survival characteristics including escape frequency. The combinations can compound the same safeguard strategy two or more times, combinations of two or more different safeguards strategies, or both.

In the most preferred embodiments, the genetically modified organism has the NIH escape frequency standard of $10^{-8}$ NIH (that is, one escape mutant per $10^8$ cells) (Health N.I.o. Office of Biotechnology Activities. Bethesda, Md.; 2013. Guidelines for Research Involving Recombinant DNA Molecules) or lower, though it will be appreciated that organisms with somewhat higher frequencies are also useful. In some embodiments, the escape frequency of the genetically modified microorganism is between about $10^{-5}$ and $10^{-12}$, or $10^{-6}$ and $10^{-12}$, or $10^{-7}$ and $10^{-12}$, $10^{-8}$ and $10^{-12}$, or $10^{-9}$ and $10^{-12}$, or $10^{-10}$ and $10^{-12}$, or $10^{-11}$ and $10^{-12}$. In preferred embodiments, the escape frequency is $10^{-8}$ or lower, $10^{-9}$ or lower, $10^{-10}$ or lower, $10^{-11}$ or lower, or $10^{-12}$ or lower. In particular embodiments, the escape frequency of the genetically modified microorganism is between about $10^{-6}$ and $10^{-12}$, or $10^{-7}$ and $10^{-11}$, or $10^{-8}$ and $10^{-10}$. In some preferred embodiments, the escape frequency is less than about $10^{-12}$.

Preferably, the genetically modified organism survives and replicates in permissive media with little or no reduction in fitness relative to its parental or precursor stain. In some embodiments, fitness is measured as doubling time of the GMO in permissive media. In preferred embodiments, the fitness of the GMO is between about 20% and 120% of the parental strain grown under the same or similar conditions. In preferred embodiments, the fitness of the GMO is about 50%, 60%, 70%, 80%, 85%, 90%, 95%, 100%, 105%, 110% of the parental strain. In some embodiment, the reduction in fitness or fitness defect in the GMO compared to its parental or precursor strain is 50%, 25%, 20%, 15%, 10%, 5%, or less. The Examples below show GMO with a fitness within 4% of the parental or precursor strain.

The genetic safeguards are applicable to a number of organisms including both prokaryotes and eukaryotes. In some embodiments, including proof-of-concept experiments discussed in more detail below, the GMO is a bacterium, for example, *E. coli*. However, it will be appreciated that the strategies can be adapted for use in virtually any microorganism or cellular system. For example, these strategies can be extended to all bacteria, including both gram negative and gram positive strains. In some embodiments, the bacteria are those found in human microbiota (e.g., gut, skin, oral, vaginal, etc., such as, for example, *actobacillus, bacteroides*, and *firmicutes*), environmentally-relevant species (e.g., cyanobacteria, *rhizobium*, agrobacteria, etc.), industrially-relevant species (e.g., *E. coli, Subtilis* strains, *Pseudomonas*, etc.), and strains relevant for secondary metabolite biosynthesis (e.g., *Streptomyces*).

Specific examples of bacteria include, but are not limited to, *Actinomyces, Anabaena, Bacillus, Bacteroides, Bdellovibrio, Bordetella, Borrelia, Campylobacter, Caulobacter, Chlamydia, Chlorobium, Chromatium, Clostridium, Corynebacterium, Cytophaga, Deinococcus, Escherichia, Francisella, Halobacterium, Heliobacter, Haemophilus, Hemophilus influenza* type B (HIB), *Hyphomicrobium, Legionella, Leptspirosis, Listeria, Meningococcus* A, B and C, *Methanobacterium, Micrococcus, Myobacterium, Mycoplasma, Myxococcus, Neisseria, Nitrobacter, Oscillatoria, Prochloron, Proteus, Pseudomonas, Phodospirillum, Rickettsia, Salmonella, Shigella, Spirillum, Spirochaeta, Staphylococcus, Streptococcus, Streptomyces, Sulfolobus, Thermoplasma, Thiobacillus*, and *Treponema, Vibrio*, and *Yersinia*.

Other suitable organisms include, but are not limited to, eukaryotes such as yeast (e.g., *S. cerevisaie, Pichia, S. pombe*, etc.). Although the disclosed strategies, compositions, and methods are generally discussed in the context of microorganisms, they are also applicable to tissue culture and other therapeutic, industrial, and environmental cell systems that may need safeguarding. Accordingly, in some embodiments, the subject of the safeguard is not a microorganism, but rather a cell or cell population from a non-microorganism such as a mammal, or more particularly a human or non-human primate. For example, the cells can be human cells such as engineered T-cells for immunotheraphy.

A. Synthetic Auxotrophy—Non-Standard Amino Acid Approach

Figure 1B:
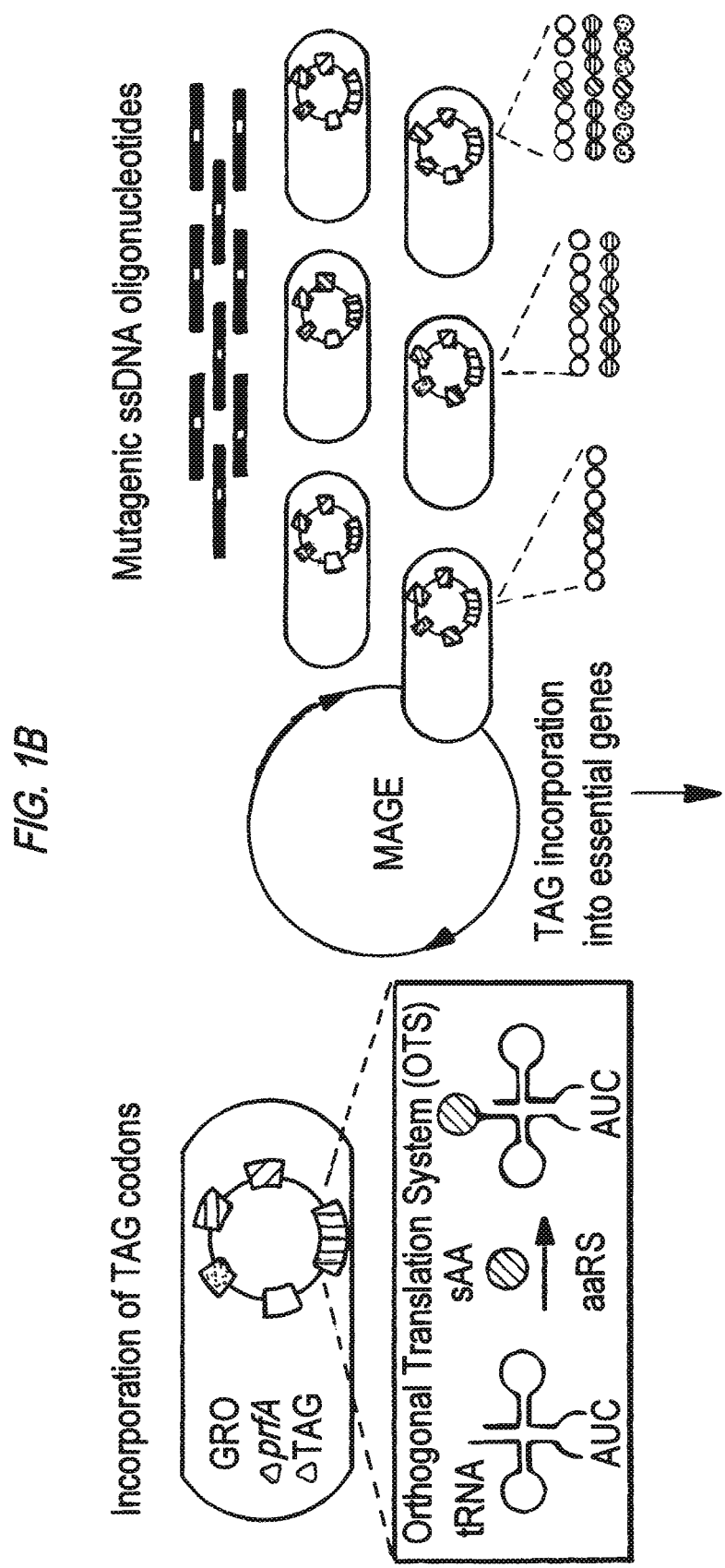
FIG. 1B is an illustration showing a MAGE-based process used for site-specific incorporation of TAG codons into essential genes of a GRO lacking all natural TAG codons (ΔTAG) and release factor 1 (ΔprfA), and containing an OTS (green) consisting of the *M. jannaschii* aaRS and cognate UAG-decoding tRNA.
Figure 1C:
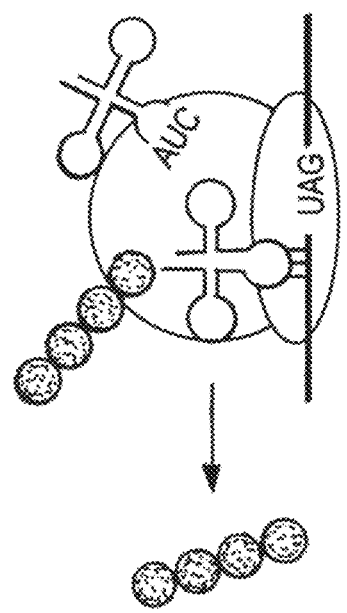
FIG. 1C is an illustration showing synthetic auxotrophs that depend on sAAs for growth.
Figure 1C:
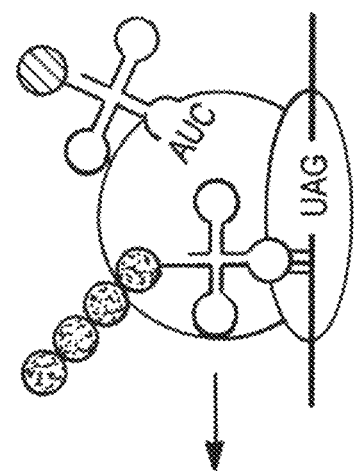

One approach to engineering biocontainment utilizes a genomically recoded organism (GRO) lacking all instances of a codon, typically a stop codon. The codon is then converted to a sense codon through the introduction of an orthogonal translation system (OTS) containing an aminoacyl-tRNA synthetase (aaRS):tRNA pair, permitting site-specific incorporation of synthetic amino acids (sAAs) or non-standard (nsAAs) into proteins. Preferably, the at least one recoded codon is introduced into an essential gene such that when the microorganism is cultured in the presence of media including the synthetic amino acid (permissive media), the protein encoded by the essential gene is a translated and the microorganism grows and survives (i.e., viability). However, when the microorganism is cultured in the absence of the synthetic amino acid (non-permissive media), translation cannot proceed through the recoded codon, leading to production of truncated essential protein and ultimately to growth inhibition or death of the microorganism (i.e., lethality). Preferably the GMO grows in permissive media with limited or no impairment to cellular fitness. A general strategy for preparing GRO with one or more essential proteins including a non-standard amino acid is depicted in FIGS. 1A-1C.

1. Exemplary Strategies and Modifications

In the most preferred embodiments, synthetic auxotrophs that requires a synthetic amino acid are engineered from a parental GRO strain wherein the TAG codon has been reassigned and is absent from the genome. Release factor 1 can be deleted or non-functional. An exemplary parental GRO is 321.ΔA (CP006698.1, GI:54981157) into essential genes to restrict growth to defined media containing sAAs.

In preferred embodiments, the synthetic auxotroph does not require multi-copy plasmid, and more preferably does not require any plasmids. Plasmids, particularly high-copy plasmids, can reduce the viability and growth, impose biosynthetic burden, persist poorly in host cells over time, and increase the risk of acquiring genetic escape mutants of some microorganisms. Therefore, in the most preferred embodiments, the OTS and the recoded essential gene(s) are incorporated into the genome of the microorganism. A recoded essential gene can be the native, chromosomal gene, which has modified or mutated to be recoded, but remains in its endogenous location. In some embodiments, the recoded gene is introduced into a new location in the genome and the corresponding endogenous gene is deleted or mutated.

The synthetic auxotrophs can have one or more genes, preferable one or more essential genes recoded to include at least one codon that encodes a synthetic amino acid. In some embodiments, multiple (e.g., two or more) genes are recoded. When two or more genes are recoded, the genes can be recoded to incorporate the same or different synthetic amino acids. For example, the GRO can include two, three or more genes recoded such that each gene includes at least one iteration of the same synthetic amino acid. Each of the one or more recoded genes can also include one or more iterations of two or more different synthetic amino acids. This can be accomplished by, for example, including a different recoded codon and corresponding orthogonal tRNA:AARS pair for each of the synthetic amino acids.

a. Gene Selection

The one or more gene to be recoded and the synthetic amino acid(s) that can be substituted for the cognate amino acid(s) can be selected by the practitioner. Several exemplary recoded genes and several synthetic amino acid substitutions were tested in the working Examples below. Preferred essential genes are also discussed in more detail below. For example, in some embodiments, wherein two or more essential genes are recoded, essential genes of varying expression levels are selected. In preferred embodiments, the one or more essential genes are ones whose functions (for example, replication or translation) cannot be complemented by cross-feeding of metabolites. When two or more genes are recoded, it is preferred that the genes be dispersed throughout the genome to prevent a single HGT event from compromising containment.

b. Residue Selection

Once a gene is selected, one or residues within the gene is selected and recoded. Criteria for selecting the one or more residues can include: (1) insertion at the amino terminus (leading to a short and therefore nonfunctional protein in non-permissive media); (2) substitution of residues with computationally predicted tolerances (so that the protein is functional when the synthetic amino acid is substituted for the cognate amino acid); and (3) substitution of conserved residues at functional sites. The residue(s) should also be selected such that a non-natural or synthetic amino acid is a viable substitution for the endogenous encoded amino acid and when introduced into the essential protein during translation yields a functional, active protein and a viable organism. Preferably, when the non-natural or synthetic amino acid is absent, translation cannot proceed through the recoded codon and yields a truncated protein that has reduced function or is non-functional and results in reduced viability or non-viability of the organism. If two or more codons are recoded more than one different species of truncated proteins can be produced.

The synthetic amino acid can be selected by the practitioner and can be virtually any non-standard or synthetic amino acid. In some embodiments, a tyrosine residue is substituted for a synthetic tyrosine derivative. WO 2015/120287 provides a non-exhaustive list of exemplary non-standard and synthetic amino acids that are known in the art (see, e.g., Table 11 of WO 2015/120287).

Target genes can be selected by the practitioner, and can be based on the subject organism or cell type. Although any gene, preferably any essential gene can be targeted in this way, some preferred target genes are dnaX, lspA, secY, serS, murG, and dnaA. Other preferred essential genes include those discussed in more detail below including genes whose disruption at the native loci will not have polar effects on neighboring genes, whose expression level does not need to fluctuate according to growth state, and whose function is not readily complemented by a crossfeeding metabolite. Examples fitting these criteria in *E. coli* include adk, nadE, ribA, and gmk. Other suitable target genes are described in Baba, et al., *Mol. Syst. Biol.*, 2, 2006.0008 (2006) (see, e.g., Baba, et al., Supplementary Table 6) and GenoBase, which provide over 300 essential genes in *E. coli*.

2. Exemplary Systems

Biocontainable microorganisms designed according to the disclosed non-standard amino acid auxotrophic strategies typically include a genomically recoded organism (GRO) expressing an aminoacyl-tRNA synthetase (AARS) and paired transfer RNA (tRNA) pair (i.e., an orthogonal pair). The AARS and paired tRNA are typically heterologous to the host organism. A GRO is an organism that has been recoded such that at least one codon is deleted from most, or preferable all, its iterations in the organism's genome. In the disclosed biocontainment strategies, the reduced or missing codon is reintroduced into the GRO by substituting it for one or more endogenous codons in an essential gene (also referred to a recoded gene of interest, recoded essential gene, etc.).

The heterologous tRNA typically includes an anticodon that recognizes the reduced or missing codon. The heterologous AARS is one that can charge it's paired heterologous tRNA with a non-standard amino acid. When a heterologous mRNA including at least one iteration of the GRO-deleted codon is expressed in the host in the presence of the non-standard amino acid, the non-standard amino acid is incorporated into the polypeptide by the heterologous tRNA during translation of the heterologous mRNA.

When used in the disclosed microorganisms, nucleic acids encoding the orthogonal AARS and tRNA operably linked to one or more expression control sequences are introduced or integrated into cells or organisms. The recoded essential gene (or ORF linked to a heterologous expression control sequence, etc.) can be introduced into the GRO and the endogenous unmodified copy can be deleted using methods that are known in the art and described in the Examples below. As discussed in more detail below, the AARS-tRNA pair and gene of interest can be transformed or transfected into the host and expressed extrachomasomally, for example by plasmid(s) or another vector(s) or an episome, or can be integrated into the host's genome. In some embodiments, release factor 1 is deleted or interrupted in the GRO (terminates translation at UAA and UAG), eliminating termination of translation at UAG and endowing the organism with increased viral resistance, a common form of horizontal gene transfer (HGT).

The GRO are typically viable when cultured under permissive conditions including the synthetic amino acid or non-standard amino acid. Such conditions result in translation of a full-length protein encoded by the essential gene. The protein includes one or more iterations of the non-standard or synthetic amino acid, but is nonetheless active and functional. Culturing of the GRO in non-permissive media that does not include the necessary synthetic amino acid or non-standard amino acid leads to truncation of the full-length protein encoded by the essential gene, and preferably results in reduced viability or non-viability of the GRO.

a. GRO

The GRO host organism, prior to recoding of the gene of interest and transfection or integration of the AARS-tRNA pair, can be referred to as a precursor or parental GRO. Typically, the precursor GRO is a bacterial strain, for example, an *E. coli* bacterial strain, wherein a codon has been replaced by a synonymous codon. Because there are 64 possible 3-base codons, but only 20 canonical amino acids (plus stop codons), some amino acids are coded for by 2, 3, 4, or 6 different codons (referred to herein as "synonymous codons"). In a GRO, most or all of the iterations of a particular codon are replaced with a synonymous codon. The precursor strain of the GRO is recoded such at a least one codon is completely absent from the genome. Removal of a codon from the precursor GRO allows reintroduction of the deleted codon in a gene of interest, for example, an essential gene. As discussed in more detail below, the reintroduced codon is typically dedicated to a non-standard amino acid, which in the presence of the appropriate orthogonal translation machinery, can be incorporated in the nascent peptide chain of during translation of the mRNA.

Different organisms often show particular preferences for one of the several codons that encode the same amino acid, and some codons are considered rare or infrequent. Preferably, the replaced codon is one that is rare or infrequent in the genome. The replaced codon can be one that codes for an amino acid (i.e., a sense codon) or a translation termination codon (i.e., a stop codon). GRO that are suitable for use as host or parental strains for the disclosed systems and methods are known in the art, or can be constructed using known methods. See, for example, Isaacs, et al., *Science*, 333, 348-53 (2011), Lajoie, et al., *Science* 342, 357-60 (2013), Lajoie, et al., *Science*, 342, 361-363 (2013).

Preferably, the replaced codon is one that codes for a rare stop codon. In a particular embodiment, the GRO is one in which all instances of the UAG (TAG) codon have been removed and replaced by another stop codon (e.g., TAA, TGA), and preferably wherein release factor 1 (RF1; terminates translation at UAG and UAA) has also been deleted, eliminating translational termination at UAG codons (Lajoie, et al., *Science* 342, 357-60 (2013)). In a particular embodiment, the host or precursor GRO is C321.Δ A [321 UAG→UAA conversions and deletion of prfA (encodes RF1)] (genome sequence at GenBank accession CP006698). This GRO allows the reintroduction of UAG codons in a heterologous mRNA, along with orthogonal translation machinery (i.e., aminoacyl-tRNA synthetases (aaRSs) and tRNAs as discussed in more detail below), to permit efficient and site specific incorporation of non-standard amino acids into protein encoded by the recoded gene of interest. That is, UAG has been transformed from a nonsense codon (terminates translation) to a sense codon (incorporates amino acid of choice), provided the appropriate translation machinery is present. UAG is a preferred codon for recoding because it is the rarest codon in *Escherichia coli* MG1655 (321 known instances) and a rich collection of translation machinery capable of incorporating non-standard amino acids has been developed for UAG (Liu and Schultz, *Annu. Rev. Biochem.*, 79:413-44 (2010), discussed in more detail below).

Stop codons include TAG (UAG), TAA (UAA), and TGA (UGA). Although recoding to UAG (TAG) is discussed in more detail above, it will be appreciated that either of the other stop codons (or any sense codon) can be recoded using the same strategy. Accordingly, in some embodiments, a sense codon is reassigned, e.g., AGG or AGA to CGG, CGA, CGC, or CGG (arginine), e.g., as the principles can be extended to any set of synonymous or even non-synonymous codons, that are coding or non-coding. Similarly, the cognate translation machinery can be removed/mutated/deleted to remove natural codon function (UAG-RF1, UGA-RF2). The OTS system, particularly the antisense codon of the tRNA, can be designed to match the reassigned codon.

GRO can have two, three, or more codons replaced with a synonymous or non-synonymous codon. Such GRO allow for reintroduction of the two, three, or more deleted codons in one or more recoded genes of interest, each dedicated to a different non-standard amino acid. Such GRO can be used in combination with the appropriate orthogonal translation machinery to produce polypeptides having two, three, or more different non-standard amino acids.

Prokaryotes useful as GRO cells include, but are not limited to, gram negative or gram positive organisms such as *E. coli* or Bacilli, and although the most preferred host organism is a bacterial GRO, it will be appreciated the methods and compositions disclosed herein can be adapted for use on other host GRO organisms.

It will be understood by one of ordinary skill in the art that regardless of the system used, expression of genes encoding orthogonal AARS and tRNA will result in site specific incorporation of non-standard amino acids into the target polypeptides or proteins encoded by the specific recoded gene(s) of interest transfected or integrated into the organism. In some embodiments, host cells are genetically engineered (e.g., transformed, transduced, or transfected) with the vectors encoding orthogonal AARS, tRNA and/or recoded gene(s) of interest which can be, for example, a cloning vector or an expression vector. The vector can be, for example, in the form of a plasmid, a bacterium, a virus, a naked polynucleotide, or a conjugated polynucleotide. The vectors are introduced into cells and/or microorganisms by standard methods including electroporation, infection by viral vectors, high velocity ballistic penetration by small particles with the nucleic acid either within the matrix of small beads or particles, or on the surface. Such vectors can optionally contain one or more promoter. A "promoter" as used herein is a DNA regulatory region capable of initiating transcription of a gene of interest.

Kits are commercially available for the purification of plasmids from bacteria, (see, e.g., GFX™ Micro Plasmid Prep Kit from GE Healthcare; STRATAPREP® Plasmid Miniprep Kit and STRATAPREP® EF Plasmid MIDIPREP Kit from Stratagene; GENELUTE™ HP Plasmid Midiprep and MAXIPREP Kits from Sigma-Aldrich, and, Qiagen plasmid prep kits and QIAfilter™ kits from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. To construct an expression vector using pBR322, an appropriate promoter and a DNA sequence are inserted into the pBR322 vector. Other commercially available vectors include, for example, T7 expression vectors from Invitrogen, pET vectors from Novagen and pALTER® vectors and PinPoint® vectors from Promega Corporation.

Yeasts useful as host cells include, but are not limited to, those from the genus *Saccharomyces, Pichia, K. actinomycetes* and *Kluyveromyces*. Yeast vectors will often contain an origin of replication sequence, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., J. Biol. Chem. 255:2073, (1980)) or other glycolytic enzymes (Holland et al., Biochem. 17:4900, (1978)) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Fleer et al., *Gene*, 107:285-195 (1991), in Li, et al., *Lett Appl Microbiol.* 40(5):347-52 (2005), Jansen, et al., *Gene* 344:43-51 (2005) and Daly and Hearn, *J. Mol. Recognit.* 18(2):119-38 (2005). Other suitable promoters and vectors for yeast and yeast transformation protocols are well known in the art.

Mammalian or insect host cell culture systems well known in the art can also be employed. Commonly used promoter sequences and enhancer sequences are derived from Polyoma virus, Adenovirus 2, Simian Virus 40 (SV40), and human cytomegalovirus. DNA sequences derived from the SV40 viral genome may be used to provide other genetic elements for expression of a structural gene sequence in a mammalian host cell, e.g., SV40 origin, early and late promoter, enhancer, splice, and polyadenylation sites. Viral early and late promoters are particularly useful because both are easily obtained from a viral genome as a fragment which may also contain a viral origin of replication. Exemplary expression vectors for use in mammalian host cells are well known in the art.

b. Orthogonal Translation System

Translation systems include most or all of the translation machinery of the host organism and additionally include a heterologous aminoacyl-tRNA synthetase (AARS)-rRNA pair (also referred to as an orthogonal translation system (OTS)) that can incorporate one or more non-standard amino acids into a growing peptide during translation of the recoded gene of interest. AARS are enzymes that catalyze the esterification of a specific cognate amino acid or its precursor to one or all of its compatible cognate tRNAs to form an aminoacyl-tRNA. An AARS can be specific for a single amino acid or a non-standard amino acid, or can be polyspecific for two or more non-standard amino acids, canonical amino acids, or a combination thereof. The heterologous AARS used in the disclosed systems typical can recognize, bind to, and transfer at least one non-standard amino acid to a cognate tRNA. Accordingly, the AARS can be selected by the practitioner based on the non-standard amino acid on interest. Some of the disclosed systems include two or more heterologous AARS.

tRNA is an adaptor molecule composed of RNA, typically about 76 to about 90 nucleotides in length that carries an amino acid to the protein synthetic machinery. Typically, each type of tRNA molecule can be attached to only one type of amino acid, so each organism has many types of tRNA (in fact, because the genetic code contains multiple codons that specify the same amino acid, there are many tRNA molecules bearing different anticodons which also carry the same amino acid). The heterologous tRNA used in the disclosed systems is one that can bind to the selected heterologous AARS and receive a non-standard amino acid to form an aminoacyl-tRNA. Because the transfer of the amino acid to the tRNA is dependent in-part on the binding of the tRNA to the AARS, these two components are typically selected by the practitioner based on their ability to interact with each other and participate in protein synthesis including the non-standard amino acid of choice in the host organism. Therefore, a selected heterologous AARS and tRNA are often referred to herein together as a heterologous AARS-tRNA pair, or an orthogonal translation system. Preferably, the heterologous AARS-tRNA pair does not cross-react with the existing host cell's pool of synthetases and tRNAs, or do so a low level (e.g., inefficiently), but is recognized by the host ribosome. Therefore, preferably the heterologous AARS cannot charge an endogenous tRNA with a non-standard amino acid (or does so a low frequency), and/or an endogenous AARS cannot charge the heterologous tRNA with a standard amino acid. Furthermore, preferably, the heterologous AARS cannot charge its paired heterologous tRNA with a standard amino acid (or does so at low frequency).

The heterologous tRNA also includes an anticodon that recognizes the codon of the codon in the heterologous mRNA that encodes the non-standard amino acid of choice. In the most preferred embodiment, the anticodon is one that hybridizes with a codon that is reduced or deleted in the host organism and reintroduced by the heterologous mRNA. For example, if the reduced or deleted codon is UAG (TAG), as in C321.ΔA, the heterologous tRNA anticodon is typically CUA.

The OTS can be derived from a bacterial or eukaryotic species (e.g., yeast translational components in bacteria). In some embodiments, the AARS-tRNA pair can be from an achaea, such as *Methanococcus maripaludis, Methanocaldococcus jannaschii, Methanopyrus kandleri, Methanococcoides burtonii, Methanospirillum hungatei, Methanocorpusculum labreanum, Methanoregula boonei, Methanococcus aeolicus, Methanococcus vannieli, Methanosarcina mazei, Methanosarcina barkeri, Methanosarcina acetivorans, Methanosaeta thermophila, Methanoculleus* marisnigri, *Methanocaldococcus vulcanius*, *Methanocaldococcus fervens*, or *Methanosphaerula palustris*, or can be variant evolved therefrom.

Suitable heterologous AARS-tRNA pairs for use in the disclosed systems and methods are known in the art. For example, Table 1 and the electronic supplementary information provided in Dumas, et al., *Chem. Sci.*, 6:50-69 (2015), provide non-natural amino acids that have been genetically encoded into proteins, the reported mutations in the AARS that enable their binding to the non-natural amino acid, the corresponding tRNA, and a host organism in which the translation system is operational. See also (Schultz, et al., *J Am Chem Soc*, 128:13984-5 (2006)), Liu and Schultz, *Annu. Rev. Biochem.*, 79:413-44 (2010), Davis and Chin, *Nat. Rev. Mol. Cell Biol.*, 13:168-82 (2012), which provide additional examples of AARS-tRNA pairs which can be used in the disclosed systems and methods. Preferred AARS with improved activity and specificity for the specific non-naturally occurring amino acids are described in more detail below.

The AARS and tRNA can be provided separately, or together, for example, as part of a single construct. In a particular embodiment, the AARS-tRNA pair is evolved from a *Methanocaldococcus jannaschii* aminoacyl-tRNA synthetase(s) (AARS)/suppressor tRNA pairs and suitable for use in an *E. coli* host organism. See, for example, Young, *J. Mol. Biol.*, 395(2):361-74 (2010), which describes an OTS including constitutive and inducible promoters driving the transcription of two copies of a *M. jannaschii* AARS gene in combination with a suppressor tRNA (CUA)(opt) in a single-vector construct.

During protein synthesis, tRNAs with attached amino acids are delivered to the ribosome by proteins called elongation factors (EF-Tu in bacteria, eEF-1 in eukaryotes), which aid in decoding the mRNA codon sequence. If the tRNA's anticodon matches the mRNA, another tRNA already bound to the ribosome transfers the growing polypeptide chain from its 3' end to the amino acid attached to the 3' end of the newly delivered tRNA, a reaction catalyzed by the ribosome. Accordingly, the heterologous AARS-tRNA pair should be one that can be processed by the host organism's elongation factor(s). Additional or alternatively, the system can include additional or alternative elongation factor variants or mutants that facilitate delivery of the heterologous aminoacyl-tRNA to the ribosome.

It will also be appreciated that methods of altering the anticodon of tRNA are known in the art. Any suitable tRNA selected for use in the disclosed systems and methods can be modified to hybridize to any desired codon. For example, although many of the heterologous tRNA disclosed here and elsewhere have a CUA anticodon, CUA can be substituted for another stop anticodon (e.g., UUA or UCA), or anticodon for any desired sense codon. The tRNA anticodon can be selected based on the GRO and the sequence of the heterologous mRNA as discussed in more detail above.

i. Exemplary tRNA and AARS

In some embodiments, the AARS is a variant of *Methanocaldococcus jannaschii* TyrRS: MDEFEMIKRNTSEII-SEEELREVLKKDEKSA
YIGFEPSGKIHLGHYLQIKKMIDLQ NAGFDIIILLADL-HAYLNQKGELDEIRKIG-
DYNKKVFEAMGLKAKYVYGSEFQLDK DYTLN-VYRLALKTTLKRARRSMELIAREDENPKVAEV
IYPIMQVNDIHYLGVDVAV GGMEQRKIHM-LARELLPKKVVCIHNPVLTGLDGEGKMSSSKGNFIA-
VDDSPEEIRA KIKKAYCPAGVVEGNPIMEIAKYFLEY-PLTIKRPEKFGGDLTVNSYEELESLFKNK ELHPM
DLKNAVAEELIKILEPIRKRL
(SEQ ID NO:1, TyrRS(WT)), wherein, one or more of residues 32, 107, 108, 109, 158, 162, or 286 are mutated relative to SEQ ID NO:1.

Table 1 illustrates the conversion of *Methanocaldococcus jannaschii* TyrRS to exemplary AARS (SEQ ID NOS:2-6) with specificity for various non-standard amino acids used in Examples 1-4 below.

TABLE 1

Conversion of aaRS specificity.

| Residue | TyrRS (WT) | pAcF-RS | pIF-RS | pAzF-RS | pCNF-RS |
|---------|------------|---------|--------|---------|---------|
| 32      | Y          | L       | L      | T       | L       |
| 107     | E          | E       | S      | N       | D[a]    |
| 108     | F          | F       | F      | F       | W       |
| 109     | Q          | Q       | Q      | Q       | M       |
| 158     | D          | G       | P      | P       | G       |
| 159     | I          | C       | L      | L       | A       |
| 162     | L          | R       | E      | Q       | L       |
| 286     | D          | R       | R      | R       | R       |

MDEFEMIKRNTSEIISEEELREVLKKDEKSALIGFEPSGKIHLGHYLQIKKMIDLQ
NAGFDIIILLADLHAYLNQKGELDEIRKIGDYNKKVFEAMGLKAKYVYGSEFQLDK
DYTLNVYRLALKTTLKRARRSMELIAREDENPKVAEVIYPIMQVNGCHYRGVDVAV
GGMEQRKIHMLARELLPKKVVCIHNPVLTGLDGEGKMSSSKGNFIAVDDSPEEIRA
KIKKAYCPAGVVEGNPIMEIAKYFLEYPLTIKRPEKFGGDLTVNSYEELESLFKNK
ELHPMRLKNAVAEELIKILEPIRKRL
(SEQ ID NO: 2, pAcF-RS) (Young, et al., J Mol Biol,
395:361-74 (2010));

MDEFEMIKRNTSEIISEEELREVLKKDEKSALIGFEPSGKIHLGHYLQIKKMIDLQ
NAGFDIIILLADLHAYLNQKGELDEIRKIGDYNKKVFEAMGLKAKYVYGSSFQLDK
DYTLNVYRLALKTTLKRARRSMELIAREDENPKVAEVIYPIMQVNPLHYEGVDVAV
GGMEQRKIHMLARELLPKKVVCIHNPVLTGLDGEGKMSSSKGNFIAVDDSPEEIRA
KIKKAYCPAGVVEGNPIMEIAKYFLEYPLTIKRPEKFGGDLTVNSYEELESLFKNK
ELHPMRLKNAVAEELIKILEPIRKRL
(SEQ ID NO: 3, pIF-RS);

MDEFEMIKRNTSEIISEEELREVLKKDEKSATIGFEPSGKIHLGHYLQIKKMIDLQ
NAGFDIIILLADLHAYLNQKGELDEIRKIGDYNKKVFEAMGLKAKYVYGSNFQLDK

TABLE 1-continued

Conversion of aaRS specificity.

```
DYTLNVYRLALKTTLKRARRSMELTAREDENPKVAEVIYPIMQVNPLHYQGVDVAV
GGMEQRKIHMLARELLPKKVVCIHNPVLTGLDGEGKMSSSKGNFIAVDDSPEEIRA
KIKKAYCPAGVVEGNPIMEIAKYFLEYPLTIKRPEKFGGDLTVNSYEELESLFKNK
ELHPMRLKNAVAEELIKILEPIRKRL
(SEQ ID NO: 4, pAzF-RS);

MDEFEMIKRNTSEIISEEELREVLKKDEKSALIGFEPSGKIHLGHYLQIKKMIDLQ
NAGFDIIILLADLHAYLNQKGELDEIRKIGDYNKKVFEAMGLKAKYVYGSDWMLDK
DYTLNVYRLALKTTLKRARRSMELIAREDENPKVAEVIYPIMQVNGAHYLGVDVAV
GGMEQRKIHMLARELLPKKVVCIHNPVLTGLDGEGKMSSSKGNFIAVDDSPEEIRA
KIKKAYCPAGVVEGNPIMEIAKYFLEYPLTIKRPEKFGGDLTVNSYEELESLFKNK
ELHPMRLKNAVAEELIKILEPIRKRL
(SEQ ID NO: 5, pCNF-RS-D107);

MDEFEMIKRNTSEIISEEELREVLKKDEKSALIGFEPSGKIHLGHYLQIKKMIDLQ
NAGFDIIILLADLHAYLNQKGELDEIRKIGDYNKKVFEAMGLKAKYVYGSEWMLDK
DYTLNVYRLALKTTLKRARRSMELIAREDENPKVAEVIYPIMQVNGAHYLGVDVAV
GGMEQRKIHMLARELLPKKVVCIHNPVLTGLDGEGKMSSSKGNFIAVDDSPEEIRA
KIKKAYCPAGVVEGNPIMEIAKYFLEYPLTIKRPEKFGGDLTVNSYEELESLFKNK
ELHPMRLKNAVAEELIKILEPIRKRL
(SEQ ID NO: 6, pCNF-RS-E107);
```

In some embodiments, the AARS are variants of any one of SEQ ID NO:1-6, that have one or more mutations relative to SEQ ID NO:1, 2, 3, 4, 5, or 6. The variants can have altered specificity and/or activity toward one or more non-standard amino acids and/or altered specificity and/or activity toward a paired tRNA relative to the protein of SEQ ID NO:1, 2, 3, 4, 5, or 6. In some embodiments, the variant includes at least 30%, 40%, 50%, 60%, 70%, 80%, 90%, 95% or 99% or more sequence identity with the parent AARS, or a functional fragment thereof.

The variants typically have one or more substitution mutations in the non-standard amino acid (amino acid ligand) binding pocket of any one of SEQ ID NO:1-6, the tRNA anticodon recognition interface of any of SEQ ID NO:1-6, or a combination thereof. For example, the variants can have a substitution mutation at one or more of amino acid positions 32, 65, 107, 108, 109, 158, 159, 162, 167, 257, 261, or 286 of any of SEQ ID NO:1, 2, 3, 4, 5, or 6 relative to the N-terminal methionine of SEQ ID NO:1, 2, 3, 4, 5, or 6, respectively.

Exemplary variants are discussed in published PCT application WO 2015/120287 and provided below, and have nsAA specificities at least as provided. The relative polyspecificities (or monospecificy) of each are discussed in more detail in the working Examples of WO 2015/120287.

pAcFRS.1 (polyspecificity for at least pAcF, pAzF, StyA, 4IF, 4BrF, 4ClF, 4MeF, 4Cf3F, MeY, 4NO2F, 4BuF, BuY, 2NaA, PheF):

(SEQ ID NO: 7)

```
MDEFEMIKRNTSEIISEEELREVLKKDEKSALIGFEPSGKIHLGHYLQIKKMIDLQ

NAGFDIIILLADLHAYLNQKGELDEIRKIGDYNKKVFEAMGLKAKYVYGSEFQLDK

DYTLNVYRLALKTTLKRARRSMELIAREDENPKVAEVIYPIMQVNGCHYRGVDVDV

GGMEQRKIHMLARELLPKKVVCIHNPVLTGLDGEGKMSSSKGNFIAVDDSPEEIRA

KIKKAYCPAGVVEGNPIMEIAKYFLEYPLTIKRPEKFGGDLTVNSYEELESLFKNK

ELHPMRLKNAVAEELIKILEPIRKRL;
``` pAcFRS.t1 (polyspecificity for at least pAcF, pAzF, StyA):

(SEQ ID NO: 8)

```
MDEFEMIKRNTSEIISEEELREVLKKDEKSALIGFEPSGKIHLGHYLQIKKMIDLQ

NAGFDIIILLADLHAYLNQKGELDEIRKIGDYNKKVFEAMGLKAKYVYGSEFQLDK

DYTLNVYRLALKTTLKRARRSMELIAREDENPKVAEVIYPIMQVNGCHYRGVDVAV

GGMEQRKIHMLARELLPKKVVCIHNPVLTGLDGEGKMSSSKGNFIAVDDSPEEIRA

KIKKAYCPAGVVEGNPIMEIAKYFLEYPLTIKGPEKFGGDLTVNSYEELESLFKNK

ELHPMRLKNAVAEELIKILEPIRKRL;
``` pAcFRS.t2 (polyspecificity for at least pAcF, pAzF, StyA):

(SEQ ID NO: 9)

```
MDEFEMIKRNTSEIISEEELREVLKKDEKSALIGFEPSGKIHLGHYLQIKKMIDLQ

NAGFDIIILLADLHAYLNQKGELDEIRKIGDYNKKVFEAMGLKAKYVYGSEFQLDK

DYTLNVYRLALKTTLKRARRSMELIAREDENPKVAEVIYPIMQVNGCHYRGVDVAV
```

GGMEQRKIHMLARELLPKKVVCIHNPVLTGLDGEGKMSSSKGNFIAVDDSPEEIRA

KIKKAYCPAGVVEGNPIMEIAKYFLEYPLTIKCPEKEGGDLTVNSYEELESLFKNK

ELHPMRLKNAVAEELIKILEPIRKRL;

pAcFRS.1.t1 (polyspecificity for at least pAcF, pAzF, StyA, 4IF,
4BrF, 4ClF, 4MeF, 4Cf3F, MeY, 4NO2F, 4BuF, BuY, 2NaA, PheF):
(SEQ ID NO: 10)
MDEFEMIKRNTSEIISEEELREVLKKDEKSALIGFEPSGKIHLGHYLQIKKMIDLQ

NAGFDIIILLADLHAYLNQKGELDEIRKIGDYNKKVFEAMGLKAKYVYGSEFQLDK

DYTLNVYRLALKTTLKRARRSMELIAREDENPKVAEVIYPIMQVNGCHYRGVDVDV

GGMEQRKIHMLARELLPKKVVCIHNPVLTGLDGEGKMSSSKGNFIAVDDSPEEIRA

KIKKAYCPAGVVEGNPIMEIAKYFLEYPLTIKGPEKEGGDLTVNSYEELESLEKNK

ELHPMRLKNAVAEELIKILEPIRKRL;

pAcFRS.1.t2 (polyspecificity for at least pAcF, pAzF, StyA, 4IF,
4BrF, 4ClF, 4MeF, 4Cf3F, MeY, 4NO2F, 4BuF, BuY, 2NaA, PheF):
(SEQ ID NO: 11)
MDEFEMIKRNTSEIISEEELREVLKKDEKSALIGFEPSGKIHLGHYLQIKKMIDLQ

NAGFDIIILLADLHAYLNQKGELDEIRKIGDYNKKVFEAMGLKAKYVYGSEFQLDK

DYTLNVYRLALKTTLKRARRSMELIAREDENPKVAEVIYPIMQVNGCHYRGVDVDV

GGMEQRKIHMLARELLPKKVVCIHNPVLTGLDGEGKMSSSKGNFIAVDDSPEEIRA

KIKKAYCPAGVVEGNPIMEIAKYFLEYPLTIKCPEKEGGDLTVNSYEELESLFKNK

ELHPMRLKNAVAEELIKILEPIRKRL;

pAcFRS.2 (polyspecificity for at least pAcF, pAzF, StyA, 4IF, 4BrF,
4ClF, 4MeF, 4Cf3F, MeY, 4NO2F, 4BuF, BuY, 2NaA, PheF).
(SEQ ID NO: 12)
MDEFEMIKRNTSEIISEEELREVLKKDEKSALIGFEPSGKIHLGHYLQIKKMIDLQ

NAGFDIIIVLADLHAYLNQKGELDEIRKIGDYNKKVFEAMGLKAKYVYGSEFQLDK

DYTLNVYRLALKTTLKRARRSMELIAREDENPKVAEVIYPIMQVNGCHYRGVDVDV

GGMEQRKIHMLARELLPKKVVCIHNPVLTGLDGEGKMSSSKGNFIAVDDSPEEIRA

KIKKAYCPAGVVEGNPIMEIAKYFLEYPLTIKRPEKFGGDLTVNSYEELESLFKNK

ELHPMRLKNAVAEELIKILEPIRKRL;

pAcFRS.2.t1 (polyspecificity for at least pAcF, pAzF, StyA, 4IF,
4BrF, 4ClF, 4MeF, 4Cf3F, MeY, 4NO2F, 4BuF, BuY, 2NaA, PheF)
(SEQ ID NO: 13)
MDEFEMIKRNTSEIISEEELREVLKKDEKSALIGFEPSGKIHLGHYLQIKKMIDLQ

NAGFDIIIVLADLHAYLNQKGELDEIRKIGDYNKKVFEAMGLKAKYVYGSEFQLDK

DYTLNVYRLALKTTLKRARRSMELIAREDENPKVAEVIYPIMQVNGCHYRGVDVDV

GGMEQRKIHMLARELLPKKVVCIHNPVLTGLDGEGKMSSSKGNFIAVDDSPEEIRA

KIKKAYCPAGVVEGNPIMEIAKYFLEYPLTIKGPEKFGGDLTVNSYEELESLFKNK

ELHPMRLKNAVAEELIKILEPIRKRL;

pAcFRS.2.t2 (polyspecificity for at least pAcF, pAzF, StyA, 4IF,
4BrF, 4ClF, 4MeF, 4Cf3F, MeY, 4NO2F, 4BuF, BuY, 2NaA, PheF):
(SEQ ID NO: 14)
MDEFEMIKRNTSEIISEEELREVLKKDEKSALIGFEPSGKIHLGHYLQIKKMIDLQ

NAGFDIIIVLADLHAYLNQKGELDEIRKIGDYNKKVFEAMGLKAKYVYGSEFQLDK

DYTLNVYRLALKTTLKRARRSMELIAREDENPKVAEVIYPIMQVNGCHYRGVDVDV

GGMEQRKIHMLARELLPKKVVCIHNPVLTGLDGEGKMSSSKGNFIAVDDSPEEIRA

KIKKAYCPAGVVEGNPIMEIAKYFLEYPLTIKCPEKEGGDLTVNSYEELESLFKNK

ELHPMRLKNAVAEELIKILEPIRKRL;

-continued pAzFRS.1 (specific for pAzF):
(SEQ ID NO: 15)
MDEFEMIKRNTSEIISEEELREVLKKDEKSALIGFEPSGKIHLGHYLQIKKMIDLQ

NAGFDIIILLADLHAYLNQKGELDEIRKIGDYNKKVFEAMGLKAKYVYGSEFQLDK

DYTLNVYRLALKTTLKRARRSMELIAREDENPKVAEVIYPIMQVNVMHYDGVDVYV

GGMEQRKIHMLARELLPKKVVCIHNPVLTGLDGEGKMSSSKGNFIAVDDSPEEIRA

KIKKAYCPAGVVEGNPIMEIAKYFLEYPLTIKRPEKFGGDLTVNSYEELESLFKNK

ELHPMRLKNAVAEELIKILEPIRKRL;

pAzFRS.1.t1(specific for pAzF):
(SEQ ID NO: 16)
MDEFEMIKRNTSEIISEEELREVLKKDEKSALIGFEPSGKIHLGHYLQIKKMIDLQ

NAGFDIIILLADLHAYLNQKGELDEIRKIGDYNKKVFEAMGLKAKYVYGSEFQLDK

DYTLNVYRLALKTTLKRARRSMELIAREDENPKVAEVIYPIMQVNVMHYDGVDVYV

GGMEQRKIHMLARELLPKKVVCIHNPVLTGLDGEGKMSSSKGNFIAVDDSPEEIRA

KIKKAYCPAGVVEGNPIMMEIAKYFLEYPLTIKGPEKFGGDLTVNSYEELESLFKN

KELHPMRLKNAVAEELIKILEPIRKRL;

pAzFRS.1.t2 (specific for pAzF):
(SEQ ID NO: 17)
MDEFEMIKRNTSEIISEEELREVLKKDEKSALIGFEPSGKIHLGHYLQIKKMIDLQ

NAGFDIIILLADLHAYLNQKGELDEIRKIGDYNKKVFEAMGLKAKYVYGSEFQLDK

DYTLNVYRLALKTTLKRARRSMELIAREDENPKVAEVIYPIMQVNVMHYDGVDVYV

GGMEQRKIHMLARELLPKKVVCIHNPVLTGLDGEGKMSSSKGNFIAVDDSPEEIRA

KIKKAYCPAGVVEGNPIMMEIAKYFLEYPLTIKCPEKEGGDLTVNSYEELESLFKN

KELHPMRLKNAVAEELIKILEPIRKRL;

pAzRS.2 (polyspecific for at least pAcF, pAzF, StyA, 4IF, 4BrF,
4C1F, 4MeF, 4Cf3F, MeY, 4NO2F, 4BuF, BuY, 2NaA, PheF):
(SEQ ID NO: 18)
MDEFEMIKRNTSEIISEEELREVLKKDEKSALIGFEPSGKIHLGHYLQIKKMIDLQ

NAGFDIIILLADLHAYLNQKGELDEIRKIGDYNKKVFEAMGLKAKYVYGSTYMLDK

DYTLNVYRLALKTTLKRARRSMELIAREDENPKVAEVIYPIMQVNGCHYRGVDVAV

GGMEQRKIHMLARELLPKKVVCIHNPVLTGLDGEGKMSSSKGNFIAVDDSPEEIRA

KIKKAYCPAGVVEGNPIMEIAKYFLEYPLTIKRPEKFGGDLTVNSYEELESLFKNK

ELHPMRLKNAVAEELIKILEPIRKRL;

pAzRS.2.t1(polyspecific for at least pAcF, pAzF, StyA, 4IF, 4BrF,
4C1F, 4MeF, 4Cf3F, MeY, 4NO2F, 4BuF, BuY, 2NaA, PheF):
(SEQ ID NO: 19)
MDEFEMIKRNTSEIISEEELREVLKKDEKSALIGFEPSGKIHLGHYLQIKKMIDLQ

NAGFDIIILLADLHAYLNQKGELDEIRKIGDYNKKVFEAMGLKAKYVYGSTYMLDK

DYTLNVYRLALKTTLKRARRSMELIAREDENPKVAEVIYPIMQVNGCHYRGVDVAV

GGMEQRKIHMLARELLPKKVVCIHNPVLTGLDGEGKMSSSKGNFIAVDDSPEEIRA

KIKKAYCPAGVVEGNPIMEIAKYFLEYPLTIKGPEKFGGDLTVNSYEELESLFKNK

ELHPMRLKNAVAEELIKILEPIRKRL;
and pAzRS.2.t2 (polyspe-
cific for at least pAcF, pAzF, StyA, 4IF, 4BrF,
4C1F, 4MeF, 4Cf3F, MeY, 4NO2F, 4BuF, BuY, 2NaA, PheF):
(SEQ ID NO: 20)
MDEFEMIKRNTSEIISEEELREVLKKDEKSALIGFEPSGKIHLGHYLQIKKMIDLQ

NAGFDIIILLADLHAYLNQKGELDEIRKIGDYNKKVFEAMGLKAKYVYGSTYMLDK

-continued

DYTLNVYRLALKTTLKRARRSMELIAREDENPKVAEVIYPIMQVNGCHYRGVDVAV

GGMEQRKIHMLARELLPKKVVCIHNPVLTGLDGEGKMSSSKGNFIAVDDSPEEIRA

KIKKAYCPAGVVEGNPIMEIAKYFLEYPLTIKCPEKEGGDLTVNSYEELESLFKNK

ELHPMRLKNAVAEELIKILEPIRKRL.

Abbreviations: pAcF (p-acetylphenylalanine), pIF (p-iodo-L-phenylalanine), pAzF (p-azido-L-phenylalanine), pCNF (p-cyanophenylalanine), StyA (3-Styryl-L-alanine), 4IF (L-4-Iodo phenylalanine), 4BrF (4-Bromo-L-phenylalanine), 4ClF (4-Chloro-L-phenylalanine), 4MeF (L-4-Methyl phenylalanine), 4Cf3F (L-4-Trifluoromethyl phenylalanine), MeY (L-4-Methoxy phenylalanine), 4NO2F (L-4-Nitro phenylalanine), 4BuF (L-4-tert-butyl phenylalanine), BuY (O-tert-Butyl-L-tyrosine), 2NaA (3-(2-Naphthyl)-L-alanine), PheF (L-4-Phenyl phenylalanine).

In some embodiments, the variant is a polypeptide including the amino acids of the non-standard amino acid (amino acid ligand) binding pocket of any of SEQ ID NO:1-20; a polypeptide including the amino acids of the tRNA anticodon recognition interface of any of SEQ ID NO:1-20; or a polypeptide including the non-standard amino acid (amino acid ligand) binding pocket and the amino acids of the tRNA anticodon recognition interface of any of SEQ ID NO:1-20. In some embodiments, the variant is a polypeptide including amino acids 65-261 of any of SEQ ID NO:1-20. All of SEQ ID NOS:1-20 are also specifically provided both with and without the N-terminal methionine. In some embodiments, the AARS is a variant of any of SEQ ID NOS:1-20 with at least 30%, 40%, 50%, 60%, 70%, 80%, 90%, 95% or 99% or more sequence identity to SEQ ID NO:1-20, or a functional fragment thereof, for example those functional fragments described above.

A nucleic acid sequence encoding a cognate tRNA of the AARS describe above (e.g., SEQ ID NO:1-20) is CCGGCGGTAGTTCAGCAGGGCAGAACGGC GGACTCTAAATCCGCATGGCAGGGGTT CAAATCCCCTCCGCCGGACCA
SEQ ID NO:21. In some embodiments, the tRNA is a variant of any of SEQ ID NOS:1-20 with at least 30%, 40%, 50%, 60%, 70%, 80%, 90%, 95% or 99% or more sequence identity to SEQ ID NO:21, or a functional fragment thereof, the can be paired with a selected AARS and incorporate the desired synthetic amino acid into a growing polypeptide chain at the desired location. In some embodiments, the tRNA is a variant of SEQ ID NO:21, wherein the anticodon sequence is substitute for an alternative anticodon sequence. Other suitable tRNAs, including non-optimized tRNAs, are known can the art and can also be used in the disclosed strategies.

ii. Nucleic Acids

Polynucleotides encoding each of the proteins of SEQ ID NO:1-20, and fragments thereof are also disclosed. The polynucleotides can be isolated nucleic acids, incorporated into in a vector, or part of a host genome. The polynucleotides can also be part of a cassette including nucleic acid sequences encoding other translational components such as a paired tRNA, selection marker, promoter and/or enhancer elements, integration sequences (e.g., homology arms), etc.

Nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

Therefore, polynucleotides encoding each of the proteins of SEQ ID NO:1-20 operably linked to an expression control sequence are also provided.

Suitable promoters are generally obtained from viral genomes (e.g., polyoma, Simian Virus 40 (SV40), adenovirus, retroviruses, hepatitis-B virus, and cytomegalovirus) or heterologous mammalian genes (e.g. beta actin promoter). Enhancer generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 bp in length, and they function in cis. Enhancers function to increase transcription from nearby promoters. Enhancers also often contain response elements that mediate the regulation of transcription. Many enhancer sequences are now known from mammalian genes (globin, elastase, albumin, α-fetoprotein and insulin). However, enhancer from a eukaryotic cell virus are preferably used for general expression. Suitable examples include the SV40 enhancer on the late side of the replication origin, the cytomegalovirus early promoter enhancer, the polyoma enhancer on the late side of the replication origin, and adenovirus enhancers.

In certain embodiments the promoter and/or enhancer region can act as a constitutive promoter and/or enhancer to maximize expression of the region of the transcription unit to be transcribed. In certain constructs the promoter and/or enhancer region is active in all eukaryotic cell types, even if it is only expressed in a particular type of cell at a particular time. A preferred promoter of this type is the CMV promoter. In other embodiments, the promoter and/or enhancer is tissue or cell specific.

In certain embodiments the promoter and/or enhancer region is inducible. Induction can occur, e.g., as the result of a physiologic response, a response to outside signals, or as the result of artificial manipulation. Such promoters are well known to those of skill in the art. For example, in some embodiments, the promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs.

The OTS can also include mutated EF-Tu, in addition to AARS and tRNA, especially for bulky and/or highly charged NSAAs (e.g., phosphorylated amino acids) (Park, et al., *Science,* 333:1151-4 (2011)).

B. Synthetic Auxotrophy—Engineered Auxotrophy and Essential Gene Regulation

Another approach to engineering biocontainment utilizes control cell growth by engineered auxotrophy by essential gene regulation. The strategy generally includes constructing strains dependent on an exogenous supplement, typically a small molecule, for essential gene expression. Although essential gene expression can be control by an inducible promoter alone, the disclosed safeguards more typically employ riboregulation.

1. Riboregulation

Riboregulation refers to a post-transcriptional regulation system in *Escherichia coli* that uses RNA to both silence and activate gene expression. Riboregulation typically includes inserting a complementary cis sequence downstream of a promoter and directly upstream of the ribosome binding site in a target gene. Upon transcription, the cis-repressive sequence (crRNA) causes a stem-loop structure to form at the 5'-untranslated region of the mRNA. The stem-loop structure interferes with ribosome binding, silencing gene expression. To relieve repression, a small noncoding RNA (taRNA) that targets the cis-repressed RNA transcript with high specificity is expressed in trans. The taRNA causes an alteration in the stem-loop structure and activates expression of the target mRNA sequence. Materials and methods of riboregulation in *E. coli* are generally known in the art and discussed in Isaacs, et al., *Nat. Biotechnol.,* 22, 841-847 (2004), and Callura, et al., *Proc. Natl. Acad. Sci. U.S.A.,* 107, 15898-15903 (2010)).

The disclosed safeguard strategies most typically employ riboregulation to control expression of one or more essential genes in the GMO. Essential genes are generally considered genes that an organism cannot survive without. For example, an essential gene can be one that when deleted, knocked-out, or otherwise disrupted, the host organism's fitness is significantly reduced. Most preferably, the organism cannot be propagated in culture when the essential gene is inactive. Absence of an essential gene can be lethal to the organism. Essential genes for numerous organisms are known in the art. For example, a collection of ~300 essential genes in *E. coli* are discussed in Baba, et al., *Mol. Syst. Biol.,* 2, 2006.0008 (2006) (see, e.g., Baba, et al., Supplementary Table 6). See also, GenoBase, which serves as a data base for functional analyses for individual targeted genes and global analyses of the entire gene set in *E. coli*, and also a repository for plasmid clone and deletion strain libraries (GenoBase: Y. Otsuka, et al. (2015) "GenoBase: comprehensive resource database of *Escherichia coli* K-12." Nucleic Acids Research, database issue).

In the most preferred embodiments, the gene is one whose function cannot be complemented by cross-feeding, either due to limited permeability of the gene's small molecule product (e.g. ribA), or because the gene's product carries out an essential intracellular enzymatic function (e.g. glnS). Preferably, essential genes for which knockout by a selectable cassette would cause polar effects are excluded. Specific preferred essential genes are ribA, adk, pyrH, glmS, gmk, nadE, acpP, tmk, and lpxC. The most preferred targets are genes whose disruption at the native loci will not have polar effects on neighboring genes, whose expression level does not need to fluctuate according to growth state, and whose function is not readily complemented by a crossfeeding metabolite. Examples fitting these criteria in *E. coli* include adk, nadE, ribA, and gmk.

In some embodiments, two or more genes are each riboregulated. Typically, at least one of the genes, more preferably two or more of the genes is essential. In some embodiments, the two or more genes are riboregulated by the same crRNA and taRNA pair. In some embodiments, two or more different crRNA and taRNA pairs are employed. CrRNA and taRNA sequences can be designed de novo using the guidelines discussed above and known in the art, or known crRNA and taRNA sequences can be used. Numerous crRNA/taRNA sequences are known in the art, see, for example, Isaacs, et al., *Nat. Biotechnol.,* 22, 841-847 (2004), and Callura, et al., *Proc. Natl. Acad. Sci. U.S.A.,* 107, 15898-15903 (2010)).

Accordingly, in some preferred embodiments the disclosed GMO includes riboregulation of at least one essential gene. Achieving biocontainment by regulating cell viability through essential genes typically requires an expression system that when induced causes high enough expression to sustain viability, and when uninduced causes low enough expression to prevent cell growth. If these requirements are not met, the cell will either die even in the presence of inducers, or live even in the absence of inducers, respectively. These requirements are not trivial as most expression systems are too leaky for use in biocontainment. Riboregulation solves this problem of leaky promoters through use of RNA structures engineered to permit translation of an ORF only upon an intermolecular folding interaction. Since the two riboregulator molecules—a trans activating RNA (taRNA) and a cis repressive RNA (crRNA)—must fold together to reveal the cloned ORF's RBS and allow translation, both species must be produced at high amounts before expression occurs. The amount of leaked transcription from both promoters is not enough to allow this. The riboregulator system therefore combines transcriptional and translational control to reduce leakage in gene expression. To employ this biocontainment technology, one or more genes essential for *E. coli* viability can be cloned into a riboregulated expression vector, integrated as individual riboregulated essential gene cassettes into the bacterial genome, then the native copy of the cloned essential gene can be deleted. As discussed in more detail below, the strains can be designed or further modified to be dependent on provision of aTc and IPTG for viability. Riborepressed GMO are typically viable when cultured under permissive conditions including the inducers needed to express the cis-regulating fusion construct and the trans-activating construct. Such conditions result in translation of a full-length protein encoded by the essential gene. Culturing of the GMO in non-permissive media that does not include the necessary inducers leads to non-transcription and non-translation the full-length protein encoded by the essential gene, and preferably results in reduced viability or non-viability of the GMO.

a. Promoter Selection

As discussed above, heterologous, inducible promoters can be used to control essential gene expression. However, additionally or alternatively, the disclosed safeguards include control of one or more essential genes riboregulation controlled with a heterologous promoter. In the most preferred embodiments, the crRNA and taRNA are under control of separate promoters. Suitable promoters and combinations thereof for use in the disclosed safeguards are known in the art and selected based on a repression/activation strategy selected by the practitioner.

Typically, the crRNA and the taRNA are driven by inducible promoters. Inducible promoters are generally those whose activity is induced by the presence or absence of biotic or abiotic factors. For example, in some embodiments, a crRNA is driven by an inducible promoter that requires a supplemental agent to relieve repression or induce transcription. The taRNA promoter can also be an inducible promoter that requires a supplemental agent to relieve repression or induce transcription.

Although the same promoter can be used to drive expression of the crRNA and the taRNA, in the most preferred embodiments, two different promoters are used. In such embodiments, two exogenous supplemental agents are needed to activate gene expression of the essential gene. A first promoter drives expression of the essential gene including a crRNA sequence only when the first supplemental agent is present. In the presence of the first supplemental agent the essential gene is transcribed, but translation is block by the crRNA hairpin. Translation can only occur in the presence of the taRNA, which is only transcribed in the presence of the second supplemental agent. This combination provides a layered safeguard. Even if transcription of the essential gene occurs due to a leaky promoter or a fitness improving mutation, the translation is blocked by the hairpin. In this way, the organism only propagates when both supplemental agents are present. Withdrawal of even one of the supplements can be lethal to the organism, resulting in tight biocontainment of the organism. For example, the practitioner can grow the organism in permissive media that includes the supplemental agent(s) and allows derepression of the target essential gene(s). Withdrawal of the supplements needed to relieve repression (e.g., non-permissive media) control growth. Therefore, if the organism escapes the conditions tightly control by the practitioner, or growth within the practitioner's control is no longer desired and switched to non-permissive, the organism cannot survive.

The layers of safeguards can be increased by increasing the number of genes that are controlled by riboregulation. In some embodiments, the two or more genes are driven by the same promoter. The two or more genes can also be driven by two or more different promoters. The crRNA for each gene can be the same or different. Accordingly, the taRNA for each gene can be the same or different. If two or more different taRNAs are employed, the same or different promoters can be used to drive expression of each of the taRNAs. In this way, the number of supplemental agents needed to drive translation of gene(s) necessary to maintain the fitness of the organism can be increased.

Suitable promoters for use in the disclosed safeguards are known in the art. In some embodiments, one or more of the promoter is repressed by expression of a repressor. The repressor can, for example, be an agent encoded by gene introduced into the organism. The repressor can be driven by a promoter that can be constitutive, inducible, synthetic etc. Most typically, the promoter for the repressor is constitutively active so that the target gene is constitutively repressed unless the supplemental agent is present to block the repressor. Such systems are well known in the art. Two preferred examples are pLtetO and pLlacO. In the pLtetO system, TetR can be (e.g., constitutively) expressed by the organism. pLtetO, which drives expression of the target gene, is repressed by Tet Repressor Protein (TetR) unless a supplemental agent, anhydrotetracycline (ATc), is added to the culture conditions to block TetR repression. In the pLlacO system, lac Repressor (LacI) can be (e.g., constitutively) expressed by the organism. pLlacO, which drives expression of the target gene, is repressed by LacI unless a supplemental agent, isopropyl β-D-1-thiogalactopyranoside (IPTG), is added to the culture conditions to block LacI repression. These systems are others are discussed in, for example, Lutz and Bujard, Nucleic Acids Research, 25(6): 1203-1210 (1997), and U.S. Pat. Nos. 4,495,280, 4,868,111, 5,362,646, 5,464,758, 5,589,362, 5,650,298, 5,654,168, 5,789,156, 5,814,618, 5,888,981, 5,922,927, 6,004,941, 6,087,166, 6,136,954, 6,242,667, 6,252,136, 6,271,341, 6,271,348, and 6,783,756.

Inducible promoters that are inactive unless activated by a supplemental agent are also known in the art and can be employed the disclosed safeguards. For example, pAra is induced only in the presence of arabinose, and pRha which is induced only in the presence of rhamnose. These promoters and others can be used addition, combination, or alternative to pLlacO and pLtet to control expression of the crRNA-linked target gene and taRNA.

Although specific exemplary promoters are provided, the provided strategies are modular and can be used with any native or synthetic promoter as determined by the designer. For example, availability of inducible promoters for eukaryotic systems (e.g., Gal in yeast and Dox in mammalian systems) enables the application of strategies including controlled toxin and essential gene-based containment mechanisms across a diverse range of microorganisms and cell types.

b. Repressor Supplementation

Sequencing of escape mutants routinely failed to identify cis-acting mutations in the riboregulation apparatus. It is believed that a likely target for a trans-acting mutation is the repressor proteins governing ribo-essential expression (lacI, tetR). Knockout of either repressor could deregulate expression of essential gene causing loss of containment. The Examples below illustrate that increasing the number of copies of the repressor can combat this phenomenon by increasing the amount of repressor in the organism even if expression from one or more copies is reduced or completely compromised by mutation. As described in more detail below, escape mutants were undetectable in assays designed to test this strategy and indicate that integrating an extra copy of both repressors in the E. coli chromosome can cause about a 1,000-fold reduction in escape frequency.

The strategy of including two or more copies of a repressor can be referred to as repression supplementation. The two or more copies of repressor can be operably linked (e.g., part of single cassette) or expressed completely separately. For example, the two or more separate copies can be driven by a single or two separate promoters. The separate promoters can be the same or different. The two or more copies can be located physically adjacent to either other or physically separated from each other. For example, the two or more copies can be expressed from the same or different plasmids, or can be integrated into the same or different locations within the organism's genome.

In some embodiments, there are two or more copies of one repressor. Preferably, if the system includes two repressors (e.g., TetR and LacI), there are two or more copies of both repressors. For example, the number of copies that are introduced can depend on factors such as the copies of the plasmid if the repressors is expressed extrachromosomally, or the tolerance of the organism for expression of the repressor without an unintended loss in fitness (e.g., due to toxicity of the repressor). In some embodiments, the number of copies can range from about 1 to 100, 1 to 50, 1 to 25, 1 to 10, or 1 to 5. In particular embodiments, the organism has 1, 2, 3, 4, 5, 6, 7, 8, 9, or 10 copies of a repressed expressed extrachromosomally, integrated into the genome, or a combination thereof.

2. Toxicity

Although repression of a target gene, particularly an essential target gene, can reduce or prevent growth of a GMO, it has been discovered that some biocontainment strategies result in a non-escape, non-proliferating persister-like population. Although the toxicity strategies discussed below were developed into part to combat the persister-like population, it will be appreciated that they can employed alone or in combination with any other biocontainment strategies. Generally, the toxicity-based strategies include introducing into an organism, a polynucleotide encoding a toxic agent, for example a nuclease, operably linked to an expression control sequence. Suitable nucleases include, but are not limited to, EcoRI, and can include any sequence-specific restriction endonuclease. Typically, the nuclease is one that when expressed in the organism destroys the organism's genome, transcripts, or a combination thereof, leading to the death of the organism. For example, the *E. coli* genome contains 645 EcoRI sites (GAATTC) that are cleavage substrates for the EcoRI endonuclease. When expressed in the cell, the EcoRI overwhelms the cell's ability to repair double-stranded breaks across its chromosome.

Although a preferred toxic agent is a nuclease, other toxic agents can also be used. In addition to EcoRI, other specific exemplary agents include the gyrase poison ccdB and the transcription repressor pasB.

In some embodiments, the toxicity agent is a CRISPR/cas9 system.

a. Inducible Toxicity

In some embodiments, the nuclease is under the control of an inducible promoter, wherein a supplemental agent is added to permissive media when induction is desired. In such embodiments, addition of the supplemental agent turns permissive media into non-permissive media by activating expression of the nuclease and leading to death of the organism. Examples of suitable inducible promoters are discussed above and include, for example, pAra which is induced only in the presence of arabinose, and pRha which is induced only in the presence of rhamnose. Accordingly, in some embodiments, expression of a nuclease such as EcoRI under control of a pAra or pRha promoter is induced when the practitioner adds to the media or otherwise contacts the GMO with arabinose or rhamnose respectively, leading to death (e.g., biocontainment) of the GMO.

EcoRI, ccdB and pasB were all tested and shown to escape containment at a frequency of ~$10^{-6}$ in an unmodified strain background, when under the control of an inducible arabinose promoter. In a ribo-essential strain background, the combination of toxin and essential gene containment give escape rates around $10^{-8}$, a 100-fold improvement over ribo-essential containment alone.

In another embodiment, the nuclease is under the control of a repressible promoter such as pLtetO and pLlacO, the permissive media must be supplemented with aTc or IPTG, respectively, to induce expression of the nuclease. However, leaky expression by pLtetO and pLlacO, even in the absence of aTc or IPTG, could result in untimely or unintended killing of the GMO.

GMO with inducible toxicity are typically viable when cultured under permissive conditions that do not include the inducers needed to express the toxic agent. Such conditions prevent or otherwise fail to induce transcription and translation of the toxic agent. Culturing of the GMO in non-permissive media that includes the necessary inducer leads to transcription and translation of the toxic agent, and preferably results in reduced viability or non-viability of the GMO.

b. Engineered Addiction

In some embodiments, the toxic agent is paired with a cognate rescue agent and regulatory logic is reversed so that safeguarded cells are killed upon removal of a supplemental agent in the permissive media. In a particular embodiment the toxic agent is nuclease and the rescue agent is a cognate methylase. When expressed, the cognate methylase methylates the GMO's genome, protecting the organism from the nuclease. When expression of the methylase is discontinued, the methylation-based protection of the genome is depleted, particularly during subsequent rounds of replication, exposing the genome to the activity of the nuclease and killing the organism. Although numerous promoter combinations are envisioned, most typically the methylase is under the control of an inducible, repressible promoter, and the nuclease is either constitutively expressed or under the control of an inducible promoter.

For example, in a particular embodiment, the methylase is under the control of pLtetO and pLlacO. Accordingly, permissive media generally includes aTc or IPTG, respectively, which blocks the TetR or LacI, relieving repression and allowing expression of the methylase. The aTc or IPTG supplement is needed to maintain expression of the methylase and viability of the organism by protecting its genome from the nuclease. The nuclease can be controlled by an inducible promoter, for example, pAra and pRh, or more preferably a constitutively active promoter. When expression of the nucleus is constitutive, the organism can be contained simply by removing the supplement (e.g., aTc or IPTG) from its environment. This strategy is also referred to herein as an "engineered addiction" because the organism is addicted to the supplement. This strategy facilitates intrinsic biocontainment because both the nuclease expression construct does not require induction. The default is constitutive expression of the nuclease and death of the organism unless it is protected by methylation controlled by the supplement. Furthermore, both the nuclease and methylase can be integrated into the genome relieving the requirement of antibiotics to maintain the default status.

The disclosed engineered addition strategies are generally predicated on a relationship between a nuclease and protective enzyme such as a cognate methylase that can protect the genome or other endogenous nucleic acids (e.g., mRNA) from the activity of the nuclease. A particularly preferred nuclease/methylase pair is EcoRI and EcoRI methylase, but other are also envisioned. See, for example, Wilson, et al, *Annu. Rev. Genet,* 25:585-627 (1991), which provide a number of known nuclease/methylase pairs. Examples of other toxin/antitoxin pairs include, but are not limited to, the CcdA/CcdB and PasA/PasB systems.

In other embodiments, riboregulated production of a rescue agent or antitoxin (i.e. ccdA, EcoRI methylase, or pasA) prevents toxicity of constitutive toxin only in the presence of synthetic small molecule inducers.

Other engineered addiction strategies include, but are not limited to, riboregulated production of a rescue or antitoxin protein that prevents expression of toxin only in the presence of synthetic small molecule inducers—like those used to control essential genes expression (as discussed above); and stress-responsive promoter (i.e. the rpoS or lexA core promoter sequences) fused to toxin so that killing is activated during the stress response induced by essential gene starvation (i.e., when inducers are withheld).

GMO with an engineered addiction system are typically viable when cultured under permissive conditions including the inducer needed to de-repress or induce the rescue agent. Such conditions result in translation of a full-length protein encoded by the essential gene. Culturing of the GMO in non-permissive media that does not include the necessary inducers leads to non-transcription and non-translation the rescue agent encoded by the essential gene, leading to exposure of the organism to the toxic agent, and preferably results in reduced viability or non-viability of the GMO.

III. Exemplary GMO and Advantages Thereof

The major advantages of the disclosed strategies include: reliability of low or no escape frequency; independence from complementation by natural compounds; modularity; limited fitness defect; generalizability; and customizability. It is believed that the exemplary strains provided in the Examples below result in the lowest frequency of escape from containment of any design yet reported that is based on inducible control of viability. Since escape frequency determines the scale on which a strain engineered for containment can be used—the lower the escape frequency, the more cells one can safely challenge. The disclosed strains therefore should allow reliable, safe, and secure use of much larger contained cell populations than was previously possible.

Containment strategies based on auxotrophy also regularly fail to show evidence of mutation leading to escape, but any auxotrophy can always be complemented by provision of natural compounds that are likely to exist in the environment. The strategies presented herein decouple essential gene processes from the chemical used to control them. This is an important design component because it means completely synthetic small molecules can be used to control viability, substantially reducing the odds that the cell could find a permissive environment outside the practitioner's control.

The Examples below show that the promoters controlling riboregulators and the essential genes to which they are attached can be changed without affecting system performance. Therefore, virtually any sequence capable of controlling transcription can be used to control riboregulated essential gene expression with the stringency needed for containment. Others have shown the ability to control expression using RNA aptamers sensitive to the synthetic compound theophylline. It is believed that any transcription regulation device, including but not limited to, inducible promoters, RNA aptamers, dependence on synthetic RNA bases needed to transcribe the RNA (e.g., Seo, et al., *J Am Chem Soc.*, 131(14):5046-7 (2009)) can be used in combination with any suitable ligand, natural or synthetic, to control gene expression in the disclosed GMO, particularly when coupled with the second layer of translational control imparted by riboregulation.

Any attempt to regulate the availability of an essential gene can lead to a substantial fitness defect. Either too much or too little of the gene product can be toxic. Many of strains exemplified below have a very small fitness (~4%) defect when compared to an uncontained ancestor strain, measured either separately as two clonal cultures, or together as the two strains compete in a mixed co-culture. This robust growth phenotype means that use of contained cells is feasible for applications that require rapid production.

The GMO can also be customized based on the type(s) of safeguard(s) employed, the one or more specific essential genes selected for regulation, or a combination thereof. Depending on the application, different strains can be used and by adding extra safeguard layers and the appropriate level of containment can be selected. This feature is particularly useful for applications involving more than one biocontained strain at once—for instance, a community of different contained genetically modified microorganisms that collaborate to remediate a polluted environment. Accordingly, mixtures of different GMO employing the same or different safeguards are also provided.

The Examples described in more detail below illustrate exemplary strategies for linking a cell's viability to the presence of one or more supplemental agents. For example, the inducible gene switches permit regulation of cell viability and diminish the chance of GMO escape, thereby permit use of engineered microorganisms outside controlled laboratory environments. By bringing essential genes under the control of engineered RNA-based dual transcriptional and translational regulators, the Examples describe a collection of *E. coli* strains capable of growth only in the presence of synthetic small molecule inducers or synthetic amino acids. Because any of hundreds of essential genes can be re-engineered in this manner, the effectiveness of such a safety switch can be increased by multiplexing essential genes (e.g., guanylate, adenylate and thymidylate kinase genes in *E. coli* are all essential and deeply rooted in central metabolism).

Escape from biocontainment is often achieved by mutation of the organism that weakens, destroys, circumvents or otherwise overcomes the engineered safeguard(s). To prevent mutation from occurring in the first place, the strain background can be genetically optimized for biocontainment. For example, the *E coli* chromosome encodes nonessential transcription factors, polymerases, mobile genetic elements, and signaling cascades that increase the rate of mutation during stress. A modifiable mutation rate helps bacteria mount a response to selective pressures while preserving genomic integrity at other times. These elements can be deleted alone or in combination and the basal mutation rate of mutants determined to find a genetic background whose capacity for stress-induced mutagenesis is reduced or ablated.

In particularly preferred examples, viability of the GMO is controlled using the synthetic small molecules anhydrotetracycline (aTc), isopropyl thiogalactoside (IPTG), or a combination thereof. In some embodiments, the strains are capable of expressing essential genes only in the presence of both inducers. Genome integration and engineered riboregulation ensure that the rate of uninduced expression for these essential genes is too low to support growth in the absence of aTc or IPTG. The experiments described in more detail below show that in the presence of both inducers, the fitness defect entailed by these safeguard strategies is extremely low.

Alternative or additional layers of genetic safeguards including supplemental copies of transcription factors governing inducible promoters; toxin expression to actively kill cells that persist after withdrawal of supplemental agent (e.g., aTc and IPTG); additional riboregulated essential genes integrated into the same strain; knockout or attenuation mutations in a variety of genomic loci involved in resistance, stress response, adaptive mutation, etc.; layered strategies to regulate cell viability using both chromosomal and episomal components. *E. coli* genomic loci involved in the stress induced mutagenesis (SIM), error-prone replication, persistence, adaptive mutation, and stress response phenotypes are known to occur in diverse bacteria. Exemplary targets are discussed in Example 11 and Table 15 below.

Moreover, the strong selections available for essential gene function (viability) allows assessment of riboregulated essential gene safeguard effectiveness to be made rapidly. For strains containing just a single safeguard—e.g., riboregulated expression of a single gene—the frequency of escape from containment is ~$10^{-6}$. Combining such a strain with a second layer safeguard reduces the frequency of escape by 100×-1,000× depending on the second layer added. When three safeguards are combined in one strain, some stains exhibit undetectable escape mutant colony forming units (CFUs). Accordingly, in preferred embodiments, the disclosed GMO exhibit undetectable escape mutant colony forming units (CFUs) according to the fitness assays described herein or otherwise known in the art.

The nature of the disclosed strategies are such that they can readily be adapted to any microbe, multicellular organism or even viruses; any organism with one or more essential genes. Accordingly, the disclosed strategies can be generalized to numerous microorganisms. Many of the strategies are based on regulated production of essential genes and might therefore be implemented in any species containing one or more essential genes. When working with essential genes, the tools available for genetic manipulation in any species become much more powerful because selections based on essential gene function (i.e. viability) allow rapid assessment of performance. The engineered riboregulators used to tightly control expression have also been shown to work well in other species, for example cyanobacteria, and eukaryotes such as *S. cerevisiae* (see, e.g., Bayer and Smolke, *Nat Biotechnol.*, 23(3):337-43 2005)).

Methods of using GMO are discussed in more detail below and include, but are not limited to: biocontainment to prevent dissemination of GMOs; security of proprietary GMOs, for example, prevention of industrial biotech espionage; open application of GMO in the clinic or elsewhere (e.g., probiotics, tumor killing bacteria); and environmental applications (e.g., bioremediation).

IV. GMO and Methods of Making GMO

Genetically modified organisms including one or more of the disclosed safeguards are provided. The disclosed GMO can be transformed or genetically engineered to express the nucleic acids needed to carry out the disclosed biocontainment strategies. For example, nucleic acids encoding components such as AARS and cognate tRNA, mRNA of interest, elements of riboregulatory machinery (e.g., crRNA cassette, taRNA cassette, etc.), elements of toxicity and engineered addiction modules (e.g., nuclease, methylase, and combinations thereof), can be transformed or transfected into the host expressed extrachomasomally, for example by plasmid(s) or another vector(s) or an episome, or can be integrated into the host's genome, or combination thereof. The nucleic acids introduced into the host GMO are typically heterologous. In some embodiments, the introduced nucleic acids include exogenous sequences that not naturally exist in the host organism's genome. In some embodiments, the nucleic acids include naturally occurring sequences that are rearranged or assembled in a way that is not naturally occurring in the host. The host's genome can be further modified as discussed throughout and known in the art, to delete or recode certain genes of interest, particularly essential genes.

The host organism can be referred to as a precursor or parental strain prior to transfection or integration of the heterologous nucleic acid, the deletion or recoding or certain genes of interest, or a combination thereof. In some embodiments, the parental GMO is a GRO as discussed in more detail above.

In some embodiments preparation of the disclosed GMO include plasmid construction and transfection into the GMO. Basic molecular biology techniques are well known and the art and can be employed in plasmid construction. For example, genes and other constructs of interest can be amplified by PCR including restriction sites and can be inserted into an expression plasmid by restriction digestion-based cloning techniques. Inserts can also be amplified using primers that added homologies to the vector termini and designed to anneal to the vector. Genome integration of heterologous expression constructs, delete or recoding cassettes, etc. can also be carried by methods known in the art. In preferred embodiments, double-stranded DNA recombination is carried out using λ-red recombineering as previously described (Sharan, et al., *Nat. Protoc.*, 2009; 4:206-223 (2009)). Briefly, dsDNA containing the cassette of interest can be amplified from purified plasmids using primers that added about 50-bp genome homology arms at both ends, targeting specific genomic loci for integration. These fragments can be transformed into a recombination-competent strain. In some embodiments, recombinants are isolated by TolC negative selection as described in DeVito, et al., *Nucleic Acids Res.*, 36:e4 (2008). Briefly, strains are transformed with dsDNAs designed to replace tolC with a desired cassette. After dsDNA recombination and recovery, cultures are incubated with purified colicin E1 protein. Counter-selected cultures are then plated on solid media and single colonies can be screened for the expected recombination by PCR or by growth in SDS to confirm loss of resistance.

Other methods of genome modification include ssDNA recombination (Ellis, et al., *Proc. Natl. Acad. Sci. U.S.A.*, 98:6742-6746 (2001), Wang, et al., *Nature*, 460:894-898 (2009)). Briefly, a 5'-phosphorothioated oligonucleotide can be targeted to the lagging strand of the replication fork at the desired chromosomal locus. The oligonucleotide can include the modification to be made (e.g., insertion, deletion, mutation or one or more nucleotides). Recombination can be verified by Sanger sequencing the insertion loci as-needed. Exemplary parental strains and other reagents are described in more detail in the Examples below.

Any suitable combination of the disclosed methods and reagents and other methods and reagents known in the art can be used to create the disclosed GMO. For example, the Examples below disclose essential gene knockout by replacing essential gene native sites with the tolC gene and selecting for sodium dodecyl sulphate (SDS) resistance, use of dsDNA cassettes for native site knockout with 50-bp homologies targeted to the ends of the gene to be replaced, and introduction of the lacIq1 allele at the lad locus by ssDNA recombination.

Methods of deleting, interrupting, and mutating organismal genomes are also known in the art. The mutagenesis can be random, semi-random, targeted, or a combination thereof. Preferably, the mutagenesis includes substituting one or more specific residues. In the most preferred embodiments, the mutagenesis includes one or more rounds of MAGE-based evolution. MAGE refers to multiplex automated genome evolution, and generally includes introducing multiple nucleic acid sequences into one or more cells such that the entire cell culture approaches a state involving a set of changes to each genome or targeted region (Wang et al., *Nature,* 460:894 (2009)). The method can be used to generate one specific configuration of alleles or can be used for combinatorial exploration of designed alleles optionally including additional random, i.e., not-designed, changes. This can be used with any of a variety of devices that allow the cyclic addition of many DNAs in parallel in random or specific order, with or without use of one or more selectable markers.

Compositions and methods for carrying out MAGE are described in U.S. Pat. No. 8,153,432. Briefly, MAGE-based methods typically include introducing multiple nucleic acid sequences into a cell including the steps transforming or transfecting a cell(s) using transformation medium or transfection medium including at least one nucleic acid oligomer containing one or more mutations, replacing the transformation medium or transfection medium with growth medium, incubating the cell in the growth medium, and repeating the steps if necessary or desired until multiple nucleic acid sequences have been introduced into the cell. In some embodiments, the one or more nucleic acid oligomers is a pool of oligomers having a diversity of different random or non-random mutations at the location(s) of desired mutagenesis. Cells are transfected with a variety of combination of nucleotides leading to the formation of a diverse genomic library of mutants. The diversity of the library can be increased by increasing the number of MAGE cycles. The oligomers can be single-stranded DNA. In preferred embodiments, multiple mutations are generated in a chromosome or in a genome.

Genetic diversity of the mutants can be tuned by the number of cycles of mutagenesis. For example, increasing the number of cycles of mutagenesis generally increases the diversity of the library. In particular embodiments, a library is prepared by one or more cycles of MAGE, for example, 1, 2, 3, 4, 5, 6, 7, 8, 9, 10, 11, 12, 13, 14, 15, or more cycles, with or without intervening cycles of selection. In a particular embodiment, a library of mutants is prepared by, for example, between 1 and 50, between 3 and 15, between 5 and 9 cycles of MAGE. The cycles can occur without intervening rounds of selection to increase the diversity of library prior to selection. The methods can also be modified to include additional or alternative steps to improve genetic diversity. See, for example, Carr, et al., *Nucleic Acids Research,* 1; 40(17):e132, 12 pages (2012), and Gregg, et al., *Nucleic Acids Research,* 42(7):4779-90 (2014).

Genetic diversity can also be tuned by selecting the number and diversity of the oligonucleotides introduced during any step of the mutagenesis processes. It will be appreciated that the number of oligonucleotides can be increased, that the oligonucleotides can include one or multiple mutations per oligonucleotide and therefore target multiple position (e.g., amino acid positions encoded by the target DNA); that the oligonucleotides can introduce various types of mutations (mismatches, insertions, deletions and with varying degrees of degeneracy (4N—A, T, G, C, 2 selected therefrom, or 3 selected therefrom) or specificity (N equals specific nt).

In general, MAGE experiments can be divided into three classes, characterized by varying degrees of scale and complexity: (i) many target sites, single genetic mutations; (ii) single target site, many genetic mutations; and (iii) many target sites, many genetic mutations. In the first class, MAGE has been used to recode all 321 instances of the TAG stop codon for the synonymous TAA codon using 321 discrete ssDNAs. This project yielded a strain of *E. coli* with only 63 'active' codons and a 64th 'blank' codon available for site-specific incorporation of nonstandard amino acids. In the second class, MAGE can be used to explore the effects of all possible amino acid substitutions at a single target locus. In such an experiment, it is possible, for example, to use a single degenerate ssDNA containing the NNN triplet at its center to introduce all possible amino acid substitutions. In the third class, MAGE has been used to construct diverse cell populations containing combinations of alleles across many loci involved in the biosynthesis of lycopene or aromatic amino acids. In this implementation, discrete oligos designed to knockout competing pathways by deletion can be mixed with degenerate oligos designed to randomize target positions in the coding sequence or regulatory regions of key pathway enzymes (FIG. 2). The highly diverse population resulting from a MAGE experiment can be used downstream to screen or select for mutants with a prescribed phenotype (e.g., overproduction of a metabolite or small molecule).

The use of MAGE for OTS optimization provides at least three advantages. First, MAGE permits the generation of sequence library sizes of $>10^9$, much larger than is possible with other in vivo randomization techniques. Second, MAGE can target multiple genetic components, enabling simultaneous co-evolution of all OTS components. Third, MAGE is an in vivo method, which permits the cell to adopt compensatory changes that will be critical for the isolation of optimized and highly efficient OTSs. This MAGE-based approach in GROs enables creation of more catalytically efficient OTSs for multi-site incorporation of nsAAs. Furthermore, this approach may be broadly used as a genetic platform to encode new chemically diverse naAAs.

Although MAGE-based mutagenesis is preferred, suitable alternative methods of mutagenesis which are well known in the art can be used to create a library of variants. Exemplary methods includes, but are not limited to, error prone PCR, PCR or overlap-elongation PCR with degenerate primers, custum DNA synthesis of degenerate DNA fragments encoding the library of interest.

Additional and alternative methods of engineering a microorganism or cell line to incorporate a nucleic acid sequence into its genome are known in the art. For example, cloning vectors expressing a transposase and containing a nucleic acid sequence of interest between inverted repeats transposable by the transposase can be used to clone the stably insert the gene of interest into a bacterial genome (Barry, *Gene,* 71:75-84 (1980)). Stably insertion can be obtained using elements derived from transposons including, but not limited to Tn7 (Drahos, et al., *Bio/Tech.* 4:439-444 (1986)), Tn9 (Joseph-Liauzun, et al., *Gene,* 85:83-89 (1989)), Tn10 (Way, et al., *Gene,* 32:369-379 (1984)), and Tn5 (Berg, In *Mobile DNA.* (Berg, et al., Ed.), pp. 185-210 and 879-926. Washington, D.C. (1989)). Additional methods for inserting heterologous nucleic acid sequences in *E. coli* and other gram-negative bacteria include use of specialized lambda phage cloning vectors that can exist stably in the lysogenic state (Silhavy, et al., Experiments with gene fusions, Cold Spring Harbor Laboratory, Cold Spring Harbor, N.Y. (1984)), homologous recombination (Raibaud, et al., *Gene,* 29:231-241 (1984)), and transposition (Grinter, et al., *Gene,* 21:133-143 (1983), and Herrero, et al., *J. Bacteriology,* 172(11):6557-6567 (1990)). Integrative plasmids can be used to incorporate nucleic acids sequences into yeast chromosomes. See for example, Taxis and Knop, *Bio/Tech.,* 40(1):73-78 (2006), and Hoslot and Gaillardin, *Molecular Biology and Genetic Engineering of Yeasts.* CRC Press, Inc. Boca Raton, Fla. (1992). Methods of incorporating nucleic acid sequence into the genomes of mammalian lines are also well known in the art using, for example, engineered retroviruses such lentiviruses.

V. Methods of Using Biocontainable GMO

Since the Asilomar Conference on recombinant DNA technology in 1975, scientists have called for the development of genetic safeguards that enable intrinsic biological containment. Physical containment and sterile technique can limit the spread of genetically modified organisms (GMOs), and genetic strategies that prevent lateral transfer of recombinant episomes have been reported, but the problem of genetically containing engineered cells remains unsolved. The disclosed strategies including engineered riboregulators, reliance on synthetic amino acids, engineered toxicity and addiction can link a cell's viability to the presence of synthetic or supplemental agents for the purpose of containing GMOs. A bacterial strain with such a 'synthetic auxotrophy' would be unable to grow effectively outside a controlled environment where the supplemental agent(s) is available.

Such genetic safeguards enable use of GMOs across an array of biomedical, environmental and biotechnology applications—for instance as cellular chassis for the delivery of therapeutic compounds, for bioremediation, or simply for safe and secure cell-based production. Because the level of containment available using the disclosed strategies is believed to be unprecedented, this technology represents an important new avenue for the development of strains that can safely and securely produce industrial or medical compounds in vitro, produce therapeutic compounds in vivo, facilitate research into dangerous pathogens (i.e. as a host for viral reverse genetic systems), permit release of engineered organisms for the purpose of remediation, sensing, agriculture, energy production, waste management, and medicine. For example, the disclosed GMOs can improve efficiency of engineered organisms, which are now being used in closed systems, such as the production of pharmaceuticals, fuels, and new chemicals. Importantly, the GMO can also be used in open systems, which include improved food production, designer probiotics to combat a host of diseases, and specialized microorganisms that clean up oil spills and landfills.

Methods of applying the disclosed GMO in wide range of applications are known in the art. The methods generally include growing or culturing the GMO in permissive conditions during the application and switching the GMO to non-permissive conditions (e.g., removing the supplemental agent needed for survival), when the application has concluded. The disclosed safeguards afford containment in "open," unrestricted environments, because the GMO cannot survive without the supplemental agent. Any GMO that escapes that control environment will not survive.

The GMO can be further modified to carryout the particular task or application. For example, production of a therapeutic protein would generally include modifying the GMO to include an expression construct the expresses the desired protein. Likewise, methods of bioremediation, energy production, etc., can include similar steps of modifying the GMO to express an enzyme or even an entire metabolic or synthetic pathway need to carry out the desired application. Such enzymes, pathways, etc. are known in the art. The additional constructs can be expressed episomally or integrated into the genome of the organism as discussed herein and otherwise known in the art.

In an exemplary embodiment, the GMO is used to express a recombinant protein. Accordingly, the GMO can be further genetically engineered (e.g., transformed, transduced or transfected) with the vectors encoding a nucleic acid encoding the protein of interest, which can be, for example, a cloning vector or an expression vector. The vector can be, for example, in the form of a plasmid, a bacterium, a virus, a naked polynucleotide, or a conjugated polynucleotide. The vectors are introduced into cells and/or microorganisms by standard methods including electroporation (From et al., *Proc. Natl. Acad. Sci. USA* 82, 5824 (1985), infection by viral vectors, high velocity ballistic penetration by small particles with the nucleic acid either within the matrix of small beads or particles, or on the surface (Klein et al., *Nature* 327, 70-73 (1987)). Methods of expressing recombinant proteins in various recombinant expression systems including bacteria, yeast, insect, and mammalian cells are known in the art, see for example *Current Protocols in Protein Science* (Print ISSN: 1934-3655 Online ISSN: 1934-3663, Last updated January 2012).

Kits are commercially available for the purification of plasmids from bacteria, (see, e.g., GFX™ Micro Plasmid Prep Kit from GE Healthcare; Strataprep® Plasmid Miniprep Kit and StrataPrep® EF Plasmid Midiprep Kit from Stratagene; GenElute™ HP Plasmid Midiprep and Maxiprep Kits from Sigma-Aldrich, and, Qiagen plasmid prep kits and QIAfilter™ kits from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems.

Useful prokaryotic and eukaryotic systems for expressing and producing polypeptides are well known in the art include, for example, *Escherichia coli* strains such as BL-21, and cultured mammalian cells such as CHO cells.

In eukaryotic host cells, a number of viral-based expression systems can be utilized to express non-naturally occurring tRNA$^{Sec}$ and mRNA for producing proteins or polypeptides containing selenocysteine. Viral based expression systems are well known in the art and include, but are not limited to, baculoviral, SV40, retroviral, or vaccinia based viral vectors.

Eukaryotic expression vectors include, for example, pCR3.1 (Invitrogen Life Technologies) and p91023(B) (see Wong et al. (1985) *Science* 228:810-815) which are suitable for expression of recombinant proteins in, for example, Chinese hamster ovary (CHO) cells, COS-1 cells, human embryonic kidney 293 cells, NIH3T3 cells, BHK21 cells, MDCK cells, and human vascular endothelial cells (HU-VEC). Additional suitable expression systems include the GS Gene Expression System™ available through Lonza Group Ltd.

Following introduction of an expression vector by electroporation, lipofection, calcium phosphate, or calcium chloride co-precipitation, DEAE dextran, or other suitable transfection method, stable cell lines can be selected (e.g., by metabolic selection, or antibiotic resistance to G418, kanamycin, or hygromycin or by metabolic selection using the Glutamine Synthetase-NS0 system). The transfected cells can be cultured such that the polypeptide of interest is expressed, and the polypeptide can be recovered from, for example, the cell culture supernatant or from lysed cells.

Other assays, methods, and applications in which the disclosed biocontained organisms can be employed or adapted are known in the art. See, for example, Moe-Behrens, et al., "Preparing synthetic biology for the world," *Frontiers in Microbiology* (2013); 4:5, doi:10.3389/fmicb.2013.00005; Paddon, et al., "High-level semi-synthetic production of the potent antimalarial artemisinin," *Nature*, 496:528-532 (2013); Pieper and Reineke, "Engineering bacteria for bioremediation," *Curr. Opin. Biotechnol.*, 11, 262-270 (2000); Steidler, L., et al., "Genetically engineered probiotics," *Best Pract. Res. Clin. Gastroenterol.*, 17, 861-876 (2003); Schmidt, M. and de Lorenzo, "Synthetic constructs in/for the environment: managing the interplay between natural and engineered biology," *FEBS Lett.*, 586, 2199-2206 (2012); Steidler, et al., "Biological containment of genetically modified *Lactococcus lactis* for intestinal delivery of human interleukin," Nat. Biotechnol., 21(7):785-789 (2003); Ronchel, M. C. and Ramos, J. L., "Dual system to reinforce biological containment of recombinant bacteria designed for rhizoremediation," *Appl. Environ. Microbiol.*, 67, 2649-2656 (2001); Jensen, et al., "A substrate-dependent biological containment system for *Pseudomonas putida* based on the *Escherichia coli* gef gene," *Appl. Environ. Microbiol.*, 59, 3713-3717 (1993); Garmory, et al., "The use of live attenuated bacteria as a delivery system for heterologous antigens," *J. Drug Target.*, 11, 471-479 (2003); Anderson, et al., "Environmentally controlled invasion of cancer cells by engineered bacteria," *J. Mol. Biol.*, 355, 619-627 (2006); Dang, et al., Combination bacteriolytic therapy for the treatment of experimental tumors, *Proc. Natl. Acad. Sci. U.S.A.*, 98, 15155-15160 (2001); and Kotula, et al., "Programmable bacteria detect and record an environmental signal in the mammalian gut," *Proc. Natl. Acad. Sci. U.S.A.*, 111, 4838-4843 (2014).

EXAMPLES

The advent of recombinant DNA technologies in the 1970s established genetic cloning methods (Cohen, et al., *Proc. Natl Acad. Sci. USA*, 70:3240-3244 (1973)), ushering in the era of biotechnology. Over the past decade, synthetic biology has fueled the emergence of GMOs with increased sophistication as common and valued solutions in clinical, industrial and environmental settings (Way, J. C., Collins, et al., *Cell*, 157:151-161 (2014); Pieper, et al., *Curr. Opin. Biotechnol*, 11:262-270 (2000); Steidler, *Best Pract. Res. Clin. Gastroenterol*, 17: 861-876 (2003)), necessitating the development of safety and security measures first outlined in the 1975 Asilomar conference on recombinant DNA (Berg, et al, *Proc. Natl Acad. Sci. USA*, 72:1981-1984 (1975)). While guidelines for physical containment and safe use of organisms have been widely adopted, intrinsic biocontainment—biological barriers limiting the spread and survival of microorganisms in natural environments—remains a defining challenge. Existing biocontainment strategies employ natural auxotrophies or conditional suicide switches where top safeguards meet the $10^8$ NIH standard for escape frequencies (that is, one escape mutant per $10^8$ cells), but can be compromised by metabolic cross-feeding or genetic mutation (Ronchel, et al, *Appl. Environ. Microbiol*, 67:2649-2656 (2001); Jensen, et al., *Appl. Environ. Microbiol*, 59:3713-3717 (1993)).

Example 1: Engineered of Synthetic Auxotrophs have Minimal Fitness Impairment and Escape at Low Frequency Materials and Methods
Primary Accessions
GenBank/EMBL/DDBJ
CP010455
CP010456
Reagents Oligonucleotide synthesis was performed by Integrated DNA Technologies (IDT) and Keck Foundation Biotechnology Resource Laboratory at Yale University. Unless otherwise stated, all cultures were grown in LB media. The following selective agents and inducers were used at the specified concentrations: ampicillin (amp, 50 µg ml$^{-1}$), carbenicillin (carb, 50 µg ml$^{-1}$), zeocin (zeo, 10 µg ml$^{-1}$), spectinomycin (spec, 95 µg ml$^{-1}$) and sodium dodecyl sulphate (SDS, 0.005% w/v), isopropyl-β-D-1-thiogalactopyranoside (IPTG, 100 µM), 5-bromo-4-chloro-3-indolyl-β-D-galacto-pyranoside (X-Gal, 40 µg ml$^{-1}$), and L-arabinose (ara, 0.2% w/v unless otherwise indicated). sAAs were used at 1 mM unless otherwise indicated and purchased from PepTech (pAcF, AL624-2), BaChem (pIF, F-3075.0005) and Chem-Impex International (pAzF, 03376).

Plasmids

All tRNAs used to assess tolerance for tryptophan and phenylalanine at TAG codons were contained within the pTech plasmid backbone and driven by the lpp promoter (Normanly, et al., *Proc. Natl Acad. Sci. USA*, 83:6548-6552 (1986)). Isothermal assembly (Gibson, et al, *Nature Methods*, 6: 343-345 (2009)) was used to replace the chloramphenicol acetyltransferase (cat) gene with the sh blegene for resistance to zeocin. The supU amber suppressor tRNA (Fan, et al, *Chem Bio Chem*, 15:1805-1809 (2014)) was used to assess tolerance for tryptophan and a phenylalanine amber suppressor (Normanly, et al., *Proc. Natl Acad. Sci. USA*, 83:6548-6552 (1986)) was used to assess tolerance for phenylalanine. pTech-supU was provided by the laboratory of D. Söll and supPhe was synthesized by IDT and isothermally assembled into the pTech plasmid backbone to obtain pTech-supPhe.

Conversion of Aminoacyl-tRNA Synthetase Specificity

The pAcF OTS was integrated into the genome of the GRO linked to a counter-selectable genetolC. Co-selection multiplex automated genome engineering (CoS-MAGE (Carr, et al, *Nucleic Acids Res*, 40:e132 (2012)) was used as described previously to introduce annotated mutations (Young, et al, *J. Mol. Biol*, 395:361-374 (2010)) to the sAA binding pocket of the aaRS for specificity towards pAzF or pIF (Table 1).

TABLE 1

Conversion of aaRS specificity.

| Residue | TyrRS (WT) | pAcF-RS | pIF-RS | pAzF-RS | pCNF-RS |
|---------|------------|---------|--------|---------|---------|
| 32      | Y          | L       | L      | T       | L       |
| 107     | E          | E       | S      | N       | D$^a$   |
| 108     | F          | F       | F      | F       | W       |
| 109     | Q          | Q       | Q      | Q       | M       |
| 158     | D          | G       | P      | P       | G       |
| 159     | I          | C       | L      | L       | A       |
| 162     | L          | R       | E      | Q       | L       |
| 286     | D          | R       | R      | R       | R       |

$^a$The published pCNF-RS contain E107, however a D107 variant was pursued here.

*Methanocaldococcus jannaschii* TyrRS (SEQ ID NO: 1)
MDEFEMIKRNTSEIISEEELREVLKKDEKSAYIGFEPSGKIHLGHYLQIK

KMIDLQNAGFDIIILLADLHAYLNQKGELDEIRKIGDYNKKVFEAMGLKA

KYVYGSEFQLDKDYTLNVYRLALKTTLKRARRSMELIAREDENPKVAEVI

YPIMQVNDIHYLGVDVAVGGMEQRKIHMLARELLPKKVVCIHNPVLTGLD

GEGKMSSSKGNFIAVDDSPEEIRAKIKKAYCPAGVVEGNPIMEIAKYFLE

YPLTIKRPEKFGGDLTVNSYEELESLFKNKELHPMDLKNAVAEELIKILE

PIRKRL.

Residues changed relative to wild type (WT) TyrRS to convert the synthetic amino acid (sAA) specificity, are underlined in the sequence above. pCNF-RS is the relevant aaRS in all pAzF auxotrophs listed in Table 4 (below).

Sanger sequencing was used to verify these mutations. Conversion of sAA-specificity was assessed in sequence-verified clones upon growth in the presence of sAA incorporation and episomally-expressed GFP containing an in-frame TAG codon at residue 151 within the protein product. OTS-mediated suppression of this codon with the sAA (that is, pAzF, pIF) generated a full-length fluorescent product, indicating that sAA incorporation had occurred and specificity was achieved.

TAG Codon Incorporation into Essential Genes

Three unique strategies were applied to identify permissive sites in essential genes for TAG codon incorporation (FIG. 1A-1C). In a first strategy, a subset of essential genes (Baba, et al, *Mol. Syst. Biol,* 2:2006-0008 (2006)) were chosen for the incorporation of one or more TAG codons immediately after the start codon to encode a sAA at the amino terminus. To explore a diverse library of incorporation targets within the *E. coli* proteome, in a second strategy the sorting intolerant from tolerant (SIFT) algorithm was applied (Kumar, et al, *Nature Protocols,* 4:1073-1081 (2009)) (downloaded on the Yale Biomedical High Performance Computing Cluster) to the entire panel of essential *E. coli* proteins (Baba, et al, *Mol. Syst. Biol,* 2:2006-0008 (2006)). SIFT is an algorithm that uses sequence homology to predict the tolerance of amino acid substitutions at different indices. In the workflow, genes were first split into three categories on the basis of wild-type expression level (Richmond, et al, *Nucleic Acids Res,* 27:3821-3835 (1999)), and a further four subgroups by genomic location with the goal of targeting essential genes dispersed throughout the *E. coli* chromosome. Next, genes shown to be essential by multiple studies (Baba, et al, *Mol. Syst. Biol,* 2:2006-0008 (2006)) were passed through SIFT. For each essential gene, two high, medium, and low tolerance sites were targeted for TAG incorporation by MAGE. By this approach, diverse residue types in proteins with varying wild-type expression levels were sampled.

In a third strategy, using the conserved domain database (Marchler-Bauer, et al, *Nucleic Acids Res,* 33:D192-D196 (2005)), a search was carried out within all annotated essential proteins for tyrosine, tryptophan and phenylalanine residues predicted to participate in essential enzymatic reactions or protein-protein interactions (e.g., dimerization). To minimize the probability that the added functionality of the sAA would perturb protein function, sites that were observed to occur as tyrosine or tryptophan in different homologues were targeted.

GROs containing an OTS integrated into the chromosome were grown to mid-log phase in liquid permissive LB media and four cycles of MAGE were performed per pool of mutagenic oligonucleotides (oligonucleotide concentration ≤15 µM) as described previously (Wang, et al, *Nature,* 460:894-898 (2009); Sharan, et al, *Nature Protocols,* 4:206-223 (2009)). To isolate synthetic auxotrophs, mutagenized cultures were plated on solid media and replica plated onto non-permissive media. To identify TAG incorporation loci, multiplex allele-specific colony (MASC) PCR was used to interrogate pools of up to eleven targeted loci as previously described (Sharan, et al, *Nature Protocols,* 4:206-223 (2009)), followed by verification using Sanger sequencing.

Genotyping

Sanger sequencing was performed by the Keck DNA Sequencing Facility at Yale University or by GENEWIZ, Inc. Genomic DNA for whole genome sequencing was prepared using a Qiagen Genomic DNA purification kit. Illumina libraries were prepared by the Yale Center for Genomic Analysis or the Dana Farber Cancer Institute. Illumina HiSeq or MiSeq sequencing systems were used for whole genome sequencing to generate 50- or 150-base-pair (bp) paired-end reads, respectively.

Whole-genome sequencing was used to analyse three escape mutants per background. In all cases, the direct ancestor to the escape mutant was also analysed. SNPs in escape mutants were identified relative to the reference genome *E. coli* C321.ΔA (CP006698.1, GI:54981157) using a previously described (Lajoie, et al, *Science,* 342:357-360 (2013)) software pipeline. SNPs were called by Freebayes in escape mutants.

Strains

All GROs used in this study are derived from C321.ΔA (CP006698.1, GI:54981157) (Sharan, et al, *Nature Protocols,* 4:206-223 (2009)) which lacks all TAG codons and release factor 1. This strain is derived from strain EcNR2 (ΔmutS:catΔ(ybhB-bioAB):[cI857Δ(cro-ea59):tetR-bla]), modified from *E. coli* K-12 substr. MG1655. In all synthetic auxotrophs, the *M. jannaschii*-derived OTS was genomically integrated into the GRO fused to the counter-selectable gene tolC. The OTS consists of an L-arabinose-inducible aaRS driven by the araBAD promoter, and a constitutively expressed cognate amber-decoding tRNA driven by the proK promoter. All genome modifications that required incorporation of dsDNA (for example, modifications to the mutS gene or incorporation of antibiotic selectable markers) were performed via λ-Red recombination (Sharan, et al, *Nature Protocols,* 4:206-223 (2009)).

Nomenclature of Genomically Recoded Organisms and Synthetic Auxotrophs

To succinctly name strains, a new one-letter amino acid code for sAAs was introduced using Greek lettering (pAcF=α, pIF=β, and pAzF=γ). Non-contained GROs lacking essential TAG codons are named according to the one letter sAA code for the specific OTS present in the organism. For example, a ΔTAG GRO with a genomically integrated pAcF OTS is rEc.α.

Biocontained GROs containing essential TAG codons are named according to two conventions based on the number of essential TAG codons in the auxotroph: (1) Strains with one essential TAG are named by the essential protein containing the sAA and the position and identity of the residue substituted therein (for example, a strain containing pAcF at residue 113 in DnaX is DnaX.Y113α); (2) Strains containing more than one essential TAG are named using the one letter sAA code for which the organism is auxotrophic. This is followed by a dependency code, d, indicating the presence of two (dB), three (dC) or four (dD) essential TAG codons, and then by a TAG combination number that uniquely identifies the specific combination of TAGs in the strain. Combinations are numbered from one through 46 and are listed in Table 4 (below).

Escape Mutant Identity

At least three escape mutants were characterized per strain background that permitted an escape mutant. An escape mutant is designated by a number following the letter 'E' (for example, E1). Strains were grown at 34° C. in flat-bottomed 96-well plates containing 150 µL of LB media permissive for sAA incorporation, unless otherwise indicated. Strains were washed twice with sterile dH$_2$O before assessing growth in non-permissive media. Kinetic growth (OD$_{600}$) was monitored on a BioTek plate reader at ten-minute intervals in triplicate. Raw OD$_{600}$ data from the plate reader were normalized to standard absorbance (OD$_{600}$ at 1 cm path length) values using an empirically derived calibration curve (Y=1.9704x−0.1183, where y=OD$_{600}$ at 1 cm path length and x=OD$_{600}$ from plate reader; R$^2$=0.998). DTs were calculated in MATLAB using custom code. Reported values are the average between three technical replicates where error bars represent ±s.d. All reported results repeated at least three times in independent experiments. Maximum OD$_{600}$ values were obtained after 24 h of growth and represent the average of three technical replicates. Reported results repeated at least three times in independent experiments.

Mass Spectrometry

Histidine-tagged proteins were purified on NiNTA resin (Qiagen). Resolution of purity was assessed via SDS-PAGE. In-gel digestion was performed similarly to previously described methods (Rinehart, et al, *J. Biol. Chem*, 286: 30171-30180 (2011)). Proteins were stained and imaged within the gel using Coomassie blue (R-250). A band corresponding to the molecular weight of DnaX was excised. Gel slices were processed into 1-mm cubes, washed in 1:1 (v/v) 50% CH$_3$CN/50 mM NH$_4$HCO$_3$, and then washed in 1:1 (v/v) 50% CH$_3$CN/10 mM NH$_4$CO$_3$. 13.33 ng µl$^{-1}$ trypsin solution in 9:1 (v/v) 50 mM NH$_4$CO$_3$/50% CH$_3$CN was added and samples were incubated overnight at 37° C. Peptides were extracted with 1:2 (v/v) 5% formic acid/50% CH$_3$CN and dried. Peptides were desalted by reconstitution in 3:8 (v/v) 70% formic acid/0.1% TFA, followed by loading onto a custom-made stage tip (2×1.06 mm punches of Empore C18 extraction disks [3 M] in a 200 µl pipette tip) (Rappsilber, et al, *Anal. Chem*, 75:663-670 (2003)) activated with 80% CH$_3$CN and 0.1% TFA. Tips were washed twice with 0.1% TFA and peptides eluted with 80% CH$_3$CN and 0.1% TFA. Peptides were dried and reconstituted for LC/MS/MS analysis. Capillary LC/MS/MS was carried out using an LTQ Orbitrap Velos (Thermo Scientific) with a nanoAcquity uHPLC (Waters) system as described previously (Heinemann, et al, *FEBS Lett*, 586: 3716-3722 (2012)). The data were processed as described previously (Lajoie, et al, *Science*, 342:357-360 (2013)). MASCOT scores were above the identity or extensive homology threshold and representative spectra are illustrated in FIG. 2C.

Selectable Markers

\>cat (1,015 bp)

(SEQ ID NO: 22)
CCTGTGACGGAAGATCACTTCGCAGAATAAATAAATCCTGGTGTCCCTGT

TGATACCGGGAAGCCCTGGGCCAACTTTTGGCGAAAATGAGACGTTGATC

GGCACGTAAGAGGTTCCAACTTTCACCATAATGAAATAAGATCACTACCG

GGCGTATTTTTTGAGTTGTCGAGATTTTCAGGAGCTAAGGAAGCTAAAAT

GGAGAAAAAAATCACTGGATATACCACCGTTGATATATCCCAATGGCATC

GTAAAGAACATTTTGAGGCATTTCAGTCAGTTGCTCAATGTACCTATAAC

CAGACCGTTCAGCTGGATATTACGGCCTTTTTAAAGACCGTAAAGAAAAA

TAAGCACAAGTTTTATCCGGCCTTTATTCACATTCTTGCCCGCCTGATGA

ATGCTCATCCGGAATTACGTATGGCAATGAAAGACGGTGAGCTGGTGATA

TGGGATAGTGTTCACCCTTGTTACACCGTTTTCCATGAGCAAACTGAAAC

GTTTTCATCGCTCTGGAGTGAATACCACGACGATTTCCGGCAGTTTCTAC

ACATATATTCGCAAGATGTGGCGTGTTACGGTGAAAACCTGGCCTATTTC

CCTAAAGGGTTTATTGAGAATATGTTTTTCGTCTCAGCCAATCCCTGGGT

GAGTTTCACCAGTTTTGATTTAAACGTGGCCAATATGGACAACTTCTTCG

CCCCCGTTTTCACCATGGGCAAATATTATACGCAAGGCGACAAGGTGCTG

ATGCCGCTGGCGATTCAGGTTCATCATGCCGTTTGTGATGGCTTCCATGT

CGGCAGAATGCTTAATGAATTACAACAGTACTGCGATGAGTGGCAGGGCG

GGGCGTAATTTTTTTAAGGCAGTTATTGGTGCCCTTAAACGCCTGGTTGC

TACGCCTGAATAAGTGATAATAAGCGGATGAATGGCAGAAATTCGAAAGC

AAATTCGACCCGGTCGTCGGTTCAGGGCAGGGTCGTTAAATAGCCGCTTA

TGTCTATTGCTGGTT.

\>kanR (1,165 bp)

(SEQ ID NO: 23)
CCTGTGACGGAAGATCACTTCGCAGAATAAATAAATCCTGGTGTCCCTGT

TGATACCGGGAAGCCCTGGGCCAACTTTTGGCGAAAATGAGACGTTGATC

GGCACGTAAGAGGTTCCAACTTTCACCATAATGAAATAAGATCACTACCG

GGCGTATTTTTTGAGTTGTCGAGATTTTCAGGAGCTAAGGAAGCTAAAAT

GAGCCATATTCAACGGGAAACGTCGAGGCCGCGATTAAATTCCAACATGG

ATGCTGATTTATATGGGTATAAATGGGCTCGCGATAATGTCGGGCAATCA

GGTGCGACAATCTATCGCTTGTATGGGAAGCCCGATGCGCCAGAGTTGTT

TCTGAAACATGGCAAAGGTAGCGTTGCCAATGATGTTACAGATGAGATGG

TCAGACTAAACTGGCTGACGGAATTTATGCCTCTTCCGACCATCAAGCAT

TTTATCCGTACTCCTGATGATGCATGGTTACTCACCACTGCGATCCCCGG

AAAAACAGCATTCCAGGTATTAGAAGAATATCCTGATTCAGGTGAAAATA

TTGTTGATGCGCTGGCAGTGTTCCTGCGCCGGTTGCATTCGATTCCTGTT

TGTAATTGTCCTTTTAACAGCGATCGCGTATTTCGTCTCGCTCAGGCGCA

ATCACGAATGAATAACGGTTTGGTTGATGCGAGTGATTTTGATGACGAGC

GTAATGGCTGGCCTGTTGAACAAGTCTGGAAAGAAATGCATAAACTTTTG

CCATTCTCACCGGATTCAGTCGTCACTCATGGTGATTTCTCACTTGATAA

CCTTATTTTTGACGAGGGGAAATTAATAGGTTGTATTGATGTTGGACGAG

TCGGAATCGCAGACCGATACCAGGATCTTGCCATCCTATGGAACTGCCTC

GGTGAGTTTTCTCCTTCATTACAGAAACGGCTTTTTCAAAAATATGGTAT

TGATAATCCTGATATGAATAAATTGCAGTTTCATTTGATGCTCGATGAGT

-continued

TTTTCTAATTTTTTTAAGGCAGTTATTGGTGCCCTTAAACGCCTGGTTGC

TACGCCTGAATAAGTGATAATAAGCGGATGAATGGCAGAAATTCGAAAGC

AAATTCGACCCGGTCGTCGGTTCAGGGCAGGGTCGTTAAATAGCCGCTTA

TGTCTATTGCTGGTT.

>spec<sup>R</sup> (1,201 bp)

(SEQ ID NO: 24)

CAGCCAGGACAGAAATGCCTCGACTTCGCTGCTGCCCAAGGTTGCCGGGT

GACGCACACCGTGGAAACGGATGAAGGCACGAACCCAGTGGACATAAGCC

TGTTCGGTTCGTAAGCTGTAATGCAAGTAGCGTATGCGCTCACGCAACTG

GTCCAGAACCTTGACCGAACGCAGCGGTGGTAACGGCGCAGTGGCGGTTT

TCATGGCTTGTTATGACTGTTTTTTTGGGGTACAGTCTATGCCTCGGGCA

TCCAAGCAGCAAGCGCGTTACGCCGTGGGTCGATGTTTGATGTTATGGAG

CAGCAACGATGTTACGCAGCAGGGCAGTCGCCCTAAAACAAAGTTAAACA

TCATGAGGGAAGCGGTGATCGCCGAAGTATCGACTCAACTATCAGAGGTA

GTTGGCGTCATCGAGCGCCATCTCGAACCGACGTTGCTGGCCGTACATTT

GTACGGCTCCGCAGTGGATGGCGGCCTGAAGCCACACAGTGATATTGATT

TGCTGGTTACGGTGACCGTAAGGCTTGATGAAACAACGCGGCGAGCTTTG

ATCAACGACCTTTTGGAAACTTCGGCTTCCCCTGGAGAGAGCGAGATTCT

CCGCGCTGTAGAAGTCACCATTGTTGTGCACGACGACATCATTCCGTGGC

GTTATCCAGCTAAGCGCGAACTGCAATTTGGAGAATGGCAGCGCAATGAC

ATTCTTGCAGGTATCTTCGAGCCAGCCACGATCGACATTGATCTGGCTAT

CTTGCTGACAAAAGCAAGAGAACATAGCGTTGCCTTGGTAGGTCCAGCGG

CGGAGGAACTCTTTGATCCGGTTCCTGAACAGGATCTATTTGAGGCGCTA

AATGAAACCTTAACGCTATGGAACTCGCCGCCCGACTGGGCTGGCGATGA

GCGAAATGTAGTGCTTACGTTGTCCCGCATTTGGTACAGCGCAGTAACCG

GCAAAATCGCGCCGAAGGATGTCGCTGCCGACTGGGCAATGGAGCGCCTG

CCGGCCCAGTATCAGCCCGTCATACTTGAAGCTAGACAGGCTTATCTTGG

ACAAGAAGAAGATCGCTTGGCCTCGCGCGCAGATCAGTTGGAAGAATTTG

TCCACTACGTGAAAGGCGAGATCACCAAGGTAGTCGGCAAATAAAGCTTT

ACTGAGCTAATAACAGGACTGCTGGTAATCGCAGGCCTTTTTATTTCTGC

A.

>tolC (1,746 bp)

(SEQ ID NO: 25)

TTGAGGCACATTAACGCCCTATGGCACGTAACGCCAACCTTTTGCGGTAG

CGGCTTCTGCTAGAATCCGCAATAATTTTACAGTTTGATCGCGCTAAATA

CTGCTTCACCACAAGGAATGCAAATGAAGAAATTGCTCCCCATTCTTATC

GGCCTGAGCCTTTCTGGGTTCAGTTCGTTGAGCCAGGCCGAGAACCTGAT

GCAAGTTTATCAGCAAGCACGCCTTAGTAACCCGGAATTGCGTAAGTCTG

CCGCCGATCGTGATGCTGCCTTTGAAAAAATTAATGAAGCGCGCAGTCCA

TTACTGCCACAGCTAGGTTTAGGTGCAGATTACACCTATAGCAACGGCTA

CCGCGACGCGAACGGCATCAACTCTAACGCGACCAGTGCGTCCTTGCAGT

TAACTCAATCCATTTTTGATATGTCGAAATGGCGTGCGTTAACGCTGCAG

GAAAAAGCAGCAGGGATTCAGGACGTCACGTATCAGACCGATCAGCAAAC

-continued

CTTGATCCTCAACACCGCGACCGCTTATTTCAACGTGTTGAATGCTATTG

ACGTTCTTTCCTATACACAGGCACAAAAAGAAGCGATCTACCGTCAATTA

GATCAAACCACCCAACGTTTTAACGTGGGCCTGGTAGCGATCACCGACGT

GCAGAACGCCCGCGCACAGTACGATACCGTGCTGGCGAACGAAGTGACCG

CACGTAATAACCTTGATAACGCGGTAGAGCAGCTGCGCCAGATCACCGGT

AACTACTATCCGGAACTGGCTGCGCTGAATGTCGAAAACTTTAAAACCGA

CAAACCACAGCCGGTTAACGCGCTGCTGAAAGAAGCCGAAAAACGCAACC

TGTCGCTGTTACAGGCACGCTTGAGCCAGGACCTGGCGCGCGAGCAAATT

CGCCAGGCGCAGGATGGTCACTTACCGACTCTGGATTTAACGGCTTCTAC

CGGGATTTCTGACACCTCTTATAGCGGTTCGAAAACCCGTGGTGCCGCTG

GTACCCAGTATGACGATAGCAATATGGGCCAGAACAAAGTTGGCCTGAGC

TTCTCGCTGCCGATTTATCAGGGCGGAATGGTTAACTCGCAGGTGAAACA

GGCACAGTACAACTTTGTCGGTGCCAGCGAGCAACTGGAAAGTGCCCATC

GTAGCGTCGTGCAGACCGTGCGTTCCTCCTTCAACAACATTAATGCATCT

ATCAGTAGCATTAACGCCTACAAACAAGCCGTAGTTTCCGCTCAAAGCTC

ATTAGACGCGATGGAAGCGGGCTACTCGGTCGGTACGCGTACCATTGTTG

ATGTGTTGGATGCGACCACCACGTTGTACAACGCCAAGCAAGAGCTGGCG

AATGCGCGTTATAACTACCTGATTAATCAGCTGAATATTAAGTCAGCTCT

GGGTACGTTGAACGAGCAGGATCTGCTGGCACTGAACAATGCGCTGAGCA

AACCGGTTTCCACTAATCCGGAAAACGTTGCACCGCAAACGCCGGAACAG

AATGCTATTGCTGATGGTTATGCGCCTGATAGCCCGGCACCAGTCGTTCA

GCAAACATCCGCACGCACTACCACCAGTAACGGTCATAACCCTTTCCGTA

ACTGATGACGACGACGGGGAAGCTTAATTAGCTGATCTAGAGGCATCAAA

TAAAACGAAAGGCTCAGTCGAAAGACTGGGCCTTTCGTTTTATCTGTTGT

TTGTCGGTGAACGCTCTCCTGAGTAGGACAAATCCGCCGCCCTAGA.

>zeo<sup>R</sup> (762 bp)

(SEQ ID NO: 26)

GGTGTTGACAATTAATCATCGGCATAGTATATCGGCATAGTATAATACGA

CAAGGTGAGGAACTAAACCATGGCCAAGTTGACCAGTGCCGTTCCGGTGC

TCACCGCGCGCGACGTCGCCGGAGCGGTCGAGTTCTGGACCGACCGGCTC

GGGTTCTCCCGGGACTTCGTGGAGGACGACTTCGCCGGTGTGGTCCGGGA

CGACGTGACCCTGTTCATCAGCGCGGTCCAGGACCAGGTGGTGCCGGACA

ACACCCTGGCCTGGGTGTGGGTGCGCGGCCTGGACGAGCTGTACGCCGAG

TGGTCGGAGGTCGTGTCCACGAACTTCCGGGACGCCTCCGGGCCGGCCAT

GACCGAGATCGGCGAGCAGCCGTGGGGGCGGGAGTTCGCCCTGCGCGACC

CGGCCGGCAACTGCGTGCACTTCGTGGCCGAGGAGCAGGACTGACACGTC

CGACGGCGGCCCACGGGTCCCAGGCCTCGGAGATCCGTCCCCCTTTTCCT

TTGTCGATATCATGTAATTAGTTATGTCACGCTTACATTCACGCCCTCCC

CCCACATCCGCTCTAACCGAAAAGGAAGGAGTTAGACAACCTGAAGTCTA

GGTCCCTATTTATTTTTTATAGTTATGTTAGTATTAAGAACGTTATTTA

TATTTCAAATTTTTCTTTTTTTTCTGTACAGACGCGTGTACGCATGTAAC

-continued
ATTATACTGAAAACCTTGCTTGAGAAGGTTTTGGGACGCTCGAAGGCTTT

AATTTGCAAGCT.

Results

One approach to engineering biocontainment used a GRO lacking all instances of the TAG codon and release factor 1 (terminates translation at UAA and UAG), eliminating termination of translation at UAG and endowing the organism with increased viral resistance, a common form of horizontal gene transfer (HGT). The TAG codon was then converted to a sense codon through the introduction of an orthogonal translation system (OTS) containing an aminoacyl-tRNA synthetase (aaRS):tRNA pair, permitting site-specific incorporation of sAAs into proteins without impairing cellular fitness (Lajoie, et al, *Science,* 342:357-360 (2013)). Leveraging these unique properties of the GRO, the TAG codon was reintroduced into essential genes to restrict growth to defined media containing sAAs. Use of multi-copy plasmids, which reduce viability and growth (Betenbaugh, et al., *Biotechnol. Bioeng,* 33:1425-1436 (1989)), impose biosynthetic burden, persist poorly in host cells over time (Sørensen, et al., *Nature Rev. Microbiol,* 3:700-710 (2005)), and increase the risk of acquiring genetic escape mutants (Moe-Behrens, et al., *Microbiol,* 4:5 (2013)), were eliminated by manipulating native chromosomal essential genes and integrating the OTS into the genome. To engineer synthetic auxotrophies, essential genes of varying expression levels (see Materials and Methods), many of whose functions (for example, replication or translation) cannot be complemented by cross-feeding of metabolites, were chosen. Genes dispersed throughout the genome were selected to prevent a single HGT event from compromising containment.

Three strategies to engineer dependence on non-toxic, membrane-permeable, and well-characterized sAAs through the introduction of TAG codons into essential genes were pursued: (1) insertion at the amino terminus; (2) substitution of residues with computationally predicted tolerances (Kumar, et al, *Nature Protocols,* 4:1073-1081 (2009)); and (3) substitution of conserved (Marchler-Bauer, et al, *Nucleic Acids Res,* 33:D192-D196 (2005)) residues at functional sites (FIG. 1A). The first two strategies were initially pursued in a GRO containing an OTS optimized for the sAA p-acetyl-L-phenylalanine (pAcF, α; see Methods for a detailed explanation of the nomenclature used). Using multiplex automated genome engineering (MAGE) (Wang, et al, *Nature,* 460:894-898 (2009)), 155 codons were targeted for TAG incorporation via 4 pools of oligonucleotides in permissive media containing pAcF and L-arabinose (aaRS induction) (FIG. 1B). After replica plating on non-permissive media lacking pAcF and L-arabinose, eight pAcF auxotrophs with one strain containing two TAGs in essential genes were isolated (FIG. 1C and Table 2).

Table 2: Analysis of sAA-Dependence Screens.

SUPPLEMENTARY TABLE 3

Analysis of sAA-dependence screens

| sAA | aaRS | Pool[a] | MAGE cycles | Total screened | Total dependent | Unique dependent | Unique 1TAG | Unique 2TAG | Unique 3TAG | Unique 4TAG |
|---|---|---|---|---|---|---|---|---|---|---|
| pAcF | pAcF-RS | Y | 4 | 88 | 3 | 3 | 2 | 1 | 0 | 0 |
| pAcF | pAcF-RS | NY | 4 | 88 | 0 | 0 | n/a[b] | n/a[b] | n/a[b] | n/a[b] |
| pAcF | pAcF-RS | N | 4 | 88 | 2 | 2 | 2 | 0 | 0 | 0 |
| pAcF | pAcF-RS | C1 | 4 | 93 | 3 | 3 | 3 | 0 | 0 | 0 |
| pAcF | pAcF-RS | F | 8 | 86 | 0 | 0 | n/a[b] | n/a[b] | n/a[b] | n/a[b] |
| pAzF | pAzF-RS | C2 | 3 | 255 | 0 | 0 | n/a[b] | n/a[b] | n/a[b] | n/a[b] |
| pAzF | pCNF-RS | Y | 4 | 130 | 13 | 8 | 4 | 3 | 0 | 1 |
| pAzF | pCNF-RS | N | 4 | 84 | 8 | 4 | 3 | 1 | 0 | 0 |
| pAzF | pCNF-RS | C2 | 4 | 124 | 8 | 6 | 3 | 1 | 2 | 0 |
| pAzF | pCNF-RS | F | 8 | 344 | 57 | 14 | 6 | 8 | 0 | 0 |
| pIF | pIF-RS | C2 | 3 | 172 | 6 | 3 | 2 | 1 | 0 | 0 |
| pIF | pIF-RS | F | 8 | 62 | 0 | 0 | n/a[b] | n/a[b] | n/a[b] | n/a[b] |

[a]Pool names are abbreviated as follows: Tolerant tyrosine (Y), tolerant non-tyrosine (NY), amino-terminal (N), complex 1 (C1), complex 2 (C2), and functional (F) pools.
[b]Only stains that were sAA-dependent were quantitatively assessed. Other successful TAG incorporations that generated viable or nonviable non-contained clones were not assessed.

To determine whether the strategy was capable of creating synthetic auxotrophs dependent on other sAAs, MAGE was used to mutagenize annotated residues in the sAA binding pocket of the pAcF aaRS (Table 1) to accommodate p-iodo-L-phenylalanine (pIF, β) or p-azido-L-phenylalanine (pAzF, γ) in two strains. After MAGE-based incorporation of TAGs and selections on permissive and non-permissive solid media, 8 pIF and 23 pAzF auxotrophs harbouring 1-4 TAGs at 30 distinct loci across 20 essential genes (dxs, ftsI, metK, murD, pgsA, can, dnaX, fabG, ispH, lptD, IspA, pheT, rpoA, secY, serS, topA, tyrS, dnaA, fusA, glyQ, lnt, and murG) were obtained. Together, these data demonstrate the modularity of the approach and that synthetic auxotrophs can be engineered across many essential genes using multiple sAAs.

Figures 2A, 2B:
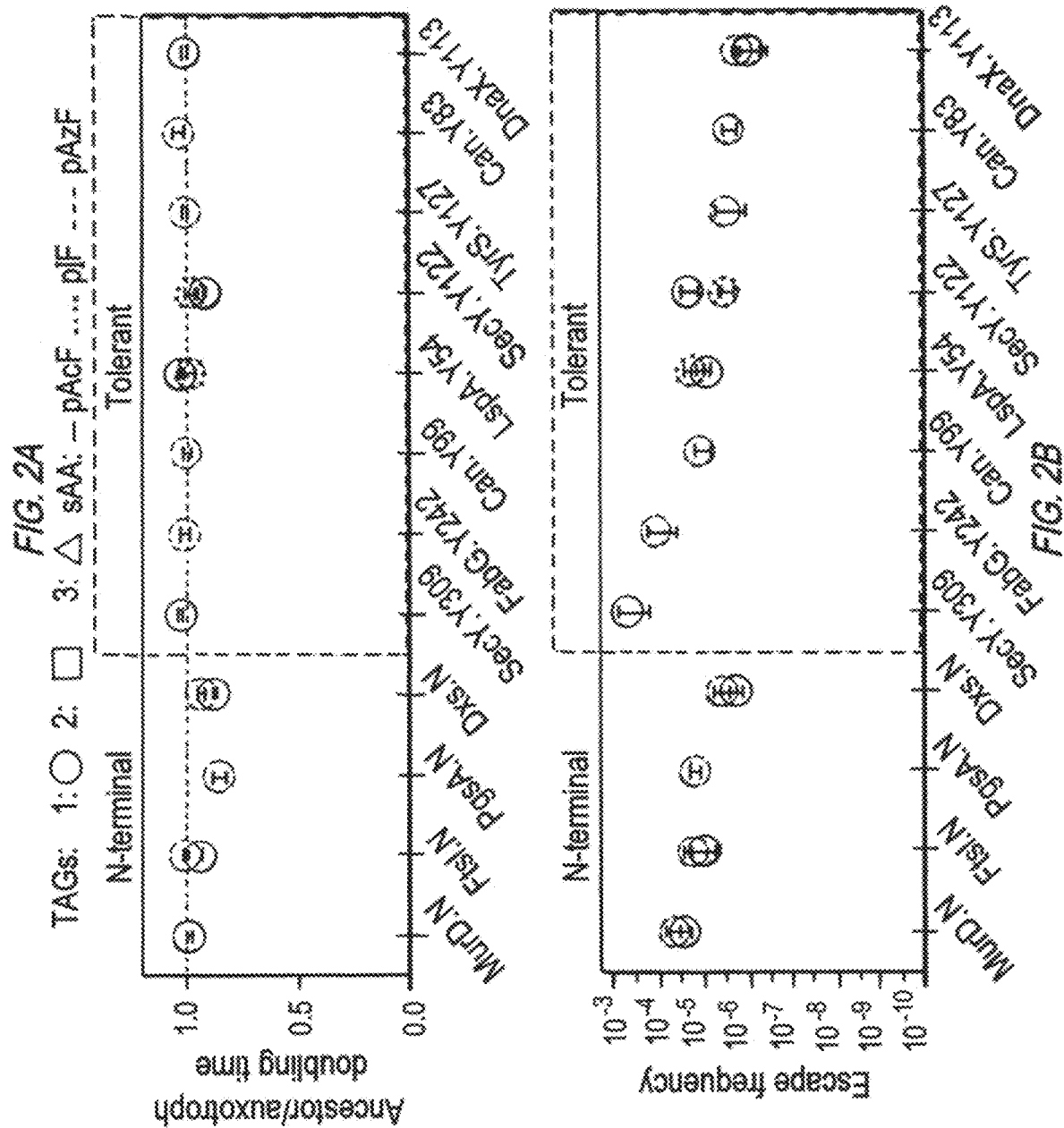
FIG. 2A is a plot showing doubling time ratios for the non-contained ancestor to synthetic auxotroph containing one TAG.
FIG. 2B is a plot showing escape frequencies.
Figure 2C:
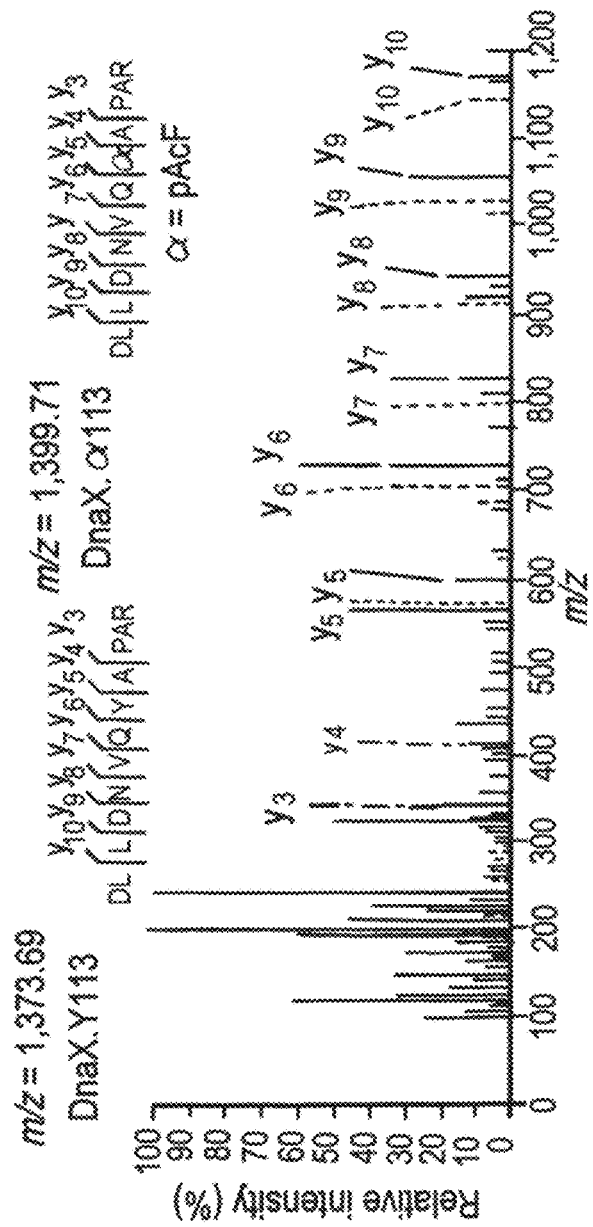
FIG. 2C is superimposed MS/MS spectra for DnaX peptides from DnaX.Y113α (right hand "Y" for each of Ys 5-10) and the non-contained ancestor rEc.α (left hand "Y" for each of Ys 5-10). Overlapping peaks are present at Y3 and Y4, and a mass shift relative to rEc.α identifies Y113 as the pAcF incorporation site in DnaX.Y113α.

Measurements of doubling time in permissive media revealed minimal or no fitness impairment of synthetic auxotrophs relative to their non-contained ancestors with a genomically integrated OTS (FIG. 2A, and Tables 3 and 4).

TABLE 3

Doubling time ratios for the non-contained ancestor
to synthetic auxotroph containing one TAG (FIG. 2A)

| Strain | Average DT (mins) 1 mM sAA | s.d. |
|---|---|---|
| rEc.γ | 58.63 | 0.87 |
| rEc.β | 60.21 | 0.46 |
| rEc.α | 54.25 | 0.19 |
| MurD.αN | 55.28 | 0.41 |
| MurD.γN | 59.01 | 0.54 |
| FtsI.αN | 57.72 | 0.03 |
| FtsI.γN | 58.67 | 0.13 |
| PgsA.γN | 68.74 | 1.34 |
| Dxs.αN | 61.77 | 0.15 |
| Dxs.γN | 62.25 | 0.54 |

TABLE 3-continued

Doubling time ratios for the non-contained ancestor to synthetic auxotroph containing one TAG (FIG. 2A)

| Strain | Average DT (mins) 1 mM sAA | s.d. |
|---|---|---|
| SecY.Y309α | 52.79 | 0.39 |
| FabG.Y242γ | 57.86 | 0.14 |
| Can.Y99γ | 58.34 | 0.28 |
| LspA.Y54α | 52.9 | 0.11 |
| LspA.Y54β | 61.68 | 1.52 |
| SecY.Y122α | 58.9 | 0.27 |
| SecY.Y122β | 62.57 | 0.36 |
| SecY.Y122γ | 59.82 | 0.66 |
| TyrS.Y127γ | 58.45 | 0.27 |
| Can.Y83γ | 57.03 | 0.27 |
| DnaX.Y113α | 54.51 | 0.6 |
| DnaX.Y113β | 60.29 | 0.68 |
| DnaX.Y113γ | 58.79 | 0.36 |

TABLE 4

Summary of escape frequencies and doubling times for 60 sAA-dependent strains

| Nickname | Synthetic amino acid | Essential protein(s) | IAG location(s) | Escape frequency (EF) (Day 1) | Doubling time (minutes)[a] 1 mM sAA | 5 mM sAA |
|---|---|---|---|---|---|---|
| rEc.α | pAcF, α | n/a | n/a | n/a | 54.25 ± 0.19 | data not collected |
| DnaX.Y113α | pAcF, α | DnaX | Y113 | 6.73E−07 ± 1.89E−07 | 54.51 ± 0.60 | data not collected |
| DnaX.Y113α' | pAcF, α | DnaX | Y113 | 1.95E−07 ± 5.09E−08 | 64.97 ± 0.73 | data not collected |
| LspA.Y54α | pAcF, α | LspA | Y54 | 8.39E−06 ± 1.16E−06 | 52.90 ± 0.11 | data not collected |
| SecY.Y122α | pAcF, α | SecY | Y122 | 2.05E−05 ± 8.38E−06 | 58.90 ± 0.27 | data not collected |
| SecY.Y309α | pAcF, α | SecY | Y309 | 4.97E−04 ± 3.15E−04 | 52.79 ± 0.39 | data not collected |
| Dxs.αN | pAcF, α | Dxs | N-term | 1.85E−06 ± 5.65E−07 | 61.77 ± 0.15 | data not collected |
| FtsI.αN | pAcF, α | FtsI | N-term | 1.07E−05 ± 6.27E−06 | 57.72 ± 0.03 | data not collected |
| MurD.αN | pAcF, α | MurD | N-term | 2.97E−05 ± 2.88E−06 | 55.28 ± 0.41 | data not collected |
| rEc.α.dB.8 | pAcF, α | TopA LspA | Y728 Y28 | 6.54E−04 ± 4.45E−04 | 51.47 ± 0.37 | data not collected |
| rEc.β | pIF, β | n/a | n/a | n/a | 60.21 ± 0.46 | data not collected |
| DnaX.Y113β | pIF, β | DnaX | Y113 | 8.71E−07 ± 5.31E−07 | 60.29 ± 0.68 | data not collected |
| LspA.Y54β | pIF, β | LspA | Y54 | 1.86E.05 ± 5.57E−06 | 61.68 ± 1.52 | data not collected |
| Sec.Y122β | pIF, β | SecY | Y122 | 2.62E−06 ± 6.47E−07 | 62.57 ± 0.36 | data not collected |
| rEc.β.dB.9 | pIF, β | DnaX LspA | Y113 Y54 | 1.31E−08 ± 9.52E−09 | 59.63 ± 0.29 | data not collected |
| rEc.β.dB.9' | pIF, β | DnaX LspA | Y113 Y54 | 4.92E−09 ± 1.62E−09 | 60.58 ± 0.28 | data not collected |
| rEc.β.dC.11 | pIF, β | DnaX LspA Dxs | Y113 Y54 N-term | 5.01E−09 ± 3.61E−09 | 61.62 ± 0.19 | data not collected |
| rEc.β.dC.11' | pIF, β | DnaX LspA Dxs | Y113 Y54 N-term | 3.31E−09 ± 4.90E−10 | 61.97 ± 0.22 | data not collected |
| rEc.β.dC.12 | pIF, β | DnaX LspA SecY | Y113 Y54 Y122 | 4.68E−09 ± 1.99E−09 | 60.04 ± 0.29 | data not collected |
| rEc.β.dC.12' | pIF, β | DnaX LspA SecY | Y113 Y54 Y122 | 2.17E−09 ± 3.69E−10 | 61.81 ± 0.65 | data not collected |
| rEc.β.dC.12'.ΔtY | pIF, β | DnaX LspA SecY | Y113 Y54 Y122 | <4.85E−12 | 60.99 ± 0.70 | data not collected |
| rEc.γ | pAzF, γ | n/a | n/a | n/a | 58.63 ± 0.87 | 59.41 ± 0.13 |
| Can.Y83γ | pAzF, γ | Can | Y83 | 2.39E−06 ± 7.90E−07 | 57.03 ± 0.27 | data not collected |
| Can.Y99γ | pAzF, γ | Can | Y99 | 1.05E−05 ± 3.84E−06 | 58.34 ± 0.28 | data not collected |
| DnaX.Y113γ | pAzF, γ | DnaX | Y113 | 1.37E−06 ± 2.08E−07 | 58.79 ± 0.36 | data not collected |

TABLE 4-continued

Summary of escape frequencies and doubling times for 60 sAA-dependent strains

| Nickname | Synthetic amino acid | Essential protein(s) | IAG location(s) | Escape frequency (EF) (Day 1) | Doubling time (minutes)[a] 1 mM sAA | 5 mM sAA |
|---|---|---|---|---|---|---|
| FabG.Y242γ | pAzF, γ | FabG | Y242 | 1.16E−04 ± 6.96E−05 | 57.86 ± 0.14 | data not collected |
| LptD.Y212γ | pAzF, γ | LptD | Y212 | data not collected | data not collected | data not collected |
| LptD.Y354γ | pAzF, γ | LptD | Y354 | data not collected | data not collected | data not collected |
| SecY.Y122γ | pAzF, γ | SecY | Y122 | 3.38E−06 ± 5.28E−07 | 59.82 ± 0.66 | data not collected |
| TyrS.Y127γ | pAzF, γ | TyrS | Y127 | 2.88E−06 ± 1.75E−06 | 58.45 ± 0.27 | data not collected |
| Dxs.γN | pAzF, γ | Dxs | N-term | 3.41E−06 ± 2.10E−06 | 62.25 ± 0.54 | data not collected |
| FtsI.γN | pAzF, γ | FtsI | N-term | 1.53E−05 ± 1.15E−05 | 58.67 ± 0.13 | data not collected |
| MurD.γN | pAzF, γ | MurD | N-term | 4.24E−05 ± 2.57E−05 | 59.01 ± 0.54 | data not collected |
| PgsA.γN | pAzF, γ | PgsA | N-term | 1.36E−05 ± 3.22E−06 | 68.74 ± 1.34 | data not collected |
| Dna.W6γ | pAzF, γ | DnaA | W6 | 5.14E−07 ± 1.69E−07 | 65.20 ± 0.89 | 66.23 ± 0.28 |
| FusA.F32γ | pAzF, γ | FusA | F32 | 5.00E−03 ± 4.14E−03 | 73.76 ± 0.17 | 62.93 ± 0.28 |
| GlyQ.Y226γ | pAzF, γ | GlyQ | Y226 | 1.01E−05 ± 3.10E−06 | 65.32 ± 1.22 | 60.66 ± 1.19 |
| Lnt.Y388γ | pAzF, γ | Lnt | Y388 | 6.80E−06 ± 3.19E−06 | 60.98 ± 0.26 | 62.27 ± 0.06 |
| MurG.F243γ | pAzF, γ | MurG | F243 | 8.05E−07 ± 4.00E−07 | 59.16 ± 0.15 | 60.41 ± 0.52 |
| SerS.F213γ | pAzF, γ | SerS | F213 | 1.29E−06 ± 8.75E−07 | 58.68 ± 0.19 | 59.52 ± 0.36 |
| rEc.γ.dB.16 | pAzF, γ | PgsA MetK | N-term | 9.87E−07 ± 4.24E−07 | 61.51 ± 1.02 | data not collected |
| rEc.γ.dB.17 | pAzF, γ | SecY | Y122 Y309 | 1.77E−06 ± 1.14E−06 | 64.02 ± 1.13 | data not collected |
| rEc.γ.dC.18 | pAzF, γ | TopA SecY122 Dxs | Y728 Y122 N-term | 3.38E−05 ± 2.65E−05 | 61.15 ± 0.88 | data not collected |
| rEc.γ.dD.20 | pAzF, γ | LspA LspA PheT IspH | Y28 Y50 Y615 Y142 | 1.02E−05 ± 5.70E−06 | 62.61 ± 0.32 | data not collected |
| rEc.γ.dB.22 | pAzF, γ | SecY PheT | Y309 Y615 | 2.93E−05 ± 1.53E−05 | 59.97 ± 0.57 | data not collected |
| rEc.γ.dB.23 | pAzF, γ | PheT | Y558 Y601 | 5.48E−06 ± 3.73E−06 | 58.22 ± 0.30 | data not collected |
| rEc.γ.dC.24 | pAzF, γ | TopA LspA Dxs | Y728 Y28 N-term | 2.85E−06 ± 2.10E−06 | 62.12 ± 0.83 | data not collected |
| rEc.γ.dB.26 | pAzF, γ | DnaX | Y113 Y328 | 1.42E−07 ± 8.69E−08 | 60.49 ± 0.15 | data not collected |
| rEc.γ.dB.28 | pAzF, γ | LptD | Y212 Y354 | data not collected | data not collected | data not collected |
| rEc.γ.dB.29 | pAzF, γ | LptD | Y458 Y514 | data not collected | data not collected | data not collected |
| rEc.γ.dB.31 | pAzF, γ | LptD | Y212 Y244 | data not collected | data not collected | data not collected |
| rEc.γ.dB.38 | pAzF, γ | FusA RpoA | F32 Y152 | data not collected | data not collected | data not collected |
| rEc.γ.dB.39 | pAzF, γ | FusA MurG | F32 F243 | data not collected | data not collected | data not collected |
| rEc.γ.dB.40 | pAzF, γ | DnaA GlyQ | W6 Y226 | data not collected | data not collected | data not collected |
| rEc.γ.dB.41 | pAzF, γ | DnaA MurG | W6 F243 | 1.56E−09 ± 1.02E−09 | 63.78 ± 0.26 | 62.62 ± 0.04 |
| rEc.γ.dB.41' | pAzF, γ | DnaA MurG | W6 F243 | 5.98E−10 | 62.22 ± 0.31 | 60.90 ± 0.21 |
| rEc.γ.dB.42 | pAzF, γ | DnaA FusA | W6 F32 | data not collected | data not collected | data not collected |
| rEc.γ.dB.43 | pAzF, γ | DnaA SerS | W6 F213 | 2.32E−09 ± 6.53E−10 | 75.89 ± 2.79 | 59.85 ± 0.10 |
| rEc.γ.dB.44 | pAzF, γ | DnaA RpoA | W6 Y152 | data not collected | data not collected | data not collected |
| rEc.γ.dB.45 | pAzF, γ | Lnt MurG | Y388 F243 | data not collected | data not collected | data not collected |
| rEc.γ.dC.46 | pAzF, γ | DnaA MurG SerS | W6 F243 F213 | <7.88E−11 | 71.01 ± 0.36 | 63.42 ± 0.30 |
| rEc.γ.dC.46' | pAzF, γ | DnaA MurG SerS | W6 F243 F213 | <4.36E−11 | 71.86 ± 0.59 | 64.27 ± 0.23 |

TABLE 4-continued

Summary of escape frequencies and doubling times for 60 sAA-dependent strains

| Nickname | Synthetic amino acid | Essential protein(s) | IAG location(s) | Escape frequency (EF) (Day 1) | Doubling time (minutes)[a] | |
|---|---|---|---|---|---|---|
| | | | | | 1 mM sAA | 5 mM sAA |
| rEc.γ.dC.46'.ΔtY | pAzF, γ | DnaA MurG SerS | W6 F243 F213 | <6.3E−12 | 64.91 ± 0.39 | 61.41 ± 0.18 |

[a]Average doubling times are shown for growth in permissive media; n = 3 technical replicates; error is +/− s.d.

Summary of all synthetic auxotrophs. Average escape frequencies (EFs) refer to day 1. Representative EFs are shown in some cases. Average doubling times refer to growth in permissive media (0.2% L-arabinose and sAA at 1 mM or 5 mM).

To quantify the degree of containment, the ratio of colony-forming units (c.f.u.) was measured on non-permissive to permissive solid media, and a range of escape frequencies spanning $10^{-3}$ to $10^{-7}$ (FIG. 2B, Table 5) was observed.

TABLE 5

Escape frequencies (FIG. 2B).

| Strain | Average EF | s.d. |
|---|---|---|
| MurD.αN | 2.97E−05 | 2.88E−06 |
| MurD.γN | 4.24E−05 | 2.57E−05 |
| FtsI.αN | 1.07E−05 | 6.27E−06 |
| FtsI.γN | 1.53E−05 | 1.15E−05 |
| PgsA.γN | 1.36E−05 | 3.22E−06 |
| Dxs.αN | 1.85E−06 | 5.65E−07 |
| Dxs.γN | 3.41E−06 | 2.10E−06 |
| SecY.Y309α | 4.97E−04 | 3.15E−04 |
| FabG.Y242γ | 1.16E−04 | 6.96E−05 |
| Can.Y99γ | 1.05E−05 | 3.84E−06 |
| LspA.Y54α | 8.39E−06 | 1.16E−06 |
| LspA.Y54β | 1.86E−05 | 5.57E−06 |
| SecY.Y122α | 2.05E−05 | 8.38E−06 |
| SecY.Y122β | 2.62E−06 | 6.47E−07 |
| SecY.Y122γ | 3.38E−06 | 5.28E−07 |
| TyrS.Y127γ | 2.88E−06 | 1.75E−06 |
| Can.Y83γ | 2.39E−06 | 7.90E−07 |
| DnaX.Y113α | 6.73E−07 | 1.89E−07 |
| DnaX.Y113β | 8.71E−07 | 5.31E−07 |
| DnaX.Y113γ | 1.37E−06 | 2.08E−07 |

One notable strain DnaX.Y113α preserved the doubling time of its non-contained ancestor (FIG. 2A) while maintaining an escape frequency of 6.7×10$^{-7}$ (FIG. 2B). pAcF incorporation in DnaX.Y113α was directly investigated using mass spectrometry and peptides containing pAcF at Y113 were identified (FIG. 2C).

To investigate escape mechanisms of escape mutants derived from synthetic auxotrophs with one essential TAG codon, targeted sequencing was performed and transition mutations (A•T to G•C and G•C to A•T) commonly observed in mismatch-repair-deficient strains (ΔmutS) were observed (Schaaper, et al, *Proc. Natl Acad. Sci. USA*, 84:6220-6224 (1987)). All isolated DnaX.Y113α escape mutants incorporate tryptophan by mutation of the TAG codon to TGG. SecY.Y122α escape mutants incorporate glutamine by mutation of glnV to form a glutamine amber suppressor or mutation of the secY.Y122 TAG codon to CAG (Table 6).

TABLE 6

Escape mechanisms of MutS-deficient strains with one essential TAG codon.

| Escape mutant | Essential gene | Causative SNP[a] | Causative SNP location[b] | Relative fitness in media without sAA[c] |
|---|---|---|---|---|
| SecY.Y122α.E1 | secY | cag→cGg | RpsD.Q54R | 0.68 ± 0.035 |
| SecY.Y122α.E2 | secY | tag→Cag | SecY.α122Q | 0.97 ± 0.006 |
| SecY.Y122α.E3 | secY | ctg→ctA | glnV→supE | 1.00 ± 0.028 |
| DnaX.Y113α.E1 | dnaX | tag→tGg | DnaX.α113W | 0.97 ± 0.011 |
| DnaX.Y113α.E2 | dnaX | tag→tGg | DnaX.α113W | 0.95 ± 0.015 |
| DnaX.Y113α.E3 | dnaX | tag→tGg | DnaX.α113W | 0.94 ± 0.014 |

One of three SecY.Y122α escape mutants was wild type at the secY.Y122 TAG codon and putative amber-suppressor loci (Eggertsson, et al, *Microbiol. Rev,* 52:354-374 (1988)), but whole-genome sequencing revealed a Q54D missense mutation in rpsD (30S ribosomal subunit S4). This site is implicated in ribosome fidelity (Maisnier-Patin, et al, *Mol. Microbiol,* 46:355-366 (2002); Holberger, et al, *J. Biol. Chem,* 284:32188-32200 (2009)) and is the causal mutation leading to escape in this mutant.

Quantitative Assessment of Amino Acid Tolerance

The following workflow was performed to assess the tolerance for natural amino acid substitution at residues chosen for sAA incorporation. Strains were grown to mid-log phase in 1 ml of permissive LB media, and MAGE was performed as described (Wang, et al, *Nature,* 460:894-898 (2009)) with modifications described here. Post induction of λ-Red proteins, cells were transferred to individual wells of a 96-well, V-bottomed plate, and washed twice at 4° C. with sterile deionized water (dH$_2$O). Cells were re-suspended in 50 μl of water or 1 μM mutagenic single-stranded DNA to convert a single in-frame essential TAG codon to one of 20 sense codons, and electroporated in a 96-well plate. Cells were electroporated using the Harvard BTX electroporation system (2.4 kV, 750Ω, 25 μF). Electroporated cells were recovered in 1.5 ml of fresh permissive media in a 96-well plate for 4 h at 34° C. shaking. Cells were pelleted, washed twice with sterile dH$_2$O, and re-suspended in 200 μl of 1×PBS. Serial dilutions were made in 1×PBS and 50 μl each of non-diluted and 100-fold diluted samples were plated on solid non-permissive LB media. 50 μl each of higher dilutions were plated on permissive solid media and all plates were incubated for 20 h at 34° C.

Colony-forming units counted on non-permissive media were expressed as a ratio of total c.f.u. on permissive media. Since the frequency of MAGE-mediated recombination (~0.3) (Wang, et al, *Nature,* 460:894-898 (2009)) exceeds the escape frequencies of these background strains (≤10$^{-5}$), these ratios were directly correlated to amino acid tolerance. MATLAB was used to calculate the log$_{10}$ of this ratio. Where no c.f.u. were observed on non-permissive media, indicative of a highly intolerant substitution, a ratio could not be calculated and these values were defaulted to NaN within MATLAB. A heat map was used to compare representative data for one experiment, where blue indicates a tolerated substitution and yellow, a non-tolerated substitution.

Twenty-one separate MAGE experiments were performed as described above for each strain, per essential genomic TAG, to assess tolerance for each of the 20 natural amino acids at each TAG site, plus a negative control (water). Strains with one TAG codon (SecY.Y122β, DnaX.Y113β, LspA.Y54β, DnaA.W6γ, SerS.F213γ, and MurG.F243γ) were assessed across 21 (including the negative control) experiments per strain, strains with two TAG codons (rEc.β.dB.9) were assessed across 42 (including two negative control) experiments per strain, and strains with three TAG codons (rEc.β.dC.12 and rEc.γ.dC.46) were assessed across 63 (including three negative control) experiments per strain. Reported results repeated at least three times in independent experiments.

Escape Assays

Strains were grown in triplicate to late-log phase in 2 ml of permissive LB media, pelleted, washed twice with sterile dH$_2$O, and re-suspended in 200 μl 1×PBS. To obtain total and escape mutant c.f.u., serial dilutions were made and equal volumes were plated on permissive and non-permissive solid media plates (100×15 mm). Plates were incubated at 34° C. and escape frequency was calculated as the total number of escape mutant c.f.u. observed per total cells plated. Reported escape frequencies are means of three technical replicates where error bars represent ±s.d. To isolate escape mutants in strains with lower escape frequencies, ~$10^{10}$-$10^{11}$ cells were plated and the resulting escape frequency from a representative escape assay is reported. When escape mutants were not detected upon plating ~$10^{10}$-$10^{11}$ cells, the escape frequency is described to be below the limit of detection and reported as less than a frequency of one over the total number of cells plated. In all cases, reported results repeated at least three times in independent experiments. Where temporal monitoring of escape frequencies on solid media is reported (FIG. 3D), representative escape assays are plotted and results repeated at least three times in independent experiments.

Example 2: Improved Synthetic Auxotrophs have Lower Escape Frequencies

Materials and Methods
Mismatch Repair

The presence of a prime symbol (') following the TAG combination number indicates that mutS has been restored at its native locus, imparting functional mismatch repair to the organism.

tRNA Redundancy

Following the TAG combination number, Δt indicates the amino acid for which tRNA redundancy has been eliminated and is followed by the relevant amino acid (for example, a strain in which two of three total tyrosine tRNAs were deleted is ΔtY).

Results

The escape mechanisms described in Example 2, informed two sets of experiments to engineer strains with lower escape frequencies. First, synthetic auxotrophs with an increased numbers of TAGs (FIG. 2D, Table 7) were created by combining TAGs from strains possessing the lowest escape frequencies (that is, dnaX.Y113, lspA.Y54 and secY.Y122) into a single strain.

TABLE 7

Figure 2E:
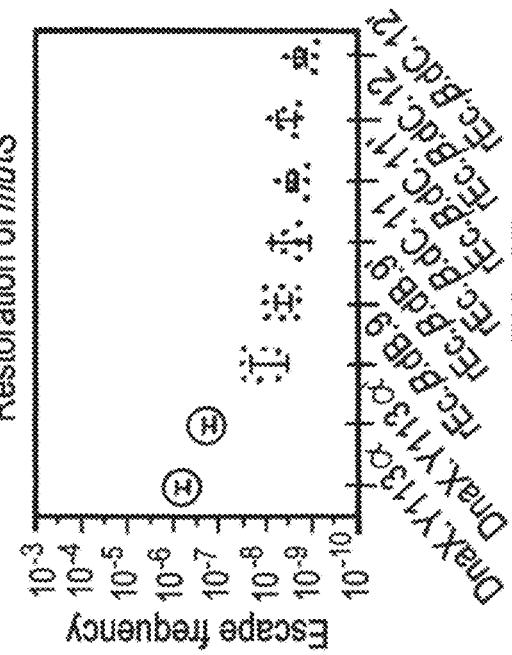
FIGS. 2D and 2E are plots showing escape frequencies for strains with multiple TAG codons (d) and/or functional mismatch repair (e) (prime, mutS+). For all plots, average values of three technical replicates are plotted with error bars representing ±s.d. Reported results repeated at least three times in independent experiments.
Figure 2D:
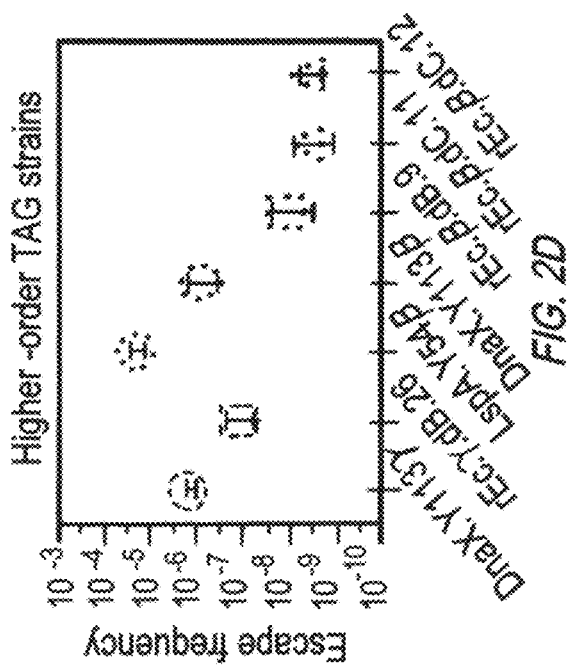

Escape frequencies for strains with multiple TAG codons (FIG. 2D).

| Strain | Average EF | s.d. |
| --- | --- | --- |
| DnaX.Y113γ | 1.37E−06 | 2.08E−07 |
| rEc.γ.dB.26 | 1.42E−07 | 8.69E−08 |
| LspA.Y54β | 1.86E−05 | 5.57E−06 |
| DnaX.Y113β | 8.71E−07 | 5.31E−07 |
| rEc.β.dB.9 | 1.31E−08 | 9.52E−09 |
| rEc.β.dC.11 | 5.01E−09 | 3.61E−09 |
| rEc.β.dC.12 | 4.68E−09 | 1.99E−09 |

In strains containing two TAGs, the escape frequency was reduced to $1.4 \times 10^{-7}$ (rEc.γ.dB.26) and $1.4 \times 10^{-8}$ (rEc.β.dB.9) (strain annotations are listed in Table 4 and a complete description of nomenclature can be found in the Methods). In strains containing three TAGs, escape frequencies were further reduced to $5.0 \times 10^{-9}$ (rEc.β.dC.11) and 4.7×10-9 (rEc.β.dC.12). MAGE was used to assess quantitatively the effects of non-synonymous mutations at individual TAG codons in strains incorporating pIF at SecY.Y122, DnaX.Y113, and LspA.Y54 by mutating the TAG site to sense codons for all 20 natural amino acids. Strains containing multiple TAGs were less likely to survive when one TAG was compromised.

In a second set of experiments, mutS (prime symbol (') denotes a mutS+ strain) was restored and a decreased escape frequency in strains by 1.5- to 3.5-fold was observed (FIG. 2E and Tables 4 and 8). Escape mutants derived from mutS+ higher-order TAG strains exhibited impaired fitness with 1.14- to 1.28-fold greater doubling times than their contained ancestors.

TABLE 8

Escape frequencies for strains with multiple TAG codons and/or functional mismatch repair (prime, mutS+) (FIG. 2E).

| Strain | Average EF | s.d. |
| --- | --- | --- |
| DnaX.Y113α | 6.73E−07 | 1.89E−07 |
| DnaX.Y113α' | 1.95E−07 | 5.09E−08 |
| rEc.β.dB.9 | 1.31E−08 | 9.52E−09 |
| rEc.β.dB.9' | 4.92E−09 | 1.62E−09 |
| rEc.β.dC.11 | 5.01E−09 | 3.61E−09 |
| rEc.β.dC.11' | 3.31E−09 | 4.90E−10 |
| rEc.β.dC.12 | 4.68E−09 | 1.99E−09 |
| rEc.β.dC.12' | 2.17E−09 | 3.69E−10 |

Whole-genome sequencing was performed on these escape mutants and revealed mutations of tyrosine tRNAs to form tyrosine amber (UAG) or ochre (UAA) suppressors (Table 9).

TABLE 9

Escape mechanisms of higher order, MutS-proficient strains with multiple essential TAG codons.

| Escape mutant | Essential genes | Causative SNP[a] | Causative SNP location[b] | Suppressor type | Relative fitness in media without sAA[c] |
|---|---|---|---|---|---|
| rEc.β.dB.9'.E1 | dnaX, lspA | Gta→Tta | tyrV→supC | ochre (TAA) | 0.83 ± 0.006 |
| rEc.β.dB.9'.E2 | dnaX, lspA | Gta→Tta | tyrV→supC | ochre (TAA) | 0.83 ± 0.009 |
| rEc.β.dB.9'.E3 | dnaX, lspA | Gta→Cta | tyrT→supF | amber (TAG) | 0.88 ± 0.010 |
| rEc.β.dC.12'.E5 | dnaX, lspA, secY | Gta→Cta | tyrU→supZ | amber (TAG) | 0.85 ± 0.019 |
| rEc.β.dC.12'.E7 | dnaX, lspA, secY | Gta→Tta | tyrT→supC | ochre (TAA) | 0.78 ± 0.012 |
| rEc.β.dC.12'.E8 | dnaX, lspA, secY | Gta→Tta | tyrT→supC | ochre (TAA) | 0.80 ± 0.012 |
| rEc.γ.dB.41'.E1 | dnaA, murG | Gta→Cta | tyrT→supF | amber (TAG) | 0.48 ± 0.008 |
| rEc.γ.dB.41'.E2 | dnaA, murG | Gta→Cta | tyrV→supF | amber (TAG) | 0.48 ± 0.063 |
| rEc.γ.dB.41'.E3 | dnaA, murG | Gta→Cta | tyrU→supZ | amber (TAG) | 0.50 ± 0.072 |
| rEc.γ.dB.46'.E4 | dnaA, murG, serS | Gta→Cta | tyrV→supF | amber (TAG) | 0.56 ± 0.093 |
| rEc.γ.dB.46'.E5 | dnaA, murG, serS | Gta→Cta | tyrV→supF | amber (TAG) | 0.62 ± 0.040 |
| rEc.γ.dB.46'.E6 | dnaA, murG, serS | Gta→Cta | tyrV→supF | amber (TAG) | 0.57 ± 0.036 |

[a]Caustive SNP is capitalized with the codon or anticodon sequence, from 5' to 3', for protein and tRNA-encoded genes, respectively.
[b]tRNA suppressor name conferred by the anticodon mutation is shown.
[c]Average ratio of doubling times are shown for contained ancestor grown to escape mutant grown in permissive and nonpermissive media, respectively;
n = 3 technical replicates; error is +/− s.d.

To reduce escape frequencies below ~$10^{-9}$ and eliminate rescue by natural amino acids, a third strategy was pursued to replace conserved and functional residues in essential proteins with sAAs (FIG. 1A). Using the Conserved Domain Database (Marchler-Bauer, et al, *Nucleic Acids Res*, 33:D192-D196 (2005)), all essential proteins for tyrosine, tryptophan and phenylalanine residues involved in protein-protein interactions (for example, dimerization) or located within active sites to identify candidates suitable for replacement with phenylalanine-derived sAAs were searched.

Figure 3C:
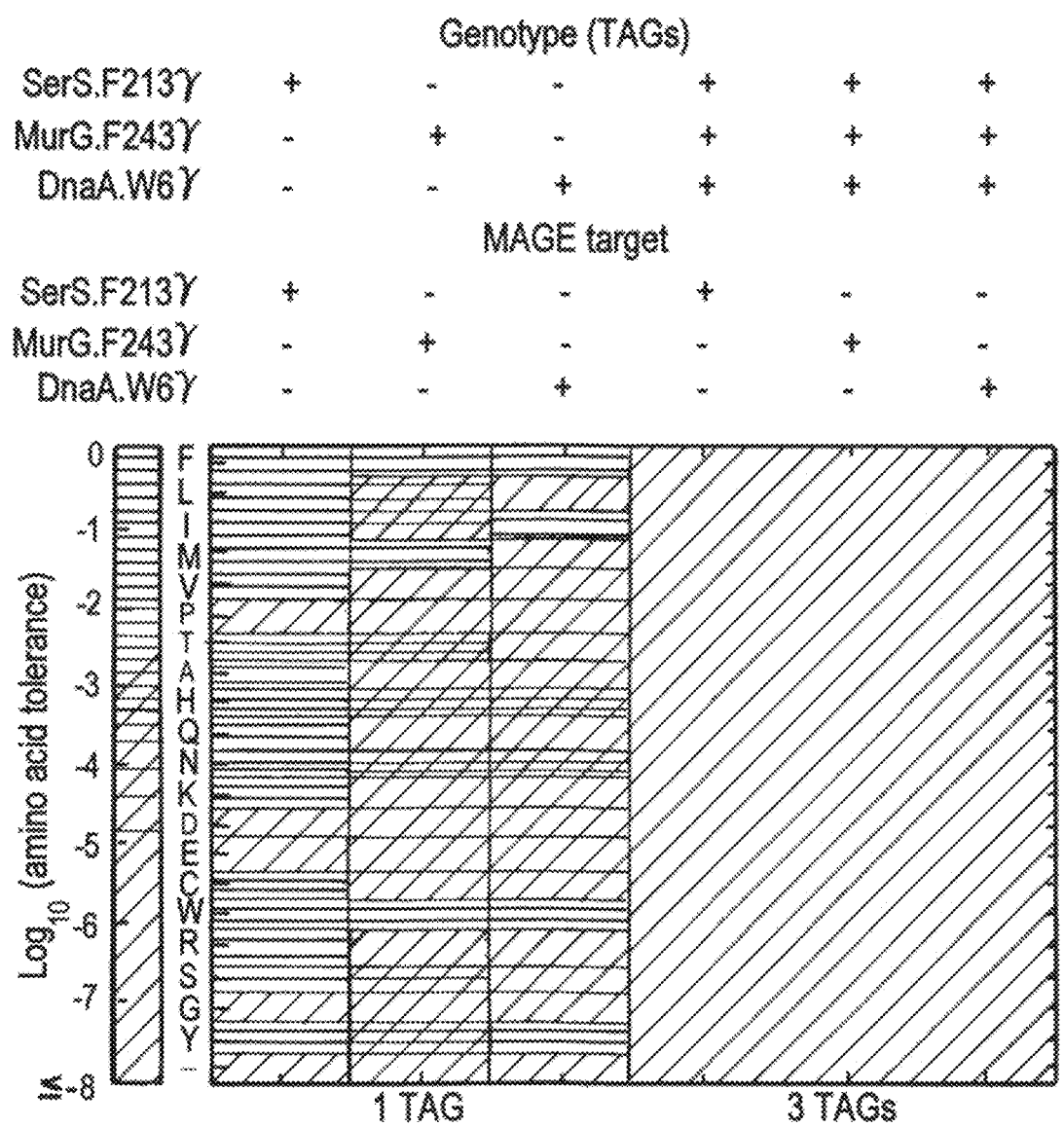
FIG. 3C is a heat map showing the results of a representative assay surveying tolerance of TAG loci to 20 amino acids in different synthetic auxotrophs and expressed as log 10 of total cell survival. A "+" symbol indicates a TAG codon at the locus in the background strain; "−" indicates the wild-type codon; dark and light indicate high and low tolerance to substitution, respectively.

After targeted insertion of TAG codons using MAGE, four synthetic auxotrophs were isolated with pAzF incorporated at GlyQ.Y226 (glycyl-tRNA synthetase α subunit, dimer interface), Lnt.Y388 (apolipoprotein N-acyltransferase, active site), MurG.F243 (N-acetylglucosaminyl transferase, active site), and DnaA.W6 (chromosomal replication initiator protein, oligomerization site (Abe, et al, *J. Biol. Chem*, 282:17816-17827 (2007)) in strains with minor fitness impairments (FIG. 3A) and escape frequencies spanning $10^{-5}$ to $10^{-7}$ (FIG. 3B).

Identical experiments to incorporate pAcF and pIF failed to generate synthetic auxotrophs, indicating that the targeted residues are recalcitrant to replacement by pAcF and pIF. Since pAzF was able to replace conserved and functional tyrosine, phenylalanine and tryptophan residues across several essential proteins, it is believed that engineering strains to contain higher-order TAG combinations would limit escape by mutations that cause incorporation of natural amino acids at multiple TAG codons. Escape frequencies of $1.6\times10^{-9}$ and $2.3\times10^{-9}$ were observed for strains containing two TAG codons: rEc.γ.dB.41 (DnaA.W6 and MurG.F243) and rEc.γ.dB.43 (DnaA.W6 and SerS.F213), respectively. Upon restoring mutS, the escape frequency of rEc.γ.dB.41' fell to $6.0\times10^{-10}$ (FIG. 3B). Merging all three sites into one strain (rEc.γ.dC.46) and its mutS+ derivative (rEc.γ.dC.46') led to escape frequencies of $<7.9\times10^{-11}$ and $<4.4\times10^{-11}$ (below the detection limit of plate-based assay utilized), respectively (Table 4).

Figure 3D:
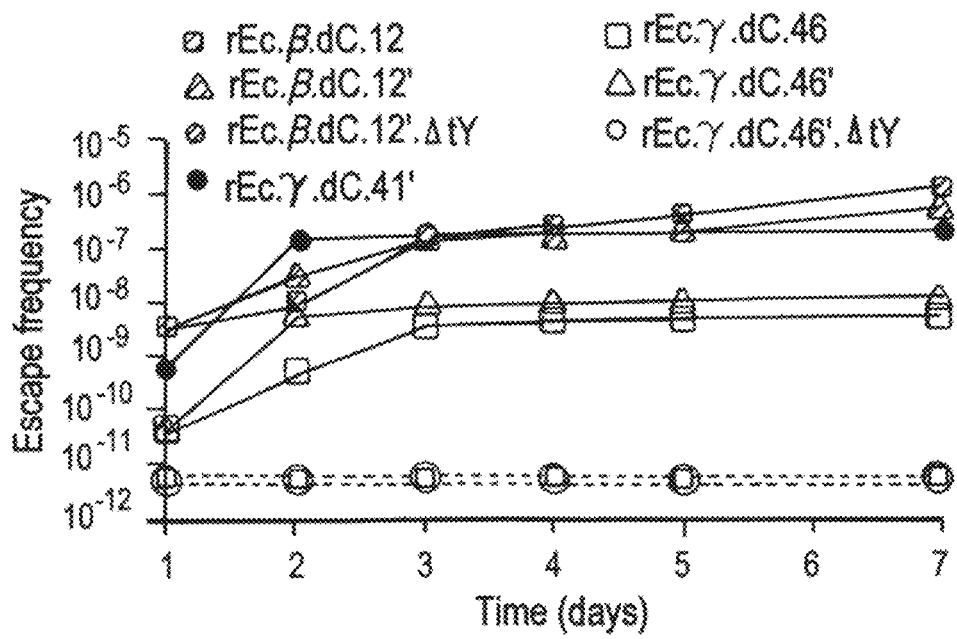
FIG. 3D is a line graph showing the results of a representative escape assay monitoring escape frequencies up to 7 days after plating on solid non-permissive media; hollow symbols/dashed lines, no observed escape mutants.

Temporal monitoring of rEc.γ.dC.46' revealed the emergence of growth-impaired escape mutants 2 days post-plating on non-permissive solid media (FIG. 3D). Sequencing of escape mutants derived from strains rEc.γ.dC.41' and rEc.γ.dC.46' revealed amber-suppressor-forming mutations at one of three tyrosine tRNAs (tyrT, tyrV, tyrU) with growth impairments spanning 1.61- to 2.10-fold increases in doubling time relative to contained ancestors (Table 9). Given that *E. coli* contains three tyrosine tRNAs, experiments were designed to determine if deletion of tyrT and tyrV24 would prevent acquisition of amber-suppressor-forming mutations at tyrU, as preservation of this single remaining copy of tRNATyr would be required to maintain fidelity of tyrosine incorporation during protein synthesis. To accomplish this, λ-Red recombination was used to delete tyrT and tyrV in rEc.β.dC.12', rEc.β.dC.12'.E7 (escape mutant of rEc.β.dC.12'), and rEc.γ.dC.46' with a chloramphenicol resistance gene. Deletion of tyrT and tyrV restored containment of the escape mutant, establishing the causal escape mechanism. Moreover, tyrT/V deletions in rEc.β.dC.12'.ΔtY and rEc.γ.dC.46'.ΔtY decreased escape frequencies below detectable levels ($<4.9\times10^{-12}$ and $<6.3\times10^{-12}$, respectively) over the 7-day observation period (FIG. 3D and Table 10).

TABLE 10

Frequencies of escape for sAA-dependent strains over time.

| Genotype | EF Day 1 | EF Day 2 | EF Day 3 | EF Day 4 | EF Day 5 | EF Day 7 |
|---|---|---|---|---|---|---|
| DnaA.W6γ | 7.81E−08 | 9.79E−06 | 1.19E−05 | 1.42E−05 | 1.42E−05 | 1.46E−05 |
| rEc.β.dC.12 | 3.31E−09 | 9.93E−09 | 1.48E−07 | 2.49E−07 | 4.51E−07 | 1.44E−06 |
| rEc.β.dC.12' | 3.79E−09 | 3.41E−08 | 1.52E−07 | 1.67E−07 | 2.02E−07 | 5.49E−07 |
| rEc.β.dC.12'.ΔtY | <4.85E−12 | <4.85E−12 | <4.85E−12 | <4.85E−12 | <4.85E−12 | <4.85E−12 |
| rEc.γ.dB.41 | 2.17E−09 | 3.62E−09 | 5.07E−09 | 5.07E−09 | 5.80E−09 | 6.52E−09 |
| rEc.γ.dB.41' | 5.98E−10 | 1.56E−07 | 1.82E−07 | 2.08E−07 | 2.08E−07 | 2.08E−07 |

TABLE 10-continued

Frequencies of escape for sAA-dependent strains over time.

| Genotype | EF Day 1 | EF Day 2 | EF Day 3 | EF Day 4 | EF Day 5 | EF Day 7 |
|---|---|---|---|---|---|---|
| rEc.γ.dC.46 | <4.03E−11 | 5.05E−10 | 3.53E−09 | 4.50E−09 | 4.75E−09 | 5.13E−09 |
| rEc.γ.dC.46' | <4.36E−11 | 5.80E−09 | 9.02E−09 | 1.05E−08 | 1.12E−08 | 1.21E−08 |
| rEc.γ.dC.46'.ΔtY | <6.30E−12 | <6.30E−12 | <6.30E−12 | <6.30E−12 | <6.30E−12 | <6.30E−12 |

Representative EFs are shown (see methods).

To challenge strains rEc.β.dC.12'.ΔtY and rEc.γ.dC.46'.ΔtY with natural amino acids and mimic a potential HGT event, constructs containing phenylalanine or tryptophan amber-suppressor tRNAs were introduced. While growth of suppressor-containing strains was equivalent to the cognate-contained ancestor in permissive liquid media, severely impaired growth or no growth was observed in non-permissive media. Such findings are further supported in experiments where a large (~$10^{11}$) inoculum of cells challenged on solid or in liquid (see below) non-permissive media do not yield escape mutants, providing ample opportunity for natural formation of a phenylalanine amber suppressor via mutation of one of two native copies of tRNAPhe. These data support the conclusion that synthetic auxotrophs containing higher-order TAG combinations depend on the sAA and limit growth from natural amino acids.

Example 3: Synthetic Auxotrophs Exhibit Long Term Stability

Materials and Methods
Liquid Escape Assays

Long-term liquid growth was assessed for two strain backgrounds: the pAzF-dependent strain, rEc.γ.dC.46'.ΔtY, and its non-contained ancestor, rEc.γ. Growth of rEc.γ.dC.46'.ΔtY was separately assessed in permissive (+sAA/+L-arabinose) and non-permissive (−sAA/−L-arabinose) media and growth of rEc.γ was assessed in non-permissive media. In all cases, flasks contained carbenicillin to prevent contamination.

Strains were grown in 100 ml of LB media overnight. Cultures were then pelleted and washed twice with the same volume of sterile dH$_2$O. Washed pellets were re-suspended in LB media plus or minus small molecules and this slurry was then added to shake flasks containing 1 l of LB media plus or minus small molecules, at time zero. At this first time point, a 1 ml sample was obtained from each flask, from which the OD$_{600}$ was measured and 50 μl was plated on both permissive (+sAA/+L-arabinose/+carbenicillin) and non-permissive (−sAA/−L-arabinose/+carbenicillin) solid LB media, in three technical replicates. Average c.f.u. counts are reported and error bars represent ±s.d. In all cases, c.f.u. on solid media were counted after 24 h of incubation at 34° C. OD$_{600\ nm}$ readings and c.f.u. counts were collected in this manner for all subsequent time points for the following 20 days.

After 20 days of growth in liquid media, the two 1-l cultures of rEc.γ.dC.46'.ΔtY grown in non-permissive and permissive media were interrogated for the presence of a single escape mutant. The entire culture was pelleted, re-suspended in 7 ml of 1×PBS, and plated across 30 large non-permissive solid media plates that were subsequently monitored for c.f.u. formation over the following 7-day period. All reported results repeated at least three times in independent experiments.

Results

Figure 3E:
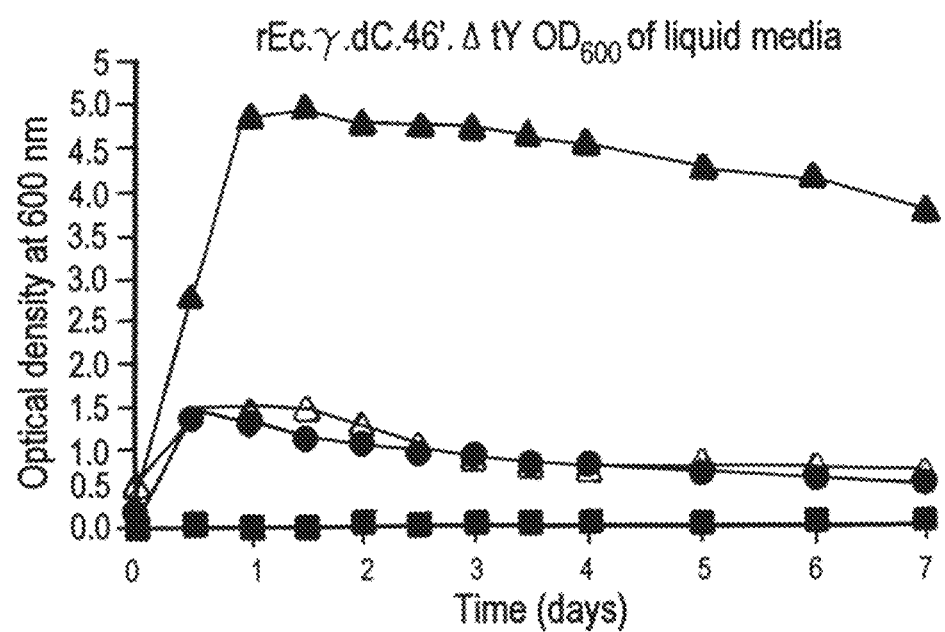
FIG. 3E is a line graph showing temporal monitoring of permissive (P, blue) and non-permissive (NP, red) cultures inoculated with ~$10^9$, $10^{10}$ or $10^{11}$ cells of rEc.γ.dC.46'.ΔtY by $OD_{600}$.
Figure 3F:
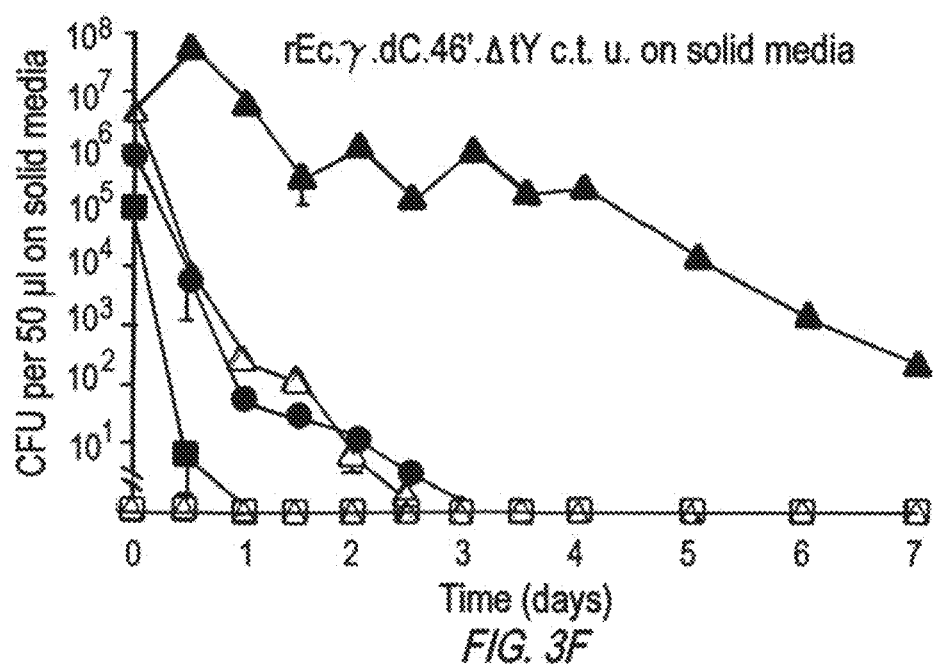
FIG. 3F is a line graph showing the associated c.f.u. from 3E as sampled on permissive (solid lines) or non-permissive (dashed lines) solid media; c.f.u. were never observed on non-permissive solid media; hollow data points indicate no observed c.f.u. For all plots, average values of three technical replicates are plotted with error bars representing ±s.d. Reported results repeated at least three times in independent experiments.
Figure 4A:
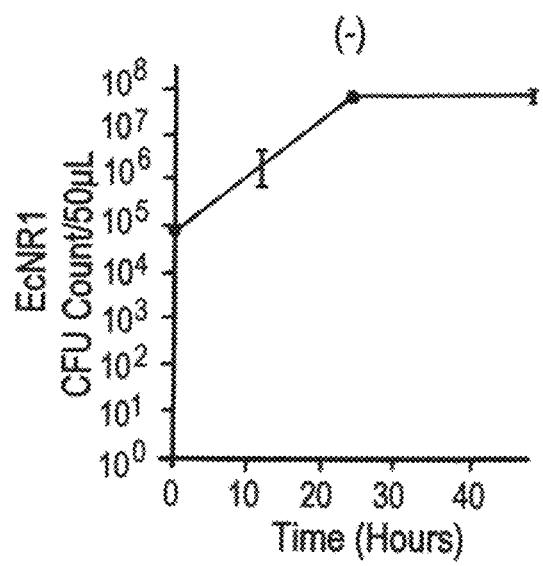
FIGS. 4A-4H is a series of line graphs showing biotin auxotrophy in sheep blood. ~$10^6$ CFUs of the EcNR1 ancestor (4A, 4C, 4E, 4G) or the EcR1ribR2nad+ riboregulated strain (4B, 4D, 4F, 4H) were inoculated into 3 mL defibrinated Sheep Blood (BD cat. 212389) alone (4A, 4B) or supplemented with biotin (4C, 4D), inducers (aTc, IPTG, arabinose) (4E, 4F), or biotin and induces (4G, 4H). Graph show CFU/50 μL sample removed every 12 hours for 48 hours for CFU counts.
Figure 4C:
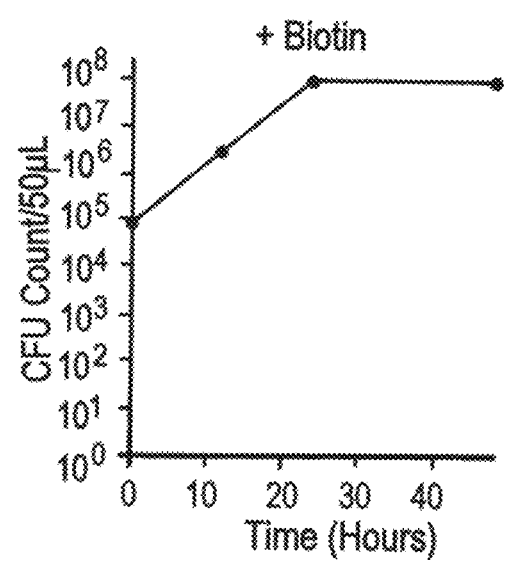
Figure 4B:
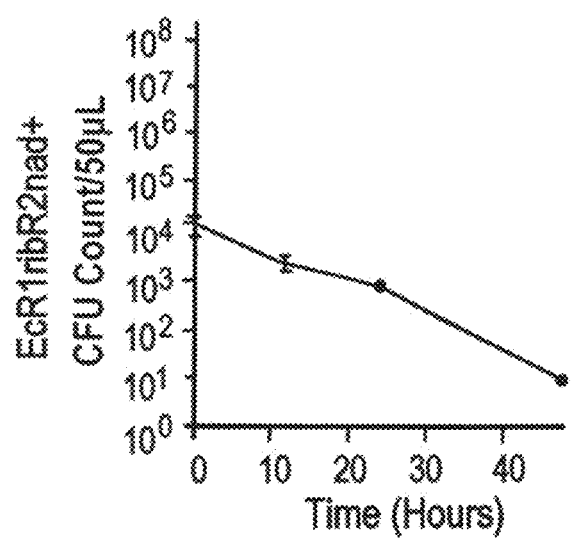
Figure 4D:
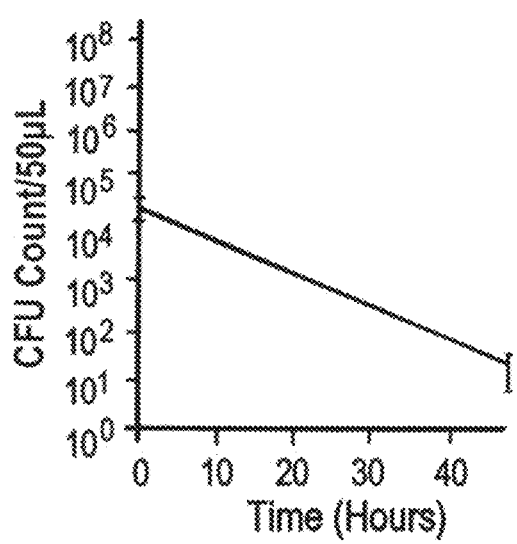
Figure 4E:
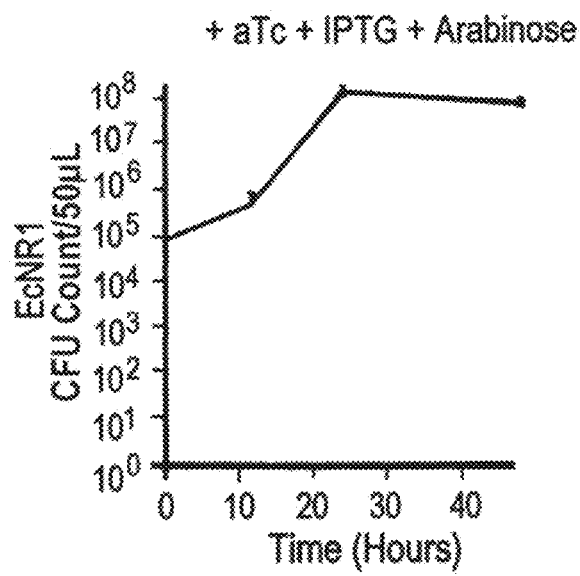
Figure 4G:
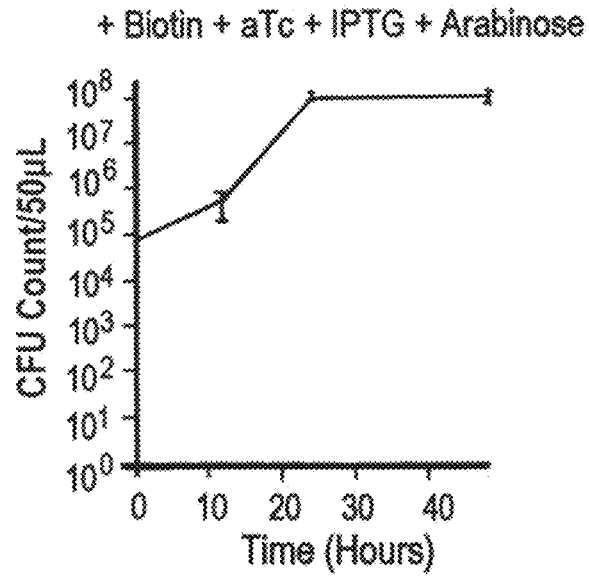
Figure 4F:
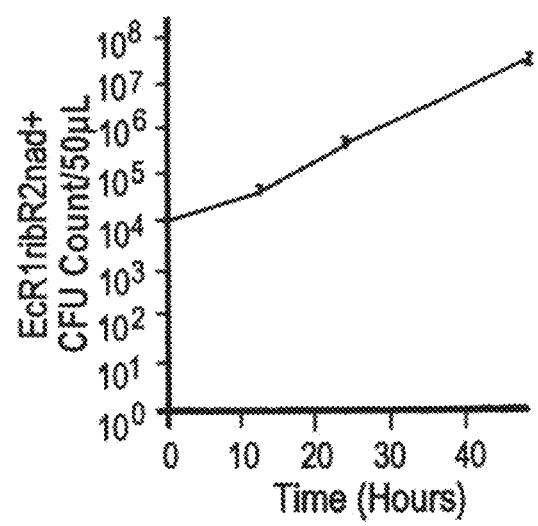
Figure 4H:
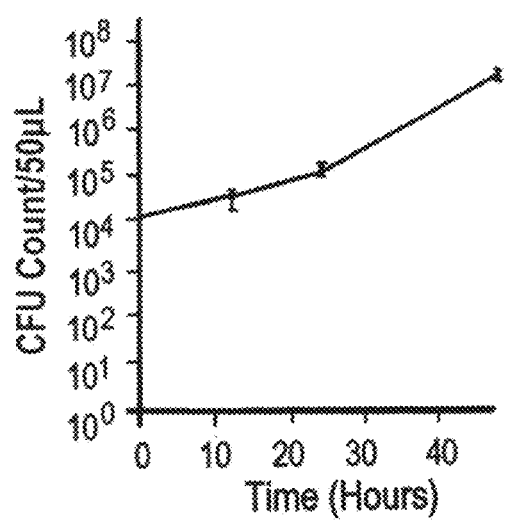

To interrogate the long-term stability of synthetic auxotrophs where escape mutant formation is not limited by a colony growth environment, temporal monitoring of rEc.γ.dC.46'.ΔtY was performed on large cell populations in liquid culture (1 litre of Luria-Bertani (LB) media) for 7 days with frequent OD$_{600}$ measurements to track cell growth (FIG. 3E). Inoculation of ~$10^{11}$ cells in permissive media led to a confluent culture of contained cells within 24 h. Inoculation of ~$10^9$, ~$10^{10}$ and ~$10^{11}$ cells into non-permissive media revealed transient growth, which is believed to be due to residual pAzF and L-arabinose from large inoculums, followed by a sustained decrease in cell density and growth termination. Cell survival and escape from liquid cultures was monitored by quantifying c.f.u. on permissive and non-permissive solid media, respectively (FIG. 3F). Plating on permissive solid media revealed a drop in c.f.u. to below the limit of detection within 1 day from the non-permissive flask inoculated with ~$10^9$ cells and 3 days from non-permissive flasks inoculated with ~$10^{10}$ or ~$10^{11}$ cells (FIG. 3F). No c.f.u. were observed from any culture plated on non-permissive solid media. To confirm the absence of a single escape mutant following an extended 20-day growth period, the non-permissive and permissive cultures inoculated with ~$10^{11}$ cells were plated across 30 non-permissive plates. Escape mutants were not observed and escape frequencies remained below the detection limit after 7 days, which is comparable to the solid media results. These results demonstrate that rEc.γ.dC.46'.ΔtY depends on pAzF, maintains long-term stability of biocontainment in permissive liquid media and exhibits termination of growth in non-permissive media.

To further investigate the dependency on sAAs, liquid growth profiles were collected for synthetic auxotrophs across sAA and L-arabinose concentration gradients. Growth of rEc.γ.dC.46'.ΔtY was not observed below 0.002% L-arabinose and 0.5 mM pAzF. Growth increased in a dose-dependent manner with increasing concentrations of pAzF and L-arabinose, where 5 mM pAzF and 0.2% L-arabinose was optimal for fitness (that is, maximum OD$_{600}$ and minimum doubling time). In an equivalent experiment with rEc.β.dC.12'.ΔtY, 1 mM pIF and 0.2% L-arabinose was optimal for fitness. Since growth was not observed in media lacking either L-arabinose or the sAA, these data further support the dependency of synthetic auxotrophs on sAAs.

Example 4: Synthetic Auxotrophs Resist Rescue by Cross-Feeding

Materials and Methods
Environmental Challenges

Wild-type *E. coli* K-12 substr. MG1655, and additional *E. coli* strains EcNR212, rEc.γ.dC.46' (a pAzF auxotroph), and rEc.γ (non-contained ancestor to rEc.γ.dC.46') were grown to mid-log phase in 1 ml of LB media supplemented with small molecules, where necessary. Cultures were washed three times with sterile dH$_2$O and re-suspended in 1 ml 1×PBS. A total of 16, two-fold serial dilutions were made and spotted on the following solid media types: (1) LB, (2) EZ rich defined (Neidhardt, et al., *J. Bacteriol,* 119:736-747 (1974)) (with modifications by Teknova) and containing 100× carbon source (40% glycerol), (3) blood agar (Teknova), or (4) soil extract agar (HiMedia). Prior to spotting, plates were topically supplemented with pAzF, L-arabinose, and/or biotin, and dried for at least 1 h. Spotted plates were incubated for 1 day at 34° C. and photographed in a Gel Doc XR+ running ImageLab v4.0.1 (BioRad).

Results

To determine whether a synthetic auxotroph could be rescued by metabolic cross-feeding, the viability of strains was evaluated on diverse media types. Wild-type MG1655 *Escherichia coli*, a biotin auxotroph (EcNR212), a non-contained GRO (rEc.γ), and the pAzF synthetic auxotroph (rEc.γ.dC.46') were grown on solid media containing both pAzF/L-arabinose and biotin, either pAzF/L-arabinose or biotin, and on plates lacking small molecules. Despite biotin auxotrophy, growth of EcNR2 on rich defined media without biotin was rescued in close proximity to wild-type *E. coli*, indicating cross-feeding of essential metabolites. Blood agar and soil extracts without biotin or pAzF/L-arabinose supplementation supported growth of all strains except the synthetic auxotroph, which only grew on media supplemented with pAzF and L-arabinose. These data show that synthetic auxotrophies could be a more viable containment strategy for clinical (for example, blood) and environmental (for example, soil) settings, where metabolic auxotrophies can be overcome by proximal, metabolically competent strains.

Synthetic auxotrophs utilize unnatural biochemical building blocks necessary for essential proteins with activities that cannot be complemented by naturally occurring small molecules. Studies show that genomic recoding interferes with HGT from viruses (Lajoie, et al, *Science,* 342:357-360 (2013)), and have now extended orthogonal barriers by engineering two synthetic auxotrophs using two unique sAAs that exhibit escape frequencies below detection limit (<6.3×10$^{-12}$). These synthetic auxotrophs possess three essential TAGs at loci dispersed throughout the genome (0.84, 0.86 and 2.9 megabases apart), thereby limiting the likelihood that a single HGT event could compromise containment. These orthogonal barriers can be expanded further by incorporation of additional TAG sense codons across more than three essential genes, but will probably require concurrent advances in OTS performance to maintain fitness and viability (for example, enhanced activity and specificity of aaRS:tRNA pairs (O'Donoghue, et al., *Nature Chem. Biol,* 9:594-598 (2013)).

The modular approach to biocontainment limits growth to synthetic environments containing unnatural biochemical building blocks with diverse chemistries. Further genome recoding efforts (Lajoie, et al, *Science,* 342:357-360 (2013); Isaacs, et al, *Science,* 333:348-353 (2011); Lajoie, et al, *Science,* 342:361-363 (2013)) will provide auxotrophies for multiple sAAs that could be enhanced by other synthetic components including unnatural nucleotides and extended genetic alphabets (Bain, et al, *Nature,* 356:537-539 (1992); Pinheiro, et al, *Science,* 336:341-344 (2012); Hammerling, et al, *Nature Chem. Biol,* 10:178-180 (2014)). Orthogonal biological systems employing multi-level containment mechanisms are uniquely suited to provide safe GMOs for clinical, environmental and industrial applications (Way, J. C., Collins, et al., *Cell,* 157:151-161 (2014)).

Despite the breadth of genomic diversity found in nature, all species utilize the same biochemical foundation to sustain life. The semantic architecture of the GRO employs orthogonal translational components, establishing the basis for a synthetic molecular language that relieves limitations on natural biological functions by depending on the incorporation of sAAs with exotic chemistries. This work sets the stage for future experiments to probe the optimality of the natural genetic code and to explore the plasticity of proteins and whole organisms capable of sampling new evolutionary landscapes.

Example 5: Some Metabolic Auxotrophs Fail in Rich and Diverse Media

First, bioA and bioB genes were replaced with the bla resistance marker to create a safeguard layer based on biotin auxotrophy, which mimics prior efforts based on metabolic auxotrophy. In LB, this strain grew with a 56 min DT, equal in fitness to its *E. coli* MG1655 ancestor (Table 14, below). In Rich Defined Media, this strain was dependent on biotin supplementation for viability. However, biotin supplementation was not required in blood-based media (FIGS. 4A-4H) and soil-based media, showing that environmental cross-feeding can compromise biosafety strategies based on auxotrophy alone. For example, FIGS. 4A-4H show the EcNR1 ancestor, though biotin auxotrophic, was able to proliferate in the blood without biotin supplementation. The riboregulated strain also did not require biotin supplementation, but was reliant on inducer supplementation for viability. In another experiment, cultures of wild-type MG1655, the EcNR1 biotin-auxotrophic ancestor, and the EcR1ribR2nad+ riboregulated strain were grown to OD 0.8. A 5-fold dilution series was made for each of the strains. With a frogger tool, this series was stamped onto various solid media—LB agar, EZ Rich Defined Media agar (Teknova), Soil Extract agar (Himedia cat. M455), Blood agar (Teknova), and Chocolate agar (Teknova)—and incubated overnight at 34° C. The media was supplemented with biotin, inducers (aTc, IPTG, arabinose), both, or neither. Biotin-auxotrophic strains required biotin supplementation only in the defined rich media. Riboregulated strains required inducer supplementation in all media.

These results lead to the development of synthetic auxotrophs whose missing essential gene functions cannot be complemented by metabolic cross-feeding, rather only by exogenous supply of synthetic small molecules. An exemplary strategy, discussed in more detail below, is outlined in FIG. 5A.

Example 6: Riboregulated Essential Gene Strains are Dependent on Synthetic Small Molecules Materials and Methods Plasmids—Cloning and DNA Synthesis and Assembly Basic molecular biology techniques were used in plasmid construction. Riboregulated essential gene plasmids (Isaacs, et al, *Nat. Biotechnol,* 22:841-847 (2004)) were constructed by amplifying genes from *Escherichia coli* using primers to add KpnI and HindIII restriction sites. Those fragments were cloned between KpnI and HindIII sites in the pZE21Y12a12C vector. For all cloning, insert amplicons were purified using spin columns (QiaGen), digested with restriction endonucleases (NEB), agarose gel purified, extracted (QiaGen), ligated (Quick Ligase, NEB), then transformed by electroporation with parameters 1800 V; 25-µF capacitance; 200-Ω resistance; in 1-mm cuvettes (Bio-Rad). The pBAD21G plasmid was created by cloning the paraBAD promoter amplified from pBAD-HisB (Invitrogen) between XhoI and KpnI in plasmid pZE21G (Isaacs, et al, *Nat. Biotechnol,* 22:841-847 (2004)). Toxin gene plasmids were created by cloning into KpnI- and HindIII-cut pBAD21G or by Gibson Assembly (NEB) into the same vector. For Gibson Assembly (Gibson, et al, *Nat. Methods,* 6:343-345 (2009)), the cloning vector was linearized by amplification using primers annealing near KpnI and HindIII sites. Toxin inserts were amplified using primers that added homologies to the vector termini; these homology arms were designed to anneal to the vector with a Tm=60° C. (~25 bp). Toxin genes were either amplified from the *E. coli* chromosome or were synthesized in codon-optimized form (gBlocks, IDT)

Synthesized Genes:

EcoRI Nuclease Pt 1:
(SEQ ID NO: 27)
ATGAGCAACAAGAAGCAGAGCAACCGCCTGACCGAGCAGCATAAGCTGAG
CCAGGGCGTGATTGGCATCTTCGGCGATTACGCCAAAGCACACGACCTGG
CAGTGGGTGAGGTGAGTAAGCTGGTGAAGAAGGCCCTGAGTAACGAGTAC
CCGCAGCTGAGCTTCCGTTATCGCGACAGCATCAAAAAAACCGAGATCAA
CGAGGCCCTGAAGAAGATCGATCCGGACCTGGGCGGCACCCTGTTCGTGA
GCAACAGTAGCATCAAGCCGGACGGCGGCATCGTTGAAGTGAAGGACGAC
TACGGTGAGTGGCGTGTGGTGTTAGTGGCCGAGGCCAAGCATCAGGGCAA
GGATATCATCAACATCCGCAACGGCCTGCTGGTTGGCAAACGTGGTGACC
AAGATCTGATGGCAGCCGGCAACGCCATCGAGCGCAGCCACAAGAATATT
AGCGAGATCGCAAATTTCATGCTGAGCGAGAGCCACTTCCCGTATGTGC
T.

EcoRI Nuclease Pt 2:
(SEQ ID NO: 28)
CCAAGCATCAGGGCAAGGATATCATCAACATCCGCAACGGCCTGCTGGTT
GGCAAACGTGGTGACCAAGATCTGATGGCAGCCGGCAACGCCATCGAGCG
CAGCCACAAGAATATTAGCGAGATCGCAAATTTCATGCTGAGCGAGAGCC
ACTTCCCGTATGTGCTGTTCTTAGAGGGTAGTAACTTCCTGACCGAGAAC
ATTAGCATCACCCGTCCTGATGGCGCGTGGTGAACCTGGAATATAACAG
CGGCATCCTGAATCGCCTGGACCGCCTGACAGCCGCCAACTACGGCATGC
CGATCAACAGTAATCTGTGTATTAACAAGTTCGTTAATCACAAAGACAAG
AGCATCATGCTGCAGGCCGCCAGCATCTACACCCAAGGCGACGGCCGCGA
GTGGGATAGTAAAATCATGTTCGAGATCATGTTTGACATTAGCACAACCA
GCCTGCGCGTGTTAGGCCGTGATCTGTTCGAGCAGCTGACAAGCAAGTA
A.

B anthracis Ames pemK:
(SEQ ID NO: 29)
ATGATTGTAAAACGCGGCGACGTGTATTTTGCAGACCTTTCCCCAGTTGT
TGGTTCTGAGCAAGGAGGTGTTCGTCCGGTTCTTGTCATTCAAAATGACA
TCGGAAATCGTTTTAGTCCAACGGTGATTGTAGCGGCTATTACTGCACAG
ATTCAAAAAGCGAAATTACCCACTCATGTGGAAATTGATGCGAAAAAGTA
CGGTTTTGAGAGAGATTCTGTTATTTTACTTGAGCAGATTCGAACAATCG -continued ATAAGCAGCGCTTAACGGACAAAATCACTCACTTAGATGAAGTGATGATG
ATTCGTGTAGATGAAGCGCTACAAATCAGTTTAGGACTAATCGATTTCTA
G.

*E coli* O111:H8 pndA
(SEQ ID NO: 30)
ATGCCACAACGAACGTTTTTAATGATGTTAATCGTCGTCTGTGTGACGAT
ACTGTGTTTTGTCTGGATGGTGAGGGATTCGCTTTGCGGATTCCGTGTCG
AGCAGGGAAACACAGTGCTTGTGGCAACGTTAGCCTACGAAGTTAAACGT
TAA.

*E coli* pC15 hok
(SEQ ID NO: 31)
ATGAAACTACCACGAAGTTCCCTTGTCTGGTGTGTGTTGATCGTGTGTCT
CACACTGTTGATATTCACTTATCTGACACGAAAATCGCTGTGCGAGATTC
GTTACAGAGACGGACACAGGGAGGTGGCGGCTTTCATGGCTTACGAATCC
GGTAAGTAG.

*P fluorescens* pasB
(SEQ ID NO: 32)
ATGGCTTGGCGGATTGAATTTGACCGCGCTGCAGAGCGCGAGCTGGGCAA
ACTCGACCCGCAAATCGCTAAACGAATCCTGTTGTTTCTGCATGAGCGGG
TATCAAATCTGGATGATCCGCGCAGCATTGGCGAAGCATTAAAAGGCTCA
CGTTTAGGGGATTTTTGGAAGTATCGGGTAGGCGACTACCGCCTTATCAG
CAGCATCGAGGACGGCGCGTTGCGCATCCTGGTGATTAAGATTGGGAACC
GGCGAGAGGTGTACCGCTAG.

*S enterica* vapC
(SEQ ID NO: 33)
ATGCTGAAATTCATGCTTGATACCAATACCTGTATTTTCACCATCAAAAA
TAAGCCCGAACACATCAGAGAACGCTTCAACCTCAATACATCCCGAATGT
GTATCAGCTCCATCACCTTAATGGAGCTGATTTACGGTGCTGAAAAAAGC
CTGGCGCCGGAGCGTAATCTTGCCGTCGTGGAGGGATTTATCTCCCGCCT
TGAGGTTTTGGATTACGATACACAGGCAGCGATACATACCGGTCAAATCC
GTGCCGAACTGGCCCGCAAGGGAACACCTGTCGGGCCTTATGACCAGATG
ATTGCTGGCCATGCCGGTAGCCGCGGACTGGTCGTCGTCACAAACAATCT
CCGCGAATTTGAACGCATTCCGGGTATCCGAATCGAAGACTGGTGCTAA.

*Streptavidin*
(SEQ ID NO: 34)
ATGGGCATCACCGGCACCTGGTACAACCAGCTCGGCTCGACCTTCATCGT
GACCGCGGGCGCCGACGGCGCCCTGACCGGAACCTACGAGTCGGCCGTCG
GCAACGCCGAGAGCCGCTACGTCCTGACCGGTCGTTACGACAGCGCCCCG
GCCACCGACGGCAGCGGCACCGCCCTCGGTTGGACGGTGGCCTGGAAGAA
TAACTACCGCAACGCCCACTCCGCGACCACGTGGAGCGGCCAGTACGTCG
GCGGCGCCGAGGCGAGGATCAACACCCAGTGGCTGCTGACCTCCGGCACC
ACCGAGGCCAACGCCGACAAGTCCACGGACGACGGCGACGACACCTTCAC
CAAGGTGTAG.

Supplemental repressor plasmids were made by Gibson Assembly (Gibson, et al, *Nat. Methods,* 6:343-345 (2009)) into the pBAD21G vector using lacI or tetR genes amplified from *E. coli* and using synonymously recoded fragments obtained from IDT. Polymerase chain reaction (PCR) reactions were carried out using Hot-Start HiFi Mastermix enzyme (Kapa Biosystems) on a C-1000 thermal cycler (Bio-Rad). The following amplification protocol was used: 3 min at 95° C. initial denaturation; 30 cycles of 20 s at 98° C., 15 s at 58° C., 30 s/kb at 72° C.; then 3 min at 72° C. final extension. Colonies were screened by PCR then confirmed by sequencing.

Genome Integration by dsDNA Recombination

Double-stranded DNA recombination was performed using λ-red recombineering as previously described (Sharan, et al, *Nat. Protoc*, 4:206-223 (2009)). For chromosomal integration of ribo-essential switches and supplemental repressors, dsDNA containing the cassette of interest was amplified from purified plasmids using primers that added 50-bp genome homology arms at both ends, targeting specific genomic loci for integration. These fragments were transformed into a recombination-competent strain and recombinants were isolated by TolC negative selection (see below). Recombination was verified by Sanger sequencing the insertion loci. Essential gene knockout was accomplished by replacing essential gene native sites with the tolC gene and selecting for sodium dodecyl sulphate (SDS) resistance. dsDNA cassettes for native site knockout were prepared with 50-bp homologies targeted to the ends of the gene to be replaced.

Strains and Reagents

All plasmids were transformed into Mach1 (NEB; F' proA+B+ lacIq ΔlacZM15/fhuA2 Δ(lac-proAB) glnV galK16 galE15 R(zgb-210::Tn10)TetS endA1 thi-1 Δ(hsdS-mcrB)5) or DH5a (Invitrogen; F-φ80lacZΔM15 Δ(lacZYA-argF) U169 recA1 endA1 hsdR17 (rk−, mk+) phoA supE44 λ-thi-1 gyrA96 relA1) cells. All dsDNA recombination steps were carried out in EcNR1 [MG1655 Δ(ybhB-bioAB):: [λcI857 N(cro-ea59)::tetR-bla]]. All strains were grown in low salt LB-Lennox media (10-g tryptone, 5-g yeast extract, 5-g NaCl in 1-l dH2O) or for auxotrophy experiments in EZ Rich Defined Medium (Teknova) with 0.4% glycerol. Plasmids were maintained using kanamycin at 30-μg/ml final concentration. Recombination-competent strains were grown with 50-μg/ml carbenicillin final concentration. Riboregulators were induced with anhydrotetracycline (aTc), isopropyl thiogalactoside (IPTG) or L-arabinose at final concentrations of 20 ng/ml, 0.1 mM or 0.2%, respectively. The tolC gene was selected by growth in 0.005% SDS. Oligonucleotides were obtained from IDT (Coralville, Iowa, USA) or from WM Keck Oligo Synthesis Resource (Yale University, New Haven, Conn., USA).

Chromosomal Modification by ssDNA Recombination

To introduce the lacIq1 allele at the lacI locus in safeguard strains, ssDNA recombination was used (Ellis, et al, *Proc. Natl. Acad. Sci. U.S.A.*, 98:6742-6746 (2001); Wang, et al, *Nature*, 460:894-898 (2009)). Briefly, a 5'-phosphorothioated 90-bp oligonucleotide targeted to the lagging strand of the replication fork at the lacI locus was designed. The center of this oligonucleotide specified the modification to be made (multibase deletion).

Negative Selection

Counter selection for markerless replacement of the tolC gene was performed as described previously (DeVito, *Nucleic Acids Res*, 36:e4 (2008)). Briefly, strains were transformed with dsDNAs designed to replace tolC with a desired cassette. After dsDNA recombination and recovery, cultures were incubated for 10 h with purified colicin E1 protein. Counter-selected cultures were then plated on solid media and single colonies were screened for the expected recombination by PCR or by growth in SDS to confirm loss of resistance.

Fitness Assays

Multiplex growth assays were conducted in a Biotek spectrophotometric 96-well plate reader (Synergy HT) programmed to measure optical density at 600 nm every 10 min over ≥12 h. Each well was seeded with 150 μl of LB-Lennox media containing a 1:100 dilution of late log phase cells. To compute the maximum doubling time (DT), a Matlab script was used to fit the time-course OD data to a smoothed spline, and to find the growth curve inflection point of that spline.

Escape Frequency Assay

Safeguarded strains were grown in permissive conditions to late log, then washed three times with distilled water and diluted over a 10-fold series down to $10^7$-fold. Fifty microliter samples of each dilution were plated on both permissive (+inducer) and non-permissive (−inducer) solid media. Plates were grown for 24 h before colonies were counted. Escape frequencies are reported as triplicate results of (colonies on non-permissive plate×dilution)/(colonies on permissive plate×dilution) plus or minus standard deviation.

Competitive Co-Culture

The non-safeguard competitor strain was made by introduction of a marker allele (premature stop codon in lacZ) in the EcNR1 ancestor strain. A ribo-essential ribA safeguard strain was marked by integration of a kanamycin resistance cassette. The competitor strain and the safeguard strain were grown separately in permissive conditions to late log, then washed three times and resuspended in phosphate buffered saline. Washed cultures were mixed 1:1 by volume, and the mixture was diluted 1:100 into 5 ml of permissive (aTc, IPTG, carbenicillin) or non-permissive (carbenicillin only) media. Every 12 h for 60 h, each co-culture (permissive or non-permissive) was diluted 1:100 into 5 ml of fresh media. For the permissive co-culture (grown +aTc and +IPTG), at each time step, a 10-fold dilution series was plated on differential permissive media (aTc, IPTG, XGAL, carbenicillin) and the blue/total colony quotient was calculated. This quotient was reported as EcR1rib prevalence. For the non-permissive co-culture (grown −aTc and −IPTG), at each time step, a 10-fold dilution series was plated on both non-permissive plates (kanamycin only) and on permissive plates (aTc, IPTG, carbenicillin) Since only EcR1rib escape mutants grow on kanamycin, whereas carbenicillin +aTc +IPTG plates support growth of all cells, [non-permissive Colony Forming Units (CFU)]/[permissive CFU] was reported as the escape mutant frequency.

Using the relative abundances of wild type and contained populations as determined by blue/white colony counts, the mean DT for each population was determined by the following equation:

$$(A_i)(2^{T_e/T_d}) = (A_f) \times G.$$

In this equation $T_d$ represents mean DT, $T_e$ represents elapsed time (720 min per dilution step), $A_i$ represents relative abundance at the initial time point, $A_f$ the relative abundance at the final time point and G represents total growth (using plate-based CFU counts, G was found to be ~100-fold growth at each step). Solving this equation for $T_d$ yields $$T_d = \frac{T_e}{\log_2\left(\frac{G \times A_f}{A_i}\right)}.$$

$T_d$ is computed for the contained (EcR1rib) and competitor subpopulations at each dilution step. Averaging these values allowed us to calculate relative fitness of the contained strain with respect to its ancestor (Table 11).

TABLE 11

Calculations for relative fitness of contained and ancestral strains in competitive co-culture.

| Dilution Step | Relative Abundance of EcR1rib | Fraction Retained During Step | Avg Doubling Time EcR1rib (mins) | Avg Doubling Time Competitor (mins) |
|---|---|---|---|---|
| 1 | 0.430 | 0.791 | 114 | 105 |
| 2 | 0.340 | 0.853 | 112 | 107 |
| 3 | 0.290 | 0.828 | 113 | 107 |
| 4 | 0.240 | 0.975 | 109 | 108 |
| 5 | 0.234 | 0.530 | 126 | 105 |
| 6 | 0.124 | N/A | N/A | N/A |
|  |  | Average: | 115 | 106 |

Whole Genome Sequencing

Sample selection: For each switch class (EcR1rib, EcR1rib+, EcR2nad, EcR1ribR2nad+ and EcTeco), a contained clone and three escaping clones were sequenced. Additionally, the ancestral MG1655, EcNR1 and EcNR1.ΔTolC genomes were sequenced.

gDNA prep: Two milliliters of confluent cell culture in LB-Lennox broth were processed with a Qiagen DNeasy Blood and Tissue (cat: 69504) to extract genomic DNA. gDNA quality was assessed on a spectrophotometer (assay for A260/280 ratio between 1.8 and 2.0) and by gel electrophoresis (assay for a tight smear at ~50 kB).

Sequencing: 2.5 µg of gDNA, eluted in 50-µl TE pH 8.0, was sent to the Yale Center Genome Analysis for library prep. One to two micrograms of gDNA were sheared to an expected size of 500 bases with Covaris E210 in a covaris microtube (Duty cycle: 5%; Intensity: 3; Cycles per burst: 200; Time: 80 s). Post-shearing cleanup was done with SPRI magnetic beads (Beckman Coulter). QC was then performed on a DNA 1000 bioanalyzer chip. 'With Bead' fragment end repair was performed with End Repair enzyme at 20° C. for 30 min and purified with a 20% PEG, 2.5-M NaCl solution. 'With bead' A-base addition was performed with A-Tailing enzyme at 30° C. for 30 min and purified with a 20% PEG 2.5-M NaCl solution. Samples were barcoded with an adapter ligation mix (5-µl 5× buffer; 15-µl Multiplexing Adapter; 5-µl DNA ligase; 5-µl nuclease free water). Ligation was purified with a 20% PEG, 2.5-M NaCl solution. Samples were PCR enriched (26-µl DNA; 30-µl KAPA HiFi Mastermix; 2-µl 25-µM PCR Primer MP1.0; 2-µl, 25-µM barcode-specific primer). Samples were loaded onto a lane of an Illumina HiSeq 2000 for 76-base paired-end reads, providing an average genome coverage of 132X.

Data Analysis

Raw FASTA reads were sorted by barcode into individual forward and reverse sample files. After this processing, reads were exactly 76 bases long. Paired-end reads were aligned to an MG1655 reference sequence (U00096) with Bowtie2. This reference sequence had been indexed with Bowtie2-build. The aligned SAM file was converted to a BAM file with Samtools view. The BAM file was sorted and then indexed with Samtools 0.1.18. Single-nucleotide polymorphisms (SNPs) and small insertions/deletions were called from the sorted BAM file with Freebayes, using default parameters. The resulting calls were initially filtered for those with a root mean square Phred Quality Score of >20. For each sample, SNPs that were also present on the EcNR1 ancestor sequence were filtered out. After these filters, strain-specific mutations were identified. Given the manageable quantity of SNPs, these were then visually vetted using Integrative Genomics Viewer (IGV) to remove false positives. SNPs were only retained if coverage at a site was >10, and if the SNP was represented on >2 plus-strand reads and >2 minus-strand reads.

Results

Figure 5A:
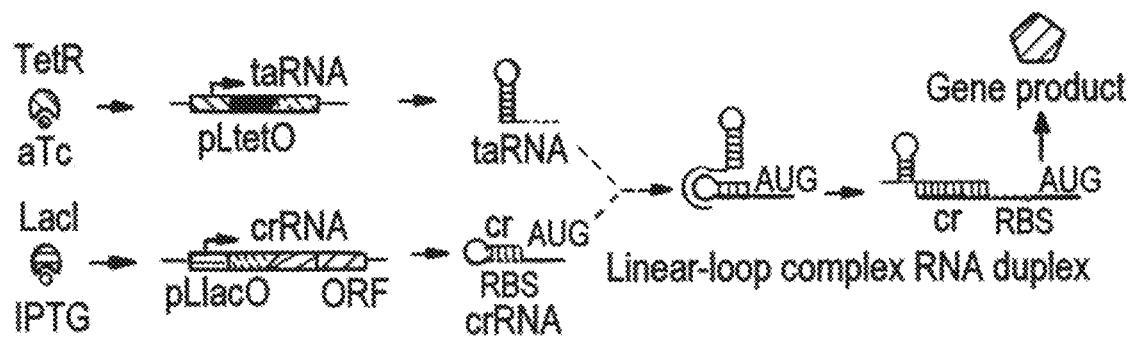
FIG. 5A is a diagram showing a design of multilayered genetic safeguards: riboregulation, engineered addiction, auxotrophy and supplemental repressors. Riboregulation system: pLtetO promoter (Lutz, et al, Nucleic Acids Res, 25:1203-1210 (1997)), repressed by TetR and induced by aTc, drives trans-activating (taRNA); pLlacO promoter, repressed by LacI and induced by IPTG, drives cis-repressed (crRNA) and essential gene. crRNA and taRNA fold through a linear loop intermediate to reveal the crRNA's RBS permitting expression. Supplementary TetR and LacI are constitutively expressed from the genome. Carbenicillin resistance gene (bla) replaces bioAB, resulting in biotin autotrophy. Constitutive EcoRI nuclease enables inducible cell killing in the absence of EcoRI methylase, which is controlled by aTc.
Figure 5A:
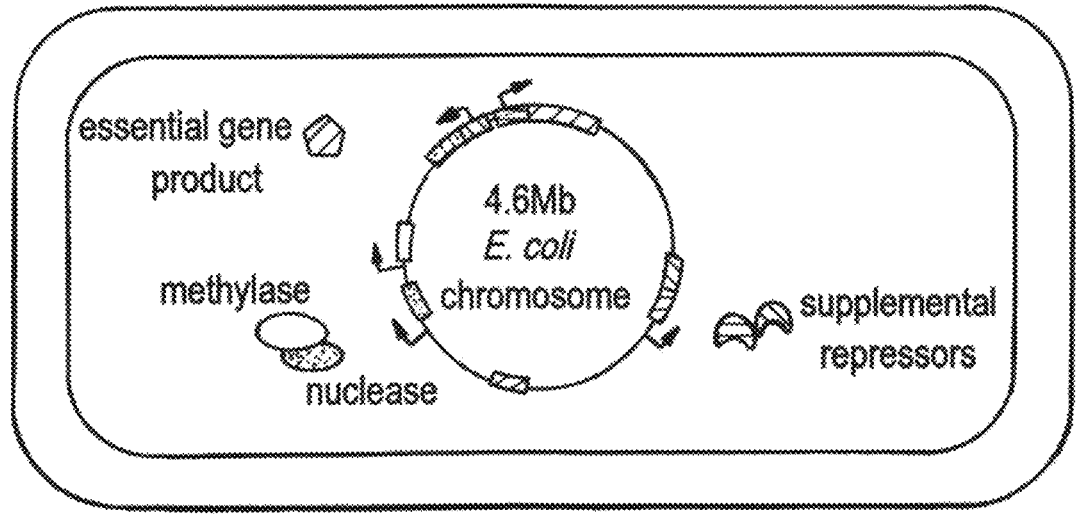
Figure 5A:
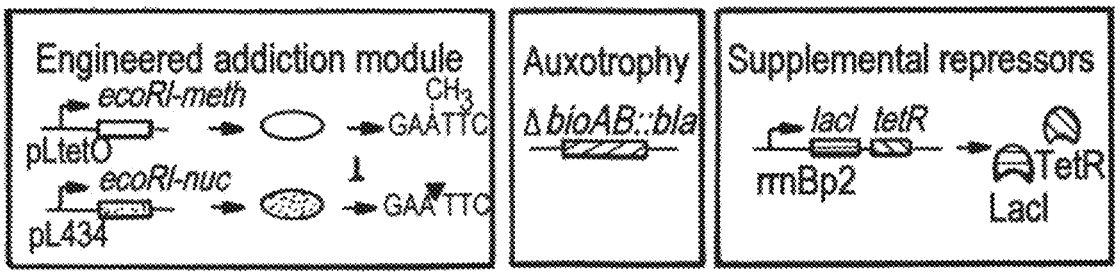
Figure 5H:
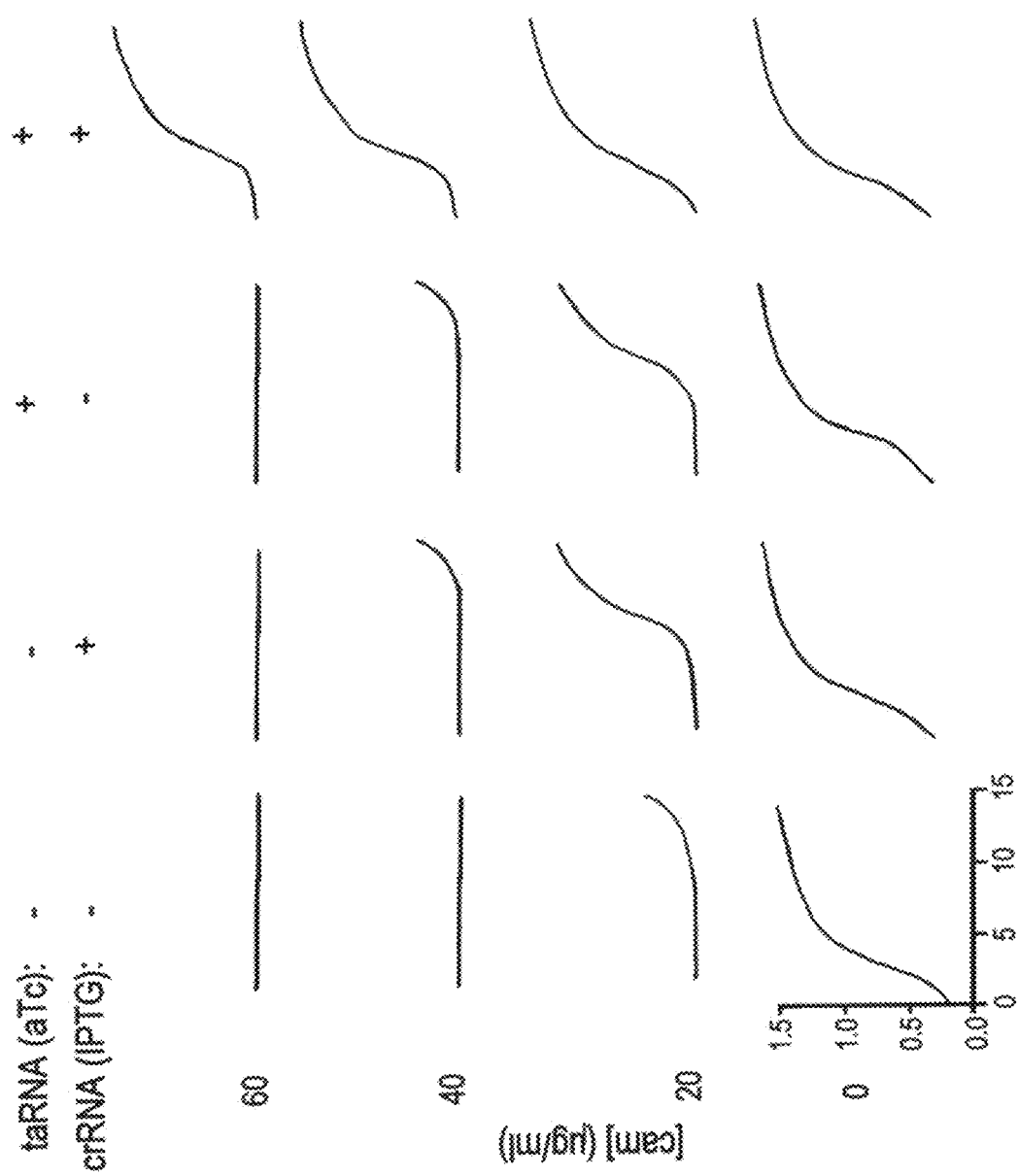
FIG. 5H is a matrix of kinetic growth curves (x-axis of each subplot: 0-15 hours) monitored by optical density at 600 nm (y-axis of each subplot: 0-1.5 OD) of strain carrying episomal riboregulated cat gene in different concentrations of inducer (aTc for taRNA at 20 ng/ml, and IPTG for crRNA at 100 μM—by column) and chloramphenicol (cam μg/ml—by row). Figure SI is a map of an exemplary plasmid (pZE21 Y12 a12C) that can be used to clone essential genes for riboregulated expression. In the mapped example, essential genes can be amplified with KpnI and HindIII overhangs for cloning into those unique restriction sites. Primers designed to amplify riboessential cassettes from the vector can be modified with genome targeting homologies to generate dsDNAs capable of site-specific integration on the E. coli chromosome.
Figure 5I:
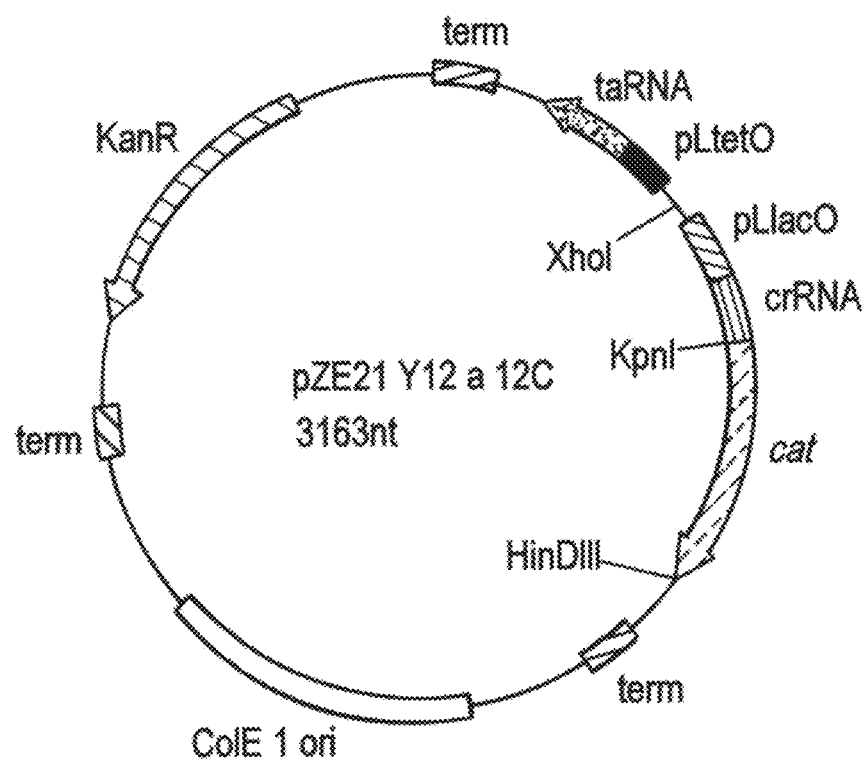
FIGS. 5B-5D are growth curves (OD600 over time) showing cell viability by chloramphenicol (cam) resistance of strains carrying cat gene regulated in different ways, all grown without inducers. Constitutive ("i" pcat (+C), positive control); pLtetO ("ii" pLtetO-cat, non-riboregulated control); riboregulated ("iii" RR-cat); no cat ("iv"Δcat (−C), negative control) at 0 ng/ml cam (5B), 3 ng/ml cam (5C), and 10 ng/ml cam (5D).
FIGS. 5E-5G are a growth curves (OD600 over time) showing cell viability of EcRN1 (wildtype) ("i") and EcEAM (engineered addiction system) ("ii") in the presence of 0 ng/ml aTc (5E) and (5F—blowup of part of 5E), and 100 ng/ml aTc (5G).

To develop a synthetic auxotroph safeguard resistant to environmental cross-feeding, strains were constructed that are dependent on exogenous supply of synthetic small molecules for essential gene expression. To identify a regulatory strategy capable of robust induction and low basal expression (leakage) necessary to control viability, the performance of an engineered promoter (Lutz, et al, Nucleic Acids Res, 25:1203-1210 (1997)) and an engineered riboregulator (Isaacs, et al, Nat. Biotechnol, 22:841-847 (2004); Callura, et al, Proc. Natl. Acad. Sci. U.S.A., 107:15898-15903 (2010)) were compared. Growth of strains was analyzed using constitutive (pcat), inducible (pLtetO-cat) or riboregulated (ribo-cat) control of the antibiotic resistance gene cat in the absence of small molecular inducers. It was determined that coupled transcriptional and translational control of engineered riboregulators confers the stringent expression required to control cell viability (FIG. 5B-5H). FIG. 5H, for example, shows that above a threshold of chloramphenicol concentration, a strain carrying episomal riboregulated cat gene only grows in the presence of both inducers thereby displaying AND logic.

Next, riboregulation was adapted for native essential genes to create synthetic auxotrophs whose viability could be controlled by synthetic small molecule inducers. From ~300 essential genes in E. coli (Baba, et al, Mol. Syst. Biol., 2:2006.0008 (2006)), 13 were selected that span a broad range of cellular processes (Table 12).

TABLE 12

Essential genes selected as targets for construction of ribo-essential strains.

| Essential Gene | Function | Class |
|---|---|---|
| acpP | Acyl carrier protein | Lipid metabolism |
| dxr | Isoprenoid synthesis, MEP pathway |  |
| lpxC | Lipid A biosynthesis |  |
| hemA | Porphyrin biosynthesis | Essential cofactor |
| nadE | Synthesis & salvage of NAD$^+$ | biosynthesis |
| ribA | First step in riboflavin biosynthesis |  |
| folA | Dihydrofolate reductase - THF synthesis |  |
| pyrH | Uridylate kinase | Nucleotide |
| adk | Adenylate kinase | metabolism |
| tmk | Thymidlyate kinase |  |
| gmk | Guanylate kinase |  |
| glnS | Glutaminyl-tRNA synthetase | Translation |
| glmS | Glucosamine biosynthesis | Aminosugar |

The selected genes were generally those whose function could not be complemented by cross-feeding, either due to limited permeability of the gene's small molecule product (e.g. ribA) (Burgess, et al, J. Bacteriol., 188:2752-2760 (2006)), or because the gene's product carries out an essential intracellular enzymatic function (e.g. glnS). Genes were selected based on criteria including: absence of internal KpnI and Hind3 restriction sites; if part of an operon must be at end so as to avoid polar effects during essential gene knockout; difficulty to complement lost function because of cell-intrinsic function of gene product (i.e., glnS) or poor permeability of small molecule product (i.e., ribA). Essential genes for which knockout by a selectable cassette would cause polar effects were excluded.

Essential genes were cloned into a riboregulator vector (ribo-essential cassettes), then ribo-essential cassettes were integrated in the *E. coli* chromosome using λ Red recombination and markerless positive/negative tolC selection. Knockout of essential gene native sites was successful for nine of the 13 cases (ribA, adk, pyrH, glmS, gmk, nadE, acpP, tmk, lpxC); these strains failed to form colonies on non-permissive media (lacking aTc and IPTG), but failed colonies on permissive media (containing aTc and IPTG). In contrast to the biotin auxotroph, non-permissive blood- and soil-based media did not support growth of ribo-essential strains (FIGS. 4A-4H). Importantly, these results show that ribo-essential regulation permits creation of auxotrophic strains that can only be rescued with synthetic small molecules rather than by supply of missing metabolites.

To determine the fitness cost of ribo-essential expression, kinetic growth curves for ancestral and ribo-essential strains were obtained in the presence or absence of inducers. Several strains possessed near wild-type fitness when grown in permissive media: 56 min per doubling compared to 57 for EcR1rib, 57 for EcR1adk and 56 for EcR1glmS (Table 14, below). Other ribo-essential strains (e.g. EcR1gmk, EcR1pyr) displayed a fitness defect compared to the ancestor. The frequency of escape mutants was also examined by plating serial dilutions of ribo-essential strains on permissive and non-permissive solid media. These experiments revealed an escape frequency of ~$10^{-6}$ for all ribo-essential strains (Table 14, below). Together, these experiments validate essential gene riboregulation as a safeguard with low escape frequencies and growth rates on par with wild-type ancestors.

Figure 6A:
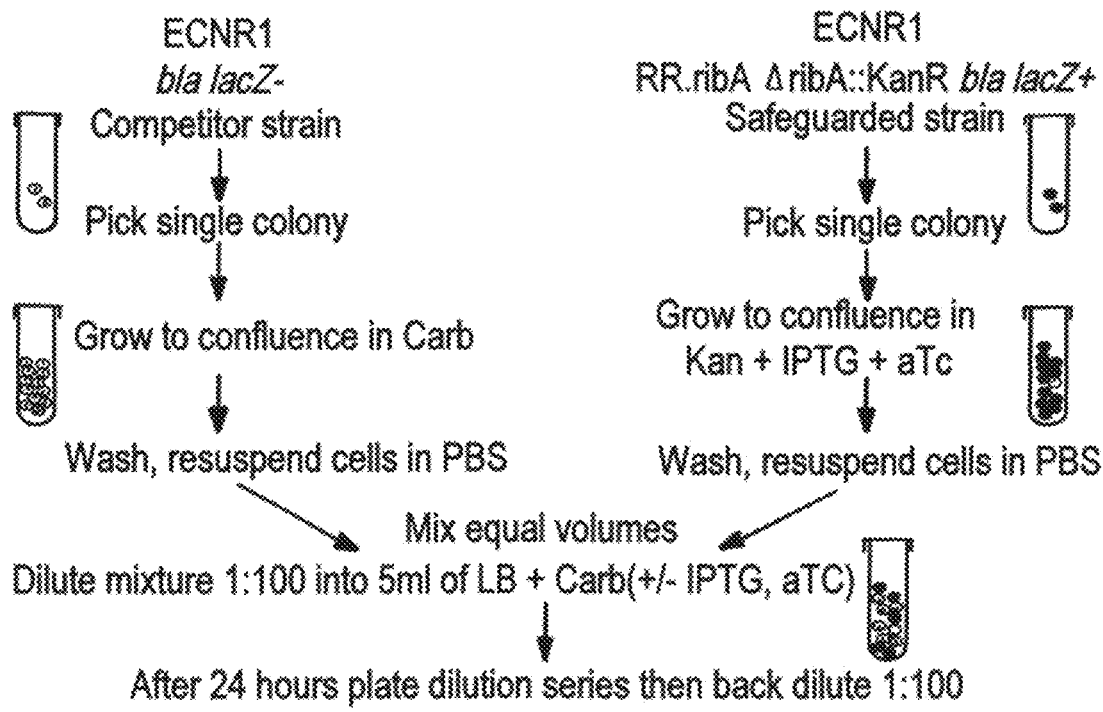
FIG. 6A is a diagram showing the workflow for a competitive co-culture experiment used to determine fitness of safeguarded strain relative to ancestral control. Competitor strain is marked with lacZ− allele (Elena, et al., Nature Reviews, Genetics, 4:457-469 (2003)) giving white colonies on IPTG+ XGAL+ media while safeguard strain has lacZ+ allele giving blue colonies on the same media. This allows the two strains to be discerned on differential permissive media (+IPTG, +aTc, +XGAL). Since only the safeguarded strain carries a kanamycin (kan) resistance gene, only escape mutants can grow on media containing kan without inducers. Both strains carry the carbenicillin (carb) resistance gene bla and can therefore both be grown on media containing carb, IPTG and aTc.
Figure 6A:
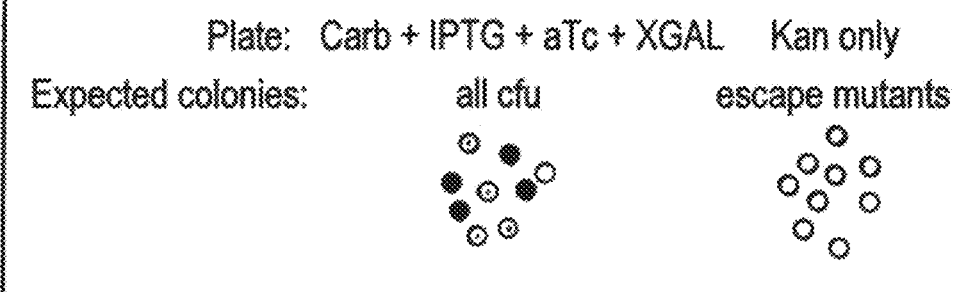
Figure 6A:
Figure 6A:
Figure 6A:
Figure 6A:
Figure 6B:
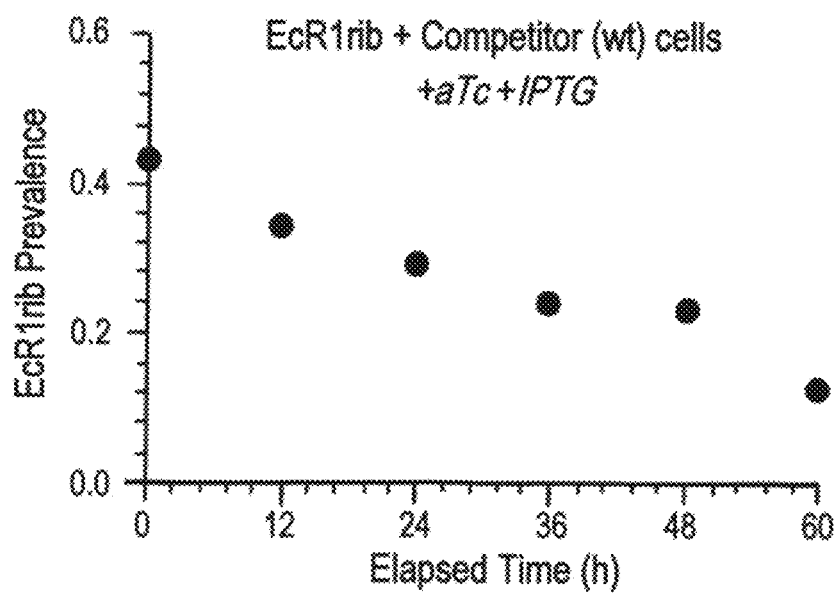
FIGS. 6B and 6C are plots showing riboregulated ribA strain grown in mixed culture with ancestral strain in permissive media (+aTc, +IPTG) (6B), or non-permissive media (−aTc, −IPTG) (6C) to compare fitness of ancestor and escape mutants.
Figure 6C:
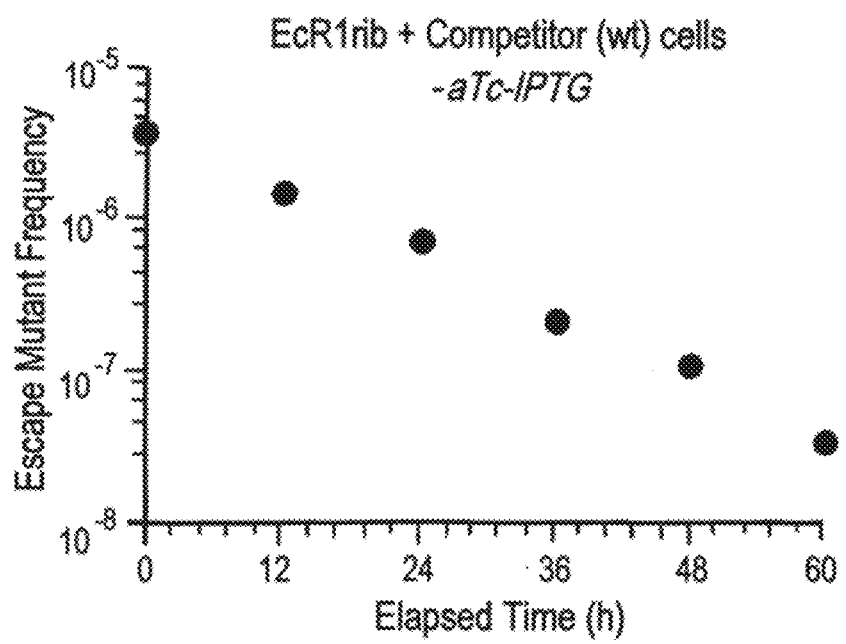

To examine fitness and escape frequency of ribo-essential strains in a competitive environment, EcR1rib was mixed with its ancestor (EcNR1) and a competitive growth experiment was performed in liquid media (FIG. 6A, FIG. 6B). Sixty hours of growth in permissive media with six 100-fold dilutions revealed an 8% fitness defect compared to the ancestral strain (Table 11). A complementary experiment mixed ancestral and ribo-essential cells in non-permissive media. Accumulation of escape mutants was not observed; instead their frequency in the population fell 100-fold over 60 h, indicating the strength of selection for escape mutants in non-permissive media is small (FIG. 6C) and that escape mutants are outcompeted by wild-type strains.

Example 7: Higher-Order Combinations of Safeguards Reduce Escape Frequency

Next, the frequency of escape was reduced by creating strains with higher-order combinations of safeguards. First, a strain with two ribo-essential cassettes was created; however, this modification gave no improvement in escape frequency (Table 14, below). Whole genome sequencing was conducted to identify the genetic basis of escape and found recurring frameshift mutations at a known mutable site in the lacI gene (Farabaugh, et al, *J. Mol. Biol.*, 126: 847-857 (1978)). Introduction of these mutations in a contained background using multiplex automated genome engineering (MAGE; (Wang, et al, *Nature*, 460:894-898 (2009); Gallagher, et al, *Nat. Protoc.*, 9:2301-2316 (2014)) leads to escape. However, in mutants isolated by growth on non-permissive media, containment could be restored by transformation with episomal lacI (Table 13).

TABLE 13

Toxin genes selected as targets for construction of inducible toxin strains.

| Gene | Class | Function | Host |
|---|---|---|---|
| pemK | Ribonuclease | Cleaves UAX sites in mRNA | *Bacillus* |
| vapC | | Cleaves tRNA-fMet (initiator) | *Salmonella* |
| pasB | | Cleaves mRNA codons in ribosome A site | *Pseudomonas* |
| higB | | Translation-dependent mRNA cleavage | *Vibrio* |
| mazF | | Cleaves upstream of ACA triplets | *E. coli* MG1655 |
| relE | | Cleaves mRNA codons in ribosome A site | *E. coli* MG1655 |
| yafQ | | Cleaves at Lys mRNA codons | *E. coli* MG1655 |
| rnlA | | 23S rRNA cleavage, some mRNAs | *E. coli* MG1655 |
| yhaV | | Degrades rRNA (16S & 23S) | *E. coli* MG1655 |
| flmA | Membrane disruptor | Pore-forming protein | *E. coli* MG1655 |
| pndA | | Pore-forming protein | *E. coli* R plasmid |
| hok | | Pore-forming protein | *E. coli* pC15 plasmid |
| ccdB | Topoisomerase poison | Inhibits gyrase | *E. coli* O157 |
| ecoRI | Deoxyribonuclease | Cleaves at GAATTC sites | *E. coli* |
| strp | Cofactor sequestration | Binds streptavidin | *Streptomyces* |

Genes native to *E. coli* MG1655 were amplified by PCR from the genome. Genes native to other organisms were obtained by codon-optimized chemical synthesis (IDT). These genes were drawn from previously described mRNA interferases, membrane destabilizers, cofactor sequesterers (Szafranski, et al., *PNAS*, 94:1059-1063 (1997)), topoisomerase poisons, dsDNA endonucleases (Yamaguchi, et al., *Annu Rev Genet*, 45:61-79 (2011)), or toxin-antitoxin loci (Smith, et al., *Journal of Bacteriology*, 180, 5458-5462 (1998)).

Figure 7B:
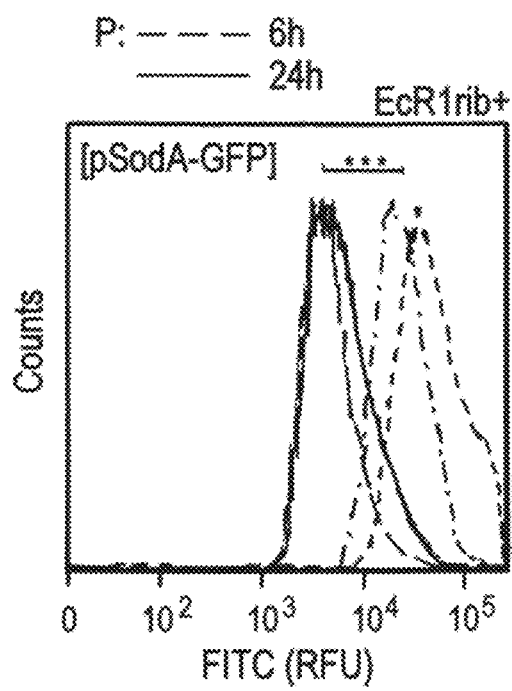
FIGS. 7B-7E are histograms showing the results of flow cytometry (fluorescence) from soda (7B, 7C) and sulA (7D, 7E) promoters in EcR1rib+ (7B, 7D)) or EcTeco (7C, 7E) when grown in non-permissive media (dashed) versus permissive (solid) media for 2, 6 or 24 hours. *** denotes P≤0.001, Student's one-tailed t-test with Welch's correction.
Figure 7D:
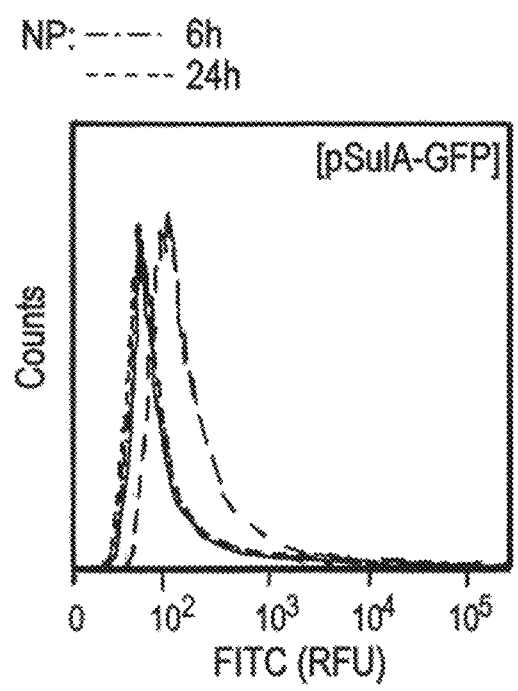
Figure 7C:
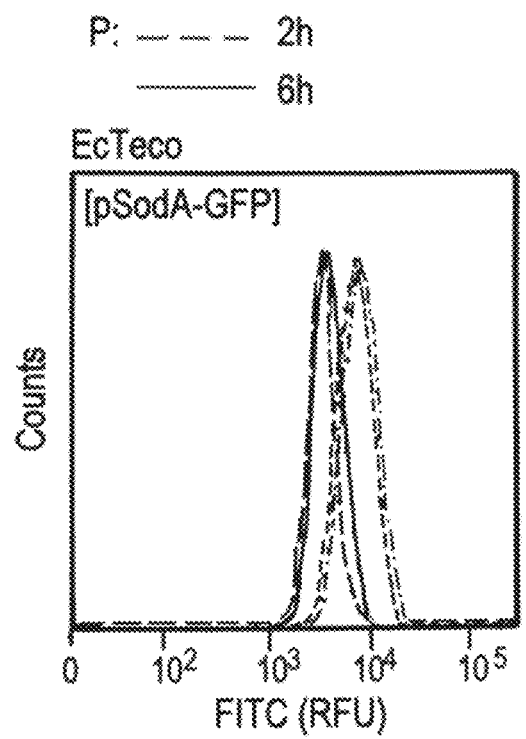
Figure 7E:
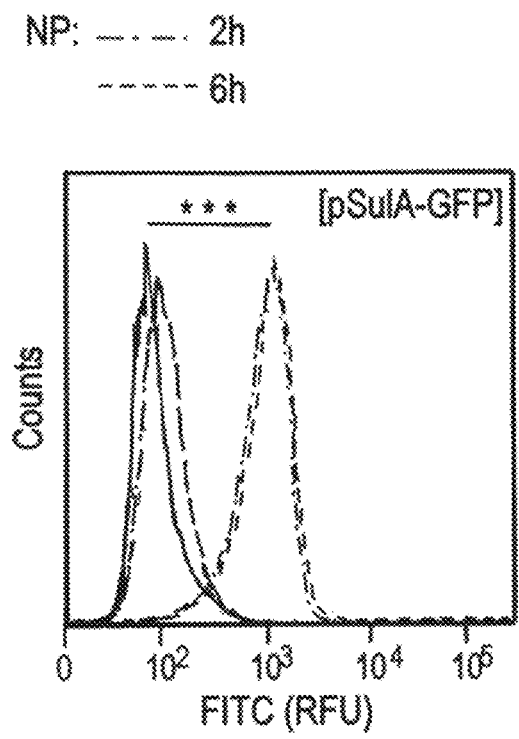
Figure 7F:
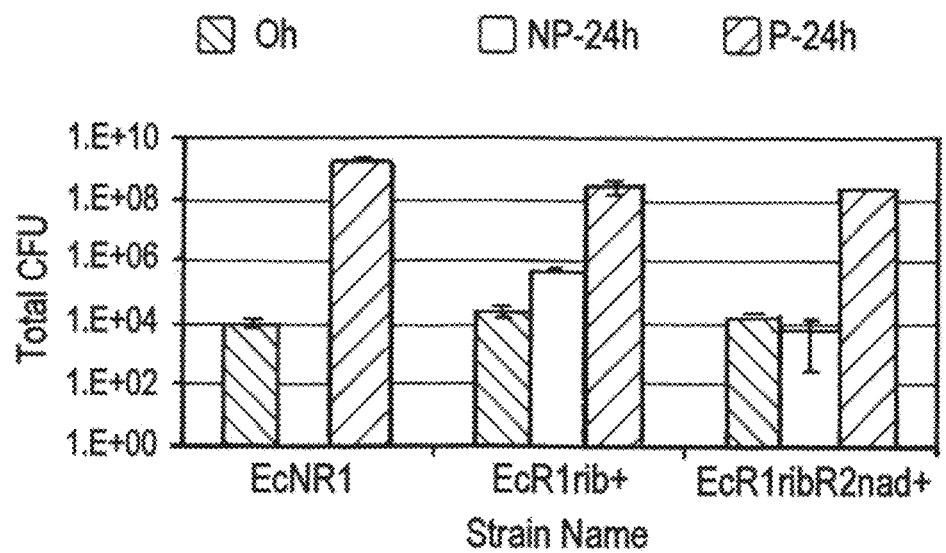
FIG. 7F is a bar graphs showing EcNR1, EcR1rib+, and EcR1ribR2nad+ grown in permissive liquid media then plated to count initial CFU (0 hr., left most bar), then washed, and inoculated into either permissive (P) or nonpermissive (NP) liquid media. After 24 h growth in P (right most bar) or NP (center bar) liquid media, cultures were plated on permissive solid media to count persistent CFU. EcNR1 in NP media not applicable (N/A).

It is believed that mutations compromising the LacI repressor deregulated both ribo-essential genes, but that intact copies of lacI restored containment. By providing supplemental repressors either episomally or chromosomally, the escape frequency of EcR1rib was reduced to ≤$9.9 \times 10^{-8}$ (Table 14, below). Finally, increasing LacI expression using the lacIq1 allele (Calos, et al, *Mol. Gen. Genet.*, 183:559-560 (1981)) diminished leaked viability in non-permissive media (FIG. 7F). The enhanced riboregulated ribA strain with supplemental repressors and lacIq1 (EcR1rib+) possessed an escape frequency of $4.6 \times 10^{-8}$ (Table 14, below).

Repressor supplementation experiments indicate that ribo-essentials could be layered to reduce escape frequency, provided different repressor proteins were used for regulation. Therefore, new riboregulators were built using pAra (arabinose induced) or pRha (rhamnose induced) promoters instead of pLlacO to control nadE or glmS essential genes, respectively. These new ribo-essential strains (EcR2nad, EcR3glm) were successfully able to link cell viability to the synthetic inducer, demonstrating the flexibility and modularity of the ribo-essential safeguard framework. Riboregulated ribA and nadE switches were integrated independently to create strain EcR1ribR2nad. This strain required arabinose and IPTG to express the two crRNAs, and aTc to express the common taRNA. Addition of supplemental repressors to create the 3-layer strain EcR1ribR2nad+ reduced the escape frequency below the detection limit ($<5\times10^{-10}$) of the solid media assay (FIG. 7A and Table 14, below), while maintaining rapid growth (58 min DT compared to 56 for MG1655).

During incubation in non-permissive media, CFU counts for this strain on media containing inducers do not drop to zero immediately, rather they decrease gradually over 24 h (FIG. 7F). Importantly, escape frequency assays and long-term challenge on non-permissive media show these cells cannot form colonies on non-permissive media (Table 14, below and FIG. 7F). This observation indicates that they are not escape mutants and instead represent a non-proliferating persister-like population similar to the low frequency, non-mutant cells that survive antibiotic exposure (Allison, et al, Curr. Opin. Microbiol, 14:593-598 (2011)).

Example 8: Engineered Addiction Modules Enable Construction of Bacteriotoxic Safeguards To counter this persister-like population, a library of toxin genes were constructed and investigated for use as bacteriotoxic safeguards (Table 13). In proof of concept experiments, cells carrying arabinose-regulated EcoRI endonuclease were killed when induced but grew without a fitness defect (DT equals wild type) when uninduced (discussed above). The E. coli genome contains 645 EcoRI sites (GAATTC) that are cleavage substrates for the EcoRI endonuclease, overwhelming the cell's ability to repair double-stranded breaks across its chromosome. As a single layer safeguard, this strain (Ec[Teco]) possesses an escape frequency of $9.4\times10^{-7}$ (Table 14, below). After transforming the inducible nuclease plasmid to create the 3-layer strain EcR1rib[Teco]+, the frequency of escape fell to $5.6\times10^{-10}$ (Table 14, below).

Figure 8:
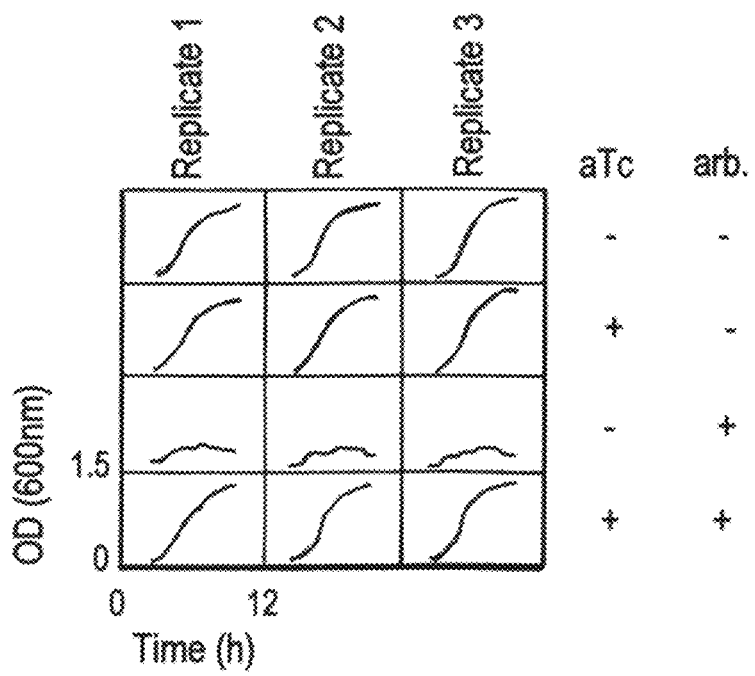
FIG. 8 is matrix of growth kinetic curves showing a 12 hour optical density time course measured over 10 minute intervals at 600 nm of a strain carrying the arabinose (arb.) induced EcoRI endonuclease plasmid from strain Ec[Teco] and having aTc induced expression of the EcoRI methylase. All wells seeded 1:100 from an overnight culture into LB with Kanamycin; arabinose supplied at final concentration of 0.1% w/v, aTc supplied at final concentration of 20 ng/ml.

To eliminate the use of antibiotics to retain plasmids and arabinose to express nucleases, which are both important design requirements for intrinsic biocontainment, an engineered addiction module (EAM) safeguard (Jensen, et al, Mol. Microbiol., 17:205-210 (1995)) was built that used the cognate methylase of EcoRI endonuclease (Polisky, et al, Proc. Natl. Acad. Sci. U.S.A., 72:3310-3314 (1975)). The EAM reversed regulatory logic so that safeguarded cells would be killed upon removal of an exogenously supplied small molecule (e.g. aTc; FIG. 5A). Preliminary experiments showed that aTc-induced EcoRI methylase could protect against the cleavage of GAATTC sites by arabinose-induced EcoRI endonuclease (FIG. 8). Strain EcEAM was constructed by genomically integrating constitutive endonuclease and inducible methylase. This safeguard displayed a delayed induction phenotype, which permitted limited cell growth before rapid killing (FIG. 5F (inset of 5E)). It is believed that this is caused by the requirement for genome replication to clear GAATTC sites that have been protected by methylation. Importantly, this strain was unviable in the absence of aTc and did not require antibiotic for maintenance of episomal nuclease. As a single-layer safeguard EcEAM displayed $2.4\times10^{-6}$ escape frequency and high fitness (61 min DT; discussed above).

Example 9: Analysis of Selected Cellular Pathways Induced by Safeguards

To investigate cellular responses in contained strains as they are challenged in non-permissive media, reporter plasmids were built containing Green Fluorescent Protein (GFP) fused to promoters of genes (umuD, polB, dinB, sulA, tisB, sodA, ribA) previously shown to be implicated in various stress responses (Little, et al, Cell, 29:11-22 (1982); Farr, et al, Microbiol. Rev., 55:561-585 (1991); Lewis, Nat. Rev. Microbiol, 5:48-56 (2007)). For EcR1rib+ cells, these experiments revealed 5- and 8-fold increases in the expression of GFP from the sodA promoter at 6 and 24 h post inducer deprivation, respectively (FIG. 7B), indicating cells grown in non-permissive media increase expression of superoxide dismutase (sodA). Since sodA is involved in the response to reactive oxygen species (ROS) (Cabiscol, et al, Int. Microbiol, 3:3-8 (2000)), this observation indicates that contained strains experience ROS stress during inducer deprivation. 8- and 10-fold upregulation of the sulA promoter in EcTeco cells were observed (FIG. 7C, 7E) at 2- and 6-h time points, respectively, which is consistent with reports implicating sulA in the response to double-strand DNA breaks (Mamun, et al, Science, 338:1344-1348 (2012)).

Example 10: Long-Term, Large-Scale Challenge of Multilayered Safeguards

To analyze the stability of the safeguards over long-term culture, single- and multilayer strains were passaged in permissive media over 110 generations (6 days).

Figure 9:
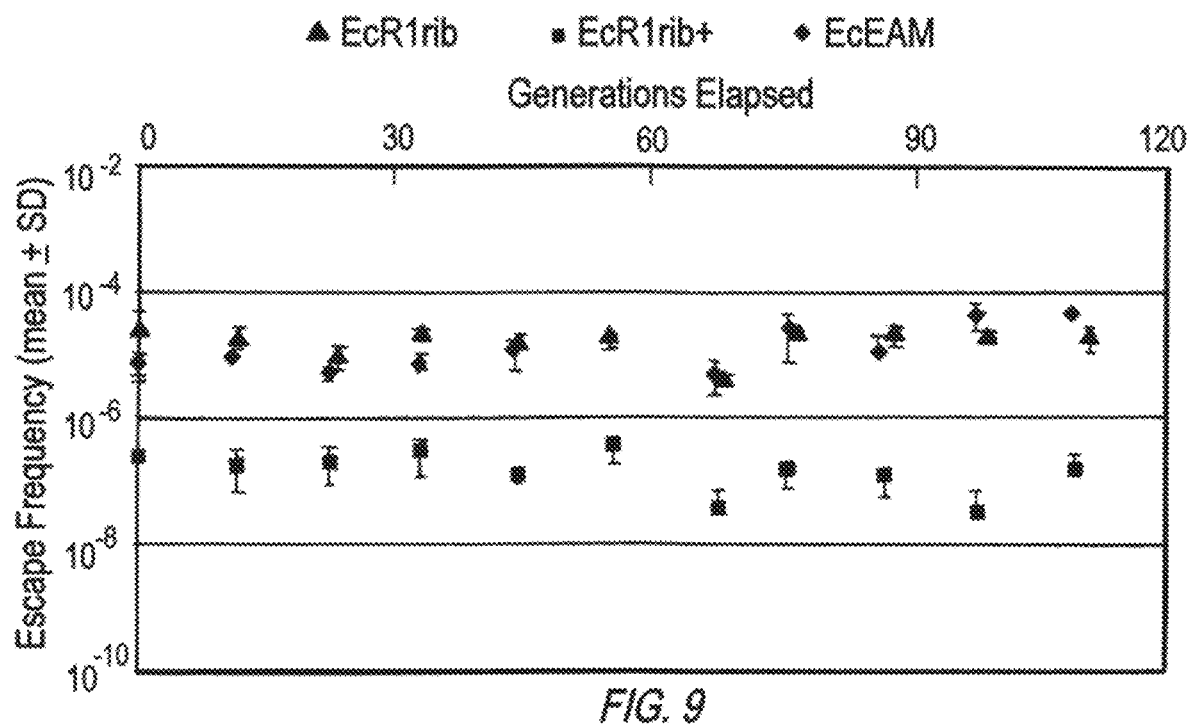
FIG. 9 is a plot showing the results of a long-term continuous culture experiment (Escape Frequency (mean+/−Standard Deviation) over Generations Elapsed). Error bars represent the standard deviation of escape frequency measurement for each strain at each timepoint (n=3).

Triplicate cultures of each strain (single layer EcR1rib and EcEAM, two layer EcR1rib+, were inoculated into permissive LB media (IPTG, aTc, and arabinose) with carbenicilin to maintain sterility. After overnight growth, each replicate was diluted 1:1,000 into fresh permissive media, and samples were plated on permissive and on nonpermissive media (carbenicilin only). Every twelve hours for 5.5 days (11 time points), cultures were diluted 1:1,000 into fresh permissive media and plated again. Total CFU counts on permissive media were used to calculate elapsed doublings (generations). The quotient of nonpermissive CFU counts divided by total CFU counts were used to calculate the escape frequency of each replicate at each timepoint (FIG. 9). Daily plating revealed that escape frequencies for each strain remained stable over time at or near values reported from single timepoint escape frequency assays (FIG. 9 and Table 14, below).

Figure 10A:
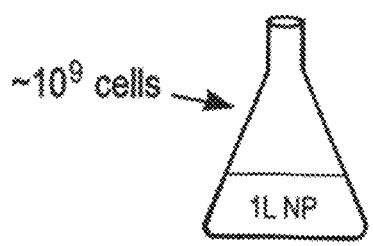
FIG. 10A is a diagram of the workflow of an escape and persistence experiment, the results of which are reported in FIGS. 10B-10C.
Figure 10B:
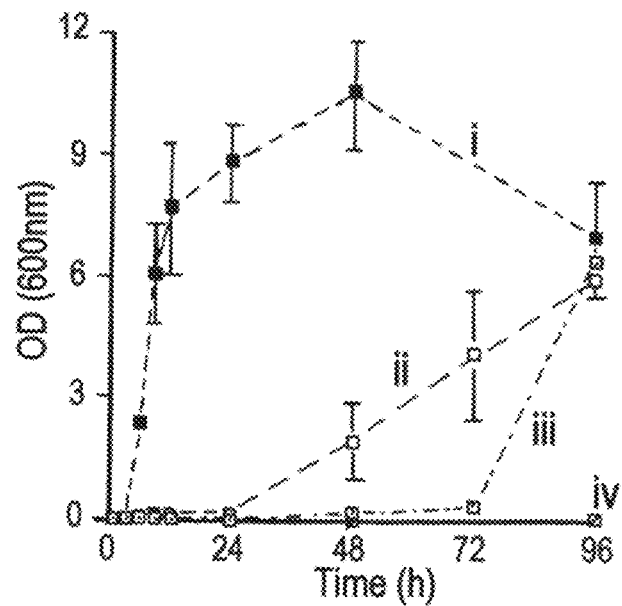
FIGS. 10B-10C are bar graphs showing the $OD_{600}$ (10B) and plating on permissive (P) and non-permissive (NP) media (10C) for EcNR1 (i), EcR1rib+ (ii), EcR1ribR2nad+ (iii), and EcR1ribTeco+ (iv) over time (hours) beginning with a ~$10^9$ CFU inoculum in 1 L of non-permissive liquid media.
Figure 10C:
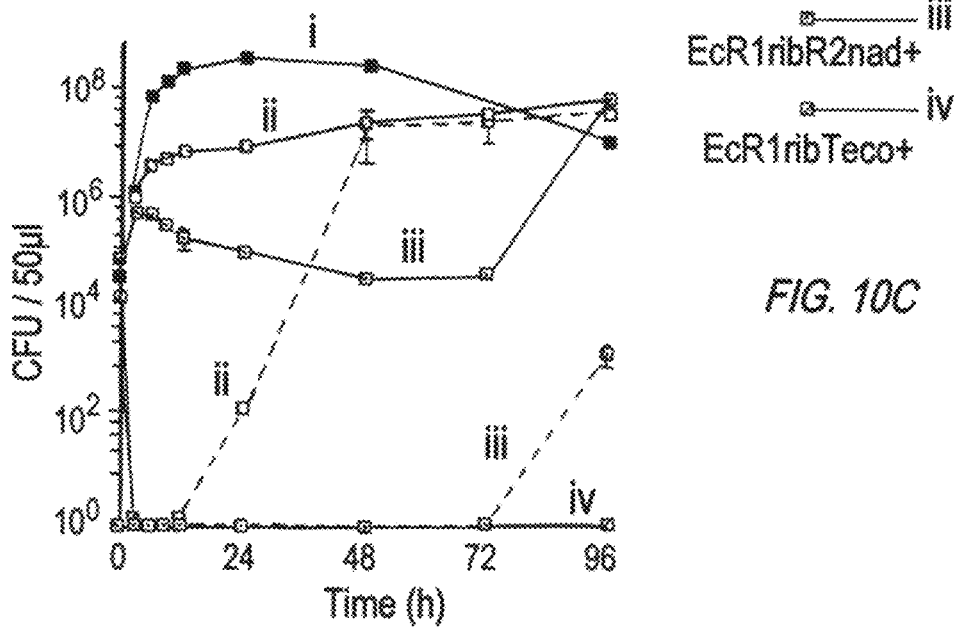

To analyze escape and persistence in large cell populations over extended time periods, flasks containing 1 L of non-permissive LB were inoculated with $\sim10^9$ CFU of safeguarded strains (FIG. 10A-C). Over 4 days of incubation, cell populations were monitored in the flask by measuring OD, and by plating samples on permissive and non-permissive media. Permissive plate counts revealed gradual growth and robust persistence for the 2-layer strain EcR1rib+. Since the inoculum CFU was significantly larger than the $4.6\times10^{-8}$ escape frequency of this strain, a proliferating population of escapers was detected within 24 h. CFU counts for 3-layer EcR1ribR2nad+ initially dropped. While the escape frequency of this strain indicates that an escape mutant was not present in the initial inoculum, an escaping population appeared after 72 h. Whole genome sequencing of 3-layer escape mutants revealed deregulating mutations in AraC (Dirla, et al, *J. Bacteriol*, 191:2668-2674 (2009); Cass, et al, *J. Bacteriol*, 166:892-900 (1986)) and in the crRNA governing ribA. In escape mutants from Ec[Teco] and EcR1ribR2nad+, sequencing also revealed identical mutations in the mismatch repair (MMR) gene mutS. These experiments highlight a persistent cell population that, while unable to form colonies on non-permissive media, can survive inducer deprivation for ribo-essential strains grown in liquid culture. It is believed that persistent cells tolerate the stress of inducer deprivation and give the population more opportunities to sequentially defeat safeguards, leading to eventual escape. In contrast to another 3-layer strain (EcR1rib[Teco]+), CFU counts dropped below detectable levels within the first 12 h and remained undetectable for the duration of the experiment. It is believed that the bacteriotoxic EcoRI safeguard degrades the host genome, preventing persistence so that an escaping population is not observed during the time course of this experiment.

Figure 10D:
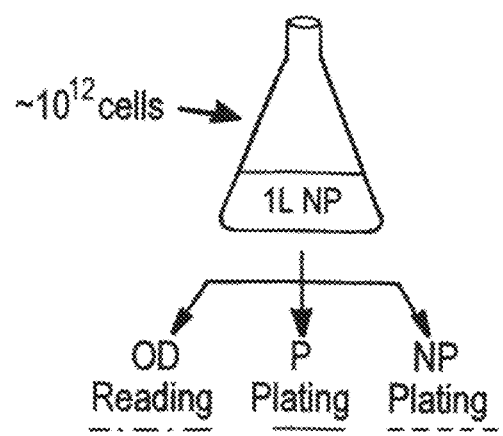
FIG. 10D is a diagram of the workflow of an escape and persistence experiment, the results of which are reported in FIGS. 10E-10F.
Figure 10E:
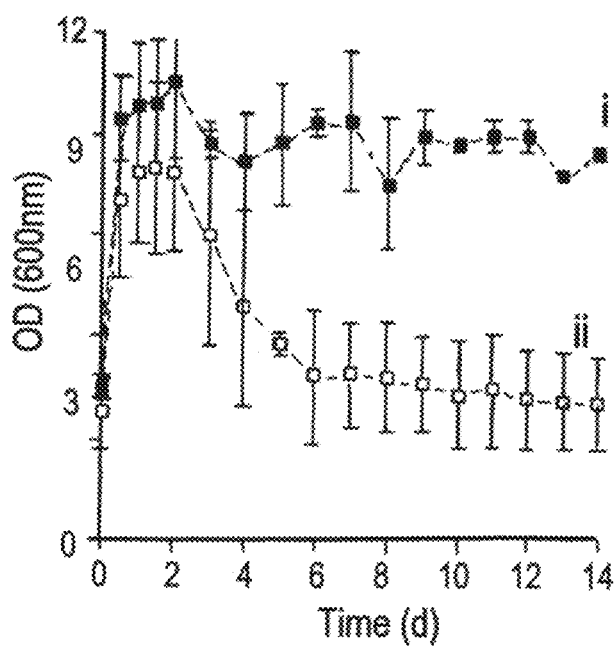
FIGS. 10E-10F are bar graphs showing the $OD_{600}$ (10E) and plating on permissive (P) and non-permissive (NP) media (10F) for EcNR1 (i) and EcR1ribR3glmEAM+ (ii) over time (hours) beginning with a ~$10^{12}$ CFU inoculum in 1 L of non-permissive liquid media.
Figure 10F:
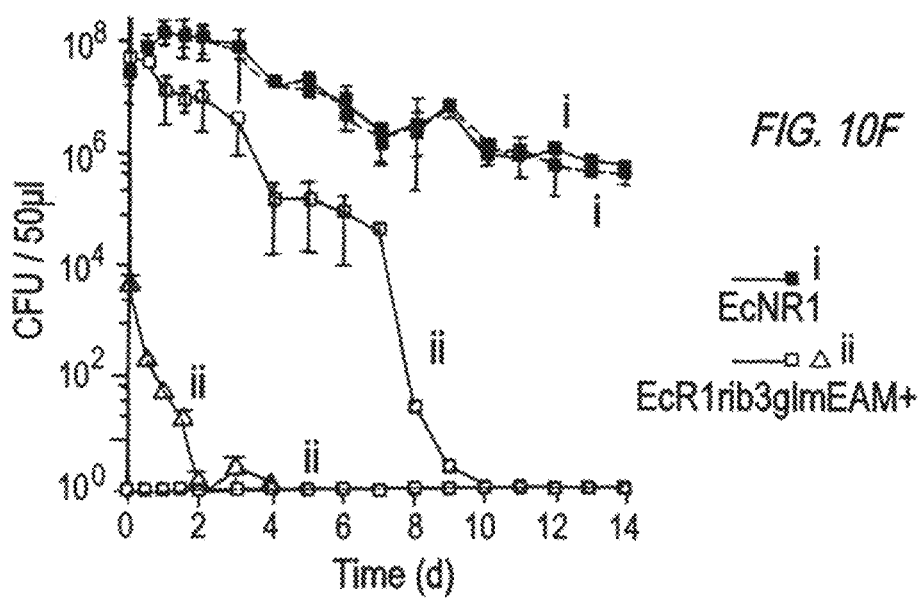

Prior work indicated that glmS deficiencies have a bacteriotoxic effect (Wu, et al, *J. Bacteriol*, 105:455-466 (1971)), indicating that a glmS synthetic auxotrophy could be used alongside ribA and EAM safeguards to counter persistence. glmS was placed under the control of a rhamnose- and aTc-induced riboregulator and this new ribo-essential was used to create a 4-layered strain (EcR1ribR3glmEAM+). 1 L of non-permissive LB was inoculated with $7.9 \times 10^{11}$ CFU of this strain and incubated for 2 weeks (FIG. 10D-F). On permissive solid media, viable CFU counts for the 4-layered strains fell ~$10^6$-fold over the first 8 days compared to ~2-fold for the EcNR1 control. No CFUs were observed on non-permissive media at any time point. Moreover, pelleting then plating the full flask volume on permissive media at day 14 revealed no CFUs, indicating an escape frequency of $<1.3 \times 10^{-12}$ ($<1/(7.9 \times 10^{11})$) Since the nuclease-based EAM requires genome replication for methylated sites to be lost, another experiment was conducted with ~$10^8$ CFU inoculum (FIG. 4F; triangles), to determine if lower cell density would reveal the dynamics of growth termination, and lead to more rapid outgrowth and faster killing of contained cells. Permissive plate CFU counts fell ~$10^4$-fold in 2 days. Taken together, these large-scale experiments show the progressive improvement in containment as additional and distinct safeguard layers are added, culminating in active termination of the inoculum population.

Examples 5-10 describe the implementation and advantages of multilayered genetic safeguards in *E. coli*, whose design is inspired by natural mechanisms of growth regulation. Because at least two independently acting regulatory pathways limit growth and division in animal cells (Hanahan, et al, *Cell*, 144:646-674 (2011)), two or more mutations are required for tumorigenesis (Knudson, et al, *Nat. Rev. Cancer*, 1:157-162 (2001)). Similarly, by integrating independently acting safeguards strains were constructed that must overcome multiple barriers to escape engineered limits on growth and division. Safeguards based on auxotrophy, independent essential gene riboregulation, repressor supplementation, and engineered addiction were employed. These safeguards were characterized individually and in combinations to show that they can be integrated in multilayered strains that exhibit limited fitness costs and reduced escape frequency, even when one layer has been compromised. This multilayered approach employs different modes of action to address the shortcomings inherent to each individual safeguard. The EAM presented here could be applied in other organisms, or could be expanded by use of other previously characterized restriction-modification enzyme pairs (Wilson, et al, *Annu. Rev. Genet*, 25:585-627 (1991)), provided that they are compatible with native methylation patterns. Importantly, by demonstrating the modularity of ribo-essential regulation through use of several essential genes (ribA, nadE, glmS, gmk) and inducible promoter (pLtetO, pLlacO, pAra, pRha) combinations, this work establishes a portable framework for engineering safeguards in other model or undomesticated microorganisms and potentially across members of a microbial community (Brenner, et al, *Trends Biotechnol*, 26:483-489 (2008)). Leveraging the modularity of this approach, future work to engineer riboregulator promoters that use native cis-acting elements could prevent the potential loss of natural essential gene regulatory functions.

Probiotic natural isolates (Altenhoefer, et al, *FEMS Immunol. Med. Microbiol*, 40:223-229 (2004)), and GMOs engineered for delivery of therapeutic DNAs (Grillot-Courvalin, et al, *Nat. Biotechnol*, 16:862-866 (1998)), RNAs (Xiang, et al, *Nat. Biotechnol*, 24:697-702 (2006)) or proteins (Galan, et al, *Nature*, 444:567-573 (2006)) to animal cells have already been demonstrated. However, their potential use in open systems such as in human (e.g., probiotic) or environmental applications (e.g., bioremediation) demands safeguard strategies that restrict their growth outside the site of delivery. The frequency of escape mutants must be low enough such that a mutant is unlikely to exist in the population demanded by an application while the strain's fitness must be high enough to ensure execution of its task. For instance, live bacterial vaccines (Kang, et al, *Infect. Immun*, 70:1739-1749 (2002); Garmory, et al, *J. Drug Target*, 11:471-479 (2003)) or oncolytic therapies delivered by live GMOs (Anderson, et al, *J. Mol. Biol*, 355:619-627 (2006); Dang, et al, *Proc. Natl. Acad. Sci. U.S.A.*, 98:15155-15160 (2001)) inoculate with ~$10^6$-$10^7$ CFU, well below the escape frequency demonstrated by the best strains. Recent work showing aTc-dependent control of a synthetic gene network in a mammalian gut commensal indicates that regulation of the safeguards is possible in vivo (Kotula, et al, *Proc. Natl. Acad. Sci. U.S.A.*, 111:4838-4843 (2014)). Future work to examine extremely large populations of safeguarded cells ($>10^{12}$) could reveal novel escape mechanisms not captured by this study and motivate creation of strains with >4 safeguards. Furthermore, future work could extend these safeguards to previously described strains, permitting safe and secure large-scale bioremediation (Pieper, et al, *Curr. Opin. Biotechnol*, 11:262-270 (2000)) and therapeutic applications (Steidler, *Best Pract. Res. Clin. Gastroenterol*, 17:861-876 (2003); Altenhoefer, et al, *FEMS Immunol. Med. Microbiol*, 40:223-229 (2004)).

TABLE 14

Strains used in Examples 5-10 with genotype, fitness, and escape frequency information.

| Strain Name | Growth Requirements | Escape Frequency | Doubling Time (min) | Genotype |
|---|---|---|---|---|
| *Ancestor Strains* | | | | |
| MG1655 | None | N/A | 56 ± 1 | |
| EcNR1 | None | N/A | 56 ± 1 | Δ{ybhB-bioAB}::{λcI857 N(cro-ea59)::tetR-bla} |
| *Single layer (episomal ribo-essential)* | | | | |
| Ec[R1gmk] | None | 1 | 57 ± 1 | EcNR1 gmk::tolC [pLtetO.taRNA pLlacO.cr.gmk] |
| *Single layer (genomic ribo-essential)* | | | | |
| EcR1rib | IPTG, aTc | $4.5 \pm 1.0 \times 10^{-6}$ | 57 ± 1 | EcNR1 13B.{pLtetO.taRNA pLlacO.cr.ribA} ribA::tolC |
| EcR1adk | IPTG, aTc | $3.4 \pm 2.0 \times 10^{-6}$ | 57 ± 1 | EcNR1 13B.{pLtetO.taRNA pLlacO.cr.adk} adk::kanR |
| EcR1pyr | IPTG, aTc | $1.1 \pm .04 \times 10^{-6}$ | 67 ± 2 | EcNR1 21B.{pLtetO.taRNA pLlacO.cr.pyrH} pyrH::tolC |
| EcR1glm | IPTG, aTc | $2.0 \pm 0.9 \times 10^{-6}$ | 56 ± 1 | EcNR1 21B.{pLtetO.taRNA pLlacO.cr.glmS} glmS::kanR |
| EcR1gmk | IPTG, aTc | $5.2 \pm 3.3 \times 10^{-6}$ | 74 ± 1 | EcNR1 21B.{pLtetO.taRNA pLlacO.cr.gmk} gmk::tolC |
| EcR1acp | None | N/A | | EcNR1 21B.{pLtetO.taRNA pLlacO.cr.acpP} acpP::tolC |
| EcR1nad | None | N/A | | EcNR1 21B.{pLtetO.taRNA pLlacO.cr.nadE} nadE::kanR |
| EcR2nad | Ara, aTc | $1.9 \pm 1.5 \times 10^{-6}$ | 56 ± 1 | EcNR1 13B.{pLtetO.taRNA pLlacO.cr.ribA} 21B.pARA$_{BAD}$.cr.nadE nadE::kanR |
| EcR3glm | Rha, aTc [1] | $3.8 \pm 0.2 \times 10^{-6}$ | 57 ± 1 | EcNR1 13B.{pLtetO.taRNA pRHA$_{BAD}$.cr.glmS} glmS::kanR |
| *Two layer (two genomic ribo-essentials, same promoter set)* | | | | |
| EcR1ribR1rib | IPTG, aTc | $1.4 \pm 0.3 \times 10^{-6}$ | 56 ± 1 | EcNR1 13B.{pLtetO.taRNA pLlacO.cr.ribA} 21B.pLlacO.cr.ribA ribA::tolC |
| EcR1ribR1adk | IPTG, aTc | $2.6 \pm 2.1 \times 10^{-6}$ | 59 ± 1 | EcNR1 13B.{pLtetO.taRNA pLlacO.cr.ribA} 21B.pLlacO.cr.adk ribA::tolC adk::kanR |
| EcR1ribR1pyr | IPTG, aTc | $7.4 \pm 5.2 \times 10^{-6}$ | 68 ± 2 | EcNR1 13B.{pLtetO.taRNA pLlacO.cr.ribA} 21B.pLlacO.cr.pyrH ribA::tolC pyrH::kanR |
| EcR1ribR1glm | IPTG, aTc | $2.3 \pm 0.9 \times 10^{-6}$ | 58 ± 1 | EcNR1 13B.{pLtetO.taRNA pLlacO.cr.ribA} 21B.LlacO.cr.glmS ribA::tolC glmS::kanR |
| EcR1ribR1dxr | IPTG, aTc | $7.0 \pm 2.1 \times 10^{-6}$ | 60 ± 1 | EcNR1 13B.{pLtetO.taRNA pLlacO.cr.ribA} 21B.pLlacO.cr.dxr ribA::tolC dxr::kanR |
| EcR1ribR1nad | IPTG, aTc | $1.3 \pm 1.1 \times 10^{-6}$ | 55 ± 1 | EcNR1 13B.{pLtetO.ta.RNA pLlacO.cr.ribA} 21B.pLlacO.cr.nadE ribA::tolC nadE::kanR |
| EcR1ribR1gmk | IPTG, aTc | $9.3 \pm 7.8 \times 10^{-6}$ | 80 ± 1 | EcNR1 13B.{pLtetO.taRNA pLlacO.cr.ribA} 21B.pLlacO.cr.gmk ribA::tolC gmk::kanR |
| EcR1ribR1lpx | IPTG, aTc | $4.2 \pm 2.0 \times 10^{-6}$ | 56 ± 1 | EcNR1 13B.{pLtetO.taRNA pLlacO.cr.ribA} 21B.pLlacO.cr.lpxC ribA::tolC lpxC::kanR |
| *Single layer enchancements (genomic ribo-essentials)* | | | | |
| EcR1ribASV | IPTG, aTc | $1.2 \pm 0.5 \times 10^{-5}$ | 60 ± 2 | EcNBR1 13B.{pLtetO.taRNA pLlacO.cr.ribA.ASV} ribA::tolC |
| EcR1ribAAV | IPTG, aTc | $3.5 \pm 2.9 \times 10^{-7}$ | 62 ± 4 | EcNR1 13B.{pLtetO.taRNA pLlacO.cr.ribA.AAV} ribA::tolC |
| EcR1riblacIq1 | IPTG, aTc | $1.4 \pm 1.0 \times 10^{-8}$ | 55 ± 3 | EcNR1 13B.{pLtetO.taRNA pLlacO.cr.ribA} ribA::tolC lacIq1 |
| EcR1rib[tetR] | IPTG, aTc | $9.9 \pm 4.2 \times 10^{-8}$ | 60 ± 1 | EcNR1 13B.{pLtetO.taRNA pLlacO.cr.ribA} ribA::tolC [pARA$_{BAD}$.tetR] |
| EcR1rib[lacI] | IPTG, aTc | $9.1 \pm 7.2 \times 10^{-8}$ | 60 ± 1 | EcNR1 13B.{pLtetO.taRNA pLlacO.cr.ribA} ribA::tolC [pARA$_{BAD}$.lacI] |
| EcR1rib+ | IPTG, aTc | $4.6 \pm 3.4 \times 10^{-8}$ | 59 ± 1 | EcNR1 13B.{pLtetO.taRNA pLlacO.cr.ribA} ribA::p$_{ma}$.tetRlacI lacIg1 |
| *Bacteriotoxic safeguard layer* | | | | |
| Ec[Teco] | None | $9.4 \pm 7.8 \times 10^{-7}$ | 56 ± 1 | EcNR1 [pARA$_{BAD}$.ecoRI] |
| Ec[Tpas] | None | $4.0 \pm 3.6 \times 10^{-7}$ | 61 ± 1 | EcNR1 [pARA$_{BAD}$.pasB] |
| EcTeco | None | $6.2 \pm 1.0 \times 10^{-8}$ | 61 ± 2 | EcNR1 13B.{pARA$_{BAD}$.ecoRI} 21B.pARA$_{BAD}$.ecoRI] |
| EcEAM | aTc | $2.4 \pm 1.2 \times 10^{-8}$ | 60 ± 2 | EcNR1 13B.{pLtetO.ecoRImet} 21B.{p434.ecoRInuc} |
| *Multilayered strains* | | | | |
| EcR1ribR2nad+ | Ara, IPTG, aTc | $<3.6 \times 10^{-10}$ | 58 ± 2 | EcNR1 13B.{pLtetO.taRNA pLlacO.cr.ribA} 21B.pARA$_{BAD}$.cr.nadE nadE::tolC ribA::p$_{ma}$.tetRlacI lacIq1 |

TABLE 14-continued

Strains used in Examples 5-10 with genotype, fitness, and escape frequency information.

| Strain Name | Growth Requirements | Escape Frequency | Doubling Time (min) | Genotype |
|---|---|---|---|---|
| EcR1rib[Teco]+ | IPTG, aTc | <5.6 × 10$^{-10}$ | 61 ± 1 | EcNR1 13B.{pLtetO.taRNA pLlacO.cr.ribA} ribA::p$_{ma}$.tetRlacI lacIq1 [pARA$_{BAD}$.ecoRI] |
| EcR1ribR3glm[Teco]+ | IPTG, aTc, Rha [1] | <3.6 × 10$^{-10}$ | 62 ± 1 | EcNR1 13B.{pLtetO.taRNA pLlacO.cr.ribA} 910B.{pRHA$_{BAD}$.cr.glmS} ribA::p$_{ma}$.tetRlacI glmS::tolC facIq1 [pARA$_{BAD}$.ecoRI] |
| EcR1ribR3glmEAM+ | IPTG, aTc, Rha [1] | <1.3 × 10$^{-12}$ | 66 ± 1 | EcNR1 13B.{pLtetO.taRNA pLlacO.cr.ribA} 910B.{pRHA$_{BAD}$.cr.glmS} ribA::p$_{ma}$.tetRlacI glmS::{pLtetO.ecoR1met} 21B.{specR.p434.ecoR1nuc} lacIq1 |

Legend:
R1 = pLtetO.taRNA pLlacO.cr.Essential gene ORF
R2 = pLtetO.taRNA pBAD$_{ARA}$.cr.Essential gene ORF
R3 = pLtetO.taRNA pBAD$_{RHA}$.cr.Essential gene ORF
+ = p$_{ma}$.tetRlacI lacIq1
taRNA = transactivating RNA
cr = cis-repressed ribosome binding site
{ } = Chromosomal Cassette
ara = arabinose
rha = rhamnose
21B = Safe genomic insertion region, coordinate: 2,428,900
13B = Safe genomic insertion region, coordinate: 1,415,470
[ ] = Plasmid Cassette - All plasmid inserts are between kpnI and hindIII on pZE21
[1] Addition of 1 mM Glucosamine improves strain fitness, but is not necessary for viability.

Example 11: Modified Background Strains

*E. coli* genomic loci involved in the stress induced mutagenesis (SIM), error-prone replication, persistence, adaptive mutation, and stress response phenotypes are known to occur in diverse bacteria. Sixteen target genes were identified and a pool of MAGE oligonucleotides were designed to introduce nonsense or attenuated alleles (Table 15).

| | Oligo Name | Oligo Target |
|---|---|---|
| lacI alleles | lacI.q | Strong -10 box for lacI repressor |
| | lacI.q1 | Strongest -10 box for lacI repressor |
| | lacI.ATG | GTG->ATG start codon for lacI repressor |
| SOS sensor alleles | recA56 | recA allele that binds ssDNA but does not cleave lexA |
| | lexA3 | lexA repressor allele that is not cleavable |
| | MutS.decoy | titrate mutS away from targeted mismatches in MMR+ strain |
| error prone pol. KOs | rpoS.KO | Stress sigma factor, Implicated in mutagenic & stringent responses |
| | dinB.KO | Error prone polymerase, dispensable |
| | polB.KO | Error prone polymerase, dispensable |
| | umuD.KO | Error prone polymerase, dispensable |
| | umuC.KO | Error prone polymerase, dispensable |
| stringence & persistence | hipA.KO | Persistence response |
| | sulA.KO | Stringent response - sequesters oriC |
| | glpD.KO | Persistence response - function unknown |
| | relA.KO | ppGppp synthase, controls stringent response |
| repair path. KOs | recA.KO | SSAP, involved in recombination & repair |
| | recB.KO | Part of nuclease complex in recombination & repair |
| | recC.KO | Part of nuclease complex in recombination & repair |
| | recD.KO | Part of nuclease complex in recombination & repair |
| | marB.KO | General purpose efflux pump - involved in MDR |

Twelve rounds of co-selection MAGE was used to drive high efficiency combinatorial mutagenesis through a population of contained cells and to isolate 96 single colonies for follow up analysis. Results showed significant phenotypic diversity in this mutant collection. Many clones showed markedly improved containment in a small-scale assay of escape frequency. It is also notable that some clones show markedly increased escape frequency in the same assay. Table 15 shows loci targeted for knockout or attenuation to develop a strain less prone to escape by mutation.

We claim:

1. A genomically recoded organism (GRO) comprising a genome wherein at least one codon is reassigned creating an available sense codon for a recombinant tRNA;
    wherein at least one instance of the available sense codon is present as a sense codon in the coding region of at least one endogenous essential gene of interest that encodes a protein whose expression is needed for the GRO's viability;
    wherein the at least one instance of the available sense codon encodes a conserved amino acid residue at a functional site of the protein; and
    wherein the recombinant tRNA can be charged by a paired recombinant aminoacyl-tRNA synthetase (aaRS) to permit site-specific incorporation of a synthetic amino acid (sAA) or non-standard amino acid (nsAA) into a nascent peptide chain of the protein during translation of the transcribed essential gene in the GRO.

2. The GRO of claim 1, wherein
    all genomic instances of a first stop codon sequence have been reassigned to a second stop codon sequence and the available sense codon consists of the sequence of the first stop codon, or
    all genomic instances of an endogenous sense codon sequence have been reassigned to a synonymous codon sequence and the available sense codon consists of the sequence of the endogenous sense codon;
    and wherein the anticodon sequence for the recombinant tRNA recognizes the available sense codon sequence.

3. The GRO of claim 2, wherein the genomic sequence of the first stop codon sequence is TAG and the second stop codon sequence is TAA or TGA.

4. The GRO of claim, 3 wherein the GRO is a variant of *E. coli* strain C321.A A (GenBank accession CP006698).

5. The GRO of claim 1 further comprising a nucleic acid encoding an expression control sequence operably linked to a sequence encoding the recombinant aminoacyl-tRNA synthetase (aaRS) and the recombinant tRNA,
    wherein the GRO has reduced viability in non-permissive media that does not include the synthetic amino acid (sAA) or non-standard amino acid (nsAA) compared to permissive media including the synthetic amino acid (sAA) or non-standard amino acid (nsAA),
    wherein the escape frequency of the GRO in the non-permissive media is about $10^{-11}$ or less.

6. The GRO of claim 1 wherein the essential gene of interest is selected from the group consisting of dnaX, lspA, secY, serS, murG, dnaA, adk, nadE, ribA, and gmk.

7. The GRO of claim 2, wherein the gene or genes encoding the endogenous cognate translation machinery corresponding to the at least one reassigned codon is interrupted or deleted.

8. The GRO of claim 1, wherein the available sense codon is only present in the essential gene of interest.

9. The GRO of claim 7, further comprising a nucleic acid encoding an expression control sequence operably linked to a sequence encoding the recombinant aminoacyl-tRNA synthetase (aaRS), the recombinant tRNA.

10. The GRO of claim 9, wherein the nucleic acid is episomal, extrachromosomal, or integrated into a chromosome of the GRO.

11. The GRO of claim 10, wherein the genomic sequence of the available sense codon is TAG, the recombinant tRNA comprises the anticodon for UAG, and the corresponding release factor or factors is deleted or interrupted.

12. The GRO of claim 9, wherein culturing the GRO with permissive media including the synthetic amino acid (sAA) or non-standard amino acid (nsAA) results in translation of the full-length protein encoded by the essential gene.

13. The GRO of claim 12, wherein culturing the GRO with non-permissive media that does not include the synthetic amino acid (sAA) or non-standard amino acid (nsAA) results in truncation of the full-length protein encoded by the essential gene.

14. The GRO of claim 12, wherein the GRO has reduced viability when cultured with non-permissive media that does not include the synthetic amino acid (sAA) or non-standard amino acid (nsAA) compared to permissive media including the synthetic amino acid (sAA) or non-standard amino acid (nsAA) that results in translation of the full-length protein encoded by the essential gene.

15. The GRO of claim 14, wherein the escape frequency of the GRO when cultured with non-permissive media is $10^{-6}$ or lower and the fitness of the GRO when cultured with permissive media is at least 70% of its parental strain grown under the same or similar conditions.

16. The GRO of claim 1, wherein two or more instances of the available sense codon are present as sense codons in at least one of the essential gene of interest.

17. The GRO of claim 1, wherein at least one instance of the available sense codon is present as a sense codon in at least a second endogenous essential gene of interest.

18. The GRO of claim 1, wherein the essential gene is one that cannot be complemented by cross-feeding of metabolites to the GRO.

19. The GRO of claim 1, where the at least one endogenous essential gene of interest is present only at its genomic locus.

20. The GRO of claim 1, wherein the protein is functional when the synthetic amino acid (sAA) or non-standard amino acid (nsAA) is substituted for the endogenously encoded cognate amino acid.

21. The GRO of claim 20, where the conserved residue is a tyrosine, phenylalanine or tryptophan.

22. The GRO of claim 1, wherein the at least one instance of the available sense codon is present at the N-terminal end of the protein.

23. The GRO of claim 21, wherein the synthetic amino acid or non-standard amino acid is pAcF (p-acetylphenylalanine), pIF (p-iodo-L-phenylalanine), or pAzF (p-azido-L-phenylalanine).

24. A genomically recoded organism (GRO) comprising a nucleic acid encoding a recombinant aminoacyl-tRNA synthetase (aaRS), a nucleic acid encoding a recombinant tRNA, and a genome wherein at least one codon is reassigned creating an available sense codon for a recombinant tRNA and the gene or genes encoding the endogenous cognate translation machinery corresponding to the at least one reassigned codon is interrupted or deleted;

at least one instance of the available sense codon is present as a sense codon in the coding region of three or more endogenous essential genes of interest that encode proteins whose expression is needed for the GRO's viability; and wherein the recombinant tRNA can be charged by a paired recombinant aminoacyl-tRNA synthetase (aaRS) to permit site-specific incorporation of a synthetic amino acid (sAA) or non-standard amino acid (nsAA) into a nascent peptide chain of the proteins during translation of the transcribed essential genes in the GRO.

25. The GRO of claim 24, wherein the available sense codons are present as sense codons at conserved amino acid residues at functional sites of the endogenous essential genes having at least one instance of the available sense codon.

26. The GRO of claim 25, wherein one or more of the essential genes having at least one instance of the available sense codon encodes a protein whose function cannot be complemented by cross-feeding of metabolites to the GRO.

27. The GRO of claim 26, wherein the escape frequency of the GRO cultured with non-permissive media is $10^{-8}$ or lower and the fitness of the GRO when cultured with permissive media is at least 70% of its parental strain grown under the same conditions.

* * * * *

SEQUENCE LISTING

<160> NUMBER OF SEQ ID NOS: 34

<210> SEQ ID NO 1
<211> LENGTH: 306
<212> TYPE: PRT
<213> ORGANISM: Methanococcus jannaschii

<400> SEQUENCE: 1

| Met | Asp | Glu | Phe | Glu | Met | Ile | Lys | Arg | Asn | Thr | Ser | Glu | Ile | Ile | Ser |
|-----|-----|-----|-----|-----|-----|-----|-----|-----|-----|-----|-----|-----|-----|-----|-----|
| 1 | | | | 5 | | | | | 10 | | | | | 15 | |

| Glu | Glu | Glu | Leu | Arg | Glu | Val | Leu | Lys | Lys | Asp | Glu | Lys | Ser | Ala | Tyr |
| | | | 20 | | | | | 25 | | | | | 30 | | |

| Ile | Gly | Phe | Glu | Pro | Ser | Gly | Lys | Ile | His | Leu | Gly | His | Tyr | Leu | Gln |
| | | | 35 | | | | | 40 | | | | | 45 | | |

| Ile | Lys | Lys | Met | Ile | Asp | Leu | Gln | Asn | Ala | Gly | Phe | Asp | Ile | Ile | Ile |
| | 50 | | | | | 55 | | | | | 60 | | | | |

| Leu | Leu | Ala | Asp | Leu | His | Ala | Tyr | Leu | Asn | Gln | Lys | Gly | Glu | Leu | Asp |
| 65 | | | | | 70 | | | | | 75 | | | | | 80 |

| Glu | Ile | Arg | Lys | Ile | Gly | Asp | Tyr | Asn | Lys | Lys | Val | Phe | Glu | Ala | Met |
| | | | | 85 | | | | | 90 | | | | | 95 | |

| Gly | Leu | Lys | Ala | Lys | Tyr | Val | Tyr | Gly | Ser | Glu | Phe | Gln | Leu | Asp | Lys |
| | | | 100 | | | | | 105 | | | | | 110 | | |

| Asp | Tyr | Thr | Leu | Asn | Val | Tyr | Arg | Leu | Ala | Leu | Lys | Thr | Thr | Leu | Lys |
| | | | 115 | | | | | 120 | | | | | 125 | | |

| Arg | Ala | Arg | Arg | Ser | Met | Glu | Leu | Ile | Ala | Arg | Glu | Asp | Glu | Asn | Pro |
| | 130 | | | | | 135 | | | | | 140 | | | | |

| Lys | Val | Ala | Glu | Val | Ile | Tyr | Pro | Ile | Met | Gln | Val | Asn | Asp | Ile | His |
| 145 | | | | | 150 | | | | | 155 | | | | | 160 |

| Tyr | Leu | Gly | Val | Asp | Val | Ala | Val | Gly | Gly | Met | Glu | Gln | Arg | Lys | Ile |
| | | | | 165 | | | | | 170 | | | | | 175 | |

| His | Met | Leu | Ala | Arg | Glu | Leu | Leu | Pro | Lys | Lys | Val | Val | Cys | Ile | His |
| | | | 180 | | | | | 185 | | | | | 190 | | |

| Asn | Pro | Val | Leu | Thr | Gly | Leu | Asp | Gly | Glu | Gly | Lys | Met | Ser | Ser | Ser |
| | | | 195 | | | | | 200 | | | | | 205 | | |

| Lys | Gly | Asn | Phe | Ile | Ala | Val | Asp | Asp | Ser | Pro | Glu | Glu | Ile | Arg | Ala |
| | 210 | | | | | 215 | | | | | 220 | | | | |

| Lys | Ile | Lys | Lys | Ala | Tyr | Cys | Pro | Ala | Gly | Val | Val | Glu | Gly | Asn | Pro |
| 225 | | | | | 230 | | | | | 235 | | | | | 240 |

| Ile | Met | Glu | Ile | Ala | Lys | Tyr | Phe | Leu | Glu | Tyr | Pro | Leu | Thr | Ile | Lys |
| | | | | 245 | | | | | 250 | | | | | 255 | |

| Arg | Pro | Glu | Lys | Phe | Gly | Gly | Asp | Leu | Thr | Val | Asn | Ser | Tyr | Glu | Glu |
| | | | 260 | | | | | 265 | | | | | 270 | | |

| Leu | Glu | Ser | Leu | Phe | Lys | Asn | Lys | Glu | Leu | His | Pro | Met | Asp | Leu | Lys |
| | | | 275 | | | | | 280 | | | | | 285 | | |

| Asn | Ala | Val | Ala | Glu | Glu | Leu | Ile | Lys | Ile | Leu | Glu | Pro | Ile | Arg | Lys |
| | 290 | | | | | 295 | | | | | 300 | | | | |

| Arg | Leu |
| 305 | |

<210> SEQ ID NO 2
<211> LENGTH: 306
<212> TYPE: PRT
<213> ORGANISM: Artificial Sequence
<220> FEATURE:
<223> OTHER INFORMATION: synthetic polypeptide - pAcF-RS

<400> SEQUENCE: 2

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile
50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Cys His
145                 150                 155                 160

Tyr Arg Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Arg Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 3
<211> LENGTH: 306
<212> TYPE: PRT
<213> ORGANISM: Artificial Sequence
<220> FEATURE:
<223> OTHER INFORMATION: synthetic polypeptide - pIF-RS

<400> SEQUENCE: 3

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45
```

```
Ile Lys Lys Met Ile Asp Leu Gln Asn Ala Gly Phe Asp Ile Ile Ile
        50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Ser Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Pro Leu His
145                 150                 155                 160

Tyr Glu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Arg Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 4
<211> LENGTH: 306
<212> TYPE: PRT
<213> ORGANISM: Artificial Sequence
<220> FEATURE:
<223> OTHER INFORMATION: synthetic polypeptide - pAzF-RS

<400> SEQUENCE: 4

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Thr
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95
```

```
Gly Leu Lys Ala Lys Tyr Val Tyr Gly Ser Asn Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Pro Leu His
145                 150                 155                 160

Tyr Gln Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Arg Leu Lys
        275                 280                 285

Asn Ala Val Ala Glu Glu Leu Ile Lys Ile Leu Glu Pro Ile Arg Lys
290                 295                 300

Arg Leu
305

<210> SEQ ID NO 5
<211> LENGTH: 306
<212> TYPE: PRT
<213> ORGANISM: Artificial Sequence
<220> FEATURE:
<223> OTHER INFORMATION: synthetic polypeptide - pCNF-RS-D107

<400> SEQUENCE: 5

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Asp Trp Met Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140
```

```
Lys Val Ala Glu Val Ile Tyr Pro Ile Met Gln Val Asn Gly Ala His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
                260                 265                 270

Leu Glu Ser Leu Phe Lys Asn Lys Glu Leu His Pro Met Arg Leu Lys
                275                 280                 285

Asn Ala Val Ala Glu Glu Leu Ile Lys Ile Leu Glu Pro Ile Arg Lys
        290                 295                 300

Arg Leu
305

<210> SEQ ID NO 6
<211> LENGTH: 306
<212> TYPE: PRT
<213> ORGANISM: Artificial Sequence
<220> FEATURE:
<223> OTHER INFORMATION: synthetic polypeptide - pCNF-RS-E107

<400> SEQUENCE: 6

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
        50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Trp Met Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
130                 135                 140

Lys Val Ala Glu Val Ile Tyr Pro Ile Met Gln Val Asn Gly Ala His
145                 150                 155                 160

Tyr Leu Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190
```

Asn Pro Val Leu Thr Gly Leu Asp Gly Glu Gly Lys Met Ser Ser Ser
            195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
                260                 265                 270

Leu Glu Ser Leu Phe Lys Asn Lys Glu Leu His Pro Met Arg Leu Lys
            275                 280                 285

Asn Ala Val Ala Glu Glu Leu Ile Lys Ile Leu Glu Pro Ile Arg Lys
        290                 295                 300

Arg Leu
305

<210> SEQ ID NO 7
<211> LENGTH: 306
<212> TYPE: PRT
<213> ORGANISM: Artificial Sequence
<220> FEATURE:
<223> OTHER INFORMATION: synthetic polypeptide - pAcFRS.1

<400> SEQUENCE: 7

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Cys His
145                 150                 155                 160

Tyr Arg Gly Val Asp Val Asp Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

```
Ile Met Glu Ile Ala Lys Tyr Phe Leu Glu Tyr Pro Leu Thr Ile Lys
            245                 250                 255

Arg Pro Glu Lys Phe Gly Gly Asp Leu Thr Val Asn Ser Tyr Glu Glu
        260                 265                 270

Leu Glu Ser Leu Phe Lys Asn Lys Glu Leu His Pro Met Arg Leu Lys
            275                 280                 285

Asn Ala Val Ala Glu Glu Leu Ile Lys Ile Leu Glu Pro Ile Arg Lys
        290                 295                 300

Arg Leu
305

<210> SEQ ID NO 8
<211> LENGTH: 306
<212> TYPE: PRT
<213> ORGANISM: Artificial Sequence
<220> FEATURE:
<223> OTHER INFORMATION: synthetic polypeptide - pAcFRS.t1

<400> SEQUENCE: 8

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
                20                  25                  30

Ile Gly Phe Glu Pro Ser Gly Lys Ile His Leu Gly His Tyr Leu Gln
            35                  40                  45

Ile Lys Lys Met Ile Asp Leu Gln Asn Ala Gly Phe Asp Ile Ile Ile
        50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Cys His
145                 150                 155                 160

Tyr Arg Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Gly Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Arg Leu Lys
        275                 280                 285
```

```
Asn Ala Val Ala Glu Glu Leu Ile Lys Ile Leu Glu Pro Ile Arg Lys
        290                 295                 300

Arg Leu
305

<210> SEQ ID NO 9
<211> LENGTH: 306
<212> TYPE: PRT
<213> ORGANISM: Artificial Sequence
<220> FEATURE:
<223> OTHER INFORMATION: synthetic polypeptide - pAcFRS.t2

<400> SEQUENCE: 9

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Cys His
145                 150                 155                 160

Tyr Arg Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Cys Pro Glu Lys Glu Gly Gly Asp Leu Thr Val Asn Ser Tyr Glu Glu
            260                 265                 270

Leu Glu Ser Leu Phe Lys Asn Lys Glu Leu His Pro Met Arg Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 10
```

```
<211> LENGTH: 306
<212> TYPE: PRT
<213> ORGANISM: Artificial Sequence
<220> FEATURE:
<223> OTHER INFORMATION: synthetic polypeptide - pAcFRS.1.t1

<400> SEQUENCE: 10
```

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Cys His
145                 150                 155                 160

Tyr Arg Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Gly Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Arg Leu Lys
        275                 280                 285

Asn Ala Val Ala Glu Glu Leu Ile Lys Ile Leu Glu Pro Ile Arg Lys
    290                 295                 300

Arg Leu
305

```
<210> SEQ ID NO 11
<211> LENGTH: 306
<212> TYPE: PRT
<213> ORGANISM: Artificial Sequence
<220> FEATURE:
<223> OTHER INFORMATION: synthetic polypeptide - pAcFRS.1.t2

<400> SEQUENCE: 11
```

Met Asp Glu Phe Glu Met Ile Lys Arg Asn Thr Ser Glu Ile Ile Ser

```
                1               5                   10                  15
            Glu Glu Glu Leu Arg Glu Val Leu Lys Lys Asp Glu Lys Ser Ala Leu
                            20                  25                  30

Ile Gly Phe Glu Pro Ser Gly Lys Ile His Leu Gly His Tyr Leu Gln
                            35                  40                  45

Ile Lys Lys Met Ile Asp Leu Gln Asn Ala Gly Phe Asp Ile Ile Ile
                50                          55                  60

Leu Leu Ala Asp Leu His Ala Tyr Leu Asn Gln Lys Gly Glu Leu Asp
             65                     70                  75                  80

Glu Ile Arg Lys Ile Gly Asp Tyr Asn Lys Lys Val Phe Glu Ala Met
                            85                  90                  95

Gly Leu Lys Ala Lys Tyr Val Tyr Gly Ser Glu Phe Gln Leu Asp Lys
                            100                 105                 110

Asp Tyr Thr Leu Asn Val Tyr Arg Leu Ala Leu Lys Thr Thr Leu Lys
                            115                 120                 125

Arg Ala Arg Arg Ser Met Glu Leu Ile Ala Arg Glu Asp Glu Asn Pro
                    130                 135                 140

Lys Val Ala Glu Val Ile Tyr Pro Ile Met Gln Val Asn Gly Cys His
            145                     150                 155                 160

Tyr Arg Gly Val Asp Val Ala Val Gly Gly Met Glu Gln Arg Lys Ile
                            165                 170                 175

His Met Leu Ala Arg Glu Leu Leu Pro Lys Lys Val Val Cys Ile His
                            180                 185                 190

Asn Pro Val Leu Thr Gly Leu Asp Gly Glu Gly Lys Met Ser Ser Ser
                        195                 200                 205

Lys Gly Asn Phe Ile Ala Val Asp Asp Ser Pro Glu Glu Ile Arg Ala
                    210                 215                 220

Lys Ile Lys Lys Ala Tyr Cys Pro Ala Gly Val Val Glu Gly Asn Pro
            225                     230                 235                 240

Ile Met Glu Ile Ala Lys Tyr Phe Leu Glu Tyr Pro Leu Thr Ile Lys
                            245                 250                 255

Cys Pro Glu Lys Glu Gly Gly Asp Leu Thr Val Asn Ser Tyr Glu Glu
                            260                 265                 270

Leu Glu Ser Leu Phe Lys Asn Lys Glu Leu His Pro Met Arg Leu Lys
                        275                 280                 285

Asn Ala Val Ala Glu Glu Leu Ile Lys Ile Leu Glu Pro Ile Arg Lys
                        290                 295                 300

Arg Leu
            305

<210> SEQ ID NO 12
<211> LENGTH: 306
<212> TYPE: PRT
<213> ORGANISM: Artificial Sequence
<220> FEATURE:
<223> OTHER INFORMATION: synthetic polypeptide - pAcFRS.2

<400> SEQUENCE: 12

Met Asp Glu Phe Glu Met Ile Lys Arg Asn Thr Ser Glu Ile Ile Ser
 1               5                   10                  15

Glu Glu Glu Leu Arg Glu Val Leu Lys Lys Asp Glu Lys Ser Ala Leu
                20                  25                  30

Ile Gly Phe Glu Pro Ser Gly Lys Ile His Leu Gly His Tyr Leu Gln
                35                  40                  45

Ile Lys Lys Met Ile Asp Leu Gln Asn Ala Gly Phe Asp Ile Ile Ile
```

```
Val Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
             85                  90                  95

Gly Leu Lys Ala Lys Tyr Val Tyr Gly Ser Glu Phe Gln Leu Asp Lys
        100                 105                 110

Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
        130                 135                 140

Lys Val Ala Glu Val Ile Tyr Pro Ile Met Gln Val Asn Gly Cys His
145                 150                 155                 160

Tyr Arg Gly Val Asp Val Asp Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
        210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
                260                 265                 270

Leu Glu Ser Leu Phe Lys Asn Lys Glu Leu His Pro Met Arg Leu Lys
            275                 280                 285

Asn Ala Val Ala Glu Glu Leu Ile Lys Ile Leu Glu Pro Ile Arg Lys
        290                 295                 300

Arg Leu
305

<210> SEQ ID NO 13
<211> LENGTH: 306
<212> TYPE: PRT
<213> ORGANISM: Artificial Sequence
<220> FEATURE:
<223> OTHER INFORMATION: synthetic polypeptide - pAcFRS.2.t1

<400> SEQUENCE: 13

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile
    50                  55                  60

Val Leu Ala Asp Leu His Ala Tyr Leu Asn Gln Lys Gly Glu Leu Asp
 65                  70                  75                  80

Glu Ile Arg Lys Ile Gly Asp Tyr Asn Lys Lys Val Phe Glu Ala Met
             85                  90                  95

Gly Leu Lys Ala Lys Tyr Val Tyr Gly Ser Glu Phe Gln Leu Asp Lys
```

```
                100                 105                 110
Asp Tyr Thr Leu Asn Val Tyr Arg Leu Ala Leu Lys Thr Thr Leu Lys
            115                 120                 125

Arg Ala Arg Arg Ser Met Glu Leu Ile Ala Arg Glu Asp Glu Asn Pro
        130                 135                 140

Lys Val Ala Glu Val Ile Tyr Pro Ile Met Gln Val Asn Gly Cys His
145                 150                 155                 160

Tyr Arg Gly Val Asp Val Asp Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Gly Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Arg Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 14
<211> LENGTH: 306
<212> TYPE: PRT
<213> ORGANISM: Artificial Sequence
<220> FEATURE:
<223> OTHER INFORMATION: synthetic polypeptide - pAcFRS.2.t2

<400> SEQUENCE: 14

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Val Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Cys His
```

```
            145                 150                 155                 160
Tyr Arg Gly Val Asp Val Asp Val Gly Met Glu Gln Arg Lys Ile
                    165                 170                 175

His Met Leu Ala Arg Glu Leu Leu Pro Lys Lys Val Val Cys Ile His
                    180                 185                 190

Asn Pro Val Leu Thr Gly Leu Asp Gly Glu Gly Lys Met Ser Ser Ser
                    195                 200                 205

Lys Gly Asn Phe Ile Ala Val Asp Asp Ser Pro Glu Glu Ile Arg Ala
210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                    245                 250                 255

Cys Pro Glu Lys Glu Gly Gly Asp Leu Thr Val Asn Ser Tyr Glu Glu
                    260                 265                 270

Leu Glu Ser Leu Phe Lys Asn Lys Glu Leu His Pro Met Arg Leu Lys
                    275                 280                 285

Asn Ala Val Ala Glu Glu Leu Ile Lys Ile Leu Glu Pro Ile Arg Lys
                    290                 295                 300

Arg Leu
305
```

<210> SEQ ID NO 15
<211> LENGTH: 306
<212> TYPE: PRT
<213> ORGANISM: Artificial Sequence
<220> FEATURE:
<223> OTHER INFORMATION: synthetic polypeptide - pAzFRS.1

<400> SEQUENCE: 15

```
Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
                    20                  25                  30

Ile Gly Phe Glu Pro Ser Gly Lys Ile His Leu Gly His Tyr Leu Gln
                    35                  40                  45

Ile Lys Lys Met Ile Asp Leu Gln Asn Ala Gly Phe Asp Ile Ile Ile
            50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                    85                  90                  95

Gly Leu Lys Ala Lys Tyr Val Tyr Gly Ser Glu Phe Gln Leu Asp Lys
                    100                 105                 110

Asp Tyr Thr Leu Asn Val Tyr Arg Leu Ala Leu Lys Thr Thr Leu Lys
                    115                 120                 125

Arg Ala Arg Arg Ser Met Glu Leu Ile Ala Arg Glu Asp Glu Asn Pro
            130                 135                 140

Lys Val Ala Glu Val Ile Tyr Pro Ile Met Gln Val Asn Val Met His
145                 150                 155                 160

Tyr Asp Gly Val Asp Val Tyr Val Gly Gly Met Glu Gln Arg Lys Ile
                    165                 170                 175

His Met Leu Ala Arg Glu Leu Leu Pro Lys Lys Val Val Cys Ile His
                    180                 185                 190

Asn Pro Val Leu Thr Gly Leu Asp Gly Glu Gly Lys Met Ser Ser Ser
```

```
                195                 200                 205
Lys Gly Asn Phe Ile Ala Val Asp Asp Ser Pro Glu Ile Arg Ala
    210                 215                 220
Lys Ile Lys Lys Ala Tyr Cys Pro Ala Gly Val Val Glu Gly Asn Pro
225                 230                 235                 240
Ile Met Glu Ile Ala Lys Tyr Phe Leu Glu Tyr Pro Leu Thr Ile Lys
                245                 250                 255
Arg Pro Glu Lys Phe Gly Gly Asp Leu Thr Val Asn Ser Tyr Glu Glu
            260                 265                 270
Leu Glu Ser Leu Phe Lys Asn Lys Glu Leu His Pro Met Arg Leu Lys
                275                 280                 285
Asn Ala Val Ala Glu Glu Leu Ile Lys Ile Leu Glu Pro Ile Arg Lys
            290                 295                 300
Arg Leu
305

<210> SEQ ID NO 16
<211> LENGTH: 307
<212> TYPE: PRT
<213> ORGANISM: Artificial Sequence
<220> FEATURE:
<223> OTHER INFORMATION: synthetic polypeptide - pAzFRS.1.t1

<400> SEQUENCE: 16

Met Asp Glu Phe Glu Met Ile Lys Arg Asn Thr Ser Glu Ile Ile Ser
1               5                   10                  15
Glu Glu Glu Leu Arg Glu Val Leu Lys Lys Asp Glu Lys Ser Ala Leu
            20                  25                  30
Ile Gly Phe Glu Pro Ser Gly Lys Ile His Leu Gly His Tyr Leu Gln
        35                  40                  45
Ile Lys Lys Met Ile Asp Leu Gln Asn Ala Gly Phe Asp Ile Ile Ile
    50                  55                  60
Leu Leu Ala Asp Leu His Ala Tyr Leu Asn Gln Lys Gly Glu Leu Asp
65                  70                  75                  80
Glu Ile Arg Lys Ile Gly Asp Tyr Asn Lys Lys Val Phe Glu Ala Met
                85                  90                  95
Gly Leu Lys Ala Lys Tyr Val Tyr Gly Ser Glu Phe Gln Leu Asp Lys
            100                 105                 110
Asp Tyr Thr Leu Asn Val Tyr Arg Leu Ala Leu Lys Thr Thr Leu Lys
        115                 120                 125
Arg Ala Arg Arg Ser Met Glu Leu Ile Ala Arg Glu Asp Glu Asn Pro
    130                 135                 140
Lys Val Ala Glu Val Ile Tyr Pro Ile Met Gln Val Asn Val Met His
145                 150                 155                 160
Tyr Asp Gly Val Asp Val Tyr Val Gly Gly Met Glu Gln Arg Lys Ile
                165                 170                 175
His Met Leu Ala Arg Glu Leu Leu Pro Lys Lys Val Val Cys Ile His
            180                 185                 190
Asn Pro Val Leu Thr Gly Leu Asp Gly Glu Gly Lys Met Ser Ser Ser
        195                 200                 205
Lys Gly Asn Phe Ile Ala Val Asp Asp Ser Pro Glu Ile Arg Ala
    210                 215                 220
Lys Ile Lys Lys Ala Tyr Cys Pro Ala Gly Val Val Glu Gly Asn Pro
225                 230                 235                 240
Ile Met Met Glu Ile Ala Lys Tyr Phe Leu Glu Tyr Pro Leu Thr Ile
```

```
                245                 250                 255
Lys Gly Pro Glu Lys Phe Gly Gly Asp Leu Thr Val Asn Ser Tyr Glu
            260                 265                 270

Glu Leu Glu Ser Leu Phe Lys Asn Lys Glu Leu His Pro Met Arg Leu
        275                 280                 285

Lys Asn Ala Val Ala Glu Glu Leu Ile Lys Ile Leu Glu Pro Ile Arg
    290                 295                 300

Lys Arg Leu
305

<210> SEQ ID NO 17
<211> LENGTH: 307
<212> TYPE: PRT
<213> ORGANISM: Artificial Sequence
<220> FEATURE:
<223> OTHER INFORMATION: synthetic polypeptide - pAzFRS.1.t2

<400> SEQUENCE: 17

Met Asp Glu Phe Glu Met Ile Lys Arg Asn Thr Ser Glu Ile Ile Ser
1               5                  10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Glu Phe Gln Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Val Met His
145                 150                 155                 160

Tyr Asp Gly Val Asp Val Tyr Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Met Glu Ile Ala Lys Tyr Phe Leu Glu Tyr Pro Leu Thr Ile
                245                 250                 255

Lys Cys Pro Glu Lys Glu Gly Gly Asp Leu Thr Val Asn Ser Tyr Glu
            260                 265                 270

Glu Leu Glu Ser Leu Phe Lys Asn Lys Glu Leu His Pro Met Arg Leu
        275                 280                 285

Lys Asn Ala Val Ala Glu Glu Leu Ile Lys Ile Leu Glu Pro Ile Arg
```

Lys Arg Leu
305

<210> SEQ ID NO 18
<211> LENGTH: 306
<212> TYPE: PRT
<213> ORGANISM: Artificial Sequence
<220> FEATURE:
<223> OTHER INFORMATION: synthetic polypeptide - pAzRS.2

<400> SEQUENCE: 18

```
Met Asp Glu Phe Glu Met Ile Lys Arg Asn Thr Ser Glu Ile Ile Ser
1               5                  10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Tyr Met Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Cys His
145                 150                 155                 160

Tyr Arg Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Arg Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Arg Leu Lys
        275                 280                 285

Asn Ala Val Ala Glu Glu Leu Ile Lys Ile Leu Glu Pro Ile Arg Lys
    290                 295                 300

Arg Leu
305
```

<210> SEQ ID NO 19
<211> LENGTH: 306
<212> TYPE: PRT

```
<213> ORGANISM: Artificial Sequence
<220> FEATURE:
<223> OTHER INFORMATION: synthetic polypeptide - pAzRS.2.t1

<400> SEQUENCE: 19

Met Asp Glu Phe Glu Met Ile Lys Arg Asn Thr Ser Glu Ile Ile Ser
1               5                   10                  15

Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Tyr Met Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Cys His
145                 150                 155                 160

Tyr Arg Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Gly Pro Glu Lys Phe Gly Gly Asp Leu Thr Val Asn Ser Tyr Glu Glu
            260                 265                 270

Leu Glu Ser Leu Phe Lys Asn Lys Glu Leu His Pro Met Arg Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 20
<211> LENGTH: 306
<212> TYPE: PRT
<213> ORGANISM: Artificial Sequence
<220> FEATURE:
<223> OTHER INFORMATION: synthetic polypeptide - pAzRS.2.t2

<400> SEQUENCE: 20

Met Asp Glu Phe Glu Met Ile Lys Arg Asn Thr Ser Glu Ile Ile Ser
1               5                   10                  15
```

```
Glu Glu Glu Leu Arg Glu Val Leu Lys Lys Asp Glu Lys Ser Ala Leu
            20                  25                  30

Ile Gly Phe Glu Pro Ser Gly Lys Ile His Leu Gly His Tyr Leu Gln
        35                  40                  45

Ile Lys Lys Met Ile Asp Leu Gln Asn Ala Gly Phe Asp Ile Ile Ile
    50                  55                  60

Leu Leu Ala Asp Leu His Ala Tyr Leu Asn Gln Lys Gly Glu Leu Asp
65                  70                  75                  80

Glu Ile Arg Lys Ile Gly Asp Tyr Asn Lys Lys Val Phe Glu Ala Met
                85                  90                  95

Gly Leu Lys Ala Lys Tyr Val Tyr Gly Ser Thr Tyr Met Leu Asp Lys
            100                 105                 110

Asp Tyr Thr Leu Asn Val Tyr Arg Leu Ala Leu Lys Thr Thr Leu Lys
        115                 120                 125

Arg Ala Arg Arg Ser Met Glu Leu Ile Ala Arg Glu Asp Glu Asn Pro
    130                 135                 140

Lys Val Ala Glu Val Ile Tyr Pro Ile Met Gln Val Asn Gly Cys His
145                 150                 155                 160

Tyr Arg Gly Val Asp Val Ala Val Gly Gly Met Glu Gln Arg Lys Ile
                165                 170                 175

His Met Leu Ala Arg Glu Leu Leu Pro Lys Lys Val Val Cys Ile His
            180                 185                 190

Asn Pro Val Leu Thr Gly Leu Asp Gly Glu Gly Lys Met Ser Ser Ser
        195                 200                 205

Lys Gly Asn Phe Ile Ala Val Asp Asp Ser Pro Glu Glu Ile Arg Ala
    210                 215                 220

Lys Ile Lys Lys Ala Tyr Cys Pro Ala Gly Val Val Glu Gly Asn Pro
225                 230                 235                 240

Ile Met Glu Ile Ala Lys Tyr Phe Leu Glu Tyr Pro Leu Thr Ile Lys
                245                 250                 255

Cys Pro Glu Lys Glu Gly Gly Asp Leu Thr Val Asn Ser Tyr Glu Glu
            260                 265                 270

Leu Glu Ser Leu Phe Lys Asn Lys Glu Leu His Pro Met Arg Leu Lys
        275                 280                 285

Asn Ala Val Ala Glu Glu Leu Ile Lys Ile Leu Glu Pro Ile Arg Lys
    290                 295                 300

Arg Leu
305

<210> SEQ ID NO 21
<211> LENGTH: 77
<212> TYPE: DNA
<213> ORGANISM: Artificial Sequence
<220> FEATURE:
<223> OTHER INFORMATION: synthetic polynucleotide - tRNA

<400> SEQUENCE: 21
ccggcggtag ttcagcaggg cagaacggcg gactctaaat ccgcatggca ggggttcaaa      60 tccccctccgc cggacca                                                    77

<210> SEQ ID NO 22
<211> LENGTH: 1015
<212> TYPE: DNA
<213> ORGANISM: Artificial Sequence
<220> FEATURE:
<223> OTHER INFORMATION: synthetic polynucleotide - selectable marker -
      cat
```

<400> SEQUENCE: 22

```
cctgtgacgg aagatcactt cgcagaataa ataaatcctg gtgtccctgt tgataccggg    60
aagccctggg ccaacttttg gcgaaaatga gacgttgatc ggcacgtaag aggttccaac   120
tttcaccata atgaaataag atcactaccg ggcgtatttt ttgagttgtc gagattttca   180
ggagctaagg aagctaaaat ggagaaaaaa atcactggat ataccaccgt tgatatatcc   240
caatggcatc gtaagaaca ttttgaggca tttcagtcag ttgctcaatg tacctataac    300
cagaccgttc agctggatat tacggccttt ttaaagaccg taagaaaaa taagcacaag    360
ttttatccgg cctttattca cattcttgcc cgcctgatga atgctcatcc ggaattacgt   420
atggcaatga agacggtga gctggtgata tgggatagtg ttcaccccttg ttacaccgtt   480
ttccatgagc aaactgaaac gttttcatcg ctctggagtg aataccacga cgatttccgg   540
cagtttctac acatatattc gcaagatgtg gcgtgttacg gtgaaaacct ggcctatttc   600
cctaaagggt ttattgagaa tatgttttc gtctcagcca atccctgggt gagtttcacc    660
agttttgatt taaacgtggc caatatggac aacttcttcg ccccgttttt caccatgggc   720
aaatattata cgcaaggcga caaggtgctg atgccgctgg cgattcaggt tcatcatgcc   780
gtttgtgatg gcttccatgt cggcagaatg cttaatgaat acaacagta ctgcgatgag    840
tggcagggcg gggcgtaatt tttttaaggc agttattggt gcccttaaac gcctggttgc   900
tacgcctgaa taagtgataa taagcggatg aatggcagaa attcgaaagc aaattcgacc   960
cggtcgtcgg ttcagggcag ggtcgttaaa tagccgctta tgtctattgc tggtt        1015
```

<210> SEQ ID NO 23
<211> LENGTH: 1165
<212> TYPE: DNA
<213> ORGANISM: Artificial Sequence
<220> FEATURE:
<223> OTHER INFORMATION: synthetic polynucleotide - selectable marker - kanR

<400> SEQUENCE: 23

```
cctgtgacgg aagatcactt cgcagaataa ataaatcctg gtgtccctgt tgataccggg    60
aagccctggg ccaacttttg gcgaaaatga gacgttgatc ggcacgtaag aggttccaac   120
tttcaccata atgaaataag atcactaccg ggcgtatttt ttgagttgtc gagattttca   180
ggagctaagg aagctaaaat gagccatatt caacgggaaa cgtcgaggcc gcgattaaat   240
tccaacatgg atgctgattt atatgggtat aaatgggctc gcgataatgt cgggcaatca   300
ggtgcgacaa tctatcgctt gtatgggaag cccgatgcgc cagagttgtt tctgaaacat   360
ggcaaaggta gcgttgccaa tgatgttaca gatgagatgg tcagactaaa ctggctgacg   420
gaatttatgc ctcttccgac catcaagcat tttatccgta ctcctgatga tgcatggtta   480
ctcaccactg cgatccccgg aaaaacagca ttccaggtat tagaagaata tcctgattca   540
ggtgaaaata ttgttgatgc gctggcagtg ttcctgcgcc ggttgcattc gattcctgtt   600
tgtaattgtc cttttaacag cgatcgcgta tttcgtctcg ctcaggcgca atcacgaatg   660
aataacggtt tggttgatgc gagtgatttt gatgacgagc gtaatggctg gcctgttgaa   720
caagtctgga agaaatgca taaacttttg ccattctcac cggattcagt cgtcactcat    780
ggtgatttct cacttgataa ccttatttt gacgagggga aattaatagg ttgtattgat    840
gttggacgag tcggaatcgc agaccgatac caggatcttg ccatcctatg gaactgcctc   900
ggtgagtttt ctccttcatt acagaaacgg ctttttcaaa aatatggtat tgataatcct   960
```

```
gatatgaata aattgcagtt tcatttgatg ctcgatgagt ttttctaatt tttttaaggc    1020
agttattggt gcccttaaac gcctggttgc tacgcctgaa taagtgataa taagcggatg    1080
aatggcagaa attcgaaagc aaattcgacc cggtcgtcgg ttcagggcag ggtcgttaaa    1140
tagccgctta tgtctattgc tggtt                                          1165
```

<210> SEQ ID NO 24
<211> LENGTH: 1201
<212> TYPE: DNA
<213> ORGANISM: Artificial Sequence
<220> FEATURE:
<223> OTHER INFORMATION: synthetic polynucleotide - selectable marker -
      specR

<400> SEQUENCE: 24

```
cagccaggac agaaatgcct cgacttcgct gctgcccaag gttgccgggt gacgcacacc      60
gtggaaacgg atgaaggcac gaacccagtg gacataagcc tgttcggttc gtaagctgta    120
atgcaagtag cgtatgcgct cacgcaactg gtccagaacc ttgaccgaac gcagcggtgg    180
taacggcgca gtggcggttt tcatggcttg ttatgactgt ttttttgggg tacagtctat    240
gcctcgggca tccaagcagc aagcgcgtta cgccgtgggt cgatgtttga tgttatggag    300
cagcaacgat gttacgcagc agggcagtcg ccctaaaaca aagttaaaca tcatgaggga    360
agcggtgatc gccgaagtat cgactcaact atcagaggta gttggcgtca tcgagcgcca    420
tctcgaaccg acgttgctgg ccgtacattt gtacggctcc gcagtggatg gcggcctgaa    480
gccacacagt gatattgatt tgctggttac ggtgaccgta aggcttgatg aaacaacgcg    540
gcgagctttg atcaacgacc ttttggaaac ttcggcttcc cctggagaga gcgagattct    600
ccgcgctgta gaagtcacca ttgttgtgca cgacgacatc attccgtggc gttatccagc    660
taagcgcgaa ctgcaatttg gagaatggca gcgcaatgac attcttgcag gtatcttcga    720
gccagccacg atcgacattg atctggctat cttgctgaca aaagcaagag aacatagcgt    780
tgccttggta ggtccagcgg cggaggaact ctttgatccg gttcctgaac aggatctatt    840
tgaggcgcta aatgaaacct taacgctatg gaactcgccg cccgactggg ctggcgatga    900
gcgaaatgta gtgcttacgt tgtcccgcat ttggtacagc gcagtaaccg gcaaaatcgc    960
gccgaaggat gtcgctgccg actgggcaat ggagcgcctg ccggcccagt atcagcccgt   1020
catacttgaa gctagacagg cttatcttgg acaagaagaa gatcgcttgg cctcgcgcgc   1080
agatcagttg gaagaatttg tccactacgt gaaaggcgag atcaccaagg tagtcggcaa   1140
ataaagcttt actgagctaa taacaggact gctggtaatc gcaggccttt ttatttctgc   1200
a                                                                    1201
```

<210> SEQ ID NO 25
<211> LENGTH: 1746
<212> TYPE: DNA
<213> ORGANISM: Artificial Sequence
<220> FEATURE:
<223> OTHER INFORMATION: synthetic polynucleotide - selectable marker -
      tolC

<400> SEQUENCE: 25

```
ttgaggcaca ttaacgccct atggcacgta acgccaacct tttgcggtag cggcttctgc      60
tagaatccgc aataatttta cagtttgatc gcgctaaata ctgcttcacc acaaggaatg    120
caaatgaaga aattgctccc cattcttatc ggcctgagcc tttctgggtt cagttcgttg    180
```

```
agccaggccg agaacctgat gcaagtttat cagcaagcac gccttagtaa cccggaattg      240
cgtaagtctg ccgccgatcg tgatgctgcc tttgaaaaaa ttaatgaagc gcgcagtcca      300
ttactgccac agctaggttt aggtgcagat tacacctata gcaacggcta ccgcgacgcg      360
aacggcatca actctaacgc gaccagtgcg tccttgcagt taactcaatc cattttgat       420 atgtcgaaat ggcgtgcgtt aacgctgcag gaaaaagcag cagggattca ggacgtcacg      480
tatcagaccg atcagcaaac cttgatcctc aacaccgcga ccgcttattt caacgtgttg      540
aatgctattg acgttctttc ctatacacag gcacaaaaag aagcgatcta ccgtcaatta      600
gatcaaacca cccaacgttt taacgtgggc ctggtagcga tcaccgacgt gcagaacgcc      660
cgcgcacagt acgataccgt gctggcgaac gaagtgaccg cacgtaataa ccttgataac      720
gcggtagagc agctgcgcca gatcaccggt aactactatc cggaactggc tgcgctgaat      780
gtcgaaaact ttaaaaccga caaccacag ccggttaacg cgctgctgaa agaagccgaa       840
aaacgcaacc tgtcgctgtt acaggcacgc ttgagccagg acctggcgcg cgagcaaatt      900
cgccaggcgc aggatggtca cttaccgact ctggatttaa cggcttctac cgggattttct     960 gacacctctt atagcggttc gaaaacccgt ggtgccgctg gtacccagta tgacgatagc     1020
aatatgggcc agaacaaagt tggcctgagc ttctcgctgc cgatttatca gggcggaatg     1080
gttaactcgc aggtgaaaca ggcacagtac aactttgtcg gtgccagcga gcaactggaa     1140
agtgcccatc gtagcgtcgt gcagaccgtg cgttcctcct tcaacaacat taatgcatct     1200
atcagtagca ttaacgccta caaacaagcc gtagtttccg ctcaaagctc attagacgcg     1260
atggaagcgg gctactcggt cggtacgcgt accattgttg atgtgttgga tgcgaccacc     1320
acgttgtaca cgccaagca agagctggcg aatgcgcgtt ataactacct gattaatcag      1380
ctgaatatta agtcagctct gggtacgttg aacgagcagg atctgctggc actgaacaat     1440
gcgctgagca aaccggtttc cactaatccg gaaaacgttg caccgcaaac gccggaacag     1500
aatgctattg ctgatggtta tgcgcctgat agcccggcac cagtcgttca gcaaacatcc     1560
gcacgcacta ccaccagtaa cggtcataac ccttttccgta actgatgacg acgacgggga     1620
agcttaatta gctgatctag aggcatcaaa taaaacgaaa ggctcagtcg aaagactggg     1680
cctttcgttt tatctgttgt ttgtcggtga acgctctcct gagtaggaca aatccgccgc     1740
cctaga                                                                1746
```

<210> SEQ ID NO 26
<211> LENGTH: 762
<212> TYPE: DNA
<213> ORGANISM: Artificial Sequence
<220> FEATURE:
<223> OTHER INFORMATION: synthetic polynucleotide - selectable marker - zeoR

<400> SEQUENCE: 26

```
ggtgttgaca attaatcatc ggcatagtat atcggcatag tataatacga caaggtgagg       60
aactaaacca tggccaagtt gaccagtgcc gttccggtgc tcaccgcgcg cgacgtcgcc      120
ggagcggtcg agttctggac cgaccggctc gggttctccc gggacttcgt ggaggacgac      180
ttcgccggtg tggtccggga cgacgtgacc ctgttcatca gcgcggtcca ggaccaggtg      240
gtgccggaca cacccctggc ctgggtgtgg gtgcgcggcc tggacgagct gtacgccgag      300
tggtcggagt tcgtgtccac gaacttccgg gacgcctccg gccggccat gaccgagatc       360 ggcgagcagc cgtgggggcg ggagttcgcc ctgcgcgacc cggccggcaa ctgcgtgcac      420
```

-continued

| | |
|---|---|
| ttcgtggccg aggagcagga ctgacacgtc cgacggcggc ccacgggtcc caggcctcgg | 480 |
| agatccgtcc ccctttcct ttgtcgatat catgtaatta gttatgtcac gcttacattc | 540 |
| acgccctccc cccacatccg ctctaaccga aaggaagga gttagacaac ctgaagtcta | 600 |
| ggtccctatt tatttttta tagttatgtt agtattaaga acgttattta tatttcaaat | 660 |
| ttttcttttt tttctgtaca gacgcgtgta cgcatgtaac attatactga aaaccttgct | 720 |
| tgagaaggtt ttgggacgct cgaaggcttt aatttgcaag ct | 762 |

<210> SEQ ID NO 27
<211> LENGTH: 500
<212> TYPE: DNA
<213> ORGANISM: Artificial Sequence
<220> FEATURE:
<223> OTHER INFORMATION: synthetic polynucleotide - EcoRI Nuclease Pt 1

<400> SEQUENCE: 27

| | |
|---|---|
| atgagcaaca agaagcagag caaccgcctg accgagcagc ataagctgag ccagggcgtg | 60 |
| attggcatct tcggcgatta cgccaaagca cacgacctgg cagtgggtga ggtgagtaag | 120 |
| ctggtgaaga aggccctgag taacgagtac ccgcagctga gcttccgtta cgcgacagc | 180 |
| atcaaaaaaa ccgagatcaa cgaggccctg aagaagatcg atccggacct gggcggcacc | 240 |
| ctgttcgtga gcaacagtag catcaagccg gacggcggca tcgttgaagt gaaggacgac | 300 |
| tacggtgagt ggcgtgtggt gttagtggcc gaggccaagc atcagggcaa ggatatcatc | 360 |
| aacatccgca acggcctgct ggttggcaaa cgtggtgacc aagatctgat ggcagccggc | 420 |
| aacgccatcg agcgcagcca caagaatatt agcgagatcg caaatttcat gctgagcgag | 480 |
| agccacttcc cgtatgtgct | 500 |

<210> SEQ ID NO 28
<211> LENGTH: 500
<212> TYPE: DNA
<213> ORGANISM: Artificial Sequence
<220> FEATURE:
<223> OTHER INFORMATION: synthetic polynucleotide - EcoRI Nuclease Pt 2

<400> SEQUENCE: 28

| | |
|---|---|
| ccaagcatca gggcaaggat atcatcaaca tccgcaacgg cctgctggtt ggcaaacgtg | 60 |
| gtgaccaaga tctgatggca gccggcaacg ccatcgagcg cagccacaag aatattagcg | 120 |
| agatcgcaaa tttcatgctg agcgagagcc acttcccgta tgtgctgttc ttagagggta | 180 |
| gtaacttcct gaccgagaac attagcatca cccgtcctga tggccgcgtg gtgaacctgg | 240 |
| aatataacag cggcatcctg aatcgcctgg accgcctgac agccgccaac tacggcatgc | 300 |
| cgatcaacag taatctgtgt attaacaagt tcgttaatca aaagacaag agcatcatgc | 360 |
| tgcaggccgc cagcatctac acccaaggcg acggccgcga gtgggatagt aaaatcatgt | 420 |
| tcgagatcat gtttgacatt agcacaacca gcctgcgcgt gttaggccgt gatctgttcg | 480 |
| agcagctgac aagcaagtaa | 500 |

<210> SEQ ID NO 29
<211> LENGTH: 351
<212> TYPE: DNA
<213> ORGANISM: Artificial Sequence
<220> FEATURE:
<223> OTHER INFORMATION: synthetic polynucleotide - B anthracis Ames

```
atgattgtaa aacgcggcga cgtgtatttt gcagaccttt ccccagttgt tggttctgag    60
caaggaggtg ttcgtccggt tcttgtcatt caaaatgaca tcggaaatcg ttttagtcca   120
acggtgattg tagcggctat tactgcacag attcaaaaag cgaaattacc cactcatgtg   180
gaaattgatg cgaaaaagta cggttttgag agagattctg ttattttact tgagcagatt   240
cgaacaatcg ataagcagcg cttaacggac aaaatcactc acttagatga agtgatgatg   300
attcgtgtag atgaagcgct acaaatcagt ttaggactaa tcgatttcta g            351

<210> SEQ ID NO 30
<211> LENGTH: 153
<212> TYPE: DNA
<213> ORGANISM: Artificial Sequence
<220> FEATURE:
<223> OTHER INFORMATION: synthetic polynucleotide - E coli O111:H8 pndA

<400> SEQUENCE: 30
atgccacaac gaacgttttt aatgatgtta atcgtcgtct gtgtgacgat actgtgtttt    60
gtctggatgg tgagggattc gctttgcgga ttccgtgtcg agcagggaaa cacagtgctt   120
gtggcaacgt tagcctacga agttaaacgt taa                                153

<210> SEQ ID NO 31
<211> LENGTH: 159
<212> TYPE: DNA
<213> ORGANISM: Artificial Sequence
<220> FEATURE:
<223> OTHER INFORMATION: synthetic polynucleotide - E coli pC15 hok

<400> SEQUENCE: 31
atgaaactac cacgaagttc ccttgtctgg tgtgtgttga tcgtgtgtct cacactgttg    60
atattcactt atctgacacg aaaatcgctg tgcgagattc gttacagaga cggacacagg   120
gaggtggcgg ctttcatggc ttacgaatcc ggtaagtag                          159

<210> SEQ ID NO 32
<211> LENGTH: 270
<212> TYPE: DNA
<213> ORGANISM: Artificial Sequence
<220> FEATURE:
<223> OTHER INFORMATION: synthetic polynucleotide - P fluorescens pasB

<400> SEQUENCE: 32
atggcttggc ggattgaatt tgaccgcgct gcagagcgcg agctgggcaa actcgacccg    60
caaatcgcta acgaatcct gttgtttctg catgagcggg tatcaaatct ggatgatccg   120
cgcagcattg gcgaagcatt aaaaggctca cgtttagggg atttttggaa gtatcgggta   180
ggcgactacc gccttatcag cagcatcgag gacggcgcgt tgcgcatcct ggtgattaag   240
attgggaacc ggcgagaggt gtaccgctag                                    270

<210> SEQ ID NO 33
<211> LENGTH: 399
<212> TYPE: DNA
<213> ORGANISM: Artificial Sequence
<220> FEATURE:
<223> OTHER INFORMATION: synthetic polynucleotide - S enterica vapC

<400> SEQUENCE: 33
atgctgaaat tcatgcttga taccaatacc tgtattttca ccatcaaaaa taagcccgaa    60
cacatcagag aacgcttcaa cctcaataca tcccgaatgt gtatcagctc catcaccttga  120 atggagctga tttacggtgc tgaaaaaagc ctggcgccgg agcgtaatct tgccgtcgtg   180
```

-continued

```
gagggattta tctcccgcct tgaggttttg gattacgata cacaggcagc gatacatacc      240
ggtcaaatcc gtgccgaact ggcccgcaag ggaacacctg tcgggcctta tgaccagatg      300
attgctggcc atgccggtag ccgcggactg gtcgtcgtca caaacaatct ccgcgaattt      360
gaacgcattc cgggtatccg aatcgaagac tggtgctaa                             399

<210> SEQ ID NO 34
<211> LENGTH: 360
<212> TYPE: DNA
<213> ORGANISM: Artificial Sequence
<220> FEATURE:
<223> OTHER INFORMATION: synthetic polynucleotide - Streptavidin

<400> SEQUENCE: 34
atgggcatca ccggcacctg gtacaaccag ctcggctcga ccttcatcgt gaccgcgggc       60
gccgacggcg ccctgaccgg aacctacgag tcggccgtcg gcaacgccga gagccgctac      120
gtcctgaccg gtcgttacga cagcgccccg gccaccgacg gcagcggcac cgccctcggt      180
tggacggtgg cctggaagaa taactaccgc aacgcccact ccgcgaccac gtggagcggc      240
cagtacgtcg gcggcgccga ggcgaggatc aacacccagt ggctgctgac ctccggcacc      300
accgaggcca acgccgacaa gtccacggac gacggcgacg acaccttcac caaggtgtag      360
```